US008920807B2

(12) United States Patent
Rome et al.

(10) Patent No.: US 8,920,807 B2
(45) Date of Patent: Dec. 30, 2014

(54) VAULT COMPLEXES FOR CYTOKINE DELIVERY

(75) Inventors: Leonard H. Rome, Los Angeles, CA (US); Valerie A. Kickhoefer, Los Angeles, CA (US); Steven M. Dubinett, Los Angeles, CA (US); Sherven Sharma, Culver City, CA (US); Upendra K. Kar, Dhenkanal (IN)

(73) Assignees: The Regents of the University of California, Oakland, CA (US); The United States of America Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 13/505,420

(22) PCT Filed: Nov. 2, 2010

(86) PCT No.: PCT/US2010/055146

§ 371 (c)(1), (2), (4) Date: May 1, 2012

(87) PCT Pub. No.: WO2011/053991

PCT Pub. Date: May 5, 2011

(65) Prior Publication Data

US 2012/0213809 A1 Aug. 23, 2012

Related U.S. Application Data

(60) Provisional application No. 61/257,358, filed on Nov. 2, 2009.

(51) Int. Cl.

| | |
|---|---|
| ***A61K 38/00*** | (2006.01) |
| ***A61K 39/00*** | (2006.01) |
| ***A61K 48/00*** | (2006.01) |
| ***A61K 35/12*** | (2006.01) |
| ***C12N 9/96*** | (2006.01) |
| ***C07H 21/00*** | (2006.01) |
| ***C07K 14/47*** | (2006.01) |
| ***C12N 15/86*** | (2006.01) |
| *C07K 7/06* | (2006.01) |
| *C12N 5/0783* | (2010.01) |
| *G01N 33/535* | (2006.01) |

(52) U.S. Cl.

CPC ................ *A61K 38/00* (2013.01); *A61K 48/00* (2013.01); *C07K 2319/00* (2013.01); *C07H 21/00* (2013.01); *C07K 7/06* (2013.01); *C07K 14/47* (2013.01); *C12N 15/86* (2013.01); *A61K 35/12* (2013.01); *C12N 5/0636* (2013.01); *C12N 9/96* (2013.01); *G01N 33/535* (2013.01)

USPC ..................... 424/185.1; 424/184.1; 424/94.3; 536/23.4; 536/23.1; 435/320.1; 435/325; 435/366; 435/372.3; 435/375; 435/188; 530/395; 530/350; 514/19.3

(58) Field of Classification Search

None

See application file for complete search history.

(56) References Cited

U.S. PATENT DOCUMENTS 5,139,941 A 8/1992 Muzyczka et al.
5,252,479 A 10/1993 Srivastava (Continued)

FOREIGN PATENT DOCUMENTS

WO WO-93/24641 A2 12/1993
WO WO-93/24641 A3 12/1993

(Continued)

OTHER PUBLICATIONS

Kickhoefer et al., (ACS Nano. 2009;3(1):27-36. Epub Dec. 19, 2008).*

(Continued)

*Primary Examiner* — Cherie M Stanfield

(74) *Attorney, Agent, or Firm* — Suzannah K. Sundby, Esq.; Canady + Lortz LLP

(57) ABSTRACT

The invention relates to compositions of vault complexes containing recombinant cytokine fusion proteins that include a cytokine and a vault targeting domain, and methods of using the vault complexes to deliver the cytokines to a cell or subject, and methods for using the compositions to treat cancer, such as lung cancer.

17 Claims, 7 Drawing Sheets

(56) References Cited

U.S. PATENT DOCUMENTS

| | | | | |
|---|---|---|---|---|
| 5,436,146 | A | 7/1995 | Shenk et al. | |
| 5,665,557 | A | 9/1997 | Murray et al. | |
| 5,981,276 | A | 11/1999 | Sodroski et al. | |
| 6,110,740 | A | 8/2000 | Rome et al. | |
| 6,143,520 | A | 11/2000 | Marasco et al. | |
| 6,156,879 | A | 12/2000 | Rome et al. | |
| 6,555,347 | B1 | 4/2003 | Rome et al. | |
| 7,482,319 | B2 * | 1/2009 | Rome et al. | 514/1.1 |
| 8,124,109 | B2 | 2/2012 | Kickhoefer et al. | |
| 8,318,182 | B2 | 11/2012 | Kickhoefer et al. | |
| 8,551,781 | B2 | 10/2013 | Rome et al. | |
| 2006/0148086 | A1 * | 7/2006 | Rome et al. | 435/455 |
| 2009/0226435 | A1 | 9/2009 | Khare | |
| 2010/0086610 | A1 | 4/2010 | Rome et al. | |
| 2012/0003201 | A1 | 1/2012 | Nicholas et al. | |
| 2013/0078273 | A1 | 3/2013 | Kickhoefer et al. | |
| 2013/0122037 | A1 | 5/2013 | Kickhoefer et al. | |

FOREIGN PATENT DOCUMENTS

| | | | |
|---|---|---|---|
| WO | WO-94/12649 | A2 | 6/1994 |
| WO | WO-94/12649 | A3 | 6/1994 |
| WO | WO-94/13788 | A1 | 6/1994 |
| WO | WO-99/49025 | A2 | 9/1999 |
| WO | WO-99/49025 | A3 | 9/1999 |
| WO | WO-99/62547 | A1 | 12/1999 |
| WO | WO-2004/081533 | A2 | 9/2004 |
| WO | WO-2004/081533 | A3 | 9/2004 |
| WO | WO 2009117566 | A1 * | 9/2009 |
| WO | WO-2011/053991 | A2 | 5/2011 |
| WO | WO-2011/053991 | A3 | 5/2011 |

OTHER PUBLICATIONS

Allen, T.M. et al. (Mar. 19, 2004). "Drug Delivery Systems: Entering the Mainstream," *Science* 303:1818-1822.

Almand, B. et al. (2001). "Increased Production of Immature Myeloid Cells in Cancer Patients: A Mechanism of Immunosuppression in Cancer," *The Journal of Immunology* 166:678-689.

Altschul, S.F. et al. (1990). "Basic Local Alignment Search Tool," *J. Mol. Biol.* 215:403-410.

Anderson, D.H. et al. (Nov. 2007). "Draft Crystal Structure of the Vault Shell at 9-Å Resolution," *PLoS Biol.* 5(11): e318, 10 pages.

Andersson, A. et al. (2009). "IL-7 promotes CXCR3 Ligand-Dependent T Cell Antitumor Reactivity in Lung Cancer," *J. Immunol.* 182:6951-6958.

Baratelli, F. et al. (Jul. 22, 2008). "Pre-Clinical Characterization of GMP Grade CCL21—Gene Modified Dendritic Cells for Application in a Phase I Trial in Non-Small Cell Lung Cancer," *Journal of Translation Medicine* 6:38, 17 pages.

Berger, W. et al. (2009, e-pub. Sep. 19, 2008). "Vaults and the Major Vault Protein: Novel Roles in Signal Pathway Regulation and Immunity," *Cell Mol. Life Sci.* 66(1):43-61.

Boesen, J.J.B. et al. (1994). "Circumvention of Chemotherapy-Induced Myelosuppression by Transfer of the *mdr1* Gene," *Biotherapy* 6:291-302.

Boon, T. et al. (1994). "Tumor Antigens Recognized by T Lymphocytes," *Annu. Rev. Immunol.* 12:337-365.

Bout, A. et al. (1994). "Lung Gene Therapy: In Vivo Adenovirus-Mediated Gene Transfer to Rhesus Monkey Airway Epithelium," *Human Gene Therapy* 5:3-10.

Champion, C.I. et al. (Apr. 2009). "A Vault Nanoparticle Vaccine Induces Protective Mucosal Immunity," *PLoS ONE* 4(4):e5409, 12 pages.

Chen, H. et al. (Feb. 24, 2009). "Anti-CTLA-4 Therapy Results in Higher $CD4^+ICOS^{hl}$ T Cell Frequency and IFN-γ Levels in Both Nonmalignant and Malignant Prostate Tissues," *PNAS* 106(8):2729-2734.

Chugani, D.C. et al. (Jan. 1991). "Vault Immunofluorescence in Brain: New Insights Regarding the Origin of Microglia," *The Journal of Neuroscience* 11:256-268.

Chugani, D.C. et al. (1993). "Evidence that Vault Ribonucleoprotein Particles Localize to the Nuclear Pore Complex," *Journal of Cell Science* 106:23-29.

Clowes, M.M. et al. (Feb. 1994). "Long-Term Biological Response of Injured Rat Carotid Artery Seeded with Smooth Muscle Cells Expressing Retrovirally Introduced Human Genes," *J. Clin. Invest.* 93:644-651.

Diaz-Montero, C.M. et al. (Jan. 2009). "Increased Circulating Myeloid-Derived Suppressor Cells Correlate with Clinical Cancer Stage, Metastatic Tumor Burden, and Doxorubicin-Cyclophosphamide Chemotherapy," *Cancer Immunol. Immunother.* 58(1):49-59.

Dieu-Nosjean, M.-C. et al. (Sep. 20, 2008). "Long-Term Survival for Patients with Non-Small-Cell Lung Cancer with Intratumoral Lymphoid Structures," *Journal of Clinical Oncology* 26(27):4410-4417.

Esfandiary, R. et al. (Apr. 2009, e-pub. Aug. 6, 2008). "Structural Stability of Vault Particles," *Journal of Pharmaceutical Sciences* 98(4):1376-1386, doi: 10.1002/jps.21508.

Fisher, K.J. et al. (Jan. 1996). "Transduction with Recombinant Adeno-Associated Virus for Gene Therapy is Limited by Leading-Strand Synthesis," *Journal of Virology* 70(1):520-532.

Goldsmith, L.E. et al. (Mar. 13, 2007, e-pub. Feb. 16, 2007). "Vault Nanocapsule Dissociation into Halves Triggered at Low pH," *Biochemistry* 46(10):2865-2875.

Goldsmith, L.E. et al. (Oct. 2009, e-pub. Sep. 23, 2009). "Utilization of a Protein 'Shuttle' to Load Vault Nanocapsules with Gold Probes and Proteins," *ACS Nano* 3(10):3175-3183.

Greish, K. (Aug.-Sep. 2007). "Enhanced Permeability and Retention of Macromolecular Drugs in Solid Tumors: A Royal Gate for Targeted Anticancer Nanomedicines," *Journal of Drug Targeting* 15(7-8): 457-464.

Grossman, M. et al. (1993). "Retroviruses: Delivery Vehicle to the Liver," *Current Opinion in Genetics and Development* 3:110-114.

Gunn, M.D. et al. (Jan. 1998). "A Chemokine Expressed in Lymphoid High Endothelial Venules Promotes the Adhesion and Chemotaxis of Naïve T Lymphocytes," *Proc. Natl. Acad. Sci. USA* 95:258-263.

Herrmann, C. et al. (Mar. 22, 1999). "Recombinant Major Vault Protein is Targeted to Neuritic Tips of PC12 Cells," *The Journal of Cell Biology* 144(6):1163-1172.

Hiraoka, K. et al. (2006). "Concurrent Infiltration by $CD8^+$ T cells and $CD4^+$ T Cells is a Favourable Prognostic Factor in Non-Small-Cell Lung Carcinoma," *British Journal of Cancer* 94(2):275-280.

Hu, Y. et al. (2002). "A Very Early Induction of Major Vault Protein is Accompanied by Increased Drug Resistance in U-937 Cells," *Int. J. Cancer* 97:149-156.

Izquierdo, M.A. et al. (1996). "Relationship of LRP-Human Major Vault Protein to in vitro and Clinical Resistance to Anticancer Drugs," *Cytotechnology* 19:191-197.

Izquierdo, M.A. et al. (Mar. 1996). "Broad Distribution of the Multidrug Resistance-Related Vault Lung Resistance Protein in Normal Human Tissues and Tumors," *American Journal of Pathology* 148(3):877-887.

Johnson, S.K. et al. (2000). "Immune Cell Infiltrates and Prognosis in Primary Carcinoma of the Lung," *Lung Cancer* 27(1):27-35.

Ju, S. et al. (Aug. 15, 2009). "$CD13^+CD4^+CD25^{hl}$ Regulatory T Cells Exhibit Higher Suppressive Function and Increase with Tumor Stage in Non-Small Cell Lung Cancer Patients," *Cell Cycle* 8(16):2578-2585.

Kaddis, C.S. et al. (2007, e-pub. Apr. 16, 2007). "Sizing Large Proteins and Protein Complexes by Electrospray Ionization Mass Spectrometry and Ion Mobility," *J. Am. Soc. Mass Spectrom* 18:1206-1216.

Kar, U.K. et al. (Jul. 2012). "Vault Nanocapsules as Adjuvants Favor Cell-Mediated Over Antibody-Mediated Immune Responses Following Immunization of Mice," *PLoS ONE* 7(7):e38553, 13 pages.

Kedersha, N.L. et al. (Sep. 1986). "Isolation and Characterization of a Novel Ribonucleoprotein Particle: Large Structures Contain a Single Species of Small RNA," *J. Cell Biol.* 103:699-709.

Kedersha, N.L. et al. (Apr. 1990). "Vaults. II. Ribonucleoprotein Structures are Highly Conserved Among Higher and Lower Eukaryotes," *J. Cell Biol.* 110:895-901.

Kedersha, N.L. et al. (1990). "Vaults: Large Cytoplasmic RNP's that Associate with Cytoskeletal Elements," *Molecular Biology Reports* 14:121-122.

(56) References Cited

OTHER PUBLICATIONS

Kedersha, N.L. et al. (Jan. 1991). "Vaults. III. Vault Ribonucleoprotein Particles Open into Flower-like Structures with Octagonal Symmetry," *J. Cell Biol.* 112:225-235.
Kickhoefer, V.A. et al. (Apr. 15, 1993). "Vault Ribonucleoprotein Particles from Rat and Bullfrog Contain a Related Small RNA that is Transcribed by RNA Polymerase III," *J. Biol. Chem.* 268(11):7868-7873.
Kickhoefer, V.A. et al. (1994). "The Sequence of a cDNA Encoding the Major Vault Protein from *Rattus norvegicus," Gene* 151:257-260.
Kickhoefer, V.A. et al. (May 1996). "Vaults are the Answer, What is the Question?" *Trends in Cell Biology* 6:174-178.
Kickhoefer, V.A. et al. (Apr. 10, 1998). "Vaults are Up-Regulated in Multidrug Resistant Cancer Cell Lines," *J. Biol. Chem.* 273(15):8971-8974.
Kickhoefer, V.A. et al. (Sep. 6, 1999). "The 193-kD Vault Protein, VPARP, is a Novel Poly(ADP-ribose) Polymerase," *J. Cell Biol.* 146(5):917-928.
Kickhoefer, V.A. et al. (Nov. 12, 1999). "Vaults and Telomerase Share a Common Subunit, TEP1," *J. Biol. Chem.* 274:32712-32717.
Kickhoefer, V.A. et al. (Jan. 8, 2001). "The Telomerase/Vault-Associated Protein TEP1 is Required for Vault RNA Stability and Its Association with the Vault Particle," *J. Cell Biol.* 152:157-164.
Kickhoefer, V.A. et al. (Mar. 22, 2005). "Engineering of Vault Nanocapsules with Enzymatic and Fluorescent Properties," *PNAS* 102(12):4348-4352.
Kiem, H.-P. et al. (Mar. 15, 1994). "Retrovirus-Mediated Gene Transduction Into Canine Peripheral Blood Repopulating Cells," *Blood* 83(6):1 467-1473.
Kirk, C.J. et al. (Dec. 15, 2001). "The Dynamics of the T-Cell Antitumor Response: Chemokine-Secreting Dendritic Cells Can Prime Tumor-Reactive T Cells Extranodally," *Cancer Research* 61:8794-8802.
Kong, L.B. et al. (Apr. 1999). "Structure of the Vault, a Ubiquitous Cellular Component," *Structure* 7:371-379.
Kong, L.B. et al. (2000). "RNA Location and Modeling of a WD40 Repeat Domain within the Vault," *RNA* 6:890-900.
Kozarsky, K.F. et al. (1993). "Gene Therapy: Adenovirus Vectors," *Current Opinion in Genetics and Development* 3:499-503.
Kusmartsev, S.A. et al. (1989). "Suppressor Activity of Bone Marrow and Spleen Cells in C57Bl/6 Mice During Carcinogenesis Induced by 7,12-Dimethylbenz(a)anthracene," *Eksp Onkol* 11(5):23-26. (English Abstract Only).
Kusmartsev, S.A. et al. (1998). "Immunosuppressive Cells in Bone Marrow of Patients with Stomach Cancer," *Adv. Exp. Med. Biol.* 451:189-194.
Kusmartsev, S.A. et al. (2000). "Gr-$1^+$ Myeloid Cells Derived from Tumor-Bearing Mice Inhibit Primary T Cell Activation Induced Through CD3/CD28 Costimulation," *The Journal of Immunology* 165:779-785.
Lai, C.-Y. et al. (2009, e-pub. Feb. 18, 2009). "Vault Nanoparticles Containing an Adenovirus-Derived Membrane Lytic Protein Facilitate Toxin and Gene Transfer," *ACS Nano* 3(3):691-699.
Li, C. et al. (Feb. 1, 2007). "Identification of Pancreatic Cancer Stem Cells," *Cancer Research* 67(3):1030-1037.
Li, L. et al. (2009). "The Prevalence of FOXP$3^+$ Regulatory T-Cells in Peripheral Blood of Patients with NSCLC," *Cancer Biotherapy Radiopharmaceuticals* 24(3):357-367.
Liang, C.-M. et al. (Sep. 2007, e-pub. Jun. 13, 2007). "Local Expression of Secondary Lymphoid Tissue Chemokine Delivered by Adeno-Associated Virus within the Tumor Bed Stimulates Strong Anti-Liver Tumor Immunity," *Journal of Virology* 81(17):9502-9511.
Liu, C. et al. (May 15, 2007). "Expansion of Spleen Myeloid Suppressor Cells Represses NK Cell Cytotoxicity in Tumor-Bearing Host," *Blood* 109(10):4336-4342.
Liu, C.-Y. et al. (2010, e-pub. Jul. 2, 2009). "Population Alterations of L-Arginase- and Inducible Nitric Oxide Synthase-Expressed CD11$b^+$/CD$14^-$/CD$15^+$/CD$33^+$ Myeloid-Derived Suppressor Cells and CD$8^+$ T Lymphocytes in Patients with Advanced-Stage Non-Small Cell Lung Cancer," *J. Cancer Res. Clin. Oncol.* 136:35-45.
Liu, Y. et al. (Jun. 2004). "Vault Poly(ADP-Ribose) Polymerase is Associated with Mammalian Telomerase and is Dispensable for Telomerase Function and Vault Structure In Vivo," *Molecular and Cell Biology* 24(12):5314-5323.
Maeda, H. et al. (2000). "Tumor Vascular Permeability and the EPR Effect in Macromolecular Therapeutics: A Review," *Journal of Controlled Release* 65:271-284.
Mastrangeli, A. et al. (1993). "Diversity of Airway Epithelial Cell Targets for In Vivo Recombinant Adenovirus-Mediated Gene Transfer," *J. Clin. Invest.* 91:225-234.
Mikyas, Y. et al. (2004). "Cryoelectron Microscopy Imaging of Recombinant and Tissue Derived Vaults: Localization of the MVP N Termini and VPARP," *J. Mol. Biol.* 344:91-105.
Needleman, S.B. et al. (1970). "A General Method Applicable to the Search for Similarities in the Amino Acid Sequence of Two Proteins," *J. Mol. Biol.* 48:443-453.
Ng, B.C. et al. (Oct. 2008, e-pub on Sep. 20, 2008). "Encapsulation of Semiconducting Polymers in Vault Protein Cages," *Nano Letters* 8(10):3503-3509.
Novak, L. et al. (Jun. 2007). "Characterization of the CCL21-Mediated Melanoma-Specific Immune Responses and in situ Melanoma Eradication," *Mol. Cancer Ther.* 6(6):1755-1764.
Pearson, W.R. et al. (Apr. 1988). "Improved Tools for Biological Sequence Comparison," *Proc. Natl. Acad. Sci. USA* 85:2444-2448.
Poderycki, M.J. et al. (2005). "The p80 Homology Region of TEP1 is Sufficient for its Association with the Telomerase and Vault RNAs, and the Vault Particle," *Nucleic Acids Research* 33(3):893-902.
Poderycki, M.J. et al. (Oct. 3, 2006, e-pub. Sep. 7, 2006). "The Vault Exterior Shell is a Dynamic Structure that Allows Incorporation of Vault-Associated Proteins into Its Interior," *Biochemistry* 45(39):12184-12193.
Raval-Fernandes, S. et al. (1999). "Cloning of a cDNA Encoding a Sequence-Specific Single-Stranded-DNA-Binding Protein from *Rattus norvegicus," Gene* 237:201-207.
Raval-Fernandes, S. et al. (Oct. 1, 2005). "Increased Susceptibility of Vault Poly(ADP-Ribose) Polymerase-Deficient Mice to Carcinogen-Induced Tumorigenesis," *Cancer Res.* 65(19):8846-8852.
Rome, L. et al. (Aug./Sep. 1991). "Unlocking Vaults: Organelles in Search of a Function," *Trends in Cell Biology* 1:47-50.
Rome, L.H. (Jun. 1995). "Multidrug Resistance: Locked in the Vault?" *Nature Medicine* 1(6):527.
Rosenfeld, M.A. et al. (Apr. 19, 1991). "Adenovirus-Mediated Transfer of a Recombinant $\alpha$1-Antitrypsin Gene to the Lung Epithelium in Vivo," *Science* 252:431-434.
Rosenfeld, M.A. et al. (Jan. 10, 1992). "In Vivo Transfer of the Human Cystic Fibrosis Transmembrane Conductance Regulator Gene to the Airway Epithelium," *Cell* 68:143-155.
Sakaguchi, S. (May 26, 2000). Regulatory T Cells: Key Controllers of Immunologic Self-Tolerance. *Cell* 101(5):455-458.
Salmons, B. et al. (1993). "Targeting of Retroviral Vectors for Gene Therapy," *Human Gene Therapy* 4:129-141.
Samulski, R.J. et al. (Oct. 1987). "A Recombinant Plasmid from Which an Infectious Adeno-Associated Virus Genome Can Be Excised In Vitro and Its Use to Study Viral Replication," *Journal of Virology* 61(10):3096-3101.
Samulski, R.J. et al. (Sep. 1989). "Helper-Free Stocks of Recombinant Adeno-Associated Viruses: Normal Integration Does Not Require Viral Gene Expression," *Journal of Virology* 63(9):3822-3828.
Scheper, R.J. et al. (1996). "Role of LRP/Major Vault Protein in Multidrug Resistance," Chapter 7 in *Multidrug Resistance in Cancer Cells: Molecular, Biochemical, Physiological and Biological Aspects*, Gupta, S. et al. eds., John Wiley & Sons, Chichester, England.
Schroeijers, A.B. et al. (Feb. 15, 2000). "The $M_r$ 193,000 Vault Protein is Up-Regulated in Multidrug-Resistant Cancer Cell Lines," *Cancer Research* 60:1104-1110.
Sharma, S. et al. (2000). "Secondary Lymphoid Tissue Chemokine Mediates T Cell-Dependent Antitumor Responses In Vivo," *J. Immunol.* 164(9):4558-4563.

(56) References Cited

OTHER PUBLICATIONS

Sharma, S. et al. (2001). "Secondary Lymphoid Organ Chemokine Reduces Pulmonary Tumor Burden in Spontaneous Murine Bronchoalveolar Cell Carcinoma," *Cancer Research* 61(17):6406-6412.
Sharma, S. et al. (Apr. 15, 2003). "SLC/CCL21-Mediated Anti-Tumor Responses Require IFNγ, MIG/CXCL9 and IP-10/CXCL10," *Molecular Cancer* 2:22, 6 pages.
Sinha, P. et al. (2005). "Reduction of Myeloid-Derived Suppressor Cells and Induction of MI Macrophages Facilitate the Rejection of Established Metastatic Disease," *The Journal of Immunology* 174(2):636-645.
Siva, A.C. et al. (2001). "Up-Regulation of Vaults May Be Necessary But Not Sufficient for Multidrug Resistance," *Int. J. Cancer* 92:195-202.
Slesina, M. et al. (2005, e-pub. May 18, 2005). "Nuclear Localization of the Major Vault Protein in U373 Cells," *Cell Tissue Res.* 321:97-104.
Slesina, M. et al. (2006, e-pub. Feb. 28, 2006). "Movement of Vault Particles Visualized by GFP-Tagged Major Vault Protein," *Cell Tissue Res.* 324:403-410.
Smith, T.R. et al. (1981). "Comparison of Biosequences," *Advances in Applied Mathematics* 2:482-489.
Smyth, M.J. et al. (2006). "$CD4^+CD25^+$ T Regulatory Cells Suppress NK Cell-Mediated Immunotherapy of Cancer," *The Journal of Immunology* 176(3):1582-1587.
Srivastava, M.K. et al. (Oct. 2008). "Lung Cancer Patients' $CD4^+$ T Cells are Activated in Vitro by MHC II Cell-Based Vaccines Despite the Presence of Myeloid-Derived Suppressor Cells," *Cancer Immunol. Immunother.* 57(10):1493-1504.
Stephen, A.G. et al. (Jun. 29, 2001). "Assembly of Vault-Like Particles in Insect Cells Expressing Only the Major Vault Protein," *J. Biol. Chem.* 276(26):23217-23220.
Subiza, J.L. et al. (1989). "Development of Splenic Natural Suppressor (NS) Cells in Ehrlich Tumor-Bearing Mice," *Int. J. Cancer* 44(2):307-314.
Suprenant, K.A. (Dec. 10, 2002, e-pub. Oct. 23, 2002). "Vault Ribonucleoprotein Particles: Sarcophagi, Gondolas, or Safety Deposit Boxes?" *Biochemistry* 41(49):14447-14454.
Tanaka, H. et al. (Jan. 16, 2009). "The Structure of Rat Liver Vault at 3.5 Angstrom Resolution," *Science* 323:384-388.
Vasu, S.K. et al. (Jul. 25, 1993). "cDNA Cloning and Disruption of the Major Vault Protein α Gene (*mvpA*) in *Dictyostelium discoideum," J. Biol. Chem.* 268(21):15356-15360.
Vilalta, A. et al. (Nov. 25, 1994). "The Rat Vault RNA Gene Contains a Unique RNA Polymerase III Promoter Composed of Both External and Internal Elements that Function Synergistically," *J. Biol. Chem.* 269(47):29752-29759.
Walsh, C.E. et al. (1993). "Gene Therapy for Human Hemoglobinopathies," *Exp. Biol. Med.* 204:289-300.
Wang, Q. et al. (1995). "A Packaging Cell Line for Propagation of Recombinant Adenovirus Vectors Containing Two Lethal Gene-Region Deletions," *Gene Therapy* 2:775-783.
Warnock, R.A. et al. (Jan. 3, 2000). "The Role of Chemokines in the Microenvironment Control of T Versus B Cell Arrest in Peyer's Patch High Endothelial Venules," *The Journal of Experimental Medicine* 191(1):77-88.
Willimann, K. et al. (1998). "The Chemokine SLC is Expressed in T Cell Areas of Lymph Nodes and Mucosal Lymphoid Tissues and Attracts Activated T Cells Via CCR7," *Eur. J. Immunol.* 28:2025-2034.
Woo, E.Y. et al. (2002). "Cutting Edge: Regulatory T Cells from Lung Cancer Patients Directly Inhibit Autologous T Cell Proliferation," *The Journal of Immunology* 168:4272-4276.
Wu, S. et al. (2008). "Tumor Transfected with CCL21 Enhanced Reactivity and Apoptosis Resistance of Human Monocyte-Derived Dendritic Cells," *Immunobiology* 213:417-426.
Xia, H. et al. (Oct. 2002, e-pub. Sep. 16, 2002). "siRNA-Mediated Gene Silencing in vitro and in vivo," *Nature Biotechnology* 20:1006-1010.
Xia, T. et al. (Jul. 2008). "Nanobiology: Particles Slip Cell Security," *Nature Materials* 7:519-520.
Xia, Y. et al. (2010, e-pub. Feb. 10, 2010). "Immobilization of Recombinant Vault Nanoparticles on Solid Substrates," *ACS Nano* 4(3):1417-1424.
Yang, J. et al. (2010, e-pub. Dec. 1, 2010). "Vaults Are Dynamically Unconstrained Cytoplasmic Nanoparticles Capable of Half Vault Exchange," *ACS Nano* 4(12):7229-7240.
Yang, S.-C. et al. (Apr. 15, 2004). "Intratumoral Administration of Dendritic Cells Overexpressing CCL21 Generates Systemic Antitumor Responses and Confers Tumor Immunity," *Clinical Cancer Research* 10:2891-2901.
Yang, S.-C. et al. (Mar. 15, 2006). "Intrapulmonary Administration of CCL21 Gene-Modified Dendritic Cells Reduces Tumor Burden in Spontaneous Murine Bronchoalveolar Cell Carcinoma," *Cancer Res* 66(6):3205-3213.
Yannelli, J.R. et al. (2009). "Characteristics of PBMC Obtained from Leukapheresis Products and Tumor Biopsies of Patients with Non-Small Cell Lung Cancer," *Oncology Reports* 22:1459-1471.
Young, M.R. et al. (1987). "Hematopoiesis and Suppressor Bone Marrow Cells in Mice Bearing Large Metastatic Lewis Lung Carcinoma Tumors," *Cancer Research* 47(1):100-105.
Young, M.R. et al. (Jul. 15, 1997). "Myeloid Differentiation Treatment to Diminish the Presence of Immune-Suppressive $CD34^+$ Cells Within Human Head and Neck Squamous Cell Carcinomas," *The Journal of Immunology* 159(2):990-996.
Yousefieh, N. et al. (2009, e-pub. May 6, 2009). "Regulated Expression of CCL21 in the Prostate Tumor Microenvironment Inhibits Tumor Growth and Metastasis in an Orthotopic Model of Prostate Cancer," *Cancer Microenvironment* 2:59-67.
Yu, M. et al. (Oct. 2008, e-pub. Sep. 20, 2008). "Reversible pH Liability of Cross-Linked Vault Nanocapsules," *Nano Letters* 8(10):3510-3515.
Final Office Action mailed on Aug. 6, 2013 for U.S. Appl. No. 13/737,963, filed Jan. 10, 2013, 12 pages.
Non-Final Office Action mailed on Mar. 21, 2013 for U.S. Appl. No. 13/737,963, filed Jan. 10, 2013, 11 pages.
Extended European Search Report for European Application No. 10827661.9-1402/2496607; mailed Nov. 15, 2013.
Communication pursuant to Rules 70(2) and 70a(2) EPC for European Application No. 10827661.9-1402/2496607; mailed Dec. 3, 2013.
Seok-Chul Yang, et al., "Intratumoral Administration of Dendritic Cells Overexpressing CCL21 Generates Systemic Antitumor Responses and Confers Tumor Immunity", Clinical Cancer Research, Apr. 15, 2004, pp. 2891-2901, vol. 10.
Chun-Min Liang, et al., "More than chemotaxis: A new anti-tumor DC vaccine modified by rAAV2-SLC", Molecular Immunology, 2007, pp. 3797-3804, vol. 44.
Cheng-Yu Lai, et al. "Vault Nanoparticles Containing an Adenovirus-Derived Membrane Lytic Protein Facilitate Toxin and Gene Transfer", American Chemical Society, 2009, pp. 691-699, vol. 3; No. 3.
Cheryl I. Champion, et al., "A Vault Nanoparticle Vaccine Induces Protective Mucosal Immunity", PLoS ONE, Apr. 2009, 12 pp., vol. 4; Issue 4.
Australian Office Action mailed on Feb. 26, 2014 for Australian Patent Application No. 2010313112, filed on Nov. 2, 2010, two pp.
Canadian Office Action mailed on Jul. 30, 2013 for Canadian Patent Application No. 2,779,512, filed on Nov. 2, 2010, three pp.
Chinese Office Action mailed on Jul. 10, 2013 for Chinese Patent Application No. 201080060374.2, filed on Nov. 2, 2010, nine pp.
Chinese Office Action mailed on Mar. 9, 2014 for Chinese Patent Application No. 201080060374.2, filed on Nov. 2, 2010, six pp.
European Communication mailed on Jun. 20, 2012 for Ep Patent Application No. 10 827 661.9, filed on Nov. 2, 2010, two pp.
International Preliminary Report on Patentability mailed on May 8, 2012 for PCT Patent Application No. PCT/US2010/055146, filed on Nov. 2, 2010, seven pp.
Xie, F.Q. et al. (May 2008). "Vault and Tum or Multidrug Resistance," Medical Recapitulate 14(9):1326-1328 (with English Machine Translation).
Written Opinion of the International Searching Authority mailed on Oct. 19, 2011 for PCT Patent Application No. PCT/US2010/055146, filed on Nov. 2, 2010, six pp.

* cited by examiner

SEQUENCE LISTING

```
<160> NUMBER OF SEQ ID NOS: 69

<210> SEQ ID NO 1
<211> LENGTH: 133
<212> TYPE: PRT
```

-continued

<213> ORGANISM: Mus sp.

<400> SEQUENCE: 1

Met Ala Gln Met Met Thr Leu Ser Leu Leu Ser Leu Val Leu Ala Leu
1               5                   10                  15

Cys Ile Pro Trp Thr Gln Gly Ser Asp Gly Gly Gly Gln Asp Cys Cys
            20                  25                  30

Leu Lys Tyr Ser Gln Lys Lys Ile Pro Tyr Ser Ile Val Arg Gly Tyr
        35                  40                  45

Arg Lys Gln Glu Pro Ser Leu Gly Cys Pro Ile Pro Ala Ile Leu Phe
    50                  55                  60

Ser Pro Arg Lys His Ser Lys Pro Glu Leu Cys Ala Asn Pro Glu Glu
65                  70                  75                  80

Gly Trp Val Gln Asn Leu Met Arg Arg Leu Asp Gln Pro Pro Ala Pro
                85                  90                  95

Gly Lys Gln Ser Pro Gly Cys Arg Lys Asn Arg Gly Thr Ser Lys Ser
            100                 105                 110

Gly Lys Lys Gly Lys Gly Ser Lys Gly Cys Lys Arg Thr Glu Gln Thr
        115                 120                 125

Gln Pro Ser Arg Gly
    130

<210> SEQ ID NO 2
<211> LENGTH: 134
<212> TYPE: PRT
<213> ORGANISM: Homo sapiens

<400> SEQUENCE: 2

Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
            20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
    130

<210> SEQ ID NO 3
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggctcaga tgatgactct gagcctcctt agcctggtcc tggctctctg catcccctgg     60

```
acccaaggca gtgatggagg gggtcaggac tgctgcctta agtacagcca gaagaaaatt    120

ccctacagta ttgtccgagg ctataggaag caagaaccaa gtttaggctg tcccatcccg    180

gcaatcctgt tctcaccccg gaagcactct aagcctgagc tatgtgcaaa ccctgaggaa    240

ggctgggtgc agaacctgat gcgccgcctg gaccagcctc cagccccagg gaaacaaagc    300

cccggctgca ggaagaaccg gggaacctct aagtctggaa agaaaggaaa gggctccaag    360

ggctgcaaga gaactgaaca gacacagccc tcaagagga                           399
```

<210> SEQ ID NO 4
<211> LENGTH: 402
<212> TYPE: DNA
<213> ORGANISM: Mus sp.

<400> SEQUENCE: 4

```
atggctcaga tgatgactct gagcctcctt agcctggtcc tggctctctg catcccctgg     60

acccaaggca gtgatggagg gggtcaggac tgctgcctta agtacagcca gaagaaaatt    120

ccctacagta ttgtccgagg ctataggaag caagaaccaa gtttaggctg tcccatcccg    180

gcaatcctgt tctcaccccg gaagcactct aagcctgagc tatgtgcaaa ccctgaggaa    240

ggctgggtgc agaacctgat gcgccgcctg gaccagcctc cagccccagg gaaacaaagc    300

cccggctgca ggaagaaccg gggaacctct aagtctggaa agaaaggaaa gggctccaag    360

ggctgcaaga gaactgaaca gacacagccc tcaagaggat ag                       402
```

<210> SEQ ID NO 5
<211> LENGTH: 405
<212> TYPE: DNA
<213> ORGANISM: Homo sapiens

<400> SEQUENCE: 5

```
atggctcagt cactggctct gagcctcctt atcctggttc tggcctttgg catccccagg     60

acccaaggca gtgatggagg ggctcaggac tgttgcctca agtacagcca aaggaagatt    120

cccgccaagg ttgtccgcag ctaccggaag caggaaccaa gcttaggctg ctccatccca    180

gctatcctgt tcttgccccg caagcgctct caggcagagc tatgtgcaga cccaaaggag    240

ctctgggtgc agcagctgat gcagcatctg gacaagacac catccccaca gaaaccagcc    300

cagggctgca ggaaggacag gggggcctcc aagactggca agaaaggaaa gggctccaaa    360

ggctgcaaga ggactgagcg gtcacagacc cctaaagggc catag                    405
```

<210> SEQ ID NO 6
<211> LENGTH: 489
<212> TYPE: DNA
<213> ORGANISM: Mus sp.

<400> SEQUENCE: 6

```
tgcacacaac actggcagga tgctgtgcct tggacagaac tcctcagtct acagacagag     60

gatggcttct ggaaacttac accagaactg ggacttatat taaatcttaa tacaaatggt    120

ttgcacagct ttcttaaaca aaaaggcatt caatctctag gtgtaaaagg aagagaatgt    180

ctcctggacc taattgccac aatgctggta ctacagttta ttcgcaccag gttggaaaaa    240

gagggaatag tgttcaaatc actgatgaaa atggatgacc cttctatttc caggaatatt    300

ccctgggctt ttgaggcaat aaagcaagca agtgaatggg taagaagaac tgaaggacag    360

tacccatcta tctgcccacg gcttgaactg gggaacgact gggactctgc caccaagcag    420

ttgctgggac tccagcccat aagcactgtg tcccctcttc atagagtcct ccattacagt    480
```

caaggctaa 489

<210> SEQ ID NO 7
<211> LENGTH: 489
<212> TYPE: DNA
<213> ORGANISM: Homo sapiens

<400> SEQUENCE: 7
tgcacacaac actggcagga tgctgtgcct tggacagaac tcctcagtct acagacagag 60
gatggcttct ggaaacttac accagaactg ggacttatat taaatcttaa tacaaatggt 120
ttgcacagct ttcttaaaca aaaaggcatt caatctctag gtgtaaaagg aagagaatgt 180
ctcctggacc taattgccac aatgctggta ctacagttta ttcgcaccag gttggaaaaa 240
gagggaatag tgttcaaatc actgatgaaa atggatgacc cttctatttc caggaatatt 300
ccctgggctt ttgaggcaat aaagcaagca agtgaatggg taagaagaac tgaaggacag 360
tacccatcta tctgcccacg gcttgaactg ggaacgact gggactctgc caccaagcag 420
ttgctgggac tccagcccat aagcactgtg tcccctcttc atagagtcct ccattacagt 480
caaggctaa 489

<210> SEQ ID NO 8
<211> LENGTH: 162
<212> TYPE: PRT
<213> ORGANISM: Homo sapiens

<400> SEQUENCE: 8

Cys Thr Gln His Trp Gln Asp Ala Val Pro Trp Thr Glu Leu Leu Ser
1 5 10 15

Leu Gln Thr Glu Asp Gly Phe Trp Lys Leu Thr Pro Glu Leu Gly Leu
20 25 30

Ile Leu Asn Leu Asn Thr Asn Gly Leu His Ser Phe Leu Lys Gln Lys
35 40 45

Gly Ile Gln Ser Leu Gly Val Lys Gly Arg Glu Cys Leu Leu Asp Leu
50 55 60

Ile Ala Thr Met Leu Val Leu Gln Phe Ile Arg Thr Arg Leu Glu Lys
65 70 75 80

Glu Gly Ile Val Phe Lys Ser Leu Met Lys Met Asp Asp Pro Ser Ile
85 90 95

Ser Arg Asn Ile Pro Trp Ala Phe Glu Ala Ile Lys Gln Ala Ser Glu
100 105 110

Trp Val Arg Arg Thr Glu Gly Gln Tyr Pro Ser Ile Cys Pro Arg Leu
115 120 125

Glu Leu Gly Asn Asp Trp Asp Ser Ala Thr Lys Gln Leu Leu Gly Leu
130 135 140

Gln Pro Ile Ser Thr Val Ser Pro Leu His Arg Val Leu His Tyr Ser
145 150 155 160

Gln Gly

<210> SEQ ID NO 9
<211> LENGTH: 162
<212> TYPE: PRT
<213> ORGANISM: Mus sp.

<400> SEQUENCE: 9

Cys Thr Gln His Trp Gln Asp Ala Val Pro Trp Thr Glu Leu Leu Ser
1 5 10 15

```
Leu Gln Thr Glu Asp Gly Phe Trp Lys Leu Thr Pro Glu Leu Gly Leu
            20                  25                  30

Ile Leu Asn Leu Asn Thr Asn Gly Leu His Ser Phe Leu Lys Gln Lys
        35                  40                  45

Gly Ile Gln Ser Leu Gly Val Lys Gly Arg Glu Cys Leu Leu Asp Leu
    50                  55                  60

Ile Ala Thr Met Leu Val Leu Gln Phe Ile Arg Thr Arg Leu Glu Lys
65                  70                  75                  80

Glu Gly Ile Val Phe Lys Ser Leu Met Lys Met Asp Asp Pro Ser Ile
                85                  90                  95

Ser Arg Asn Ile Pro Trp Ala Phe Glu Ala Ile Lys Gln Ala Ser Glu
            100                 105                 110

Trp Val Arg Arg Thr Glu Gly Gln Tyr Pro Ser Ile Cys Pro Arg Leu
        115                 120                 125

Glu Leu Gly Asn Asp Trp Asp Ser Ala Thr Lys Gln Leu Leu Gly Leu
    130                 135                 140

Gln Pro Ile Ser Thr Val Ser Pro Leu His Arg Val Leu His Tyr Ser
145                 150                 155                 160

Gln Gly


<210> SEQ ID NO 10
<211> LENGTH: 888
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

atggctcaga tgatgactct gagcctcctt agcctggtcc tggctctctg catcccctgg      60

acccaaggca gtgatggagg gggtcaggac tgctgcctta agtacagcca gaagaaaatt     120

ccctacagta ttgtccgagg ctataggaag caagaaccaa gtttaggctg tcccatcccg     180

gcaatcctgt tctcaccccg gaagcactct aagcctgagc tatgtgcaaa ccctgaggaa     240

ggctgggtgc agaacctgat gcgccgcctg gaccagcctc cagccccagg gaaacaaagc     300

cccggctgca ggaagaaccg gggaacctct aagtctggaa agaaaggaaa gggctccaag     360

ggctgcaaga gaactgaaca gacacagccc tcaagaggat gcacacaaca ctggcaggat     420

gctgtgcctt ggacagaact cctcagtcta cagacagagg atggcttctg gaaacttaca     480

ccagaactgg gacttatatt aaatcttaat acaaatggtt tgcacagctt tcttaaacaa     540

aaaggcattc aatctctagg tgtaaaagga agagaatgtc tcctggacct aattgccaca     600

atgctggtac tacagtttat tcgcaccagg ttggaaaaag agggaatagt gttcaaatca     660

ctgatgaaaa tggatgaccc ttctatttcc aggaatattc cctgggcttt tgaggcaata     720

aagcaagcaa gtgaatgggt aagaagaact gaaggacagt acccatctat ctgcccacgg     780

cttgaactgg ggaacgactg ggactctgcc accaagcagt tgctgggact ccagcccata     840

agcactgtgt cccctcttca tagagtcctc cattacagtc aaggctaa                  888


<210> SEQ ID NO 11
<211> LENGTH: 897
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 11
atggctcagt cactggctct gagcctcctt atcctggttc tggcctttgg catccccagg 60
acccaaggca gtgatggagg ggctcaggac tgttgcctca agtacagcca aaggaagatt 120
cccgccaagg ttgtccgcag ctaccggaag caggaaccaa gcttaggctg ctccatccca 180
gctatcctgt tcttgccccg caagcgctct caggcagagc tatgtgcaga cccaaaggag 240
ctctgggtgc agcagctgat gcagcatctg gacaagacac catccccaca gaaaccagcc 300
cagggctgca ggaaggacag gggggcctcc aagactggca agaaaggaaa gggctccaaa 360
ggctgcaaga ggactgagcg gtcacagacc cctaaagggc cagctagctg cacacaacac 420
tggcaggatg ctgtgccttg gacagaactc ctcagtctac agacagagga tggcttctgg 480
aaacttacac cagaactggg acttatatta aatcttaata caaatggttt gcacagcttt 540
cttaaacaaa aaggcattca atctctaggt gtaaaaggaa gagaatgtct cctggaccta 600
attgccacaa tgctggtact acagtttatt cgcaccaggt tggaaaaaga gggaatagtg 660
ttcaaatcac tgatgaaaat ggatgaccct tctatttcca ggaatattcc ctgggctttt 720
gaggcaataa agcaagcaag tgaatgggta agaagaactg aaggacagta cccatctatc 780
tgcccacggc ttgaactggg gaacgactgg gactctgcca ccaagcagtt gctgggactc 840
cagcccataa gcactgtgtc ccctcttcat agagtcctcc attacagtca aggctaa 897

<210> SEQ ID NO 12
<211> LENGTH: 295
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Ala Gln Met Met Thr Leu Ser Leu Leu Ser Leu Val Leu Ala Leu
1               5                   10                  15

Cys Ile Pro Trp Thr Gln Gly Ser Asp Gly Gly Gly Gln Asp Cys Cys
            20                  25                  30

Leu Lys Tyr Ser Gln Lys Lys Ile Pro Tyr Ser Ile Val Arg Gly Tyr
        35                  40                  45

Arg Lys Gln Glu Pro Ser Leu Gly Cys Pro Ile Pro Ala Ile Leu Phe
    50                  55                  60

Ser Pro Arg Lys His Ser Lys Pro Glu Leu Cys Ala Asn Pro Glu Glu
65                  70                  75                  80

Gly Trp Val Gln Asn Leu Met Arg Arg Leu Asp Gln Pro Pro Ala Pro
                85                  90                  95

Gly Lys Gln Ser Pro Gly Cys Arg Lys Asn Arg Gly Thr Ser Lys Ser
            100                 105                 110

Gly Lys Lys Gly Lys Gly Ser Lys Gly Cys Lys Arg Thr Glu Gln Thr
        115                 120                 125

Gln Pro Ser Arg Gly Cys Thr Gln His Trp Gln Asp Ala Val Pro Trp
    130                 135                 140

Thr Glu Leu Leu Ser Leu Gln Thr Glu Asp Gly Phe Trp Lys Leu Thr
145                 150                 155                 160

Pro Glu Leu Gly Leu Ile Leu Asn Leu Asn Thr Asn Gly Leu His Ser
                165                 170                 175

Phe Leu Lys Gln Lys Gly Ile Gln Ser Leu Gly Val Lys Gly Arg Glu
            180                 185                 190

Cys Leu Leu Asp Leu Ile Ala Thr Met Leu Val Leu Gln Phe Ile Arg
195 200 205

Thr Arg Leu Glu Lys Glu Gly Ile Val Phe Lys Ser Leu Met Lys Met
210 215 220

Asp Asp Pro Ser Ile Ser Arg Asn Ile Pro Trp Ala Phe Glu Ala Ile
225 230 235 240

Lys Gln Ala Ser Glu Trp Val Arg Arg Thr Glu Gly Gln Tyr Pro Ser
245 250 255

Ile Cys Pro Arg Leu Glu Leu Gly Asn Asp Trp Asp Ser Ala Thr Lys
260 265 270

Gln Leu Leu Gly Leu Gln Pro Ile Ser Thr Val Ser Pro Leu His Arg
275 280 285

Val Leu His Tyr Ser Gln Gly
290 295

<210> SEQ ID NO 13
<211> LENGTH: 298
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

Met Ala Gln Ser Leu Ala Leu Ser Leu Leu Ile Leu Val Leu Ala Phe
1 5 10 15

Gly Ile Pro Arg Thr Gln Gly Ser Asp Gly Gly Ala Gln Asp Cys Cys
20 25 30

Leu Lys Tyr Ser Gln Arg Lys Ile Pro Ala Lys Val Val Arg Ser Tyr
35 40 45

Arg Lys Gln Glu Pro Ser Leu Gly Cys Ser Ile Pro Ala Ile Leu Phe
50 55 60

Leu Pro Arg Lys Arg Ser Gln Ala Glu Leu Cys Ala Asp Pro Lys Glu
65 70 75 80

Leu Trp Val Gln Gln Leu Met Gln His Leu Asp Lys Thr Pro Ser Pro
85 90 95

Gln Lys Pro Ala Gln Gly Cys Arg Lys Asp Arg Gly Ala Ser Lys Thr
100 105 110

Gly Lys Lys Gly Lys Gly Ser Lys Gly Cys Lys Arg Thr Glu Arg Ser
115 120 125

Gln Thr Pro Lys Gly Pro Ala Ser Cys Thr Gln His Trp Gln Asp Ala
130 135 140

Val Pro Trp Thr Glu Leu Leu Ser Leu Gln Thr Glu Asp Gly Phe Trp
145 150 155 160

Lys Leu Thr Pro Glu Leu Gly Leu Ile Leu Asn Leu Asn Thr Asn Gly
165 170 175

Leu His Ser Phe Leu Lys Gln Lys Gly Ile Gln Ser Leu Gly Val Lys
180 185 190

Gly Arg Glu Cys Leu Leu Asp Leu Ile Ala Thr Met Leu Val Leu Gln
195 200 205

Phe Ile Arg Thr Arg Leu Glu Lys Glu Gly Ile Val Phe Lys Ser Leu
210 215 220

Met Lys Met Asp Asp Pro Ser Ile Ser Arg Asn Ile Pro Trp Ala Phe
225 230 235 240

Glu Ala Ile Lys Gln Ala Ser Glu Trp Val Arg Arg Thr Glu Gly Gln

-continued

```
                245                 250                 255

Tyr Pro Ser Ile Cys Pro Arg Leu Glu Leu Gly Asn Asp Trp Asp Ser
            260                 265                 270

Ala Thr Lys Gln Leu Leu Gly Leu Gln Pro Ile Ser Thr Val Ser Pro
        275                 280                 285

Leu His Arg Val Leu His Tyr Ser Gln Gly
    290                 295


<210> SEQ ID NO 14
<211> LENGTH: 1724
<212> TYPE: PRT
<213> ORGANISM: Homo sapiens

<400> SEQUENCE: 14

Met Val Met Gly Ile Phe Ala Asn Cys Ile Phe Cys Leu Lys Val Lys
1               5                   10                  15

Tyr Leu Pro Gln Gln Gln Lys Lys Lys Leu Gln Thr Asp Ile Lys Glu
            20                  25                  30

Asn Gly Gly Lys Phe Ser Phe Ser Leu Asn Pro Gln Cys Thr His Ile
        35                  40                  45

Ile Leu Asp Asn Ala Asp Val Leu Ser Gln Tyr Gln Leu Asn Ser Ile
    50                  55                  60

Gln Lys Asn His Val His Ile Ala Asn Pro Asp Phe Ile Trp Lys Ser
65                  70                  75                  80

Ile Arg Glu Lys Arg Leu Leu Asp Val Lys Asn Tyr Asp Pro Tyr Lys
                85                  90                  95

Pro Leu Asp Ile Thr Pro Pro Pro Asp Gln Lys Ala Ser Ser Ser Glu
            100                 105                 110

Val Lys Thr Glu Gly Leu Cys Pro Asp Ser Ala Thr Glu Glu Glu Asp
        115                 120                 125

Thr Val Glu Leu Thr Glu Phe Gly Met Gln Asn Val Glu Ile Pro His
    130                 135                 140

Leu Pro Gln Asp Phe Glu Val Ala Lys Tyr Asn Thr Leu Glu Lys Val
145                 150                 155                 160

Gly Met Glu Gly Gly Gln Glu Ala Val Val Val Glu Leu Gln Cys Ser
                165                 170                 175

Arg Asp Ser Arg Asp Cys Pro Phe Leu Ile Ser Ser His Phe Leu Leu
            180                 185                 190

Asp Asp Gly Met Glu Thr Arg Arg Gln Phe Ala Ile Lys Lys Thr Ser
        195                 200                 205

Glu Asp Ala Ser Glu Tyr Phe Glu Asn Tyr Ile Glu Glu Leu Lys Lys
    210                 215                 220

Gln Gly Phe Leu Leu Arg Glu His Phe Thr Pro Glu Ala Thr Gln Leu
225                 230                 235                 240

Ala Ser Glu Gln Leu Gln Ala Leu Leu Leu Glu Glu Val Met Asn Ser
                245                 250                 255

Ser Thr Leu Ser Gln Glu Val Ser Asp Leu Val Glu Met Ile Trp Ala
            260                 265                 270

Glu Ala Leu Gly His Leu Glu His Met Leu Leu Lys Pro Val Asn Arg
        275                 280                 285

Ile Ser Leu Asn Asp Val Ser Lys Ala Glu Gly Ile Leu Leu Leu Val
    290                 295                 300

Lys Ala Ala Leu Lys Asn Gly Glu Thr Ala Glu Gln Leu Gln Lys Met
305                 310                 315                 320
```

-continued

```
Met Thr Glu Phe Tyr Arg Leu Ile Pro His Lys Gly Thr Met Pro Lys
                325                 330                 335

Glu Val Asn Leu Gly Leu Leu Ala Lys Lys Ala Asp Leu Cys Gln Leu
            340                 345                 350

Ile Arg Asp Met Val Asn Val Cys Glu Thr Asn Leu Ser Lys Pro Asn
        355                 360                 365

Pro Pro Ser Leu Ala Lys Tyr Arg Ala Leu Arg Cys Lys Ile Glu His
    370                 375                 380

Val Glu Gln Asn Thr Glu Glu Phe Leu Arg Val Arg Lys Glu Val Leu
385                 390                 395                 400

Gln Asn His His Ser Lys Ser Pro Val Asp Val Leu Gln Ile Phe Arg
                405                 410                 415

Val Gly Arg Val Asn Glu Thr Thr Glu Phe Leu Ser Lys Leu Gly Asn
            420                 425                 430

Val Arg Pro Leu Leu His Gly Ser Pro Val Gln Asn Ile Val Gly Ile
        435                 440                 445

Leu Cys Arg Gly Leu Leu Leu Pro Lys Val Val Glu Asp Arg Gly Val
    450                 455                 460

Gln Arg Thr Asp Val Gly Asn Leu Gly Ser Gly Ile Tyr Phe Ser Asp
465                 470                 475                 480

Ser Leu Ser Thr Ser Ile Lys Tyr Ser His Pro Gly Glu Thr Asp Gly
                485                 490                 495

Thr Arg Leu Leu Leu Ile Cys Asp Val Ala Leu Gly Lys Cys Met Asp
            500                 505                 510

Leu His Glu Lys Asp Phe Pro Leu Thr Glu Ala Pro Pro Gly Tyr Asp
        515                 520                 525

Ser Val His Gly Val Ser Gln Thr Ala Ser Val Thr Thr Asp Phe Glu
    530                 535                 540

Asp Asp Glu Phe Val Val Tyr Lys Thr Asn Gln Val Lys Met Lys Tyr
545                 550                 555                 560

Ile Ile Lys Phe Ser Met Pro Gly Asp Gln Ile Lys Asp Phe His Pro
                565                 570                 575

Ser Asp His Thr Glu Leu Glu Glu Tyr Arg Pro Glu Phe Ser Asn Phe
            580                 585                 590

Ser Lys Val Glu Asp Tyr Gln Leu Pro Asp Ala Lys Thr Ser Ser Ser
        595                 600                 605

Thr Lys Ala Gly Leu Gln Asp Ala Ser Gly Asn Leu Val Pro Leu Glu
    610                 615                 620

Asp Val His Ile Lys Gly Arg Ile Ile Asp Thr Val Ala Gln Val Ile
625                 630                 635                 640

Val Phe Gln Thr Tyr Thr Asn Lys Ser His Val Pro Ile Glu Ala Lys
                645                 650                 655

Tyr Ile Phe Pro Leu Asp Asp Lys Ala Ala Val Cys Gly Phe Glu Ala
            660                 665                 670

Phe Ile Asn Gly Lys His Ile Val Gly Glu Ile Lys Glu Lys Glu Glu
        675                 680                 685

Ala Gln Gln Glu Tyr Leu Glu Ala Val Thr Gln Gly His Gly Ala Tyr
    690                 695                 700

Leu Met Ser Gln Asp Ala Pro Asp Val Phe Thr Val Ser Val Gly Asn
705                 710                 715                 720

Leu Pro Pro Lys Ala Lys Val Leu Ile Lys Ile Thr Tyr Ile Thr Glu
                725                 730                 735

Leu Ser Ile Leu Gly Thr Val Gly Val Phe Phe Met Pro Ala Thr Val
```

-continued

```
            740                 745                 750

Ala Pro Trp Gln Gln Asp Lys Ala Leu Asn Glu Asn Leu Gln Asp Thr
        755                 760                 765

Val Glu Lys Ile Cys Ile Lys Glu Ile Gly Thr Lys Gln Ser Phe Ser
    770                 775                 780

Leu Thr Met Ser Ile Glu Met Pro Tyr Val Ile Glu Phe Ile Phe Ser
785                 790                 795                 800

Asp Thr His Glu Leu Lys Gln Lys Arg Thr Asp Cys Lys Ala Val Ile
                805                 810                 815

Ser Thr Met Glu Gly Ser Ser Leu Asp Ser Ser Gly Phe Ser Leu His
            820                 825                 830

Ile Gly Leu Ser Ala Ala Tyr Leu Pro Arg Met Trp Val Glu Lys His
        835                 840                 845

Pro Glu Lys Glu Ser Glu Ala Cys Met Leu Val Phe Gln Pro Asp Leu
    850                 855                 860

Asp Val Asp Leu Pro Asp Leu Ala Ser Glu Ser Glu Val Ile Ile Cys
865                 870                 875                 880

Leu Asp Cys Ser Ser Ser Met Glu Gly Val Thr Phe Leu Gln Ala Lys
                885                 890                 895

Gln Ile Thr Leu His Ala Leu Ser Leu Val Gly Glu Lys Gln Lys Val
            900                 905                 910

Asn Ile Ile Gln Phe Gly Thr Gly Tyr Lys Glu Leu Phe Ser Tyr Pro
        915                 920                 925

Lys His Ile Thr Ser Asn Thr Thr Ala Ala Glu Phe Ile Met Ser Ala
    930                 935                 940

Thr Pro Thr Met Gly Asn Thr Asp Phe Trp Lys Thr Leu Arg Tyr Leu
945                 950                 955                 960

Ser Leu Leu Tyr Pro Ala Arg Gly Ser Arg Asn Ile Leu Leu Val Ser
                965                 970                 975

Asp Gly His Leu Gln Asp Glu Ser Leu Thr Leu Gln Leu Val Lys Arg
            980                 985                 990

Ser Arg Pro His Thr Arg Leu Phe  Ala Cys Gly Ile Gly  Ser Thr Ala
        995                 1000                1005

Asn Arg  His Val Leu Arg Ile  Leu Ser Gln Cys Gly  Ala Gly Val
    1010                1015                1020

Phe Glu  Tyr Phe Asn Ala Lys  Ser Lys His Ser Trp  Arg Lys Gln
    1025                1030                1035

Ile Glu  Asp Gln Met Thr Arg  Leu Cys Ser Pro Ser  Cys His Ser
    1040                1045                1050

Val Ser  Val Lys Trp Gln Gln  Leu Asn Pro Asp Ala  Pro Glu Ala
    1055                1060                1065

Leu Gln  Ala Pro Ala Gln Val  Pro Ser Leu Phe Arg  Asn Asp Arg
    1070                1075                1080

Leu Leu  Val Tyr Gly Phe Ile  Pro His Cys Thr Gln  Ala Thr Leu
    1085                1090                1095

Cys Ala  Leu Ile Gln Glu Lys  Glu Phe Cys Thr Met  Val Ser Thr
    1100                1105                1110

Thr Glu  Leu Gln Lys Thr Thr  Gly Thr Met Ile His  Lys Leu Ala
    1115                1120                1125

Ala Arg  Ala Leu Ile Arg Asp  Tyr Glu Asp Gly Ile  Leu His Glu
    1130                1135                1140

Asn Glu  Thr Ser His Glu Met  Lys Lys Gln Thr Leu  Lys Ser Leu
    1145                1150                1155
```

```
Ile Ile  Lys Leu Ser Lys Glu  Asn Ser Leu Ile Thr  Gln Phe Thr
    1160                 1165                 1170

Ser Phe  Val Ala Val Glu Lys  Arg Asp Glu Asn Glu  Ser Pro Phe
    1175                 1180                 1185

Pro Asp  Ile Pro Lys Val Ser  Glu Leu Ile Ala Lys  Glu Asp Val
    1190                 1195                 1200

Asp Phe  Leu Pro Tyr Met Ser  Trp Gln Gly Glu Pro  Gln Glu Ala
    1205                 1210                 1215

Val Arg  Asn Gln Ser Leu Leu  Ala Ser Ser Glu Trp  Pro Glu Leu
    1220                 1225                 1230

Arg Leu  Ser Lys Arg Lys His  Arg Lys Ile Pro Phe  Ser Lys Arg
    1235                 1240                 1245

Ser Met  Glu Leu Ser Gln Pro  Glu Val Ser Glu Asp  Phe Glu Glu
    1250                 1255                 1260

Asp Gly  Leu Gly Val Leu Pro  Ala Phe Thr Ser Asn  Leu Glu Arg
    1265                 1270                 1275

Gly Gly  Val Glu Lys Leu Leu  Asp Leu Ser Trp Thr  Glu Ser Cys
    1280                 1285                 1290

Lys Pro  Thr Ala Thr Glu Pro  Leu Phe Lys Lys Val  Ser Pro Trp
    1295                 1300                 1305

Glu Thr  Ser Thr Ser Ser Phe  Phe Pro Ile Leu Ala  Pro Ala Val
    1310                 1315                 1320

Gly Ser  Tyr Leu Thr Pro Thr  Thr Arg Ala His Ser  Pro Ala Ser
    1325                 1330                 1335

Leu Ser  Phe Ala Ser Tyr Arg  Gln Val Ala Ser Phe  Gly Ser Ala
    1340                 1345                 1350

Ala Pro  Pro Arg Gln Phe Asp  Ala Ser Gln Phe Ser  Gln Gly Pro
    1355                 1360                 1365

Val Pro  Gly Thr Cys Ala Asp  Trp Ile Pro Gln Ser  Ala Ser Cys
    1370                 1375                 1380

Pro Thr  Gly Pro Pro Gln Asn  Pro Pro Ser Ala Pro  Tyr Cys Gly
    1385                 1390                 1395

Ile Val  Phe Ser Gly Ser Ser  Leu Ser Ser Ala Gln  Ser Ala Pro
    1400                 1405                 1410

Leu Gln  His Pro Gly Gly Phe  Thr Thr Arg Pro Ser  Ala Gly Thr
    1415                 1420                 1425

Phe Pro  Glu Leu Asp Ser Pro  Gln Leu His Phe Ser  Leu Pro Thr
    1430                 1435                 1440

Asp Pro  Asp Pro Ile Arg Gly  Phe Gly Ser Tyr His  Pro Ser Ala
    1445                 1450                 1455

Tyr Ser  Pro Phe His Phe Gln  Pro Ser Ala Ala Ser  Leu Thr Ala
    1460                 1465                 1470

Asn Leu  Arg Leu Pro Met Ala  Ser Ala Leu Pro Glu  Ala Leu Cys
    1475                 1480                 1485

Ser Gln  Ser Arg Thr Thr Pro  Val Asp Leu Cys Leu  Leu Glu Glu
    1490                 1495                 1500

Ser Val  Gly Ser Leu Glu Gly  Ser Arg Cys Pro Val  Phe Ala Phe
    1505                 1510                 1515

Gln Ser  Ser Asp Thr Glu Ser  Asp Glu Leu Ser Glu  Val Leu Gln
    1520                 1525                 1530

Asp Ser  Cys Phe Leu Gln Ile  Lys Cys Asp Thr Lys  Asp Asp Ser
    1535                 1540                 1545
```

```
Ile Pro  Cys Phe Leu Glu Leu  Lys Glu Glu Asp Glu  Ile Val Cys
    1550                 1555                 1560

Thr Gln  His Trp Gln Asp Ala  Val Pro Trp Thr Glu  Leu Leu Ser
    1565                 1570                 1575

Leu Gln  Thr Glu Asp Gly Phe  Trp Lys Leu Thr Pro  Glu Leu Gly
    1580                 1585                 1590

Leu Ile  Leu Asn Leu Asn Thr  Asn Gly Leu His Ser  Phe Leu Lys
    1595                 1600                 1605

Gln Lys  Gly Ile Gln Ser Leu  Gly Val Lys Gly Arg  Glu Cys Leu
    1610                 1615                 1620

Leu Asp  Leu Ile Ala Thr Met  Leu Val Leu Gln Phe  Ile Arg Thr
    1625                 1630                 1635

Arg Leu  Glu Lys Glu Gly Ile  Val Phe Lys Ser Leu  Met Lys Met
    1640                 1645                 1650

Asp Asp  Pro Ser Ile Ser Arg  Asn Ile Pro Trp Ala  Phe Glu Ala
    1655                 1660                 1665

Ile Lys  Gln Ala Ser Glu Trp  Val Arg Arg Thr Glu  Gly Gln Tyr
    1670                 1675                 1680

Pro Ser  Ile Cys Pro Arg Leu  Glu Leu Gly Asn Asp  Trp Asp Ser
    1685                 1690                 1695

Ala Thr  Lys Gln Leu Leu Gly  Leu Gln Pro Ile Ser  Thr Val Ser
    1700                 1705                 1710

Pro Leu  His Arg Val Leu His  Tyr Ser Gln Gly
    1715                 1720
```

<210> SEQ ID NO 15
<211> LENGTH: 5175
<212> TYPE: DNA
<213> ORGANISM: Homo sapiens

<400> SEQUENCE: 15

```
atggtgatgg gaatctttgc aaattgtatc ttctgtttga aagtgaagta cttacctcag     60

cagcagaaga aaaagctaca aactgacatt aaggaaaatg gcggaaagtt ttccttttcg    120

ttaaatcctc agtgcacaca tataatctta gataatgctg atgttctgag tcagtaccaa    180

ctgaattcta tccaaaagaa ccacgttcat attgcaaacc cagattttat atggaaatct    240

atcagagaaa agagactctt ggatgtaaag aattatgatc cttataagcc cctggacatc    300

acaccacctc ctgatcagaa ggcgagcagt tctgaagtga aaacagaagg tctatgcccg    360

gacagtgcca cagaggagga agacactgtg gaactcactg agtttggtat gcagaatgtt    420

gaaattcctc atcttcctca agattttgaa gttgcaaaat ataacacctt ggagaaagtg    480

ggaatggagg gaggccagga agctgtggtg gtggagcttc agtgttcgcg ggactccagg    540

gactgtcctt tcctgatatc ctcacacttc ctcctggatg atggcatgga gactagaaga    600

cagtttgcta taaagaaaac ctctgaagat gcaagtgaat actttgaaaa ttacattgaa    660

gaactgaaga aacaaggatt tctactaaga gaacatttca cacctgaagc aacccaatta    720

gcatctgaac aattgcaagc attgcttttg gaggaagtca tgaattcaag cactctgagc    780

caagaggtga gcgatttagt agagatgatt tgggcagagg ccctgggcca cctggaacac    840

atgcttctca agccagtgaa caggattagc ctcaacgatg tgagcaaggc agaggggatt    900

ctccttctag taaaggcagc actgaaaaat ggagaaacag cagagcaatt gcaaaagatg    960

atgacagagt tttacagact gatacctcac aaaggcacaa tgcccaaaga agtgaacctg   1020

ggactattgg ctaagaaagc agacctctgc cagctaataa gagacatggt taatgtctgt   1080
```

-continued

```
gaaactaatt tgtccaaacc caacccacca tccctggcca aataccgagc tttgaggtgc   1140
aaaattgagc atgttgaaca gaatactgaa gaatttctca gggttagaaa agaggttttg   1200
cagaatcatc acagtaagag cccagtggat gtcttgcaga tatttagagt tggcagagtg   1260
aatgaaacca cagagttttt gagcaaactt ggtaatgtga ggcccttgtt gcatggttct   1320
cctgtacaaa acatcgtggg aatcttgtgt cgagggttgc ttttacccaa agtagtggaa   1380
gatcgtggtg tgcaaagaac agacgtcgga aaccttggaa gtgggattta tttcagtgat   1440
tcgctcagta caagtatcaa gtactcacac ccgggagaga cagatggcac cagactcctg   1500
ctcatttgtg acgtagccct cggaaagtgt atggacttac atgagaagga ctttccctta   1560
actgaagcac caccaggcta cgacagtgtg catggagttt cacaaacagc ctctgtcacc   1620
acagactttg aggatgatga atttgttgtc tataaaacca atcaggttaa aatgaaatat   1680
attattaaat tttccatgcc tggagatcag ataaaggact ttcatcctag tgatcatact   1740
gaattagagg aatacagacc tgagttttca aatttttcaa aggttgaaga ttaccagtta   1800
ccagatgcca aaacttccag cagcaccaag gccggcctcc aggatgcctc tgggaacttg   1860
gttcctctgg aggatgtcca catcaaaggg agaatcatag acactgtagc ccaggtcatt   1920
gtttttcaga catacacaaa taaaagtcac gtgcccattg aggcaaaata tatctttcct   1980
ttggatgaca aggccgctgt gtgtggcttc gaagccttca tcaatgggaa gcacatagtt   2040
ggagagatta aagagaagga agaagcccag caagagtacc tagaagccgt gacccagggc   2100
catggcgctt acctgatgag tcaggatgct ccggacgttt ttactgtaag tgttggaaac   2160
ttacccccta aggctaaggt tcttataaaa attacctaca tcacagaact cagcatcctg   2220
ggcactgttg gtgtcttttt catgcccgcc accgtagcac cctggcaaca ggacaaggct   2280
ttgaatgaaa accttcagga tacagtagag aagatttgta taaaagaaat aggaacaaag   2340
caaagcttct ctttgactat gtctattgag atgccgtatg tgattgaatt cattttcagt   2400
gatacacatg aactgaaaca aaagcgcaca gactgcaaag ctgtcattag caccatggaa   2460
ggcagctcct tagacagcag tggattttct ctccacatcg gtttgtctgc tgcctatctc   2520
ccaagaatgt gggttgaaaa acatccagaa aaagaaagcg aggcttgcat gcttgtcttt   2580
caacccgatc tcgatgtcga cctccctgac ctagccagtg agagcgaagt gattatttgt   2640
cttgactgct ccagttccat ggagggtgtg acattcttgc aagccaagca aatcaccttg   2700
catgcgctgt ccttggtggg tgagaagcag aaagtaaata ttatccagtt cggcacaggt   2760
tacaaggagc tattttcgta tcctaagcat atcacaagca ataccacggc agcagagttc   2820
atcatgtctg ccacacctac catggggaac acagacttct ggaaaacact ccgatatctt   2880
agcttattgt accctgctcg agggtcacgg aacatcctcc tggtgtctga tgggcacctc   2940
caggatgaga gcctgacatt acagctcgtg aagaggagcc gcccgcacac caggttattc   3000
gcctgcggta tcggttctac agcaaatcgt cacgtcttaa ggattttgtc ccagtgtggt   3060
gccggagtat ttgaatattt taatgcaaaa tccaagcata gttggagaaa acagatagaa   3120
gaccaaatga ccaggctatg ttctccgagt tgccactctg tctccgtcaa atggcagcaa   3180
ctcaatccag atgcgcccga ggccctgcag gccccagccc aggtgccatc cttgtttcgc   3240
aatgatcgac tccttgtcta tggattcatt cctcactgca cacaagcaac tctgtgtgca   3300
ctaattcaag agaaagaatt ttgtacaatg gtgtcgacta ctgagcttca gaagacaact   3360
ggaactatga tccacaagct ggcagcccga gctctaatca gagattatga agatggcatt   3420
```

```
cttcacgaaa atgaaaccag tcatgagatg aaaaaacaaa ccttgaaatc tctgattatt   3480

aaactcagta aagaaaactc tctcataaca caatttacaa gctttgtggc agttgagaaa   3540

agggatgaga atgagtcgcc ttttcctgat attccaaaag tttctgaact tattgccaaa   3600

gaagatgtag acttcctgcc ctacatgagc tggcaggggg agccccaaga agccgtcagg   3660

aaccagtctc ttttagcatc ctctgagtgg ccagaattac gtttatccaa acgaaaacat   3720

aggaaaattc cattttccaa aagaaaaatg gaattatctc agccagaagt ttctgaagat   3780

tttgaagagg atggcttagg tgtactacca gctttcacat caaatttgga acgtggaggt   3840

gtggaaaagc tattggattt aagttggaca gagtcatgta aaccaacagc aactgaacca   3900

ctatttaaga aagtcagtcc atgggaaaca tctacttcta gctttttttcc tattttggct   3960

ccggccgttg gttcctatct taccccgact acccgcgctc acagtcctgc ttccttgtct   4020

tttgcctcat atcgtcaggt agctagtttc ggttcagctg ctcctcccag acagtttgat   4080

gcatctcaat tcagccaagg ccctgtgcct ggcacttgtg ctgactggat cccacagtcg   4140

gcgtcttgtc ccacaggacc tccccagaac ccaccttctg caccctattg tggcattgtt   4200

ttttcaggga gctcattaag ctctgcacag tctgctccac tgcaacatcc tggaggcttt   4260

actaccaggc cttctgctgg caccttccct gagctggatt ctccccagct tcatttctct   4320

cttcctacag accctgatcc catcagaggt tttgggtctt atcatccctc tgcttactct   4380

ccttttcatt ttcaaccttc cgcagcctct ttgactgcca accttaggct gccaatggcc   4440

tctgctttac ctgaggctct ttgcagtcag tcccggacta ccccagtaga tctctgtctt   4500

ctagaagaat cagtaggcag tctcgaagga agtcgatgtc ctgtctttgc ttttcaaagt   4560

tctgacacag aaagtgatga gctatcagaa gtacttcaag acagctgctt tttacaaata   4620

aagtgtgata caaaagatga cagtatcccg tgctttctgg aattaaaaga agaggatgaa   4680

atagtgtgca cacaacactg gcaggatgct gtgccttgga cagaactcct cagtctacag   4740

acagaggatg gcttctggaa acttacacca gaactgggac ttatattaaa tcttaataca   4800

aatggtttgc acagctttct taaacaaaaa ggcattcaat ctctaggtgt aaaaggaaga   4860

gaatgtctcc tggacctaat tgccacaatg ctggtactac agtttattcg caccaggttg   4920

gaaaaagagg gaatagtgtt caaatcactg atgaaaatgg atgacccttc tatttccagg   4980

aatattccct gggcttttga ggcaataaag caagcaagtg aatgggtaag aagaactgaa   5040

ggacagtacc catctatctg cccacggctt gaactgggga acgactggga ctctgccacc   5100

aagcagttgc tgggactcca gcccataagc actgtgtccc ctcttcatag agtcctccat   5160

tacagtcaag gctaa                                                    5175


<210> SEQ ID NO 16
<211> LENGTH: 893
<212> TYPE: PRT
<213> ORGANISM: Homo sapiens

<400> SEQUENCE: 16

Met Ala Thr Glu Glu Phe Ile Ile Arg Ile Pro Pro Tyr His Tyr Ile
1               5                   10                  15

His Val Leu Asp Gln Asn Ser Asn Val Ser Arg Val Glu Val Gly Pro
            20                  25                  30

Lys Thr Tyr Ile Arg Gln Asp Asn Glu Arg Val Leu Phe Ala Pro Met
        35                  40                  45

Arg Met Val Thr Val Pro Pro Arg His Tyr Cys Thr Val Ala Asn Pro
    50                  55                  60
```

-continued

```
Val Ser Arg Asp Ala Gln Gly Leu Val Leu Phe Asp Val Thr Gly Gln
65                  70                  75                  80

Val Arg Leu Arg His Ala Asp Leu Glu Ile Arg Leu Ala Gln Asp Pro
                85                  90                  95

Phe Pro Leu Tyr Pro Gly Glu Val Leu Glu Lys Asp Ile Thr Pro Leu
            100                 105                 110

Gln Val Val Leu Pro Asn Thr Ala Leu His Leu Lys Ala Leu Leu Asp
        115                 120                 125

Phe Glu Asp Lys Asp Gly Asp Lys Val Val Ala Gly Asp Glu Trp Leu
    130                 135                 140

Phe Glu Gly Pro Gly Thr Tyr Ile Pro Arg Lys Glu Val Glu Val Val
145                 150                 155                 160

Glu Ile Ile Gln Ala Thr Ile Ile Arg Gln Asn Gln Ala Leu Arg Leu
                165                 170                 175

Arg Ala Arg Lys Glu Cys Trp Asp Arg Asp Gly Lys Glu Arg Val Thr
            180                 185                 190

Gly Glu Glu Trp Leu Val Thr Thr Val Gly Ala Tyr Leu Pro Ala Val
        195                 200                 205

Phe Glu Glu Val Leu Asp Leu Val Asp Ala Val Ile Leu Thr Glu Lys
    210                 215                 220

Thr Ala Leu His Leu Arg Ala Arg Arg Asn Phe Arg Asp Phe Arg Gly
225                 230                 235                 240

Val Ser Arg Arg Thr Gly Glu Glu Trp Leu Val Thr Val Gln Asp Thr
                245                 250                 255

Glu Ala His Val Pro Asp Val His Glu Glu Val Leu Gly Val Val Pro
            260                 265                 270

Ile Thr Thr Leu Gly Pro His Asn Tyr Cys Val Ile Leu Asp Pro Val
        275                 280                 285

Gly Pro Asp Gly Lys Asn Gln Leu Gly Gln Lys Arg Val Val Lys Gly
    290                 295                 300

Glu Lys Ser Phe Phe Leu Gln Pro Gly Glu Gln Leu Glu Gln Gly Ile
305                 310                 315                 320

Gln Asp Val Tyr Val Leu Ser Glu Gln Gln Gly Leu Leu Leu Arg Ala
                325                 330                 335

Leu Gln Pro Leu Glu Glu Gly Glu Asp Glu Glu Lys Val Ser His Gln
            340                 345                 350

Ala Gly Asp His Trp Leu Ile Arg Gly Pro Leu Glu Tyr Val Pro Ser
        355                 360                 365

Ala Lys Val Glu Val Val Glu Glu Arg Gln Ala Ile Pro Leu Asp Glu
    370                 375                 380

Asn Glu Gly Ile Tyr Val Gln Asp Val Lys Thr Gly Lys Val Arg Ala
385                 390                 395                 400

Val Ile Gly Ser Thr Tyr Met Leu Thr Gln Asp Glu Val Leu Trp Glu
                405                 410                 415

Lys Glu Leu Pro Pro Gly Val Glu Glu Leu Leu Asn Lys Gly Gln Asp
            420                 425                 430

Pro Leu Ala Asp Arg Gly Glu Lys Asp Thr Ala Lys Ser Leu Gln Pro
        435                 440                 445

Leu Ala Pro Arg Asn Lys Thr Arg Val Val Ser Tyr Arg Val Pro His
    450                 455                 460

Asn Ala Ala Val Gln Val Tyr Asp Tyr Arg Glu Lys Arg Ala Arg Val
465                 470                 475                 480
```

-continued

```
Val Phe Gly Pro Glu Leu Val Ser Leu Gly Pro Glu Glu Gln Phe Thr
                485                 490                 495

Val Leu Ser Leu Ser Ala Gly Arg Pro Lys Arg Pro His Ala Arg Arg
            500                 505                 510

Ala Leu Cys Leu Leu Leu Gly Pro Asp Phe Phe Thr Asp Val Ile Thr
        515                 520                 525

Ile Glu Thr Ala Asp His Ala Arg Leu Gln Leu Gln Leu Ala Tyr Asn
    530                 535                 540

Trp His Phe Glu Val Asn Asp Arg Lys Asp Pro Gln Glu Thr Ala Lys
545                 550                 555                 560

Leu Phe Ser Val Pro Asp Phe Val Gly Asp Ala Cys Lys Ala Ile Ala
                565                 570                 575

Ser Arg Val Arg Gly Ala Val Ala Ser Val Thr Phe Asp Asp Phe His
            580                 585                 590

Lys Asn Ser Ala Arg Ile Ile Arg Thr Ala Val Phe Gly Phe Glu Thr
        595                 600                 605

Ser Glu Ala Lys Gly Pro Asp Gly Met Ala Leu Pro Arg Pro Arg Asp
    610                 615                 620

Gln Ala Val Phe Pro Gln Asn Gly Leu Val Val Ser Ser Val Asp Val
625                 630                 635                 640

Gln Ser Val Glu Pro Val Asp Gln Arg Thr Arg Asp Ala Leu Gln Arg
                645                 650                 655

Ser Val Gln Leu Ala Ile Glu Ile Thr Thr Asn Ser Gln Glu Ala Ala
            660                 665                 670

Ala Lys His Glu Ala Gln Arg Leu Glu Gln Glu Ala Arg Gly Arg Leu
        675                 680                 685

Glu Arg Gln Lys Ile Leu Asp Gln Ser Glu Ala Glu Lys Ala Arg Lys
    690                 695                 700

Glu Leu Leu Glu Leu Glu Ala Leu Ser Met Ala Val Glu Ser Thr Gly
705                 710                 715                 720

Thr Ala Lys Ala Glu Ala Glu Ser Arg Ala Glu Ala Ala Arg Ile Glu
                725                 730                 735

Gly Glu Gly Ser Val Leu Gln Ala Lys Leu Lys Ala Gln Ala Leu Ala
            740                 745                 750

Ile Glu Thr Glu Ala Glu Leu Gln Arg Val Gln Lys Val Arg Glu Leu
        755                 760                 765

Glu Leu Val Tyr Ala Arg Ala Gln Leu Glu Leu Glu Val Ser Lys Ala
    770                 775                 780

Gln Gln Leu Ala Glu Val Glu Val Lys Lys Phe Lys Gln Met Thr Glu
785                 790                 795                 800

Ala Ile Gly Pro Ser Thr Ile Arg Asp Leu Ala Val Ala Gly Pro Glu
                805                 810                 815

Met Gln Val Lys Leu Leu Gln Ser Leu Gly Leu Lys Ser Thr Leu Ile
            820                 825                 830

Thr Asp Gly Ser Thr Pro Ile Asn Leu Phe Asn Thr Ala Phe Gly Leu
        835                 840                 845

Leu Gly Met Gly Pro Glu Gly Gln Pro Leu Gly Arg Arg Val Ala Ser
    850                 855                 860

Gly Pro Ser Pro Gly Glu Gly Ile Ser Pro Gln Ser Ala Gln Ala Pro
865                 870                 875                 880

Gln Ala Pro Gly Asp Asn His Val Val Pro Val Leu Arg
                885                 890
```

<210> SEQ ID NO 17
<211> LENGTH: 2682
<212> TYPE: DNA
<213> ORGANISM: Homo sapiens

<400> SEQUENCE: 17

```
atggcaactg aagagttcat catccgcatc cccccatacc actatatcca tgtgctggac     60
cagaacagca acgtgtcccg tgtggaggtc gggccaaaga cctacatccg gcaggacaat    120
gagagggtac tgtttgcccc catgcgcatg gtgaccgtcc ccccacgtca ctactgcaca    180
gtggccaacc ctgtgtctcg ggatgcccag ggcttggtgc tgtttgatgt cacagggcaa    240
gttcggcttc gccacgctga cctcgagatc cggctggccc aggacccctt cccccctgtac    300
ccaggggagg tgctggaaaa ggacatcaca cccctgcagg tggttctgcc caacactgcc    360
ctccatctaa aggcgctgct tgattttgag gataaagatg gagacaaggt ggtggcagga    420
gatgagtggc ttttcgaggg acctggcacg tacatccccc ggaaggaagt ggaggtcgtg    480
gagatcattc aggccaccat catcaggcag aaccaggctc tgcggctcag ggcccgcaag    540
gagtgctggg accgggacgg caaggagagg gtgacagggg aagaatggct ggtcaccaca    600
gtaggggcgt acctcccagc ggtgtttgag gaggttctgg atttggtgga cgccgtcatc    660
cttacggaaa agacagccct gcacctccgg gctcggcgga acttccggga cttcaggggga    720
gtgtcccgcc gcactgggga ggagtggctg gtaacagtgc aggacacaga ggcccacgtg    780
ccagatgtcc acgaggaggt gctgggggtt gtgcccatca ccaccctggg cccccacaac    840
tactgcgtga ttctcgaccc tgtcggaccg gatggcaaga atcagctggg gcagaagcgc    900
gtggtcaagg gagagaagtc ttttttcctc cagccaggag agcagctgga acaaggcatc    960
caggatgtgt atgtgctgtc ggagcagcag gggctgctgc tgagggccct gcagcccctg   1020
gaggaggggg aggatgagga gaaggtctca caccaggctg gggaccactg gctcatccgc   1080
ggacccctgg agtatgtgcc atctgccaaa gtggaggtgg tggaggagcg ccaggccatc   1140
cctctagacg agaacgaggg catctatgtg caggatgtca agaccggaaa ggtgcgcgct   1200
gtgattggaa gcacctacat gctgacccag gacgaagtcc tgtgggagaa agagctgcct   1260
cccggggtgg aggagctgct gaacaagggg caggaccctc tggcagacag gggtgagaag   1320
gacacagcta agagcctcca gcccttggcg ccccggaaca agacccgtgt ggtcagctac   1380
cgcgtgcccc acaacgctgc ggtgcaggtg tacgactacc gagagaagcg agcccgcgtg   1440
gtcttcgggc ctgagctggt gtcgctgggt cctgaggagc agttcacagt gttgtccctc   1500
tcagctgggc ggcccaagcg tccccatgcc cgccgtgcgc tctgcctgct gctggggcct   1560
gacttcttca cagacgtcat caccatcgaa acggcggatc atgccaggct gcaactgcag   1620
ctggcctaca actggcactt tgaggtgaat gaccggaagg acccccaaga gacggccaag   1680
ctcttttcag tgccagactt tgtaggtgat gcctgcaaag ccatcgcatc ccgggtgcgg   1740
ggggccgtgg cctctgtcac tttcgatgac ttccataaga actcagcccg catcattcgc   1800
actgctgtct ttggctttga gacctcggaa gcgaagggcc ccgatggcat ggccctgccc   1860
aggccccggg accaggctgt cttcccccaa aacgggctgg tggtcagcag tgtggacgtg   1920
cagtcagtgg agcctgtgga tcagaggacc cgggacgccc tgcaacgcag cgtccagctg   1980
gccatcgaga tcaccaccaa ctcccaggaa gcggcggcca agcatgaggc tcagagactg   2040
gagcaggaag cccgcggccg gcttgagcgg cagaagatcc tggaccagtc agaagccgag   2100
aaagctcgca aggaactttt ggagctggag gctctgagca tggccgtgga gagcaccggg   2160
```

-continued

```
actgccaagg cggaggccga gtcccgtgcg gaggcagccc ggattgaggg agaagggtcc   2220

gtgctgcagg ccaagctaaa agcacaggcc ttggccattg aaacggaggc tgagctccag   2280

agggtccaga aggtccgaga gctggaactg gtctatgccc gggcccagct ggagctggag   2340

gtgagcaagg ctcagcagct ggctgaggtg gaggtgaaga agttcaagca gatgacagag   2400

gccataggcc ccagcaccat cagggacctt gctgtggctg ggcctgagat gcaggtaaaa   2460

ctgctccagt ccctgggcct gaaatcaacc ctcatcaccg atggctccac tcccatcaac   2520

ctcttcaaca cagcctttgg gctgctgggg atggggcccg agggtcagcc cctgggcaga   2580

agggtggcca gtgggcccag ccctggggag gggatatccc cccagtctgc tcaggcccct   2640

caagctcctg gagacaacca cgtggtgcct gtactgcgct aa                       2682
```

```
<210> SEQ ID NO 18
<211> LENGTH: 861
<212> TYPE: PRT
<213> ORGANISM: Rattus norvegicus

<400> SEQUENCE: 18

Met Ala Thr Glu Glu Ala Ile Ile Arg Ile Pro Pro Tyr His Tyr Ile
1               5                   10                  15

His Val Leu Asp Gln Asn Ser Asn Val Ser Arg Val Glu Val Gly Pro
            20                  25                  30

Lys Thr Tyr Ile Arg Gln Asp Asn Glu Arg Val Leu Phe Ala Pro Val
        35                  40                  45

Arg Met Val Thr Val Pro Pro Arg His Tyr Cys Ile Val Ala Asn Pro
    50                  55                  60

Val Ser Arg Asp Thr Gln Ser Ser Val Leu Phe Asp Ile Thr Gly Gln
65                  70                  75                  80

Val Arg Leu Arg His Ala Asp Gln Glu Ile Arg Leu Ala Gln Asp Pro
                85                  90                  95

Phe Pro Leu Tyr Pro Gly Glu Val Leu Glu Lys Asp Ile Thr Pro Leu
            100                 105                 110

Gln Val Val Leu Pro Asn Thr Ala Leu His Leu Lys Ala Leu Leu Asp
        115                 120                 125

Phe Glu Asp Lys Asn Gly Asp Lys Val Met Ala Gly Asp Glu Trp Leu
    130                 135                 140

Phe Glu Gly Pro Gly Thr Tyr Ile Pro Gln Lys Glu Val Glu Val Val
145                 150                 155                 160

Glu Ile Ile Gln Ala Thr Val Ile Lys Gln Asn Gln Ala Leu Arg Leu
                165                 170                 175

Arg Ala Arg Lys Glu Cys Phe Asp Arg Glu Gly Lys Gly Arg Val Thr
            180                 185                 190

Gly Glu Glu Trp Leu Val Arg Ser Val Gly Ala Tyr Leu Pro Ala Val
        195                 200                 205

Phe Glu Glu Val Leu Asp Leu Val Asp Ala Val Ile Leu Thr Glu Lys
    210                 215                 220

Thr Ala Leu His Leu Arg Ala Leu Gln Asn Phe Arg Asp Leu Arg Gly
225                 230                 235                 240

Val Leu His Arg Thr Gly Glu Glu Trp Leu Val Thr Val Gln Asp Thr
                245                 250                 255

Glu Ala His Val Pro Asp Val Tyr Glu Glu Val Leu Gly Val Val Pro
            260                 265                 270

Ile Thr Thr Leu Gly Pro Arg His Tyr Cys Val Ile Leu Asp Pro Met
        275                 280                 285
```

-continued

```
Gly Pro Asp Gly Lys Asn Gln Leu Gly Gln Lys Arg Val Val Lys Gly
    290                 295                 300

Glu Lys Ser Phe Phe Leu Gln Pro Gly Glu Arg Leu Glu Arg Gly Ile
305                 310                 315                 320

Gln Asp Val Tyr Val Leu Ser Glu Gln Gln Gly Leu Leu Leu Lys Ala
                325                 330                 335

Leu Gln Pro Leu Glu Glu Gly Glu Ser Glu Glu Lys Val Ser His Gln
            340                 345                 350

Ala Gly Asp Cys Trp Leu Ile Arg Gly Pro Leu Glu Tyr Val Pro Ser
        355                 360                 365

Ala Lys Val Glu Val Val Glu Glu Arg Gln Ala Ile Pro Leu Asp Gln
    370                 375                 380

Asn Glu Gly Ile Tyr Val Gln Asp Val Lys Thr Gly Lys Val Arg Ala
385                 390                 395                 400

Val Ile Gly Ser Thr Tyr Met Leu Thr Gln Asp Glu Val Leu Trp Glu
                405                 410                 415

Lys Glu Leu Pro Ser Gly Val Glu Glu Leu Leu Asn Leu Gly His Asp
            420                 425                 430

Pro Leu Ala Asp Arg Gly Gln Lys Gly Thr Ala Lys Pro Leu Gln Pro
        435                 440                 445

Ser Ala Pro Arg Asn Lys Thr Arg Val Val Ser Tyr Arg Val Pro His
    450                 455                 460

Asn Ala Ala Val Gln Val Tyr Asp Tyr Arg Ala Lys Arg Ala Arg Val
465                 470                 475                 480

Val Phe Gly Pro Glu Leu Val Thr Leu Asp Pro Glu Glu Gln Phe Thr
                485                 490                 495

Val Leu Ser Leu Ser Ala Gly Arg Pro Lys Arg Pro His Ala Arg Arg
            500                 505                 510

Ala Leu Cys Leu Leu Leu Gly Pro Asp Phe Phe Thr Asp Val Ile Thr
        515                 520                 525

Ile Glu Thr Ala Asp His Ala Arg Leu Gln Leu Gln Leu Ala Tyr Asn
    530                 535                 540

Trp His Phe Glu Leu Lys Asn Arg Asn Asp Pro Ala Glu Ala Ala Lys
545                 550                 555                 560

Leu Phe Ser Val Pro Asp Phe Val Gly Asp Ala Cys Lys Ala Ile Ala
                565                 570                 575

Ser Arg Val Arg Gly Ala Val Ala Ser Val Thr Phe Asp Asp Phe His
            580                 585                 590

Lys Asn Ser Ala Arg Ile Ile Arg Met Ala Val Phe Gly Phe Glu Met
        595                 600                 605

Ser Glu Asp Thr Gly Pro Asp Gly Thr Leu Leu Pro Lys Ala Arg Asp
    610                 615                 620

Gln Ala Val Phe Pro Gln Asn Gly Leu Val Val Ser Ser Val Asp Val
625                 630                 635                 640

Gln Ser Val Glu Pro Val Asp Gln Arg Thr Arg Asp Ala Leu Gln Arg
                645                 650                 655

Ser Val Gln Leu Ala Ile Glu Ile Thr Thr Asn Ser Gln Glu Ala Ala
            660                 665                 670

Ala Lys His Glu Ala Gln Arg Leu Glu Gln Glu Ala Arg Gly Arg Leu
        675                 680                 685

Glu Arg Gln Lys Ile Leu Asp Gln Ser Glu Ala Glu Lys Ala Arg Lys
    690                 695                 700
```

-continued

```
Glu Leu Leu Glu Leu Glu Ala Met Ser Met Ala Val Glu Ser Thr Gly
705                 710                 715                 720

Asn Ala Lys Ala Glu Ala Glu Ser Arg Ala Glu Ala Ala Arg Ile Glu
                725                 730                 735

Gly Glu Gly Ser Val Leu Gln Ala Lys Leu Lys Ala Gln Ala Leu Ala
            740                 745                 750

Ile Glu Thr Glu Ala Glu Leu Glu Arg Val Lys Lys Val Arg Glu Met
        755                 760                 765

Glu Leu Ile Tyr Ala Arg Ala Gln Leu Glu Leu Glu Val Ser Lys Ala
    770                 775                 780

Gln Gln Leu Ala Asn Val Glu Ala Lys Lys Phe Lys Glu Met Thr Glu
785                 790                 795                 800

Ala Leu Gly Pro Gly Thr Ile Arg Asp Leu Ala Val Ala Gly Pro Glu
                805                 810                 815

Met Gln Val Lys Leu Leu Gln Ser Leu Gly Leu Lys Ser Thr Leu Ile
            820                 825                 830

Thr Asp Gly Ser Ser Pro Ile Asn Leu Phe Ser Thr Ala Phe Gly Leu
        835                 840                 845

Leu Gly Leu Gly Ser Asp Gly Gln Pro Pro Ala Gln Lys
    850                 855                 860
```

<210> SEQ ID NO 19
<211> LENGTH: 2586
<212> TYPE: DNA
<213> ORGANISM: Rattus norvegicus

<400> SEQUENCE: 19

```
atggcaactg aagaggccat catccgcatc cccccatacc actacatcca tgtgctggac     60

cagaacagta atgtgtcccg tgtggaggtt ggaccaaaga cctacatccg gcaggacaat    120

gagagggtac tgtttgcccc agttcgcatg gtgaccgtcc ccccacgcca ctactgcata    180

gtggccaacc ctgtgtcccg ggacacccag agttctgtgt tatttgacat cacaggacaa    240

gtccgactcc ggcacgctga ccaggagatc cgactagccc aggacccctt ccccctgtat    300

ccaggggagg tgctggaaaa ggacatcacc ccactgcagg tggttctgcc caacacagca    360

ctgcatctta aggcgttgct ggactttgag gataagaatg gagacaaggt catggcagga    420

gacgagtggc tatttgaggg acctggcacc tacatcccac agaaggaagt ggaagtcgtg    480

gagatcattc aggccacagt catcaaacag aaccaagcac tgcggctaag ggcccgaaag    540

gagtgctttg accgggaggg caaggggcgc gtgacaggtg aggagtggct ggtccgatcc    600

gtgggggctt acctcccagc tgtctttgaa gaggtgctgg atctggtgga tgctgtgatc    660

cttacagaaa agactgccct gcacctccgg gctctgcaga acttcaggga ccttcgggga    720

gtgctccacc gcaccgggga ggaatggtta gtgacagtgc aggacacaga agcccatgtt    780

ccagatgtct atgaggaggt gcttggggta gtacccatca ccaccctggg acctcgacac    840

tactgtgtca ttcttgaccc aatgggacca gacggcaaga accagctggg acaaaagcgt    900

gttgtcaagg gagagaagtc ctttttcctc cagccaggag agaggctgga gcgaggcatc    960

caggatgtgt atgtgctgtc agagcagcag gggctgctac tgaaggcact gcagcccctg   1020

gaggagggag agagcgagga gaaggtctcc catcaggccg gagactgctg gctcatccgt   1080

gggcccctgg agtatgtgcc atctgcaaaa gtggaggtgg tggaggagcg tcaggctatc   1140

cctctggacc aaaatgaggg catctatgtg caggatgtca agacggggaa ggtgcgggct   1200

gtgattggaa gcacctacat gctgactcag gatgaagtcc tgtgggaaaa ggagctgcct   1260
```

tctggggtgg aggagctgct gaacttgggg catgaccctc tggcagacag gggtcagaag 1320
ggcacagcca agccccttca gccctcagct ccaaggaaca agacccgagt ggtcagctac 1380
cgtgtcccgc acaatgcagc ggtgcaggtc tatgactaca gagccaagag agcccgtgtg 1440
gtctttgggc ccgagctagt gacactggat cctgaggagc agttcacagt attgtccctt 1500
tctgccgggc gacccaagcg tcctcatgcc cgccgtgcac tctgcctact gctgggacct 1560
gatttcttta ctgatgtcat caccatcgaa actgcagatc atgccaggtt gcagctgcag 1620
cttgcctaca actggcactt tgaactgaag aaccggaatg accctgcaga ggcagccaag 1680
cttttctccg tgcctgactt cgtgggtgac gcctgcaagg ccattgcatc ccgagtccgg 1740
ggggctgtag cctctgtcac ctttgatgac ttccataaaa actcagcccg gatcattcga 1800
atggctgttt ttggctttga gatgtctgaa gacacaggtc ctgatggcac actcctgccc 1860
aaggctcgag accaggcagt ctttccccaa aacgggctgg tagtcagcag tgtggatgtg 1920
cagtcagtgg agcccgtgga ccagaggacc cgggatgccc ttcagcgcag cgttcagctg 1980
gccatcgaaa ttaccaccaa ctcccaggag gcagcagcca agcacgaggc tcagagactg 2040
gaacaggaag cccgtggtcg gcttgagagg cagaagatct tggaccagtc agaagctgaa 2100
aaagcccgca aggaactctt ggagcttgag gctatgagca tggctgtgga gagcacgggt 2160
aatgccaaag cagaggctga gtcccgtgca gaggcagcga ggatcgaagg agaaggctct 2220
gtgctgcagg ccaagctcaa ggcacaggcg ctagccattg agacggaggc tgagttggag 2280
cgagtaaaga aagtacgaga gatggaactg atctatgccc gggcccagtt ggagctggag 2340
gtgagcaagg cgcagcagct tgccaatgtg gaggcaaaga agttcaagga gatgacagag 2400
gcactgggcc ccggcaccat cagggacctg gctgtggccg ggccagagat gcaggtgaaa 2460
cttctccagt ccctgggcct gaaatccact ctcatcaccg atggctcgtc tcccatcaac 2520
ctcttcagca cagccttcgg gttgctgggg ctggggtctg atggtcagcc gccagcacag 2580
aagtga 2586

<210> SEQ ID NO 20
<211> LENGTH: 12
<212> TYPE: PRT
<213> ORGANISM: Unknown
<220> FEATURE:
<223> OTHER INFORMATION: Description of Unknown: Cysteine-rich peptide (CP)

<400> SEQUENCE: 20

Met Ala Gly Cys Gly Cys Pro Cys Gly Cys Gly Ala
1 5 10

<210> SEQ ID NO 21
<211> LENGTH: 905
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Met Ala Gly Cys Gly Cys Pro Cys Gly Cys Gly Ala Met Ala Thr Glu
1 5 10 15

Glu Phe Ile Ile Arg Ile Pro Pro Tyr His Tyr Ile His Val Leu Asp
20 25 30

Gln Asn Ser Asn Val Ser Arg Val Glu Val Gly Pro Lys Thr Tyr Ile

-continued

```
        35                  40                  45

Arg Gln Asp Asn Glu Arg Val Leu Phe Ala Pro Met Arg Met Val Thr
    50                  55                  60

Val Pro Pro Arg His Tyr Cys Thr Val Ala Asn Pro Val Ser Arg Asp
65                  70                  75                  80

Ala Gln Gly Leu Val Leu Phe Asp Val Thr Gly Gln Val Arg Leu Arg
                85                  90                  95

His Ala Asp Leu Glu Ile Arg Leu Ala Gln Asp Pro Phe Pro Leu Tyr
            100                 105                 110

Pro Gly Glu Val Leu Glu Lys Asp Ile Thr Pro Leu Gln Val Val Leu
        115                 120                 125

Pro Asn Thr Ala Leu His Leu Lys Ala Leu Leu Asp Phe Glu Asp Lys
    130                 135                 140

Asp Gly Asp Lys Val Val Ala Gly Asp Glu Trp Leu Phe Glu Gly Pro
145                 150                 155                 160

Gly Thr Tyr Ile Pro Arg Lys Glu Val Glu Val Val Glu Ile Ile Gln
                165                 170                 175

Ala Thr Ile Ile Arg Gln Asn Gln Ala Leu Arg Leu Arg Ala Arg Lys
            180                 185                 190

Glu Cys Trp Asp Arg Asp Gly Lys Glu Arg Val Thr Gly Glu Glu Trp
        195                 200                 205

Leu Val Thr Thr Val Gly Ala Tyr Leu Pro Ala Val Phe Glu Glu Val
    210                 215                 220

Leu Asp Leu Val Asp Ala Val Ile Leu Thr Glu Lys Thr Ala Leu His
225                 230                 235                 240

Leu Arg Ala Arg Arg Asn Phe Arg Asp Phe Arg Gly Val Ser Arg Arg
                245                 250                 255

Thr Gly Glu Glu Trp Leu Val Thr Val Gln Asp Thr Glu Ala His Val
            260                 265                 270

Pro Asp Val His Glu Glu Val Leu Gly Val Val Pro Ile Thr Thr Leu
        275                 280                 285

Gly Pro His Asn Tyr Cys Val Ile Leu Asp Pro Val Gly Pro Asp Gly
    290                 295                 300

Lys Asn Gln Leu Gly Gln Lys Arg Val Val Lys Gly Glu Lys Ser Phe
305                 310                 315                 320

Phe Leu Gln Pro Gly Glu Gln Leu Glu Gln Gly Ile Gln Asp Val Tyr
                325                 330                 335

Val Leu Ser Glu Gln Gln Gly Leu Leu Leu Arg Ala Leu Gln Pro Leu
            340                 345                 350

Glu Glu Gly Glu Asp Glu Glu Lys Val Ser His Gln Ala Gly Asp His
        355                 360                 365

Trp Leu Ile Arg Gly Pro Leu Glu Tyr Val Pro Ser Ala Lys Val Glu
    370                 375                 380

Val Val Glu Glu Arg Gln Ala Ile Pro Leu Asp Glu Asn Glu Gly Ile
385                 390                 395                 400

Tyr Val Gln Asp Val Lys Thr Gly Lys Val Arg Ala Val Ile Gly Ser
                405                 410                 415

Thr Tyr Met Leu Thr Gln Asp Glu Val Leu Trp Glu Lys Glu Leu Pro
            420                 425                 430

Pro Gly Val Glu Glu Leu Leu Asn Lys Gly Gln Asp Pro Leu Ala Asp
        435                 440                 445

Arg Gly Glu Lys Asp Thr Ala Lys Ser Leu Gln Pro Leu Ala Pro Arg
    450                 455                 460
```

-continued

Asn Lys Thr Arg Val Val Ser Tyr Arg Val Pro His Asn Ala Ala Val
465 470 475 480

Gln Val Tyr Asp Tyr Arg Glu Lys Arg Ala Arg Val Val Phe Gly Pro
485 490 495

Glu Leu Val Ser Leu Gly Pro Glu Glu Gln Phe Thr Val Leu Ser Leu
500 505 510

Ser Ala Gly Arg Pro Lys Arg Pro His Ala Arg Arg Ala Leu Cys Leu
515 520 525

Leu Leu Gly Pro Asp Phe Phe Thr Asp Val Ile Thr Ile Glu Thr Ala
530 535 540

Asp His Ala Arg Leu Gln Leu Gln Leu Ala Tyr Asn Trp His Phe Glu
545 550 555 560

Val Asn Asp Arg Lys Asp Pro Gln Glu Thr Ala Lys Leu Phe Ser Val
565 570 575

Pro Asp Phe Val Gly Asp Ala Cys Lys Ala Ile Ala Ser Arg Val Arg
580 585 590

Gly Ala Val Ala Ser Val Thr Phe Asp Asp Phe His Lys Asn Ser Ala
595 600 605

Arg Ile Ile Arg Thr Ala Val Phe Gly Phe Glu Thr Ser Glu Ala Lys
610 615 620

Gly Pro Asp Gly Met Ala Leu Pro Arg Pro Arg Asp Gln Ala Val Phe
625 630 635 640

Pro Gln Asn Gly Leu Val Val Ser Ser Val Asp Val Gln Ser Val Glu
645 650 655

Pro Val Asp Gln Arg Thr Arg Asp Ala Leu Gln Arg Ser Val Gln Leu
660 665 670

Ala Ile Glu Ile Thr Thr Asn Ser Gln Glu Ala Ala Ala Lys His Glu
675 680 685

Ala Gln Arg Leu Glu Gln Glu Ala Arg Gly Arg Leu Glu Arg Gln Lys
690 695 700

Ile Leu Asp Gln Ser Glu Ala Glu Lys Ala Arg Lys Glu Leu Leu Glu
705 710 715 720

Leu Glu Ala Leu Ser Met Ala Val Glu Ser Thr Gly Thr Ala Lys Ala
725 730 735

Glu Ala Glu Ser Arg Ala Glu Ala Ala Arg Ile Glu Gly Glu Gly Ser
740 745 750

Val Leu Gln Ala Lys Leu Lys Ala Gln Ala Leu Ala Ile Glu Thr Glu
755 760 765

Ala Glu Leu Gln Arg Val Gln Lys Val Arg Glu Leu Glu Leu Val Tyr
770 775 780

Ala Arg Ala Gln Leu Glu Leu Glu Val Ser Lys Ala Gln Gln Leu Ala
785 790 795 800

Glu Val Glu Val Lys Lys Phe Lys Gln Met Thr Glu Ala Ile Gly Pro
805 810 815

Ser Thr Ile Arg Asp Leu Ala Val Ala Gly Pro Glu Met Gln Val Lys
820 825 830

Leu Leu Gln Ser Leu Gly Leu Lys Ser Thr Leu Ile Thr Asp Gly Ser
835 840 845

Thr Pro Ile Asn Leu Phe Asn Thr Ala Phe Gly Leu Leu Gly Met Gly
850 855 860

Pro Glu Gly Gln Pro Leu Gly Arg Arg Val Ala Ser Gly Pro Ser Pro
865 870 875 880

```
Gly Glu Gly Ile Ser Pro Gln Ser Ala Gln Ala Pro Gln Ala Pro Gly
                885                 890                 895

Asp Asn His Val Val Pro Val Leu Arg
            900                 905


<210> SEQ ID NO 22
<211> LENGTH: 2718
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

atggcaggct gcggttgtcc atgcggttgt ggcgccatgg caactgaaga gttcatcatc     60

cgcatccccc cataccacta tatccatgtg ctggaccaga acagcaacgt gtcccgtgtg    120

gaggtcgggc caaagaccta catccggcag gacaatgaga gggtactgtt tgcccccatg    180

cgcatggtga ccgtccccc acgtcactac tgcacagtgg ccaaccctgt gtctcgggat    240

gcccagggct tggtgctgtt tgatgtcaca gggcaagttc ggcttcgcca cgctgacctc    300

gagatccggc tggcccagga ccccttcccc ctgtacccag gggaggtgct ggaaaaggac    360

atcacacccc tgcaggtggt tctgcccaac actgccctcc atctaaaggc gctgcttgat    420

tttgaggata aagatggaga caaggtggtg gcaggagatg agtggctttt cgagggacct    480

ggcacgtaca tcccccggaa ggaagtggag gtcgtggaga tcattcaggc caccatcatc    540

aggcagaacc aggctctgcg gctcagggcc cgcaaggagt gctgggaccg ggacggcaag    600

gagagggtga caggggaaga atggctggtc accacagtag ggcgtacct cccagcggtg    660

tttgaggagg ttctggattt ggtggacgcc gtcatcctta cggaaaagac agccctgcac    720

ctccgggctc ggcggaactt ccgggacttc aggggagtgt cccgccgcac tggggaggag    780

tggctggtaa cagtgcagga cacagaggcc cacgtgccag atgtccacga ggaggtgctg    840

ggggttgtgc ccatcaccac cctgggcccc cacaactact gcgtgattct cgaccctgtc    900

ggaccggatg gcaagaatca gctggggcag aagcgcgtgg tcaagggaga gaagtctttt    960

ttcctccagc caggagagca gctggaacaa ggcatccagg atgtgtatgt gctgtcggag   1020

cagcaggggc tgctgctgag ggccctgcag cccctggagg agggggagga tgaggagaag   1080

gtctcacacc aggctgggga ccactggctc atccgcggac ccctggagta tgtgccatct   1140

gccaaagtgg aggtggtgga ggagcgccag gccatccctc tagacgagaa cgagggcatc   1200

tatgtgcagg atgtcaagac cggaaaggtg cgcgctgtga ttggaagcac ctacatgctg   1260

acccaggacg aagtcctgtg ggagaaagag ctgcctcccg gggtggagga gctgctgaac   1320

aaggggcagg accctctggc agacaggggt gagaaggaca cagctaagag cctccagccc   1380

ttggcgcccc ggaacaagac ccgtgtggtc agctaccgcg tgccccacaa cgctgcggtg   1440

caggtgtacg actaccgaga gaagcgagcc cgcgtggtct tcgggcctga gctggtgtcg   1500

ctgggtcctg aggagcagtt cacagtgttg tccctctcag ctgggcggcc caagcgtccc   1560

catgcccgcc gtgcgctctg cctgctgctg gggcctgact tcttcacaga cgtcatcacc   1620

atcgaaacgg cggatcatgc caggctgcaa ctgcagctgg cctacaactg gcactttgag   1680

gtgaatgacc ggaaggaccc ccaagagacg gccaagctct tttcagtgcc agactttgta   1740

ggtgatgcct gcaaagccat cgcatcccgg gtgcgggggg ccgtggcctc tgtcactttc   1800

gatgacttcc ataagaactc agcccgcatc attcgcactg ctgtctttgg ctttgagacc   1860
```

-continued

```
tcggaagcga agggccccga tggcatggcc ctgcccaggc cccgggacca ggctgtcttc   1920

ccccaaaacg ggctggtggt cagcagtgtg gacgtgcagt cagtggagcc tgtggatcag   1980

aggacccggg acgccctgca acgcagcgtc cagctggcca tcgagatcac caccaactcc   2040

caggaagcgg cggccaagca tgaggctcag agactggagc aggaagcccg cggccggctt   2100

gagcggcaga agatcctgga ccagtcagaa gccgagaaag ctcgcaagga acttttggag   2160

ctggaggctc tgagcatggc cgtggagagc accgggactg ccaaggcgga ggccgagtcc   2220

cgtgcggagg cagcccggat tgagggagaa gggtccgtgc tgcaggccaa gctaaaagca   2280

caggccttgg ccattgaaac ggaggctgag ctccagaggg tccagaaggt ccgagagctg   2340

gaactggtct atgcccgggc ccagctggag ctggaggtga gcaaggctca gcagctggct   2400

gaggtggagg tgaagaagtt caagcagatg acagaggcca taggccccag caccatcagg   2460

gaccttgctg tggctgggcc tgagatgcag gtaaaactgc tccagtccct gggcctgaaa   2520

tcaaccctca tcaccgatgg ctccactccc atcaacctct tcaacacagc ctttgggctg   2580

ctggggatgg ggcccgaggg tcagcccctg ggcagaaggg tggccagtgg gcccagccct   2640

ggggagggga tatcccccca gtctgctcag gcccctcaag ctcctggaga caaccacgtg   2700

gtgcctgtac tgcgctaa                                                 2718
```

```
<210> SEQ ID NO 23
<211> LENGTH: 873
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Ala Gly Cys Gly Cys Pro Cys Gly Cys Gly Ala Met Ala Thr Glu
1               5                   10                  15

Glu Ala Ile Ile Arg Ile Pro Pro Tyr His Tyr Ile His Val Leu Asp
            20                  25                  30

Gln Asn Ser Asn Val Ser Arg Val Glu Val Gly Pro Lys Thr Tyr Ile
        35                  40                  45

Arg Gln Asp Asn Glu Arg Val Leu Phe Ala Pro Val Arg Met Val Thr
    50                  55                  60

Val Pro Pro Arg His Tyr Cys Ile Val Ala Asn Pro Val Ser Arg Asp
65                  70                  75                  80

Thr Gln Ser Ser Val Leu Phe Asp Ile Thr Gly Gln Val Arg Leu Arg
                85                  90                  95

His Ala Asp Gln Glu Ile Arg Leu Ala Gln Asp Pro Phe Pro Leu Tyr
            100                 105                 110

Pro Gly Glu Val Leu Glu Lys Asp Ile Thr Pro Leu Gln Val Val Leu
        115                 120                 125

Pro Asn Thr Ala Leu His Leu Lys Ala Leu Leu Asp Phe Glu Asp Lys
    130                 135                 140

Asn Gly Asp Lys Val Met Ala Gly Asp Glu Trp Leu Phe Glu Gly Pro
145                 150                 155                 160

Gly Thr Tyr Ile Pro Gln Lys Glu Val Glu Val Val Glu Ile Ile Gln
                165                 170                 175

Ala Thr Val Ile Lys Gln Asn Gln Ala Leu Arg Leu Arg Ala Arg Lys
            180                 185                 190

Glu Cys Phe Asp Arg Glu Gly Lys Gly Arg Val Thr Gly Glu Glu Trp
        195                 200                 205
```

-continued

```
Leu Val Arg Ser Val Gly Ala Tyr Leu Pro Ala Val Phe Glu Glu Val
    210                 215                 220

Leu Asp Leu Val Asp Ala Val Ile Leu Thr Glu Lys Thr Ala Leu His
225                 230                 235                 240

Leu Arg Ala Leu Gln Asn Phe Arg Asp Leu Arg Gly Val Leu His Arg
                245                 250                 255

Thr Gly Glu Glu Trp Leu Val Thr Val Gln Asp Thr Glu Ala His Val
            260                 265                 270

Pro Asp Val Tyr Glu Glu Val Leu Gly Val Val Pro Ile Thr Thr Leu
        275                 280                 285

Gly Pro Arg His Tyr Cys Val Ile Leu Asp Pro Met Gly Pro Asp Gly
    290                 295                 300

Lys Asn Gln Leu Gly Gln Lys Arg Val Val Lys Gly Glu Lys Ser Phe
305                 310                 315                 320

Phe Leu Gln Pro Gly Glu Arg Leu Glu Arg Gly Ile Gln Asp Val Tyr
                325                 330                 335

Val Leu Ser Glu Gln Gln Gly Leu Leu Leu Lys Ala Leu Gln Pro Leu
            340                 345                 350

Glu Glu Gly Glu Ser Glu Glu Lys Val Ser His Gln Ala Gly Asp Cys
        355                 360                 365

Trp Leu Ile Arg Gly Pro Leu Glu Tyr Val Pro Ser Ala Lys Val Glu
    370                 375                 380

Val Val Glu Glu Arg Gln Ala Ile Pro Leu Asp Gln Asn Glu Gly Ile
385                 390                 395                 400

Tyr Val Gln Asp Val Lys Thr Gly Lys Val Arg Ala Val Ile Gly Ser
                405                 410                 415

Thr Tyr Met Leu Thr Gln Asp Glu Val Leu Trp Glu Lys Glu Leu Pro
            420                 425                 430

Ser Gly Val Glu Glu Leu Leu Asn Leu Gly His Asp Pro Leu Ala Asp
        435                 440                 445

Arg Gly Gln Lys Gly Thr Ala Lys Pro Leu Gln Pro Ser Ala Pro Arg
    450                 455                 460

Asn Lys Thr Arg Val Val Ser Tyr Arg Val Pro His Asn Ala Ala Val
465                 470                 475                 480

Gln Val Tyr Asp Tyr Arg Ala Lys Arg Ala Arg Val Val Phe Gly Pro
                485                 490                 495

Glu Leu Val Thr Leu Asp Pro Glu Glu Gln Phe Thr Val Leu Ser Leu
            500                 505                 510

Ser Ala Gly Arg Pro Lys Arg Pro His Ala Arg Arg Ala Leu Cys Leu
        515                 520                 525

Leu Leu Gly Pro Asp Phe Phe Thr Asp Val Ile Thr Ile Glu Thr Ala
    530                 535                 540

Asp His Ala Arg Leu Gln Leu Gln Leu Ala Tyr Asn Trp His Phe Glu
545                 550                 555                 560

Leu Lys Asn Arg Asn Asp Pro Ala Glu Ala Ala Lys Leu Phe Ser Val
                565                 570                 575

Pro Asp Phe Val Gly Asp Ala Cys Lys Ala Ile Ala Ser Arg Val Arg
            580                 585                 590

Gly Ala Val Ala Ser Val Thr Phe Asp Asp Phe His Lys Asn Ser Ala
        595                 600                 605

Arg Ile Ile Arg Met Ala Val Phe Gly Phe Glu Met Ser Glu Asp Thr
    610                 615                 620
```

```
Gly Pro Asp Gly Thr Leu Leu Pro Lys Ala Arg Asp Gln Ala Val Phe
625                 630                 635                 640

Pro Gln Asn Gly Leu Val Val Ser Ser Val Asp Val Gln Ser Val Glu
                645                 650                 655

Pro Val Asp Gln Arg Thr Arg Asp Ala Leu Gln Arg Ser Val Gln Leu
            660                 665                 670

Ala Ile Glu Ile Thr Thr Asn Ser Gln Glu Ala Ala Ala Lys His Glu
        675                 680                 685

Ala Gln Arg Leu Glu Gln Glu Ala Arg Gly Arg Leu Glu Arg Gln Lys
    690                 695                 700

Ile Leu Asp Gln Ser Glu Ala Glu Lys Ala Arg Lys Glu Leu Leu Glu
705                 710                 715                 720

Leu Glu Ala Met Ser Met Ala Val Glu Ser Thr Gly Asn Ala Lys Ala
                725                 730                 735

Glu Ala Glu Ser Arg Ala Glu Ala Ala Arg Ile Glu Gly Glu Gly Ser
            740                 745                 750

Val Leu Gln Ala Lys Leu Lys Ala Gln Ala Leu Ala Ile Glu Thr Glu
        755                 760                 765

Ala Glu Leu Glu Arg Val Lys Lys Val Arg Glu Met Glu Leu Ile Tyr
    770                 775                 780

Ala Arg Ala Gln Leu Glu Leu Glu Val Ser Lys Ala Gln Gln Leu Ala
785                 790                 795                 800

Asn Val Glu Ala Lys Lys Phe Lys Glu Met Thr Glu Ala Leu Gly Pro
                805                 810                 815

Gly Thr Ile Arg Asp Leu Ala Val Ala Gly Pro Glu Met Gln Val Lys
            820                 825                 830

Leu Leu Gln Ser Leu Gly Leu Lys Ser Thr Leu Ile Thr Asp Gly Ser
        835                 840                 845

Ser Pro Ile Asn Leu Phe Ser Thr Ala Phe Gly Leu Leu Gly Leu Gly
    850                 855                 860

Ser Asp Gly Gln Pro Pro Ala Gln Lys
865                 870
```

<210> SEQ ID NO 24
<211> LENGTH: 2622
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
atggcaggct gcggttgtcc atgcggttgt ggcgccatgg caactgaaga ggccatcatc      60

cgcatccccc cataccacta catccatgtg ctggaccaga acagtaatgt gtcccgtgtg     120

gaggttggac caaagaccta catccggcag gacaatgaga gggtactgtt tgccccagtt     180

cgcatggtga ccgtcccccc acgccactac tgcatagtgg ccaaccctgt gtcccgggac     240

acccagagtt ctgtgttatt tgacatcaca ggacaagtcc gactccggca cgctgaccag     300

gagatccgac tagcccagga ccccttcccc ctgtatccag gggaggtgct ggaaaaggac     360

atcaccccac tgcaggtggt tctgcccaac acagcactgc atcttaaggc gttgctggac     420

tttgaggata agaatggaga caaggtcatg gcaggagacg agtggctatt tgagggacct     480

ggcacctaca tcccacagaa ggaagtggaa gtcgtggaga tcattcaggc cacagtcatc     540

aaacagaacc aagcactgcg gctaagggcc cgaaaggagt gctttgaccg ggagggcaag     600
```

gggcgcgtga caggtgagga gtggctggtc cgatccgtgg gggcttacct cccagctgtc 660
tttgaagagg tgctggatct ggtggatgct gtgatcctta cagaaaagac tgccctgcac 720
ctccgggctc tgcagaactt cagggacctt cggggagtgc tccaccgcac cggggaggaa 780
tggttagtga cagtgcagga cacagaagcc catgttccag atgtctatga ggaggtgctt 840
ggggtagtac ccatcaccac cctgggacct cgacactact gtgtcattct tgacccaatg 900
ggaccagacg gcaagaacca gctgggacaa aagcgtgttg tcaagggaga gaagtccttt 960
ttcctccagc caggagagag gctggagcga ggcatccagg atgtgtatgt gctgtcagag 1020
cagcaggggc tgctactgaa ggcactgcag cccctggagg agggagagag cgaggagaag 1080
gtctcccatc aggccggaga ctgctggctc atccgtgggc ccctggagta tgtgccatct 1140
gcaaaagtgg aggtggtgga ggagcgtcag gctatccctc tggaccaaaa tgagggcatc 1200
tatgtgcagg atgtcaagac ggggaaggtg cgggctgtga ttggaagcac ctacatgctg 1260
actcaggatg aagtcctgtg ggaaaaggag ctgccttctg ggtggaggga gctgctgaac 1320
ttggggcatg accctctggc agacaggggt cagaagggca cagccaagcc ccttcagccc 1380
tcagctccaa ggaacaagac ccgagtggtc agctaccgtg tcccgcacaa tgcagcggtg 1440
caggtctatg actacagagc caagagagcc cgtgtggtct ttgggcccga gctagtgaca 1500
ctggatcctg aggagcagtt cacagtattg tccctttctg ccgggcgacc caagcgtcct 1560
catgcccgcc gtgcactctg cctactgctg ggacctgatt tctttactga tgtcatcacc 1620
atcgaaactg cagatcatgc caggttgcag ctgcagcttg cctacaactg gcactttgaa 1680
ctgaagaacc ggaatgaccc tgcagaggca gccaagcttt tctccgtgcc tgacttcgtg 1740
ggtgacgcct gcaaggccat tgcatcccga gtccgggggg ctgtagcctc tgtcaccttt 1800
gatgacttcc ataaaaactc agcccggatc attcgaatgg ctgtttttgg ctttgagatg 1860
tctgaagaca caggtcctga tggcacactc ctgcccaagg ctcgagacca ggcagtcttt 1920
ccccaaaacg ggctggtagt cagcagtgtg gatgtgcagt cagtggagcc cgtggaccag 1980
aggacccggg atgcccttca gcgcagcgtt cagctggcca tcgaaattac caccaactcc 2040
caggaggcag cagccaagca cgaggctcag agactggaac aggaagcccg tggtcggctt 2100
gagaggcaga agatcttgga ccagtcagaa gctgaaaaag cccgcaagga actcttggag 2160
cttgaggcta tgagcatggc tgtggagagc acgggtaatg ccaaagcaga ggctgagtcc 2220
cgtgcagagg cagcgaggat cgaaggagaa ggctctgtgc tgcaggccaa gctcaaggca 2280
caggcgctag ccattgagac ggaggctgag ttggagcgag taaagaaagt acgagagatg 2340
gaactgatct atgcccgggc ccagttggag ctggaggtga gcaaggcgca gcagcttgcc 2400
aatgtggagg caaagaagtt caaggagatg acagaggcac tgggccccgg caccatcagg 2460
gacctggctg tggccgggcc agagatgcag gtgaaacttc tccagtccct gggcctgaaa 2520
tccactctca tcaccgatgg ctcgtctccc atcaacctct tcagcacagc cttcgggttg 2580
ctggggctgg ggtctgatgg tcagccgcca gcacagaagt ga 2622

<210> SEQ ID NO 25
<211> LENGTH: 2627
<212> TYPE: PRT
<213> ORGANISM: Homo sapiens

<400> SEQUENCE: 25

Met Glu Lys Leu His Gly His Val Ser Ala His Pro Asp Ile Leu Ser
1 5 10 15

-continued

```
Leu Glu Asn Arg Cys Leu Ala Met Leu Pro Asp Leu Gln Pro Leu Glu
            20                  25                  30

Lys Leu His Gln His Val Ser Thr His Ser Asp Ile Leu Ser Leu Lys
        35                  40                  45

Asn Gln Cys Leu Ala Thr Leu Pro Asp Leu Lys Thr Met Glu Lys Pro
    50                  55                  60

His Gly Tyr Val Ser Ala His Pro Asp Ile Leu Ser Leu Glu Asn Gln
65                  70                  75                  80

Cys Leu Ala Thr Leu Ser Asp Leu Lys Thr Met Glu Lys Pro His Gly
                85                  90                  95

His Val Ser Ala His Pro Asp Ile Leu Ser Leu Glu Asn Arg Cys Leu
            100                 105                 110

Ala Thr Leu Pro Ser Leu Lys Ser Thr Val Ser Ala Ser Pro Leu Phe
        115                 120                 125

Gln Ser Leu Gln Ile Ser His Met Thr Gln Ala Asp Leu Tyr Arg Val
    130                 135                 140

Asn Asn Ser Asn Cys Leu Leu Ser Glu Pro Pro Ser Trp Arg Ala Gln
145                 150                 155                 160

His Phe Ser Lys Gly Leu Asp Leu Ser Thr Cys Pro Ile Ala Leu Lys
                165                 170                 175

Ser Ile Ser Ala Thr Glu Thr Ala Gln Glu Ala Thr Leu Gly Arg Trp
            180                 185                 190

Phe Asp Ser Glu Glu Lys Lys Gly Ala Glu Thr Gln Met Pro Ser Tyr
        195                 200                 205

Ser Leu Ser Leu Gly Glu Glu Glu Glu Val Glu Asp Leu Ala Val Lys
    210                 215                 220

Leu Thr Ser Gly Asp Ser Glu Ser His Pro Glu Pro Thr Asp His Val
225                 230                 235                 240

Leu Gln Glu Lys Lys Met Ala Leu Leu Ser Leu Leu Cys Ser Thr Leu
                245                 250                 255

Val Ser Glu Val Asn Met Asn Asn Thr Ser Asp Pro Thr Leu Ala Ala
            260                 265                 270

Ile Phe Glu Ile Cys Arg Glu Leu Ala Leu Leu Glu Pro Glu Phe Ile
        275                 280                 285

Leu Lys Ala Ser Leu Tyr Ala Arg Gln Gln Leu Asn Val Arg Asn Val
    290                 295                 300

Ala Asn Asn Ile Leu Ala Ile Ala Ala Phe Leu Pro Ala Cys Arg Pro
305                 310                 315                 320

His Leu Arg Arg Tyr Phe Cys Ala Ile Val Gln Leu Pro Ser Asp Trp
                325                 330                 335

Ile Gln Val Ala Glu Leu Tyr Gln Ser Leu Ala Glu Gly Asp Lys Asn
            340                 345                 350

Lys Leu Val Pro Leu Pro Ala Cys Leu Arg Thr Ala Met Thr Asp Lys
        355                 360                 365

Phe Ala Gln Phe Asp Glu Tyr Gln Leu Ala Lys Tyr Asn Pro Arg Lys
    370                 375                 380

His Arg Ala Lys Arg His Pro Arg Arg Pro Pro Arg Ser Pro Gly Met
385                 390                 395                 400

Glu Pro Pro Phe Ser His Arg Cys Phe Pro Arg Tyr Ile Gly Phe Leu
                405                 410                 415

Arg Glu Glu Gln Arg Lys Phe Glu Lys Ala Gly Asp Thr Val Ser Glu
            420                 425                 430

Lys Lys Asn Pro Pro Arg Phe Thr Leu Lys Lys Leu Val Gln Arg Leu
```

-continued

```
        435                 440                 445

His Ile His Lys Pro Ala Gln His Val Gln Ala Leu Leu Gly Tyr Arg
    450                 455                 460

Tyr Pro Ser Asn Leu Gln Leu Phe Ser Arg Ser Arg Leu Pro Gly Pro
465                 470                 475                 480

Trp Asp Ser Ser Arg Ala Gly Lys Arg Met Lys Leu Ser Arg Pro Glu
                485                 490                 495

Thr Trp Glu Arg Glu Leu Ser Leu Arg Gly Asn Lys Ala Ser Val Trp
            500                 505                 510

Glu Glu Leu Ile Glu Asn Gly Lys Leu Pro Phe Met Ala Met Leu Arg
        515                 520                 525

Asn Leu Cys Asn Leu Leu Arg Val Gly Ile Ser Ser Arg His His Glu
    530                 535                 540

Leu Ile Leu Gln Arg Leu Gln His Gly Lys Ser Val Ile His Ser Arg
545                 550                 555                 560

Gln Phe Pro Phe Arg Phe Leu Asn Ala His Asp Ala Ile Asp Ala Leu
                565                 570                 575

Glu Ala Gln Leu Arg Asn Gln Ala Leu Pro Phe Pro Ser Asn Ile Thr
            580                 585                 590

Leu Met Arg Arg Ile Leu Thr Arg Asn Glu Lys Asn Arg Pro Arg Arg
        595                 600                 605

Arg Phe Leu Cys His Leu Ser Arg Gln Gln Leu Arg Met Ala Met Arg
    610                 615                 620

Ile Pro Val Leu Tyr Glu Gln Leu Lys Arg Glu Lys Leu Arg Val His
625                 630                 635                 640

Lys Ala Arg Gln Trp Lys Tyr Asp Gly Glu Met Leu Asn Arg Tyr Arg
                645                 650                 655

Gln Ala Leu Glu Thr Ala Val Asn Leu Ser Val Lys His Ser Leu Pro
            660                 665                 670

Leu Leu Pro Gly Arg Thr Val Leu Val Tyr Leu Thr Asp Ala Asn Ala
        675                 680                 685

Asp Arg Leu Cys Pro Lys Ser Asn Pro Gln Gly Pro Pro Leu Asn Tyr
    690                 695                 700

Ala Leu Leu Leu Ile Gly Met Met Ile Thr Arg Ala Glu Gln Val Asp
705                 710                 715                 720

Val Val Leu Cys Gly Gly Asp Thr Leu Lys Thr Ala Val Leu Lys Ala
                725                 730                 735

Glu Glu Gly Ile Leu Lys Thr Ala Ile Lys Leu Gln Ala Gln Val Gln
            740                 745                 750

Glu Phe Asp Glu Asn Asp Gly Trp Ser Leu Asn Thr Phe Gly Lys Tyr
        755                 760                 765

Leu Leu Ser Leu Ala Gly Gln Arg Val Pro Val Asp Arg Val Ile Leu
    770                 775                 780

Leu Gly Gln Ser Met Asp Asp Gly Met Ile Asn Val Ala Lys Gln Leu
785                 790                 795                 800

Tyr Trp Gln Arg Val Asn Ser Lys Cys Leu Phe Val Gly Ile Leu Leu
                805                 810                 815

Arg Arg Val Gln Tyr Leu Ser Thr Asp Leu Asn Pro Asn Asp Val Thr
            820                 825                 830

Leu Ser Gly Cys Thr Asp Ala Ile Leu Lys Phe Ile Ala Glu His Gly
        835                 840                 845

Ala Ser His Leu Leu Glu His Val Gly Gln Met Asp Lys Ile Phe Lys
    850                 855                 860
```

-continued

Ile Pro Pro Pro Pro Gly Lys Thr Gly Val Gln Ser Leu Arg Pro Leu
865 870 875 880

Glu Glu Asp Thr Pro Ser Pro Leu Ala Pro Val Ser Gln Gln Gly Trp
885 890 895

Arg Ser Ile Arg Leu Phe Ile Ser Ser Thr Phe Arg Asp Met His Gly
900 905 910

Glu Arg Asp Leu Leu Leu Arg Ser Val Leu Pro Ala Leu Gln Ala Arg
915 920 925

Ala Ala Pro His Arg Ile Ser Leu His Gly Ile Asp Leu Arg Trp Gly
930 935 940

Val Thr Glu Glu Glu Thr Arg Arg Asn Arg Gln Leu Glu Val Cys Leu
945 950 955 960

Gly Glu Val Glu Asn Ala Gln Leu Phe Val Gly Ile Leu Gly Ser Arg
965 970 975

Tyr Gly Tyr Ile Pro Pro Ser Tyr Asn Leu Pro Asp His Pro His Phe
980 985 990

His Trp Ala Gln Gln Tyr Pro Ser Gly Arg Ser Val Thr Glu Met Glu
995 1000 1005

Val Met Gln Phe Leu Asn Arg Asn Gln Arg Leu Gln Pro Ser Ala
1010 1015 1020

Gln Ala Leu Ile Tyr Phe Arg Asp Ser Ser Phe Leu Ser Ser Val
1025 1030 1035

Pro Asp Ala Trp Lys Ser Asp Phe Val Ser Glu Ser Glu Glu Ala
1040 1045 1050

Ala Cys Arg Ile Ser Glu Leu Lys Ser Tyr Leu Ser Arg Gln Lys
1055 1060 1065

Gly Ile Thr Cys Arg Arg Tyr Pro Cys Glu Trp Gly Gly Val Ala
1070 1075 1080

Ala Gly Arg Pro Tyr Val Gly Gly Leu Glu Glu Phe Gly Gln Leu
1085 1090 1095

Val Leu Gln Asp Val Trp Asn Met Ile Gln Lys Leu Tyr Leu Gln
1100 1105 1110

Pro Gly Ala Leu Leu Glu Gln Pro Val Ser Ile Pro Asp Asp Asp
1115 1120 1125

Leu Val Gln Ala Thr Phe Gln Gln Leu Gln Lys Pro Pro Ser Pro
1130 1135 1140

Ala Arg Pro Arg Leu Leu Gln Asp Thr Val Gln Gln Leu Met Leu
1145 1150 1155

Pro His Gly Arg Leu Ser Leu Val Thr Gly Gln Ser Gly Gln Gly
1160 1165 1170

Lys Thr Ala Phe Leu Ala Ser Leu Val Ser Ala Leu Gln Ala Pro
1175 1180 1185

Asp Gly Ala Lys Val Ala Pro Leu Val Phe Phe His Phe Ser Gly
1190 1195 1200

Ala Arg Pro Asp Gln Gly Leu Ala Leu Thr Leu Leu Arg Arg Leu
1205 1210 1215

Cys Thr Tyr Leu Arg Gly Gln Leu Lys Glu Pro Gly Ala Leu Pro
1220 1225 1230

Ser Thr Tyr Arg Ser Leu Val Trp Glu Leu Gln Gln Arg Leu Leu
1235 1240 1245

Pro Lys Ser Ala Glu Ser Leu His Pro Gly Gln Thr Gln Val Leu
1250 1255 1260

```
Ile Ile  Asp Gly Ala Asp Arg  Leu Val Asp Gln Asn  Gly Gln Leu
    1265                 1270                 1275

Ile Ser  Asp Trp Ile Pro Lys  Lys Leu Pro Arg Cys  Val His Leu
    1280                 1285                 1290

Val Leu  Ser Val Ser Ser Asp  Ala Gly Leu Gly Glu  Thr Leu Glu
    1295                 1300                 1305

Gln Ser  Gln Gly Ala His Val  Leu Ala Leu Gly Pro  Leu Glu Ala
    1310                 1315                 1320

Ser Ala  Arg Ala Arg Leu Val  Arg Glu Glu Leu Ala  Leu Tyr Gly
    1325                 1330                 1335

Lys Arg  Leu Glu Glu Ser Pro  Phe Asn Asn Gln Met  Arg Leu Leu
    1340                 1345                 1350

Leu Val  Lys Arg Glu Ser Gly  Arg Pro Leu Tyr Leu  Arg Leu Val
    1355                 1360                 1365

Thr Asp  His Leu Arg Leu Phe  Thr Leu Tyr Glu Gln  Val Ser Glu
    1370                 1375                 1380

Arg Leu  Arg Thr Leu Pro Ala  Thr Val Pro Leu Leu  Leu Gln His
    1385                 1390                 1395

Ile Leu  Ser Thr Leu Glu Lys  Glu His Gly Pro Asp  Val Leu Pro
    1400                 1405                 1410

Gln Ala  Leu Thr Ala Leu Glu  Val Thr Arg Ser Gly  Leu Thr Val
    1415                 1420                 1425

Asp Gln  Leu His Gly Val Leu  Ser Val Trp Arg Thr  Leu Pro Lys
    1430                 1435                 1440

Gly Thr  Lys Ser Trp Glu Glu  Ala Val Ala Ala Gly  Asn Ser Gly
    1445                 1450                 1455

Asp Pro  Tyr Pro Met Gly Pro  Phe Ala Cys Leu Val  Gln Ser Leu
    1460                 1465                 1470

Arg Ser  Leu Leu Gly Glu Gly  Pro Leu Glu Arg Pro  Gly Ala Arg
    1475                 1480                 1485

Leu Cys  Leu Pro Asp Gly Pro  Leu Arg Thr Ala Ala  Lys Arg Cys
    1490                 1495                 1500

Tyr Gly  Lys Arg Pro Gly Leu  Glu Asp Thr Ala His  Ile Leu Ile
    1505                 1510                 1515

Ala Ala  Gln Leu Trp Lys Thr  Cys Asp Ala Asp Ala  Ser Gly Thr
    1520                 1525                 1530

Phe Arg  Ser Cys Pro Pro Glu  Ala Leu Gly Asp Leu  Pro Tyr His
    1535                 1540                 1545

Leu Leu  Gln Ser Gly Asn Arg  Gly Leu Leu Ser Lys  Phe Leu Thr
    1550                 1555                 1560

Asn Leu  His Val Val Ala Ala  His Leu Glu Leu Gly  Leu Val Ser
    1565                 1570                 1575

Arg Leu  Leu Glu Ala His Ala  Leu Tyr Ala Ser Ser  Val Pro Lys
    1580                 1585                 1590

Glu Glu  Gln Lys Leu Pro Glu  Ala Asp Val Ala Val  Phe Arg Thr
    1595                 1600                 1605

Phe Leu  Arg Gln Gln Ala Ser  Ile Leu Ser Gln Tyr  Pro Arg Leu
    1610                 1615                 1620

Leu Pro  Gln Gln Ala Ala Asn  Gln Pro Leu Asp Ser  Pro Leu Cys
    1625                 1630                 1635

His Gln  Ala Ser Leu Leu Ser  Arg Arg Trp His Leu  Gln His Thr
    1640                 1645                 1650

Leu Arg  Trp Leu Asn Lys Pro  Arg Thr Met Lys Asn  Gln Gln Ser
```

```
    1655                1660                1665

Ser Ser  Leu Ser Leu Ala Val  Ser Ser Ser Pro Thr  Ala Val Ala
    1670                1675                1680

Phe Ser  Thr Asn Gly Gln Arg  Ala Ala Val Gly Thr  Ala Asn Gly
    1685                1690                1695

Thr Val  Tyr Leu Leu Asp Leu  Arg Thr Trp Gln Glu  Glu Lys Ser
    1700                1705                1710

Val Val  Ser Gly Cys Asp Gly  Ile Ser Ala Cys Leu  Phe Leu Ser
    1715                1720                1725

Asp Asp  Thr Leu Phe Leu Thr  Ala Phe Asp Gly Leu  Leu Glu Leu
    1730                1735                1740

Trp Asp  Leu Gln His Gly Cys  Arg Val Leu Gln Thr  Lys Ala His
    1745                1750                1755

Gln Tyr  Gln Ile Thr Gly Cys  Cys Leu Ser Pro Asp  Cys Arg Leu
    1760                1765                1770

Leu Ala  Thr Val Cys Leu Gly  Gly Cys Leu Lys Leu  Trp Asp Thr
    1775                1780                1785

Val Arg  Gly Gln Leu Ala Phe  Gln His Thr Tyr Pro  Lys Ser Leu
    1790                1795                1800

Asn Cys  Val Ala Phe His Pro  Glu Gly Gln Val Ile  Ala Thr Gly
    1805                1810                1815

Ser Trp  Ala Gly Ser Ile Ser  Phe Phe Gln Val Asp  Gly Leu Lys
    1820                1825                1830

Val Thr  Lys Asp Leu Gly Ala  Pro Gly Ala Ser Ile  Arg Thr Leu
    1835                1840                1845

Ala Phe  Asn Val Pro Gly Gly  Val Val Ala Val Gly  Arg Leu Asp
    1850                1855                1860

Ser Met  Val Glu Leu Trp Ala  Trp Arg Glu Gly Ala  Arg Leu Ala
    1865                1870                1875

Ala Phe  Pro Ala His His Gly  Phe Val Ala Ala Ala  Leu Phe Leu
    1880                1885                1890

His Ala  Gly Cys Gln Leu Leu  Thr Ala Gly Glu Asp  Gly Lys Val
    1895                1900                1905

Gln Val  Trp Ser Gly Ser Leu  Gly Arg Pro Arg Gly  His Leu Gly
    1910                1915                1920

Ser Leu  Ser Leu Ser Pro Ala  Leu Ser Val Ala Leu  Ser Pro Asp
    1925                1930                1935

Gly Asp  Arg Val Ala Val Gly  Tyr Arg Ala Asp Gly  Ile Arg Ile
    1940                1945                1950

Tyr Lys  Ile Ser Ser Gly Ser  Gln Gly Ala Gln Gly  Gln Ala Leu
    1955                1960                1965

Asp Val  Ala Val Ser Ala Leu  Ala Trp Leu Ser Pro  Lys Val Leu
    1970                1975                1980

Val Ser  Gly Ala Glu Asp Gly  Ser Leu Gln Gly Trp  Ala Leu Lys
    1985                1990                1995

Glu Cys  Ser Leu Gln Ser Leu  Trp Leu Leu Ser Arg  Phe Gln Lys
    2000                2005                2010

Pro Val  Leu Gly Leu Ala Thr  Ser Gln Glu Leu Leu  Ala Ser Ala
    2015                2020                2025

Ser Glu  Asp Phe Thr Val Gln  Leu Trp Pro Arg Gln  Leu Leu Thr
    2030                2035                2040

Arg Pro  His Lys Ala Glu Asp  Phe Pro Cys Gly Thr  Glu Leu Arg
    2045                2050                2055
```

```
Gly His  Glu Gly Pro Val Ser  Cys Cys Ser Phe Ser  Thr Asp Gly
    2060                 2065                 2070

Gly Ser  Leu Ala Thr Gly Gly  Arg Asp Arg Ser Leu  Leu Cys Trp
    2075                 2080                 2085

Asp Val  Arg Thr Pro Lys Thr  Pro Val Leu Ile His  Ser Phe Pro
    2090                 2095                 2100

Ala Cys  His Arg Asp Trp Val  Thr Gly Cys Ala Trp  Thr Lys Asp
    2105                 2110                 2115

Asn Leu  Leu Ile Ser Cys Ser  Ser Asp Gly Ser Val  Gly Leu Trp
    2120                 2125                 2130

Asp Pro  Glu Ser Gly Gln Arg  Leu Gly Gln Phe Leu  Gly His Gln
    2135                 2140                 2145

Ser Ala  Val Ser Ala Val Ala  Ala Val Glu Glu His  Val Val Ser
    2150                 2155                 2160

Val Ser  Arg Asp Gly Thr Leu  Lys Val Trp Asp His  Gln Gly Val
    2165                 2170                 2175

Glu Leu  Thr Ser Ile Pro Ala  His Ser Gly Pro Ile  Ser His Cys
    2180                 2185                 2190

Ala Ala  Ala Met Glu Pro Arg  Ala Ala Gly Gln Pro  Gly Ser Glu
    2195                 2200                 2205

Leu Leu  Val Val Thr Val Gly  Leu Asp Gly Ala Thr  Arg Leu Trp
    2210                 2215                 2220

His Pro  Leu Leu Val Cys Gln  Thr His Thr Leu Leu  Gly His Ser
    2225                 2230                 2235

Gly Pro  Val Arg Ala Ala Ala  Val Ser Glu Thr Ser  Gly Leu Met
    2240                 2245                 2250

Leu Thr  Ala Ser Glu Asp Gly  Ser Val Arg Leu Trp  Gln Val Pro
    2255                 2260                 2265

Lys Glu  Ala Asp Asp Thr Cys  Ile Pro Arg Ser Ser  Ala Ala Val
    2270                 2275                 2280

Thr Ala  Val Ala Trp Ala Pro  Asp Gly Ser Met Ala  Val Ser Gly
    2285                 2290                 2295

Asn Gln  Ala Gly Glu Leu Ile  Leu Trp Gln Glu Ala  Lys Ala Val
    2300                 2305                 2310

Ala Thr  Ala Gln Ala Pro Gly  His Ile Gly Ala Leu  Ile Trp Ser
    2315                 2320                 2325

Ser Ala  His Thr Phe Phe Val  Leu Ser Ala Asp Glu  Lys Ile Ser
    2330                 2335                 2340

Glu Trp  Gln Val Lys Leu Arg  Lys Gly Ser Ala Pro  Gly Asn Leu
    2345                 2350                 2355

Ser Leu  His Leu Asn Arg Ile  Leu Gln Glu Asp Leu  Gly Val Leu
    2360                 2365                 2370

Thr Ser  Leu Asp Trp Ala Pro  Asp Gly His Phe Leu  Ile Leu Ala
    2375                 2380                 2385

Lys Ala  Asp Leu Lys Leu Leu  Cys Met Lys Pro Gly  Asp Ala Pro
    2390                 2395                 2400

Ser Glu  Ile Trp Ser Ser Tyr  Thr Glu Asn Pro Met  Ile Leu Ser
    2405                 2410                 2415

Thr His  Lys Glu Tyr Gly Ile  Phe Val Leu Gln Pro  Lys Asp Pro
    2420                 2425                 2430

Gly Val  Leu Ser Phe Leu Arg  Gln Lys Glu Ser Gly  Glu Phe Glu
    2435                 2440                 2445
```

```
Glu Arg  Leu Asn Phe Asp Ile  Asn Leu Glu Asn Pro  Ser Arg Thr
    2450                 2455                 2460

Leu Ile  Ser Ile Thr Gln Ala  Lys Pro Glu Ser Glu  Ser Ser Phe
    2465                 2470                 2475

Leu Cys  Ala Ser Ser Asp Gly  Ile Leu Trp Asn Leu  Ala Lys Cys
    2480                 2485                 2490

Ser Pro  Glu Gly Glu Trp Thr  Thr Gly Asn Met Trp  Gln Lys Lys
    2495                 2500                 2505

Ala Asn  Thr Pro Glu Thr Gln  Thr Pro Gly Thr Asp  Pro Ser Thr
    2510                 2515                 2520

Cys Arg  Glu Ser Asp Ala Ser  Met Asp Ser Asp Ala  Ser Met Asp
    2525                 2530                 2535

Ser Glu  Pro Thr Pro His Leu  Lys Thr Arg Gln Arg  Arg Lys Ile
    2540                 2545                 2550

His Ser  Gly Ser Val Thr Ala  Leu His Val Leu Pro  Glu Leu Leu
    2555                 2560                 2565

Val Thr  Ala Ser Lys Asp Arg  Asp Val Lys Leu Trp  Glu Arg Pro
    2570                 2575                 2580

Ser Met  Gln Leu Leu Gly Leu  Phe Arg Cys Glu Gly  Ser Val Ser
    2585                 2590                 2595

Cys Leu  Glu Pro Trp Leu Gly  Ala Asn Ser Thr Leu  Gln Leu Ala
    2600                 2605                 2610

Val Gly  Asp Val Gln Gly Asn  Val Tyr Phe Leu Asn  Trp Glu
    2615                 2620                 2625


<210> SEQ ID NO 26
<211> LENGTH: 7884
<212> TYPE: DNA
<213> ORGANISM: Homo sapiens

<400> SEQUENCE: 26

atggaaaaac tccatgggca tgtgtctgcc catccagaca tcctctcctt ggagaaccgg     60

tgcctggcta tgctccctga cttacagccc ttggagaaac tacatcagca tgtatctacc    120

cactcagata tcctctcctt gaagaaccag tgcctagcca cgcttcctga cctgaagacc    180

atggaaaaac cacatggata tgtgtctgcc cacccagaca tcctctcctt ggagaaccag    240

tgcctggcca cactttctga cctgaagacc atggagaaac cacatggaca tgtttctgcc    300

cacccagaca tcctctcctt ggagaaccgg tgcctggcca ccctccctag tctaaagagc    360

actgtgtctg ccagcccctt gttccagagt ctacagatat ctcacatgac gcaagctgat    420

ttgtaccgtg tgaacaacag caattgcctg ctctctgagc ctccaagttg gagggctcag    480

catttctcta agggactaga cctttcaacc tgccctatag ccctgaaatc catctctgcc    540

acagagacag ctcaggaagc aactttgggt cgttggtttg attcagaaga gaagaaaggg    600

gcagagaccc aaatgccttc ttatagtctg agcttgggag aggaggagga ggtggaggat    660

ctggccgtga agctcacctc tggagactct gaatctcatc cagagcctac tgaccatgtc    720

cttcaggaaa agaagatggc tctactgagc ttgctgtgct ctactctggt ctcagaagta    780

aacatgaaca atacatctga ccccaccctg gctgccattt ttgaaatctg tcgtgaactt    840

gccctcctgg agcctgagtt tatcctcaag gcatctttgt atgccaggca gcagctgaac    900

gtccggaatg tggccaataa catcttggcc attgctgctt tcttgccggc gtgtcgcccc    960

cacctgcgac gatatttctg tgccattgtc cagctgcctt ctgactggat ccaggtggct   1020

gagctttacc agagcctggc tgagggagat aagaataagc tggtgcccct gcccgcctgt   1080
```

```
ctccgtactg ccatgacgga caaatttgcc cagtttgacg agtaccagct ggctaagtac   1140
aaccctcgga agcaccgggc caagagacac ccccgccggc caccccgctc tccagggatg   1200
gagcctccat tttctcacag atgtttttcca aggtacatag ggtttctcag agaagagcag   1260
agaaagtttg agaaggccgg tgatacagtg tcagagaaaa agaatcctcc aaggttcacc   1320
ctgaagaagc tggttcagcg actgcacatc cacaagcctg cccagcacgt tcaagccctg   1380
ctgggttaca gatacccctc caacctacag ctcttttctc gaagtcgcct tcctgggcct   1440
tgggattcta gcagagctgg gaagaggatg aagctgtcta ggccagagac ctgggagcgg   1500
gagctgagcc tacgggggaa caaagcgtcg gtctgggagg aactcattga aaatgggaag   1560
cttcccttca tggccatgct tcggaacctg tgcaacctgc tgcgggttgg aatcagttcc   1620
cgccaccatg agctcattct ccagagactc cagcatggga agtcggtgat ccacagtcgg   1680
cagtttccat tcagatttct taacgcccat gatgccattg atgccctcga ggctcaactc   1740
agaaatcaag cattgccctt tccttcgaat ataacactga tgaggcggat actaactaga   1800
aatgaaaaga accgtcccag gcggaggttt ctttgccacc taagccgtca gcagcttcgt   1860
atggcaatga ggatacctgt gttgtatgag cagctcaaga gggagaagct gagagtacac   1920
aaggccagac agtggaaata tgatggtgag atgctgaaca ggtaccgaca ggccctagag   1980
acagctgtga acctctctgt gaagcacagc ctgcccctgc tgccaggccg cactgtcttg   2040
gtctatctga cagatgctaa tgcagacagg ctctgtccaa agagcaaccc acaagggccc   2100
ccgctgaact atgcactgct gttgattggg atgatgatca cgagggcgga gcaggtggac   2160
gtcgtgctgt gtggaggtga cactctgaag actgcagtgc ttaaggcaga agaaggcatc   2220
ctgaagactg ccatcaagct ccaggctcaa gtccaggagt ttgatgaaaa tgatggatgg   2280
tccctgaata cttttgggaa atacctgctg tctctggctg gccaaagggt tcctgtggac   2340
agggtcatcc tccttggcca aagcatggat gatggaatga taaatgtggc caaacagctt   2400
tactggcagc gtgtgaattc caagtgcctc tttgttggta tcctcctaag aagggtacaa   2460
tacctgtcaa cagatttgaa tcccaatgat gtgacactct caggctgtac tgatgcgata   2520
ctgaagttca ttgcagagca tggggcctcc catcttctgg aacatgtggg ccaaatggac   2580
aaaatattca agattccacc acccccagga aagacagggg tccagtctct ccggccactg   2640
gaagaggaca ctccaagccc cttggctcct gtttcccagc aaggatggcg cagcatccgg   2700
cttttcattt catccacttt ccgagacatg cacggggagc gggacctgct gctgaggtct   2760
gtgctgccag cactgcaggc ccgagcggcc cctcaccgta tcagccttca cggaatcgac   2820
ctccgctggg gcgtcactga ggaggagacc cgtaggaaca gacaactgga agtgtgcctt   2880
ggggaggtgg agaacgcaca gctgtttgtg gggattctgg gctcccgtta tggatacatt   2940
ccccccagct acaaccttcc tgaccatcca cacttccact gggcccagca gtacccttca   3000
gggcgctctg tgacagagat ggaggtgatg cagttcctga accggaacca acgtctgcag   3060
ccctctgccc aagctctcat ctacttccgg gattccagct tcctcagctc tgtgccagat   3120
gcctggaaat ctgactttgt ttctgagtct gaagaggccg catgtcggat ctcagaactg   3180
aagagctacc taagcagaca gaaagggata acctgccgca gatacccctg tgagtggggg   3240
ggtgtggcag ctggccggcc ctatgttggc gggctggagg agtttgggca gttggttctg   3300
caggatgtat ggaatatgat ccagaagctc tacctgcagc ctggggccct gctggagcag   3360
ccagtgtcca tcccagacga tgacttggtc caggccacct tccagcagct gcagaagcca   3420
```

-continued ccgagtcctg cccggccacg ccttcttcag gacacagtgc aacagctgat gctgccccac 3480
ggaaggctga gcctggtgac ggggcagtca ggacagggca agacagcctt cctggcatct 3540
cttgtgtcag ccctgcaggc tcctgatggg gccaaggtgg caccattagt cttcttccac 3600
ttttctgggg ctcgtcctga ccagggtctt gccctcactc tgctcagacg cctctgtacc 3660
tatctgcgtg gccaactaaa agagccaggt gccctcccca gcacctaccg aagcctggtg 3720
tgggagctgc agcagaggct gctgcccaag tctgctgagt ccctgcatcc tggccagacc 3780
caggtcctga tcatcgatgg ggctgatagg ttagtggacc agaatgggca gctgatttca 3840
gactggatcc caaagaagct tccccggtgt gtacacctgg tgctgagtgt gtctagtgat 3900
gcaggcctag gggagaccct tgagcagagc cagggtgccc acgtgctggc cttggggcct 3960
ctggaggcct ctgctcgggc ccggctggtg agagaggagc tggccctgta cgggaagcgg 4020
ctggaggagt caccatttaa caaccagatg cgactgctgc tggtgaagcg ggaatcaggc 4080
cggccgctct acctgcgctt ggtcaccgat cacctgaggc tcttcacgct gtatgagcag 4140
gtgtctgaga gactccggac cctgcctgcc actgtccccc tgctgctgca gcacatcctg 4200
agcacactgg agaaggagca cgggcctgat gtccttcccc aggccttgac tgccctagaa 4260
gtcacacgga gtggtttgac tgtggaccag ctgcacggag tgctgagtgt gtggcggaca 4320
ctaccgaagg ggactaagag ctgggaagaa gcagtggctg ctggtaacag tggagacccc 4380
taccccatgg gcccgtttgc ctgcctcgtc cagagtctgc gcagtttgct aggggagggc 4440
cctctggagc gccctggtgc ccggctgtgc ctccctgatg ggcccctgag aacagcagct 4500
aaacgttgct atgggaagag gccagggcta gaggacacgg cacacatcct cattgcagct 4560
cagctctgga agacatgtga cgctgatgcc tcaggcacct tccgaagttg ccctcctgag 4620
gctctgggag acctgcctta ccacctgctc cagagcggga accgtggact tctttcgaag 4680
ttccttacca acctccatgt ggtggctgca cacttggaat tgggtctggt ctctcggctc 4740
ttggaggccc atgccctcta tgcttcttca gtccccaaag aggaacaaaa gctccccgag 4800
gctgacgttg cagtgtttcg caccttcctg aggcagcagg cttcaatcct cagccagtac 4860
ccccggctcc tgccccagca ggcagccaac cagcccctgg actcacctct ttgccaccaa 4920
gcctcgctgc tctcccggag atggcacctc caacacacac tacgatggct taataaaccc 4980
cggaccatga aaaatcagca aagctccagc ctgtctctgg cagtttcctc atcccctact 5040
gctgtggcct tctccaccaa tgggcaaaga gcagctgtgg gcactgccaa tgggacagtt 5100
tacctgttgg acctgagaac ttggcaggag gagaagtctg tggtgagtgg ctgtgatgga 5160
atctctgctt gtttgttcct ctccgatgat acactctttc ttactgcctt cgacgggctc 5220
ctggagctct gggacctgca gcatggttgt cgggtgctgc agactaaggc tcaccagtac 5280
caaatcactg gctgctgcct gagcccagac tgccggctgc tagccaccgt gtgcttggga 5340
ggatgcctaa agctgtggga cacagtccgt gggcagctgg ccttccagca cacctacccc 5400
aagtccctga actgtgttgc cttccaccca gaggggcagg taatagccac aggcagctgg 5460
gctggcagca tcagcttctt ccaggtggat gggctcaaag tcaccaagga cctgggggca 5520
cccggagcct ctatccgtac cttggccttc aatgtgcctg ggggggttgt ggctgtgggc 5580
cggctggaca gtatggtgga gctgtgggcc tggcgagaag ggcacggct ggctgccttc 5640 cctgcccacc atggctttgt tgctgctgcg cttttcctgc atgcgggttg ccagttactg 5700
acggctggag aggatggcaa ggttcaggtg tggtcagggt ctctgggtcg gccccgtggg 5760
cacctgggtt ccctttctct ctctcctgcc ctctctgtgg cactcagccc agatggtgat 5820

```
cgggtggctg ttggatatcg agcggatggc attaggatct acaaaatctc ttcaggttcc   5880
cagggggctc agggtcaggc actggatgtg gcagtgtccg ccctggcctg gctaagcccc   5940
aaggtattgg tgagtggtgc agaagatggg tccttgcagg gctgggcact caaggaatgc   6000
tcccttcagt ccctctggct cctgtccaga ttccagaagc ctgtgctagg actggccact   6060
tcccaggagc tcttggcttc tgcctcagag gatttcacag tgcagctgtg gccaaggcag   6120
ctgctgacgc ggccacacaa ggcagaagac tttccctgtg gcactgagct gcggggacat   6180
gagggccctg tgagctgctg tagtttcagc actgatggag gcagcctggc caccgggggc   6240
cgggatcgga gtctcctctg ctgggacgtg aggacaccca aaacccctgt tttgatccac   6300
tccttccctg cctgtcaccg tgactgggtc actggctgtg cctggaccaa agataaccta   6360
ctgatatcct gctccagtga tggctctgtg gggctctggg acccagagtc aggacagcgg   6420
cttggtcagt tcctgggtca tcagagtgct gtgagcgctg tggcagctgt ggaggagcac   6480
gtggtgtctg tgagccggga tgggaccttg aaagtgtggg accatcaagg cgtggagctg   6540
accagcatcc ctgctcactc aggacccatt agccactgtg cagctgccat ggagccccgt   6600
gcagctggac agcctgggtc agagcttctg gtggtaaccg tcgggctaga tggggccaca   6660
cggttatggc atccactctt ggtgtgccaa acccacaccc tcctgggaca cagcggccca   6720
gtccgtgctg ctgctgtttc agaaacctca ggcctcatgc tgaccgcctc tgaggatggt   6780
tctgtacggc tctggcaggt tcctaaggaa gcagatgaca catgtatacc aaggagttct   6840
gcagccgtca ctgctgtggc ttgggcacca gatggttcca tggcagtatc tggaaatcaa   6900
gctggggaac taatcttgtg gcaggaagct aaggctgtgg ccacagcaca ggctccaggc   6960
cacattggtg ctctgatctg gtcctcggca cacacctttt ttgtcctcag tgctgatgag   7020
aaaatcagcg agtggcaagt gaaactgcgg aagggttcgg cacccggaaa tttgagtctt   7080
cacctgaacc gaattctaca ggaggactta ggggtgctga caagtctgga ttgggctcct   7140
gatggtcact ttctcatctt ggccaaagca gatttgaagt tactttgcat gaagccaggg   7200
gatgctccat ctgaaatctg gagcagctat acagaaaatc ctatgatatt gtccacccac   7260
aaggagtatg gcatatttgt cctgcagccc aaggatcctg gagttctttc tttcttgagg   7320
caaaaggaat caggagagtt tgaagagagg ctgaactttg atataaactt agagaatcct   7380
agtaggaccc taatatcgat aactcaagcc aaacctgaat ctgagtcctc atttttgtgt   7440
gccagctctg atgggatcct atggaacctg gccaaatgca gcccagaagg agaatggacc   7500
acaggtaaca tgtggcagaa aaaagcaaac actccagaaa cccaaactcc agggacagac   7560
ccatctacct gcagggaatc tgatgccagc atggatagtg atgccagcat ggatagtgag   7620
ccaacaccac atctaaagac acggcagcgt agaaagattc actcgggctc tgtcacagcc   7680
ctccatgtgc tacctgagtt gctggtgaca gcttcgaagg acagagatgt taagctatgg   7740
gagagaccca gtatgcagct gctgggcctg ttccgatgcg aagggtcagt gagctgcctg   7800
gaaccttggc tgggcgctaa ctccaccctg cagcttgccg tgggagacgt gcagggcaat   7860
gtgtactttc tgaattggga atga                                          7884
```

<210> SEQ ID NO 27
<211> LENGTH: 2629
<212> TYPE: PRT
<213> ORGANISM: Rattus norvegicus

<400> SEQUENCE: 27

```
Met Glu Lys Leu Cys Gly Tyr Val Pro Val His Pro Asp Ile Leu Ser
1               5                   10                  15

Leu Lys Asn Arg Cys Leu Thr Met Leu Ser Asp Ile Gln Pro Leu Glu
            20                  25                  30

Lys Ile His Gly Gln Arg Ser Val Asn Pro Asp Ile Leu Ser Leu Glu
        35                  40                  45

Asn Arg Cys Leu Thr Leu Leu Pro Asp Leu Gln Pro Met Glu Lys Ile
    50                  55                  60

His Gly Gln Arg Ser Val His Pro Asp Ile Leu Ser Ser Glu Asn Arg
65                  70                  75                  80

Cys Leu Thr Leu Leu Pro Asp Leu Gln Ser Leu Glu Lys Leu Cys Gly
                85                  90                  95

His Met Ser Ser His Pro Asp Val Leu Ser Leu Glu Asn Arg Cys Leu
            100                 105                 110

Ala Thr Leu Pro Thr Val Lys Arg Thr Val Ser Ser Gly Pro Leu Leu
        115                 120                 125

Gln Cys Leu His Arg Ser His Thr Ala Gln Ala Asp Leu Arg Asp Pro
    130                 135                 140

Asn Phe Arg Asn Cys Leu Phe Pro Glu Pro Pro Thr Ile Glu Ala Pro
145                 150                 155                 160

Cys Phe Leu Lys Glu Leu Asp Leu Pro Thr Gly Pro Arg Ala Leu Lys
                165                 170                 175

Ser Met Ser Ala Thr Ala Arg Val Gln Glu Val Ala Leu Gly Gln Arg
            180                 185                 190

Cys Val Ser Glu Gly Lys Glu Leu Gln Glu Glu Lys Glu Ser Ala Glu
        195                 200                 205

Val Pro Met Pro Leu Tyr Ser Leu Ser Leu Gly Gly Glu Glu Glu Glu
    210                 215                 220

Val Val Gly Ala Pro Val Leu Lys Leu Thr Ser Gly Asp Ser Asp Ser
225                 230                 235                 240

His Pro Glu Thr Thr Asp Gln Ile Leu Gln Glu Lys Lys Met Ala Leu
                245                 250                 255

Leu Thr Leu Leu Cys Ser Ala Met Ala Ser Ser Val Asn Val Lys Asp
            260                 265                 270

Ala Ser Asp Pro Thr Arg Ala Ser Ile His Glu Val Cys Ser Ala Leu
        275                 280                 285

Ala Pro Leu Glu Pro Glu Phe Ile Leu Lys Ala Ser Leu Tyr Ala Arg
    290                 295                 300

Gln Gln Leu Asn Leu Arg Asp Ile Ala Asn Ile Val Leu Ala Val Ala
305                 310                 315                 320

Ala Leu Leu Pro Ala Cys Arg Pro His Val Arg Arg Tyr Tyr Ser Ala
                325                 330                 335

Ile Val His Leu Pro Ser Asp Trp Ile Gln Val Ala Glu Phe Tyr Gln
            340                 345                 350

Ser Leu Ala Glu Gly Asp Glu Lys Lys Leu Val Pro Leu Pro Ala Cys
        355                 360                 365

Leu Arg Ala Ala Met Thr Asp Lys Phe Ala Gln Phe Asp Glu Tyr Gln
    370                 375                 380

Leu Ala Lys Tyr Asn Pro Arg Lys His Arg Ser Lys Thr Arg Ser Arg
385                 390                 395                 400

Gln Pro Pro Arg Pro Gln Arg Thr Lys Pro Pro Phe Ser Glu Ser Gly
                405                 410                 415

Lys Cys Phe Pro Lys Ser Val Trp Pro Leu Lys Asn Glu Gln Ile Ser
```

-continued

```
            420                 425                 430

Phe Glu Ala Ala Tyr Asn Ala Val Ser Glu Lys Lys Arg Leu Pro Arg
        435                 440                 445

Phe Thr Leu Lys Lys Leu Val Glu Gln Leu His Ile His Glu Pro Ala
    450                 455                 460

Gln His Val Gln Ala Leu Leu Gly Tyr Arg Tyr Pro Ser Thr Leu Glu
465                 470                 475                 480

Leu Phe Ser Arg Ser His Leu Pro Gly Pro Trp Asp Ser Ser Arg Ala
                485                 490                 495

Gly Gln Arg Met Lys Leu Gln Arg Pro Glu Thr Trp Glu Arg Glu Leu
            500                 505                 510

Ser Leu Arg Gly Asn Arg Ala Ser Val Trp Glu Glu Leu Ile Asp Asn
        515                 520                 525

Gly Lys Leu Pro Phe Met Ala Met Leu Arg Asn Leu Cys Asn Leu Leu
    530                 535                 540

Arg Thr Gly Ile Ser Ala His His His Glu Leu Val Leu Gln Arg Leu
545                 550                 555                 560

Gln His Glu Lys Ser Val Ile His Ser Arg Gln Phe Pro Phe Arg Phe
                565                 570                 575

Leu Asn Ala His Asp Ser Leu Asp Arg Leu Glu Ala Gln Leu Arg Ser
            580                 585                 590

Lys Ala Ser Pro Phe Pro Ser Asn Thr Thr Leu Met Lys Arg Ile Met
        595                 600                 605

Ile Arg Asn Ser Lys Lys Ile Lys Arg Pro Ala Asn Pro Arg Tyr Leu
    610                 615                 620

Cys Thr Leu Thr Gln Arg Gln Leu Arg Ala Ala Met Ala Ile Pro Val
625                 630                 635                 640

Met Tyr Glu His Leu Lys Arg Glu Lys Leu Arg Leu His Lys Ala Arg
                645                 650                 655

Gln Trp Thr Cys Asp Leu Glu Leu Leu Glu Arg Tyr Arg Gln Ala Leu
            660                 665                 670

Glu Thr Ala Val Asn Ile Ser Val Lys His Asn Leu Pro Pro Leu Pro
        675                 680                 685

Gly Arg Thr Leu Leu Val Tyr Leu Thr Asp Ala Asn Ala Asn Arg Leu
    690                 695                 700

Cys Pro Lys Ser His Leu Gln Gly Pro Pro Leu Asn Tyr Val Leu Leu
705                 710                 715                 720

Leu Ile Gly Met Met Met Ala Arg Ala Glu Gln Thr Thr Val Trp Leu
                725                 730                 735

Cys Gly Thr Gly Thr Val Lys Thr Pro Val Leu Thr Ala Asp Glu Gly
            740                 745                 750

Ile Leu Lys Thr Ala Ile Lys Leu Gln Ala Gln Val Gln Glu Leu Glu
        755                 760                 765

Glu Asn Asp Glu Trp Pro Leu Glu Thr Phe Glu Lys Tyr Leu Leu Ser
    770                 775                 780

Leu Ala Val Arg Arg Thr Pro Ile Asp Arg Val Ile Leu Phe Gly Gln
785                 790                 795                 800

Arg Met Asp Thr Glu Leu Leu Asn Val Ala Lys Gln Ile Ile Trp Gln
                805                 810                 815

His Val Asn Ser Lys Cys Leu Phe Val Ser Val Leu Leu Arg Lys Met
            820                 825                 830

Gln Tyr Met Ser Pro Asn Leu Asn Pro Asn Asp Val Thr Leu Ser Gly
        835                 840                 845
```

```
Cys Thr Asp Gly Ile Leu Lys Phe Ile Ala Glu His Gly Ala Ser Arg
    850                 855                 860

Leu Leu Glu His Val Gly Gln Leu Asp Lys Ile Phe Lys Ile Pro Pro
865                 870                 875                 880

Pro Pro Gly Lys Thr Lys Val Ser Pro Leu Arg Pro Leu Glu Glu Asn
                885                 890                 895

Asn Pro Gly Pro Phe Val Pro Ile Ser Gln His Gly Trp Arg Asn Ile
            900                 905                 910

Arg Leu Phe Ile Ser Ser Thr Phe Arg Asp Met His Gly Glu Arg Asp
        915                 920                 925

Leu Leu Met Arg Ser Val Leu Pro Ala Leu Gln Ala Arg Ala Phe Pro
    930                 935                 940

His Arg Ile Ser Leu His Ala Ile Asp Leu Arg Trp Gly Ile Thr Glu
945                 950                 955                 960

Glu Glu Thr Arg Arg Asn Arg Gln Leu Glu Val Cys Leu Gly Glu Val
                965                 970                 975

Glu Asn Ser Gln Leu Phe Val Gly Ile Leu Gly Ser Arg Tyr Gly Tyr
            980                 985                 990

Thr Pro Pro Ser Tyr Asp Leu Pro  Asp His Pro His Phe  His Trp Thr
        995                 1000                1005

Gln Arg  Tyr Pro Ser Gly Arg  Ser Val Thr Glu Met  Glu Val Met
    1010                1015                1020

Gln Phe  Leu Asn Arg Gly Gln  Arg Ser Glu Pro Ser  Asp Gln Ala
    1025                1030                1035

Leu Ile  Tyr Phe Arg Asp Pro  Gly Phe Leu Ser Ser  Val Pro Asp
    1040                1045                1050

Val Trp  Lys Pro Asp Phe Ile  Ser Glu Ser Glu Glu  Ala Ala His
    1055                1060                1065

Arg Val  Ser Glu Leu Lys Arg  Phe Leu Gln Glu Gln  Lys Glu Val
    1070                1075                1080

Thr Cys  Arg Arg Tyr Ser Cys  Glu Trp Gly Gly Val  Ala Ala Gly
    1085                1090                1095

Arg Pro  Tyr Thr Gly Gly Leu  Glu Glu Phe Gly Gln  Leu Val Leu
    1100                1105                1110

Gln Asp  Val Trp Ser Val Ile  Gln Lys Arg Tyr Leu  Gln Pro Gly
    1115                1120                1125

Ala Gln  Leu Glu Gln Pro Gly  Ser Ile Ser Glu Glu  Asp Leu Ile
    1130                1135                1140

Gln Ala  Ser Phe Gln Gln Leu  Lys Ser Pro Pro Ser  Pro Ala Arg
    1145                1150                1155

Pro Arg  Leu Leu Gln Asp Thr  Val Gln Gln Leu Met  Leu Pro His
    1160                1165                1170

Gly Arg  Leu Ser Leu Val Ile  Gly Gln Ala Gly Gln  Gly Lys Thr
    1175                1180                1185

Ala Phe  Leu Ala Ser Leu Val  Ser Ala Leu Lys Val  Pro Asp Gln
    1190                1195                1200

Pro Asn  Val Ala Pro Phe Val  Phe Phe His Phe Ser  Ala Ala Arg
    1205                1210                1215

Pro Asp  Gln Cys Leu Ala Phe  Asn Leu Leu Arg Arg  Leu Cys Thr
    1220                1225                1230

His Leu  His Gln Lys Leu Gly  Glu Pro Ser Ala Leu  Pro Ser Thr
    1235                1240                1245
```

-continued

```
Tyr Arg  Gly Leu Val Trp Glu  Leu Gln Gln Lys Leu  Leu Leu Lys
    1250                 1255                 1260

Ser Ala  Gln Trp Leu Gln Pro  Gly Gln Thr Leu Val  Leu Ile Ile
    1265                 1270                 1275

Asp Gly  Ala Asp Lys Leu Val  Asp His Asn Gly Gln  Leu Ile Ser
    1280                 1285                 1290

Asp Trp  Ile Pro Lys Ser Leu  Pro Arg Arg Val His  Leu Val Leu
    1295                 1300                 1305

Ser Val  Ser Ser Asp Ser Gly  Leu Gly Glu Thr Leu  Gln Gln Ser
    1310                 1315                 1320

Gln Ser  Ala Tyr Val Val Ala  Leu Gly Ser Leu Val  Pro Ser Ser
    1325                 1330                 1335

Arg Ala  Gln Leu Val Arg Glu  Glu Leu Ala Leu Tyr  Gly Lys Arg
    1340                 1345                 1350

Leu Glu  Glu Ser Pro Phe Asn  Asn Gln Met Arg Leu  Leu Leu Ala
    1355                 1360                 1365

Lys Gln  Gly Ser Ser Leu Pro  Leu Tyr Leu His Leu  Val Thr Asp
    1370                 1375                 1380

Tyr Leu  Arg Leu Phe Thr Leu  Tyr Glu Gln Val Ser  Glu Arg Leu
    1385                 1390                 1395

Arg Thr  Leu Pro Ala Thr Leu  Pro Leu Leu Leu Gln  His Ile Leu
    1400                 1405                 1410

Ser Thr  Leu Glu Gln Glu His  Gly His Asn Val Leu  Pro Gln Ala
    1415                 1420                 1425

Leu Thr  Ala Leu Glu Val Thr  His Ser Gly Leu Thr  Val Asp Gln
    1430                 1435                 1440

Leu His  Ala Val Leu Ser Thr  Trp Leu Thr Leu Pro  Lys Glu Thr
    1445                 1450                 1455

Lys Ser  Trp Glu Glu Ala Val  Ala Ala Ser His Ser  Gly Asn Leu
    1460                 1465                 1470

Tyr Pro  Leu Ala Pro Phe Ala  Tyr Leu Val Gln Ser  Leu Arg Ser
    1475                 1480                 1485

Leu Leu  Gly Glu Gly Pro Val  Glu Arg Pro Gly Ala  Arg Leu Cys
    1490                 1495                 1500

Leu Ser  Asp Gly Pro Leu Arg  Thr Ala Val Lys Arg  Arg Tyr Gly
    1505                 1510                 1515

Lys Arg  Leu Gly Leu Glu Lys  Thr Ala His Val Leu  Ile Ala Ala
    1520                 1525                 1530

His Leu  Trp Lys Met Cys Asp  Pro Asp Ala Ser Gly  Thr Phe Arg
    1535                 1540                 1545

Ser Cys  Pro Pro Glu Ala Leu  Lys Asp Leu Pro Tyr  His Leu Leu
    1550                 1555                 1560

Gln Ser  Gly Asn His Gly Leu  Leu Ala Lys Phe Leu  Thr Asn Leu
    1565                 1570                 1575

His Val  Val Ala Ala Tyr Leu  Glu Val Gly Leu Val  Pro Asp Leu
    1580                 1585                 1590

Leu Glu  Ala Tyr Glu Leu Tyr  Ala Ser Ser Lys Pro  Glu Val Asn
    1595                 1600                 1605

Gln Lys  Leu Pro Glu Ala Asp  Val Ala Val Phe His  Asn Phe Leu
    1610                 1615                 1620

Lys Gln  Gln Ala Ser Leu Leu  Thr Gln Tyr Pro Leu  Leu Leu Leu
    1625                 1630                 1635

Gln Gln  Ala Ala Ser Gln Pro  Glu Glu Ser Pro Val  Cys Cys Gln
```

```
    1640                1645                1650

Ala Pro  Leu Leu Thr Gln Arg  Trp His Asn Gln Cys  Ile Leu Lys
    1655                1660                1665

Trp Ile  Asn Lys Pro Gln Thr  Leu Lys Gly Gln Gln  Ser Leu Ser
    1670                1675                1680

Leu Pro  Ile Ser Ser Ser Pro  Thr Ala Val Ala Phe  Ser Pro Asn
    1685                1690                1695

Gly Gln  Arg Ala Ala Val Gly  Thr Ala Gly Gly Thr  Ile Tyr Leu
    1700                1705                1710

Leu Asn  Leu Arg Thr Trp Gln  Glu Glu Lys Ala Leu  Val Ser Gly
    1715                1720                1725

Cys Asp  Gly Ile Ser Ser Phe  Ala Phe Leu Ser Asp  Thr Ala Leu
    1730                1735                1740

Phe Leu  Thr Thr Phe Asp Gly  Leu Leu Glu Leu Trp  Asp Leu Gln
    1745                1750                1755

His Gly  Cys Trp Val Phe Gln  Thr Lys Ala His Gln  Tyr Gln Ile
    1760                1765                1770

Thr Gly  Cys Cys Leu Ser Pro  Asp Arg Arg Leu Leu  Ala Thr Val
    1775                1780                1785

Cys Leu  Gly Gly Tyr Val Lys  Leu Trp Asp Thr Val  Gln Gly Gln
    1790                1795                1800

Leu Ala  Phe Gln Tyr Thr His  Pro Lys Ser Leu Asn  Cys Ile Thr
    1805                1810                1815

Phe His  Pro Glu Gly Gln Val  Val Ala Thr Gly Asn  Trp Ser Gly
    1820                1825                1830

Ile Val  Thr Phe Phe Gln Ala  Asp Gly Leu Lys Val  Thr Lys Glu
    1835                1840                1845

Leu Gly  Gly Pro Gly Pro Ser  Val Arg Thr Leu Ala  Phe Ser Ala
    1850                1855                1860

Pro Gly  Lys Val Val Ala Leu  Gly Arg Ile Asp Gly  Thr Val Glu
    1865                1870                1875

Leu Trp  Ala Trp Gln Glu Gly  Thr Arg Leu Ala Ala  Phe Pro Ala
    1880                1885                1890

Gln Cys  Gly Gly Val Ser Thr  Val Leu Phe Leu His  Ala Gly Gly
    1895                1900                1905

Arg Phe  Leu Thr Ala Gly Glu  Asp Gly Lys Ala Gln  Leu Trp Ser
    1910                1915                1920

Gly Phe  Leu Gly Arg Pro Arg  Gly Cys Leu Gly Ser  Leu Tyr Leu
    1925                1930                1935

Ser Pro  Ala Leu Ser Val Ala  Leu Asn Pro Asp Gly  Asp Gln Val
    1940                1945                1950

Ala Val  Gly Tyr Arg Gly Asp  Gly Ile Lys Ile Tyr  Arg Ile Ser
    1955                1960                1965

Ser Gly  Pro Gln Glu Ala Gln  Cys Gln Glu Leu Asn  Val Ala Val
    1970                1975                1980

Ser Ala  Leu Val Trp Leu Ser  Pro Ser Val Leu Val  Ser Gly Ala
    1985                1990                1995

Glu Asp  Gly Ser Leu His Gly  Trp Met Leu Arg Arg  Asn Ser Leu
    2000                2005                2010

Gln Ser  Leu Trp Leu Ser Ser  Val Cys Gln Lys Pro  Val Leu Gly
    2015                2020                2025

Leu Ala  Ala Ser Gln Glu Phe  Leu Ala Ser Ala Ser  Glu Asp Phe
    2030                2035                2040
```

```
Thr Val  Arg Leu Trp Pro Arg  Gln Leu Leu Thr Gln  Pro His Ala
    2045                 2050                 2055

Val Glu  Glu Leu Pro Cys Ala  Ala Glu Leu Arg Gly  His Glu Gly
    2060                 2065                 2070

Pro Val  Cys Cys Cys Ser Phe  Ser Pro Asp Gly Arg  Ile Leu Ala
    2075                 2080                 2085

Thr Ala  Gly Arg Asp Arg Asn  Leu Leu Cys Trp Asp  Val Lys Val
    2090                 2095                 2100

Ala Gln  Ala Pro Leu Leu Ile  His Thr Phe Ser Ser  Cys His Arg
    2105                 2110                 2115

Asp Trp  Ile Thr Gly Cys Thr  Trp Thr Lys Asp Asn  Ile Leu Ile
    2120                 2125                 2130

Ser Cys  Ser Ser Asp Gly Ser  Val Gly Leu Trp Asn  Pro Glu Ala
    2135                 2140                 2145

Gly Gln  Gln Leu Gly Gln Phe  Pro Gly His Gln Ser  Ala Val Ser
    2150                 2155                 2160

Ala Val  Val Ala Val Glu Glu  His Ile Val Ser Val  Ser Arg Asp
    2165                 2170                 2175

Gly Thr  Leu Lys Val Trp Asp  Arg Gln Gly Val Glu  Leu Thr Ser
    2180                 2185                 2190

Ile Pro  Ala His Ser Gly Pro  Ile Ser Gln Cys Ala  Ala Ala Leu
    2195                 2200                 2205

Glu Pro  Arg Pro Ala Gly Gln  Pro Gly Ser Glu Leu  Met Val Val
    2210                 2215                 2220

Thr Val  Gly Leu Asp Gly Ala  Thr Lys Leu Trp His  Pro Leu Leu
    2225                 2230                 2235

Val Cys  Gln Ile His Thr Leu  Gln Gly His Ser Gly  Pro Val Thr
    2240                 2245                 2250

Ala Ala  Ala Ala Ser Glu Ala  Ser Gly Leu Leu Leu  Thr Ser Asp
    2255                 2260                 2265

Asn Ser  Ser Val Arg Leu Trp  Gln Ile Pro Lys Glu  Ala Asp Asp
    2270                 2275                 2280

Thr Cys  Lys Pro Arg Ser Ser  Ala Val Ile Thr Ala  Val Ala Trp
    2285                 2290                 2295

Ala Pro  Asp Gly Ser Leu Val  Val Ser Gly Asn Glu  Ala Gly Glu
    2300                 2305                 2310

Leu Thr  Leu Trp Gln Lys Ala  Gln Ala Val Ala Thr  Ala Arg Ala
    2315                 2320                 2325

Pro Gly  Arg Val Ser Asp Leu  Ile Trp Cys Ser Ala  Asn Ala Phe
    2330                 2335                 2340

Phe Val  Leu Ser Ala Asn Glu  Asn Val Ser Glu Trp  Gln Val Glu
    2345                 2350                 2355

Leu Arg  Lys Gly Ser Thr Cys  Thr Asn Phe Arg Leu  Tyr Leu Lys
    2360                 2365                 2370

Arg Val  Leu Gln Glu Asp Leu  Gly Val Leu Thr Gly  Met Ala Leu
    2375                 2380                 2385

Ala Pro  Asp Gly Gln Ser Leu  Ile Leu Met Lys Glu  Asp Val Glu
    2390                 2395                 2400

Leu Leu  Gln Met Lys Pro Gly  Ser Thr Pro Ser Ser  Ile Cys Arg
    2405                 2410                 2415

Arg Tyr  Ala Val His Ser Ser  Ile Leu Cys Thr Ser  Lys Asp Tyr
    2420                 2425                 2430
```

```
Gly Leu  Phe Tyr Leu Gln Gln  Gly Asn Ser Gly Ser  Leu Ser Ile
    2435                 2440                 2445

Leu Glu  Gln Glu Glu Ser Gly  Lys Phe Glu Lys Thr  Leu Asp Phe
    2450                 2455                 2460

Asn Leu  Asn Leu Asn Asn Pro  Asn Gly Ser Pro Val  Ser Ile Thr
    2465                 2470                 2475

Gln Ala  Glu Pro Glu Ser Gly  Ser Ser Leu Leu Cys  Ala Thr Ser
    2480                 2485                 2490

Asp Gly  Met Leu Trp Asn Leu  Ser Glu Cys Thr Pro  Glu Gly Glu
    2495                 2500                 2505

Trp Val  Val Asp Asn Ile Trp  Gln Lys Lys Ser Arg  Asn Pro Lys
    2510                 2515                 2520

Ser Arg  Thr Pro Gly Thr Asp  Ser Ser Pro Gly Leu  Phe Cys Met
    2525                 2530                 2535

Asp Ser  Trp Val Glu Pro Thr  His Leu Lys Ala Arg  Gln Cys Lys
    2540                 2545                 2550

Lys Ile  His Leu Gly Ser Val  Thr Ala Leu His Val  Leu Pro Gly
    2555                 2560                 2565

Leu Leu  Val Thr Ala Ser Glu  Asp Arg Asp Val Lys  Leu Trp Glu
    2570                 2575                 2580

Arg Pro  Ser Met Gln Leu Leu  Gly Leu Phe Arg Cys  Glu Gly Pro
    2585                 2590                 2595

Val Ser  Cys Leu Glu Pro Trp  Met Glu Pro Ser Ser  Pro Leu Gln
    2600                 2605                 2610

Leu Ala  Val Gly Asp Ala Gln  Gly Asn Leu Tyr Phe  Leu Ser Trp
    2615                 2620                 2625

Glu
```

<210> SEQ ID NO 28
<211> LENGTH: 7890
<212> TYPE: DNA
<213> ORGANISM: Rattus norvegicus

<400> SEQUENCE: 28

```
atggagaaac tctgtggtta tgtgcctgtc cacccagaca tcctctcctt gaagaatcgg     60

tgcctgacca tgctctctga catccaaccc ctggagaaaa tacatggaca gagatctgtc    120

aacccagaca tcctgtcctt ggagaaccgg tgcctgacct tgctccctga tctccagccc    180

atggagaaaa tacatggaca gagatctgtc cacccagaca tcctctcctc agagaaccgg    240

tgtctgacct tgctccctga cctccagtcc ctggagaagc tatgtggaca tatgtctagt    300

cacccagacg tcctctcttt ggagaaccga tgtcttgcta ccctcccgac tgtaaagaga    360

actgtttcga gtggcccctt gctccagtgt cttcacagat ctcatacggc acaagctgat    420

ctgcgtgacc cgaactttcg caactgcctg ttccctgagc ctcctaccat agaggctcca    480

tgtttcttga aggaactaga ccttccaact ggacccaggg ccctgaaatc catgtctgct    540

acagctcgag ttcaggaagt agctttgggt cagcggtgcg tctcagaagg aaaggaattg    600

caggaagaaa aagaaagcgc agaagtcccg atgcctttgt acagtctaag cttgggggga    660

gaagaagaag aagtggtggg ggcaccggtc ctaaaactca catctggaga ctctgactct    720

caccctgaaa ccactgacca gatcctgcag gagaagaaga tggctctctt gaccttgctg    780

tgctcagcta tggcctcaag tgtgaatgtg aaagatgcct ccgatcctac ccgggcatct    840

atccatgaag tctgcagtgc gctggccccc ttggaacctg agttcatcct taaggcatct    900
```

-continued

```
ttgtatgcta ggcagcagct taacctccgg gacatagcca atatagtgtt ggccgtggct    960
gccctcttgc cagcctgccg cccccatgta cgacggtatt actctgccat tgttcacctg   1020
ccttcagact ggatccaggt agccgagttc taccagagcc tggcagaagg ggatgagaag   1080
aagttggtgc ccctgcctgc ctgcctccgt gctgccatga ctgacaaatt tgcccagttt   1140
gatgagtacc agctagcgaa gtacaaccca cggaaacacc gatccaagac acgttcccgc   1200
cagccacccc gccctcaaag gacaaaacct ccattttcag agagtgggaa atgttttcca   1260
aagagcgttt ggccccttaa aaacgaacag atttcgttcg aagcagctta taatgcagtg   1320
tcagagaaga aaaggctacc aaggttcact ctgaagaagt tggtagagca actgcatatc   1380
catgagcctg cgcagcatgt ccaggccctg ctgggctaca ggtacccatc caccctagag   1440
ctcttttctc ggagtcatct ccctgggcca tgggactcta gcagggctgg gcaacggatg   1500
aagctccaaa ggccagagac ctgggagcgg gagctgagct tacgtggaaa cagagcttct   1560
gtgtgggagg aactcataga caatgggaaa ctccccttca tggccatgct ccggaacctg   1620
tgtaacctgc tgcggactgg gatcagtgcc caccaccatg aactcgttct ccagagactc   1680
cagcatgaga aatctgtgat tcacagtcgg cagtttccat tcagattcct taatgctcac   1740
gactctctcg atagactcga ggctcagctc agaagtaaag catcgccctt cccttccaat   1800
acaacattga tgaagcggat aatgattaga aactcaaaaa aaatcaagag acctgccaac   1860
ccgaggtacc tgtgcaccct gacgcagcgg cagcttcggg cggcaatggc tatcccggtg   1920
atgtatgagc atctcaagcg ggagaaactg aggctgcaca aggccagaca gtggacctgt   1980
gaccttgagt tgctggagcg gtatcgccag gccctggaaa cggccgtgaa catctctgta   2040
aagcacaacc taccccccgct gccaggccga accctcttgg tctatctcac agatgcaaat   2100
gccaacagac tttgtcccaa gagtcacttg caagggcctc ccctgaacta tgtgctgctg   2160
ttgatcggga tgatgatggc tcgggcggag cagacgacag tttggctgtg tgggacagga   2220
actgtgaaga caccagtact tacagccgac gaaggtatcc tgaagactgc catcaaactt   2280
caggctcaag tccaggagtt agaagaaaat gatgagtggc cctggaaac ttttgagaag   2340
tacctgctat ctctggctgt gcgaaggacc cctattgaca gggtcatcct gttcggccaa   2400
aggatggata cggagctgct gaatgtagcc aaacagatta tctggcagca tgtgaattcc   2460
aagtgcctct tcgtcagtgt cctcctacgg aaaatgcagt acatgtcacc aaatttgaat   2520
cccaatgatg tgacgctctc gggctgcact gacgggatcc tgaagttcat tgcggagcat   2580
ggagcctctc gtcttctgga acatgtgggc caactagata agatattcaa gatccctcca   2640
cccccaggaa agacaaaggt ctcacctctc cggccgctgg aggagaacaa ccctggtccc   2700
ttcgttccta tttcccagca tggatggcgc aacatccggc ttttcatttc gtccactttc   2760
cgagacatgc atggggaacg agacttgctg atgcgatctg ttctgccagc gctgcaggcc   2820
cgagcgttcc cccaccgcat cagccttcac gccattgacc tgcgctgggg aatcacggag   2880
gaagagaccc gcaggaacag acaactggaa gtgtgccttg gggaggtgga gaactctcag   2940
ctgttcgtgg ggatcctggg ctcccgctat ggctatactc cccccagcta tgatctgcct   3000
gaccaccccc actttcactg gacccagcga taccccttcgg ggcgctctgt aacagagatg   3060
gaggtgatgc agttcctgaa ccgtggccaa cgctcggaac cctctgacca agctctcatc   3120
tacttccgag atcctggttt ccttagctct gtgccagatg tctggaaacc tgactttatt   3180
tccgagtcag aagaggctgc acatcgggtc tcagaactga agagattcct acaggaacag   3240
aaagaggtta cctgccgcag gtactcctgt gaatggggag gcgtagcagc cggccggccc   3300
```

-continued

```
tatactgggg gcctggagga gtttggacag ttggttctcc aagatgtgtg gagcgtgatc   3360
cagaagcgtt acctgcagcc tggggcccag ttggagcagc caggatccat ctcagaagag   3420
gatttgatcc aggccagctt tcagcagctg aagagcccac cgagtcccgc acggccacgc   3480
cttcttcagg ataccgtgca acagctgatg ctgccccacg ggaggctgag cctagtgatt   3540
gggcaggcag gacagggaaa gactgccttc ctggcatccc ttgtgtcggc cctgaaggtt   3600
cccgaccagc ccaatgtggc cccgttcgtt ttcttccact tttcagcagc ccgccctgac   3660
cagtgtcttg ctttcaacct cctcagacgc ctctgtaccc atctgcatca aaaactggga   3720
gagccgagcg ctctccccag cacttacaga ggcctggtgt gggaactgca gcagaagctg   3780
ctcctcaaat ctgcccagtg gctgcaacca ggccagactt tggtccttat tatcgacggg   3840
gcagataagt tggtggacca taatggacag ctgatttcag actggatccc caagtctctt   3900
ccgcggcgag tacacctggt gctgagtgtg tctagtgact caggcctggg agagaccctt   3960
cagcaaagtc agagtgctta tgtggtggcc ttggggtctt tggtcccgtc ttcaagggct   4020
cagcttgtga gagaagagct agcactgtat gggaaacggc tggaggagtc accttttaac   4080
aaccagatgc ggctgctgct ggcaaagcag gggtcaagcc tgccactgta cctgcacctc   4140
gtcactgact acctgaggct tttcacactg tacgaacagg tgtctgagag acttcgaacc   4200
ctgcccgcca ctctcccact gctgctgcag cacatcctga gcaccttgga gcaagagcat   4260
ggccataacg tccttcctca agctttgact gcccttgagg tcacgcacag tggtctgact   4320
gtggaccagc tgcatgcagt cctgagcacg tggttgactt tgcccaagga gactaagagc   4380
tgggaagagg cagtggctgc cagtcacagt ggaaacctct acccccttggc tccatttgcc   4440
taccttgtcc agagtctacg cagtttacta ggcgagggcc ccgtggagcg ccctggcgcc   4500
cgtctctgcc tctctgatgg gcctctgagg acagcagtta aacgtcgcta tgggaaaagg   4560
ctggggctag agaagactgc gcatgtcctc attgcagctc acctctggaa gatgtgtgac   4620
cctgatgcct caggcacctt ccgaagttgc cctcccgagg ctctgaaaga tttaccttac   4680
cacctgctcc agagcgggaa ccatggtctc cttgcaaagt tccttaccaa cctccatgtg   4740
gtggctgcat atctggaagt gggtctagtc ccggacctct tggaggctta cgagctctat   4800
gcttcttcaa agcctgaagt gaaccagaag ctcccggagg cagatgttgc tgtattccac   4860
aacttcctga aacaacaggc ttcactcctt acccagtatc ctttgctcct gctccagcag   4920
gcagctagcc agcctgaaga gtcacctgtt tgctgccagg ccccccctgct cacccagcgg   4980
tggcacaacc agtgcatact gaaatggatt aataaacccc agaccttgaa gggtcagcaa   5040
agcttgtctc tgccaatttc ctcatcccca actgctgtgg ccttctctcc taatgggcaa   5100
agagcagctg tggggactgc tggtgggaca atttacctgt tgaacttgag aacctggcag   5160
gaggagaagg ctctggtgag tggctgtgat gggatttcct ctttcgcgtt cctgtcagac   5220
actgctcttt tccttaccac cttcgatggg ctcctggagc tttgggacct gcaacatggt   5280
tgttgggtgt tccagaccaa ggcccaccag taccaaatca ctggctgctg cctgagccca   5340
gaccgccgcc tgctggccac cgtgtgtttg ggaggatacg taaagctgtg ggacacagtc   5400
cagggccagc tggctttcca gtacacccat cccaagtctc taaactgcat caccttccac   5460
ccagaggggc aggtggtagc cacaggcaac tggtctggca tcgtgacctt cttccaggca   5520
gatggactca aagtcaccaa ggaactaggg ggcccaggac cctctgttcg tacgctggca   5580
ttcagtgcac ccgggaaggt tgtggctcta ggccggatag atgggacagt ggagctgtgg   5640
```

```
gcctggcaag agggcacacg gctggcagcc ttccctgcac agtgtggcgg tgtctccacc   5700
gttcttttct tgcatgctgg aggccggttc ctgacggctg gggaagatgg caaggctcag   5760
ttatggtcag gatttcttgg ccggcccagg ggttgcctgg gctctcttta tctttctcct   5820
gcgctctctg tggctctcaa cccagacggt gaccaggtgg ctgttgggta ccgaggagat   5880
ggcattaaaa tctacagaat ttcttcaggt ccccaggagg ctcaatgcca agagctaaat   5940
gtggcggtgt ctgcactggt ctggctgagt cccagcgtct tggtgagtgg tgcagaagat   6000
ggctccctgc atggctggat gctcaggaga aactcccttc agtccctgtg gctgtcatcc   6060
gtgtgccaga agcctgtgct ggggctggct gcctcccagg agttcttggc ttctgcctca   6120
gaggacttca cggtgcgact gtggccaaga cagctgctga cacagccaca tgcagtagaa   6180
gagttgccct gtgcggctga actccgggga cacgaggggc cggtgtgctg ctgtagcttc   6240
agcccggatg gacgcatctt ggccacagcg ggcagggatc ggaatctcct ctgctgggac   6300
gtcaaggtag cccaagcccc tctcctgatt cacacgttct cgtcctgtca tcgagactgg   6360
atcactggct gtacgtggac caaagacaac atcctgatct cctgctctag tgatggctct   6420
gtgggactct ggaacccaga ggcaggacag caacttggcc agttcccagg tcaccagagt   6480
gccgtgagcg ctgtggttgc tgtggaggaa cacattgtat ctgtgagtcg ggatgggacc   6540
ttgaaagtgt gggaccgtca gggtgtggag ctgaccagca tccctgccca ttccggaccc   6600
attagccagt gtgcggctgc tctggaaccc cgtccagctg gacagcctgg atcagagctt   6660
atggtggtga ctgttggact ggatggggcc acaaagctgt ggcatcccct gttggtgtgc   6720
caaatacata ccctgcaggg acacagtggt ccagtcacag ctgctgctgc ttcagaggcc   6780
tcaggcctcc tgctgacctc agacaatagc tctgtacgac tctggcagat ccctaaggaa   6840
gcagatgata cctgcaaacc taggagttct gcggtcatca ccgctgtggc gtgggcacca   6900
gatggttctc tggtggtgtc tggaaatgaa gctggggaac taacgctgtg gcagaaagcg   6960
caggctgtgg ctacggcacg ggctccaggc cgcgtcagtg acctgatctg gtgctccgca   7020
aatgcattct ttgttctcag tgctaatgaa aatgtcagtg agtggcaagt ggaactgagg   7080
aaaggttcaa catgcaccaa tttcagactt tatctgaaga gagttctgca ggaggacttg   7140
ggagtcttga caggtatggc cctggcgcct gacggccagt ctctcatttt gatgaaagag   7200
gatgtagaat tgctacagat gaagcccggg tctactccat cttcgatctg caggaggtat   7260
gcagtgcatt cttctatact gtgcaccagc aaagactatg gcctgtttta cctgcagcag   7320
ggaaactctg gatctctttc tatcttggag caggaggagt cagggaagtt tgaaaagacc   7380
ctggacttca atctgaactt aaataatcct aatgggtccc cagtatcaat cactcaggct   7440
gaacctgagt ctgggtcctc gcttttgtgt gctacctctg atgggatgct gtggaactta   7500
tctgagtgta ccccagaagg agagtgggtc gtagataaca tctggcagaa aaaatcaaga   7560
aaccctaaaa gtcgaactcc ggggacagat tcgtccccag gcttattctg catggatagc   7620
tgggtagaac ccacacattt aaaggcacgg cagtgtaaaa agattcactt gggctctgtc   7680
acggccctcc atgtgctgcc cggattgctg gtgactgctt cagaggacag agatgttaag   7740
ctgtgggaga gacccagtat gcagctgctc ggcttgttcc gatgtgaagg gccggtgagc   7800
tgtctggaac cttggatgga gcccagctct cccctgcagc ttgctgtggg agatgcacaa   7860
ggaaacttgt attttctatc ttgggaatga                                    7890
```

<210> SEQ ID NO 29
<211> LENGTH: 98

-continued

<212> TYPE: RNA
<213> ORGANISM: Homo sapiens

<400> SEQUENCE: 29
ggcuggcuuu agcucagcgg uuacuucgac aguucuuuaa uugaaacaag caaccugucu 60
ggguuguucg agacccgcgg gcgcucucca guccuuuu 98

<210> SEQ ID NO 30
<211> LENGTH: 88
<212> TYPE: RNA
<213> ORGANISM: Homo sapiens

<400> SEQUENCE: 30
ggcuggcuuu agcucagcgg uuacuucgag uacauuguaa ccaccucucu gggugguucg 60
agacccgcgg gugcuuucca gcucuuuu 88

<210> SEQ ID NO 31
<211> LENGTH: 88
<212> TYPE: RNA
<213> ORGANISM: Homo sapiens

<400> SEQUENCE: 31
ggcuggcuuu agcucagcgg uuacuucgcg ugucaucaaa ccaccucucu ggguuguucg 60
agacccgcgg gcgcucucca gcccucuu 88

<210> SEQ ID NO 32
<211> LENGTH: 143
<212> TYPE: RNA
<213> ORGANISM: Rattus norvegicus

<400> SEQUENCE: 32
ggccagcuuu agcucagcgg uuacuucgac gugcuccagu uugagcaggc uauguaacgu 60
ggucgguucg agcaacacaa ccagccgcuu gccuaucugg ugagugguug guucgagacc 120
cgcgggcgcu cucuggcccu uuu 143

<210> SEQ ID NO 33
<211> LENGTH: 814
<212> TYPE: DNA
<213> ORGANISM: Homo sapiens

<400> SEQUENCE: 33
atcactctct ttaatcacta ctcacagtaa cctcaactcc tgccacaatg tacaggatgc 60
aactcctgtc ttgcattgca ctaagtcttg cacttgtcac aaacagtgca cctacttcaa 120
gttctacaaa gaaaacacag ctacaactgg agcatttact gctggattta cagatgattt 180
tgaatggaat taataattac aagaatccca aactcaccag gatgctcaca tttaagtttt 240
acatgcccaa gaaggccaca gaactgaaac atcttcagtg tctagaagaa gaactcaaac 300
ctctggagga agtgctaaat ttagctcaaa gcaaaaactt tcacttaaga cccagggact 360
taatcagcaa tatcaacgta atagttctgg aactaaaggg atctgaaaca acattcatgt 420
gtgaatatgc tgatgagaca gcaaccattg tagaatttct gaacagatgg attacctttt 480
gtcaaagcat catctcaaca ctgacttgat aattaagtgc ttcccactta aaacgtatca 540
ggccttctat ttatttaaat atttaaattt tatatttatt gttgaatgta tggtttgcta 600
cctattgtaa ctattattct taatcttaaa actataaata tggatctttt atgattcttt 660
ttgtaagccc taggggctct aaaatggttt cacttattta tcccaaaata tttattatta 720

```
tgttgaatgt taaatatagt atctatgtag attggttagt aaaactattt aataaatttg    780

ataaatataa aaaaaaaaaa aaaaaaaaaa aaaa                                814


<210> SEQ ID NO 34
<211> LENGTH: 153
<212> TYPE: PRT
<213> ORGANISM: Homo sapiens

<400> SEQUENCE: 34

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150


<210> SEQ ID NO 35
<211> LENGTH: 1589
<212> TYPE: DNA
<213> ORGANISM: Homo sapiens

<400> SEQUENCE: 35

gaattcctct ggtcctcatc caggtgcgcg ggaagcaggt gcccaggaga gaggggataa     60

tgaagattcc atgctgatga tcccaaagat tgaacctgca gaccaagcgc aaagtagaaa    120

ctgaaagtac actgctggcg gatcctacgg aagttatgga aaaggcaaag cgcagagcca    180

cgccgtagtg tgtgccgccc cccttgggat ggatgaaact gcagtcgcgg cgtgggtaag    240

aggaaccagc tgcagagatc accctgccca acacagactc ggcaactccg cggaagacca    300

gggtcctggg agtgactatg ggcggtgaga gcttgctcct gctccagttg cggtcatcat    360

gactacgccc gcctcccgca gaccatgttc catgtttctt ttaggtatat ctttggactt    420

cctcccctga tccttgttct gttgccagta gcatcatctg attgtgatat tgaaggtaaa    480

gatggcaaac aatatgagag tgttctaatg gtcagcatcg atcaattatt ggacagcatg    540

aaagaaattg gtagcaattg cctgaataat gaatttaact tttttaaaag acatatctgt    600

gatgctaata aggaaggtat gtttttattc cgtgctgctc gcaagttgag gcaatttctt    660

aaaatgaata gcactggtga ttttgatctc cacttattaa aagtttcaga aggcacaaca    720

atactgttga actgcactgg ccaggttaaa ggaagaaaac cagctgccct gggtgaagcc    780

caaccaacaa agagtttgga agaaaataaa tctttaaagg aacagaaaaa actgaatgac    840

ttgtgtttcc taaagagact attacaagag ataaaaactt gttggaataa aattttgatg    900
```

```
ggcactaaag aacactgaaa aatatggagt ggcaatatag aaacacgaac tttagctgca    960

tcctccaaga atctatctgc ttatgcagtt tttcagagtg gaatgcttcc tagaagttac   1020

tgaatgcacc atggtcaaaa cggattaggg catttgagaa atgcatattg tattactaga   1080

agatgaatac aaacaatgga aactgaatgc tccagtcaac aaactatttc ttatatatgt   1140

gaacatttat caatcagtat aattctgtac tgatttttgt aagacaatcc atgtaaggta   1200

tcagttgcaa taatacttct caaacctgtt taaatatttc aagacattaa atctatgaag   1260

tatataatgg tttcaaagat tcaaaattga cattgcttta ctgtcaaaat aattttatgg   1320

ctcactatga atctattata ctgtattaag agtgaaaatt gtcttcttct gtgctggaga   1380

tgttttagag ttaacaatga tatatggata atgccggtga gaataagaga gtcataaacc   1440

ttaagtaagc aacagcataa caaggtccaa gatacctaaa agagatttca agagatttaa   1500

ttaatcatga atgtgtaaca cagtgccttc aataaatggt atagcaaatg ttttgacatg   1560

aaaaaaggac aatttcaaaa aaataaaat                                      1589
```

<210> SEQ ID NO 36
<211> LENGTH: 177
<212> TYPE: PRT
<213> ORGANISM: Homo sapiens

<400> SEQUENCE: 36

```
Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His
```

<210> SEQ ID NO 37
<211> LENGTH: 1968
<212> TYPE: DNA
<213> ORGANISM: Homo sapiens

<400> SEQUENCE: 37

```
actccgggtg gcaggcgccc gggggaatcc cagctgactc gctcactgcc ttcgaagtcc     60

ggcgcccccc gggagggaac tgggtggccg caccctcccg gctgcggtgg ctgtcgcccc    120
```

-continued

```
ccaccctgca gccaggactc gatggaggta cagagctcgg cttctttgcc ttgggagggg    180
agtggtggtg gttgaaaggg cgatggaatt ttccccgaaa gcctacgccc agggcccctc    240
ccagctccag cgttaccctc cggtctatcc tactggccga gctgccccgc cttctcatgg    300
ggaaaactta gccgcaactt caatttttgg tttttccttt aatgacactt ctgaggctct    360
cctagccatc ctcccgcttc cggaggagcg cagatcgcag gtccctttgc ccctggcgtg    420
cgactcccta ctgcgctgcg ctcttacggc gttccaggct gctggctagc gcaaggcggg    480
ccgggcaccc cgcgctccgc tgggagggtg agggacgcgc gtctggcggc cccagccaag    540
ctgcgggttt ctgagaagac gctgtcccgc agccctgagg gctgagttct gcacccagtc    600
aagctcagga aggccaagaa aagaatccat tccaatatat ggccatgtgg ctctttggag    660
caatgttcca tcatgttcca tgctgctgac gtcacatgga gcacagaaat caatgttagc    720
agatagccag cccatacaag atcgtattgt attgtaggag gcatcgtgga tggatggctg    780
ctggaaaccc cttgccatag ccagctcttc ttcaatactt aaggatttac cgtggctttg    840
agtaatgaga atttcgaaac cacatttgag aagtatttcc atccagtgct acttgtgttt    900
acttctaaac agtcattttc taactgaagc tggcattcat gtcttcattt tgggctgttt    960
cagtgcaggg cttcctaaaa cagaagccaa ctgggtgaat gtaataagtg atttgaaaaa   1020
aattgaagat cttattcaat ctatgcatat tgatgctact ttatatacgg aaagtgatgt   1080
tcaccccagt tgcaaagtaa cagcaatgaa gtgctttctc ttggagttac aagttatttc   1140
acttgagtcc ggagatgcaa gtattcatga tacagtagaa aatctgatca tcctagcaaa   1200
caacagtttg tcttctaatg ggaatgtaac agaatctgga tgcaaagaat gtgaggaact   1260
ggaggaaaaa aatattaaag aatttttgca gagttttgta catattgtcc aaatgttcat   1320
caacacttct tgattgcaat tgattctttt taaagtgttt ctgttattaa caaacatcac   1380
tctgctgctt agacataaca aaacactcgg catttcaaat gtgctgtcaa aacaagtttt   1440
tctgtcaaga agatgatcag accttggatc agatgaactc ttagaaatga aggcagaaaa   1500
atgtcattga gtaatatagt gactatgaac ttctctcaga cttactttac tcattttttt   1560
aatttattat tgaaattgta catatttgtg gaataatgta aaatgttgaa taaaaatatg   1620
tacaagtgtt gtttttttaag ttgcactgat attttacctc ttattgcaaa atagcatttg   1680
tttaagggtg atagtcaaat tatgtattgg tggggctggg taccaatgct gcaggtcaac   1740
agctatgctg gtaggctcct gcctgtgtgg aaccactgac tactggctct cattgacttc   1800
cttactaagc atagcaaaca gaggaagaat ttgttatcag taagaaaaag aagaactata   1860
tgtgaatcct cttctttaca ctgtaattta gttattgatg tataaagcaa ctgttatgaa   1920
ataaagaaat tgcaataact ggcaaaaaaa aaaaaaaaaa aaaaaaaa                1968

<210> SEQ ID NO 38
<211> LENGTH: 160
<212> TYPE: PRT
<213> ORGANISM: Homo sapiens

<400> SEQUENCE: 38

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45
```

```
Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160


<210> SEQ ID NO 39
<211> LENGTH: 2347
<212> TYPE: DNA
<213> ORGANISM: Homo sapiens

<400> SEQUENCE: 39

ctgtttcagg gccattggac tctccgtcct gcccagagca agatgtgtca ccagcagttg      60

gtcatctctt ggttttccct ggtttttctg gcatctcccc tcgtggccat atgggaactg     120

aagaaagatg tttatgtcgt agaattggat tggtatccgg atgcccctgg agaaatggtg     180

gtcctcacct gtgacacccc tgaagaagat ggtatcacct ggaccttgga ccagagcagt     240

gaggtcttag gctctggcaa aaccctgacc atccaagtca aagagtttgg agatgctggc     300

cagtacacct gtcacaaagg aggcgaggtt ctaagccatt cgctcctgct gcttcacaaa     360

aaggaagatg gaatttggtc cactgatatt ttaaaggacc agaaagaacc caaaaataag     420

acctttctaa gatgcgaggc caagaattat tctggacgtt tcacctgctg gtggctgacg     480

acaatcagta ctgatttgac attcagtgtc aaaagcagca gaggctcttc tgacccccaa     540

ggggtgacgt gcggagctgc tacactctct gcagagagag tcagagggga caacaaggag     600

tatgagtact cagtggagtg ccaggaggac agtgcctgcc cagctgctga ggagagtctg     660

cccattgagg tcatggtgga tgccgttcac aagctcaagt atgaaaacta caccagcagc     720

ttcttcatca gggacatcat caaacctgac ccacccaaga acttgcagct gaagccatta     780

aagaattctc ggcaggtgga ggtcagctgg gagtaccctg acacctggag tactccacat     840

tcctacttct ccctgacatt ctgcgttcag gtccagggca agagcaagag agaaaagaaa     900

gatagagtct tcacggacaa gacctcagcc acggtcatct gccgcaaaaa tgccagcatt     960

agcgtgcggg cccaggaccg ctactatagc tcatcttgga gcgaatgggc atctgtgccc    1020

tgcagttagg ttctgatcca ggatgaaaat ttggaggaaa agtggaagat attaagcaaa    1080

atgtttaaag acacaacgga atagacccaa aaagataatt tctatctgat ttgctttaaa    1140

acgttttttt aggatcacaa tgatatcttt gctgtatttg tatagttaga tgctaaatgc    1200

tcattgaaac aatcagctaa tttatgtata gattttccag ctctcaagtt gccatgggcc    1260

ttcatgctat ttaaatattt aagtaattta tgtatttatt agtatattac tgttatttaa    1320

cgtttgtctg ccaggatgta tggaatgttt catactctta tgacctgatc catcaggatc    1380

agtccctatt atgcaaaatg tgaatttaat tttatttgta ctgacaactt ttcaagcaag    1440

gctgcaagta catcagtttt atgacaatca ggaagaatgc agtgttctga taccagtgcc    1500
```

-continued

```
atcatacact tgtgatggat gggaacgcaa gagatactta catggaaacc tgacaatgca   1560

aacctgttga gaagatccag gagaacaaga tgctagttcc catgtctgtg aagacttcct   1620

ggagatggtg ttgataaagc aatttagggc cacttacact tctaagcaag tttaatcttt   1680

ggatgcctga attttaaaag ggctagaaaa aaatgattga ccagcctggg aaacataaca   1740

agaccccgtc tctacaaaaa aaatttaaaa ttagccaggc gtggtggctc atgcttgtgg   1800

tcccagctgt tcaggaggat gaggcaggag gatctcttga gcccaggagg tcaaggctat   1860

ggtgagccgt gattgtgcca ctgcatacca gcctaggtga cagaatgaga ccctgtctca   1920

aaaaaaaaaa tgattgaaat taaaattcag ctttagcttc catggcagtc ctcacccccca  1980

cctctctaaa agacacagga ggatgacaca gaaacaccgt aagtgtctgg aaggcaaaaa   2040

gatcttaaga ttcaagagag aggacaagta gttatggcta aggacatgaa attgtcagaa   2100

tggcaggtgg cttcttaaca gccctgtgag aagcagacag atgcaaagaa aatctggaat   2160

ccctttctca ttagcatgaa tgaacctgat acacaattat gaccagaaaa tatggctcca   2220

tgaaggtgct acttttaagt aatgtatgtg cgctctgtaa agtgattaca tttgtttcct   2280

gtttgtttat ttatttattt atttttgcat tctgaggctg aactaataaa aactcttctt   2340

tgtaatc                                                             2347


<210> SEQ ID NO 40
<211> LENGTH: 328
<212> TYPE: PRT
<213> ORGANISM: Homo sapiens

<400> SEQUENCE: 40

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
```

```
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325


<210> SEQ ID NO 41
<211> LENGTH: 1444
<212> TYPE: DNA
<213> ORGANISM: Homo sapiens

<400> SEQUENCE: 41

tttcattttg ggccgagctg gaggcggcgg ggccgtcccg gaacggctgc ggccgggcac     60

cccgggagtt aatccgaaag cgccgcaagc cccgcgggcc ggccgcaccg cacgtgtcac    120

cgagaagctg atgtagagag agacacagaa ggagacagaa agcaagagac cagagtcccg    180

ggaaagtcct gccgcgcctc gggacaatta taaaaatgtg gccccctggg tcagcctccc    240

agccaccgcc ctcacctgcc gcggccacag gtctgcatcc agcggctcgc cctgtgtccc    300

tgcagtgccg gctcagcatg tgtccagcgc gcagcctcct ccttgtggct accctggtcc    360

tcctggacca cctcagtttg gccagaaacc tccccgtggc cactccagac ccaggaatgt    420

tcccatgcct tcaccactcc caaaacctgc tgagggccgt cagcaacatg ctccagaagg    480

ccagacaaac tctagaattt taccccttgca cttctgaaga gattgatcat gaagatatca    540

caaaagataa aaccagcaca gtggaggcct gtttaccatt ggaattaacc aagaatgaga    600

gttgcctaaa ttccagagag acctctttca taactaatgg gagttgcctg gcctccagaa    660

agacctcttt tatgatggcc ctgtgcctta gtagtattta tgaagacttg aagatgtacc    720

aggtggagtt caagaccatg aatgcaaagc ttctgatgga tcctaagagg cagatctttc    780

tagatcaaaa catgctggca gttattgatg agctgatgca ggccctgaat ttcaacagtg    840

agactgtgcc acaaaaatcc tcccttgaag aaccggattt ttataaaact aaaatcaagc    900

tctgcatact tcttcatgct ttcagaattc gggcagtgac tattgataga gtgatgagct    960

atctgaatgc ttcctaaaaa gcgaggtccc tccaaaccgt tgtcattttt ataaaacttt   1020

gaaatgagga aactttgata ggatgtggat taagaactag ggagggggaa agaaggatgg   1080

gactattaca tccacatgat acctctgatc aagtattttt gacatttact gtggataaat   1140

tgtttttaag ttttcatgaa tgaattgcta agaagggaaa atatccatcc tgaaggtgtt   1200

tttcattcac tttaatagaa gggcaaatat ttataagcta tttctgtacc aaagtgtttg   1260

tggaaacaaa catgtaagca taacttattt taaaatattt atttatataa cttggtaatc   1320

atgaaagcat ctgagctaac ttatatttat ttatgttata tttattaaat tatttatcaa   1380

gtgtatttga aaaatatttt taagtgttct aaaaataaaa gtattgaatt aaagtgaaaa   1440
```

-continued aaaa 1444

<210> SEQ ID NO 42
<211> LENGTH: 253
<212> TYPE: PRT
<213> ORGANISM: Homo sapiens

<400> SEQUENCE: 42

Met Trp Pro Pro Gly Ser Ala Ser Gln Pro Pro Pro Ser Pro Ala Ala
1 5 10 15

Ala Thr Gly Leu His Pro Ala Ala Arg Pro Val Ser Leu Gln Cys Arg
20 25 30

Leu Ser Met Cys Pro Ala Arg Ser Leu Leu Leu Val Ala Thr Leu Val
35 40 45

Leu Leu Asp His Leu Ser Leu Ala Arg Asn Leu Pro Val Ala Thr Pro
50 55 60

Asp Pro Gly Met Phe Pro Cys Leu His His Ser Gln Asn Leu Leu Arg
65 70 75 80

Ala Val Ser Asn Met Leu Gln Lys Ala Arg Gln Thr Leu Glu Phe Tyr
85 90 95

Pro Cys Thr Ser Glu Glu Ile Asp His Glu Asp Ile Thr Lys Asp Lys
100 105 110

Thr Ser Thr Val Glu Ala Cys Leu Pro Leu Glu Leu Thr Lys Asn Glu
115 120 125

Ser Cys Leu Asn Ser Arg Glu Thr Ser Phe Ile Thr Asn Gly Ser Cys
130 135 140

Leu Ala Ser Arg Lys Thr Ser Phe Met Met Ala Leu Cys Leu Ser Ser
145 150 155 160

Ile Tyr Glu Asp Leu Lys Met Tyr Gln Val Glu Phe Lys Thr Met Asn
165 170 175

Ala Lys Leu Leu Met Asp Pro Lys Arg Gln Ile Phe Leu Asp Gln Asn
180 185 190

Met Leu Ala Val Ile Asp Glu Leu Met Gln Ala Leu Asn Phe Asn Ser
195 200 205

Glu Thr Val Pro Gln Lys Ser Ser Leu Glu Glu Pro Asp Phe Tyr Lys
210 215 220

Thr Lys Ile Lys Leu Cys Ile Leu Leu His Ala Phe Arg Ile Arg Ala
225 230 235 240

Val Thr Ile Asp Arg Val Met Ser Tyr Leu Asn Ala Ser
245 250

<210> SEQ ID NO 43
<211> LENGTH: 787
<212> TYPE: DNA
<213> ORGANISM: Homo sapiens

<400> SEQUENCE: 43
ggctaaagtt ctctggagga tgtggctgca gagcctgctg ctcttgggca ctgtggcctg 60
cagcatctct gcacccgccc gctcgcccag ccccagcacg cagccctggg agcatgtgaa 120
tgccatccag gaggcccggc gtctcctgaa cctgagtaga gacactgctg ctgagatgaa 180
tgaaacagta gaagtcatct cagaaatgtt tgacctccag gagccgacct gcctacagac 240
ccgcctggag ctgtacaagc agggcctgcg gggcagcctc accaagctca agggcccctt 300
gaccatgatg gccagccact acaagcagca ctgccctcca accccggaaa cttcctgtgc 360
aacccagatt atcacctttg aaagtttcaa agagaacctg aaggactttc tgcttgtcat 420

```
ccccttgac tgctgggagc cagtccagga gtgagaccgg ccagatgagg ctggccaagc    480

cggggagctg ctctctcatg aaacaagagc tagaaactca ggatggtcat cttggaggga    540

ccaaggggtg ggccacagcc atggtgggag tggcctggac ctgccctggg ccacactgac    600

cctgatacag gcatggcaga agaatgggaa tattttatac tgacagaaat cagtaatatt    660

tatatattta tatttttaaa atatttattt atttatttat ttaagttcat attccatatt    720

tattcaagat gttttaccgt aataattatt attaaaaata tgcttctact tgaaaaaaaa    780

aaaaaaa                                                              787
```

<210> SEQ ID NO 44
<211> LENGTH: 144
<212> TYPE: PRT
<213> ORGANISM: Homo sapiens

<400> SEQUENCE: 44

```
Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140
```

<210> SEQ ID NO 45
<211> LENGTH: 2545
<212> TYPE: DNA
<213> ORGANISM: Homo sapiens

<400> SEQUENCE: 45

```
atccaataca ggagtgactt ggaactccat tctatcacta tgaagaaaag tggtgttctt     60

ttcctcttgg gcatcatctt gctggttctg attggagtgc aaggaacccc agtagtgaga    120

aagggtcgct gttcctgcat cagcaccaac caagggacta tccacctaca atccttgaaa    180

gaccttaaac aatttgcccc aagcccttcc tgcgagaaaa ttgaaatcat tgctacactg    240

aagaatggag ttcaaacatg tctaaaccca gattcagcag atgtgaagga actgattaaa    300

aagtgggaga aacaggtcag ccaaaagaaa aagcaaaaga atgggaaaaa acatcaaaaa    360

aagaaagttc tgaaagttcg aaaatctcaa cgttctcgtc aaaagaagac tacataagag    420

accacttcac caataagtat tctgtgttaa aaatgttcta ttttaattat accgctatca    480

ttccaaagga ggatggcata taatacaaag gcttattaat ttgactagaa aatttaaaac    540

attactctga aattgtaact aaagttagaa agttgatttt aagaatccaa acgttaagaa    600

ttgttaaagg ctatgattgt ctttgttctt ctaccaccca ccagttgaat ttcatcatgc    660
```

-continued

```
ttaaggccat gattttagca atacccatgt ctacacagat gttcacccaa ccacatccca    720

ctcacaacag ctgcctggaa gagcagccct aggcttccac gtactgcagc ctccagagag    780

tatctgaggc acatgtcagc aagtcctaag cctgttagca tgctggtgag ccaagcagtt    840

tgaaattgag ctggacctca ccaagctgct gtggccatca acctctgtat ttgaatcagc    900

ctacaggcct cacacacaat gtgtctgaga gattcatgct gattgttatt gggtatcacc    960

actggagatc accagtgtgt ggctttcaga gcctcctttc tggctttgga agccatgtga   1020

ttccatcttg cccgctcagg ctgaccactt tatttctttt tgttcccctt tgcttcattc   1080

aagtcagctc ttctccatcc taccacaatg cagtgccttt cttctctcca gtgcacctgt   1140

catatgctct gatttatctg agtcaactcc tttctcatct tgtccccaac accccacaga   1200

agtgctttct tctcccaatt catcctcact cagtccagct tagttcaagt cctgcctctt   1260

aaataaacct ttttggacac acaaattatc ttaaaactcc tgtttcactt ggttcagtac   1320

cacatgggtg aacactcaat ggttaactaa ttcttgggtg tttatcctat ctctccaacc   1380

agattgtcag ctccttgagg gcaagagcca cagtatattt ccctgtttct tccacagtgc   1440

ctaataatac tgtggaacta ggttttaata attttttaat tgatgttgtt atgggcagga   1500

tggcaaccag accattgtct cagagcaggt gctggctctt tcctggctac tccatgttgg   1560

ctagcctctg gtaacctctt acttattatc ttcaggacac tcactacagg gaccagggat   1620

gatgcaacat ccttgtcttt ttatgacagg atgtttgctc agcttctcca acaataagaa   1680

gcacgtggta aaacacttgc ggatattctg gactgttttt aaaaaatata cagtttaccg   1740

aaaatcatat aatcttacaa tgaaaaggac tttatagatc agccagtgac caaccttttc   1800

ccaaccatac aaaaattcct tttcccgaag gaaaagggct ttctcaataa gcctcagctt   1860

tctaagatct aacaagatag ccaccgagat ccttatcgaa actcatttta ggcaaatatg   1920

agttttattg tccgtttact tgtttcagag tttgtattgt gattatcaat taccacacca   1980

tctcccatga agaaagggaa cggtgaagta ctaagcgcta gaggaagcag ccaagtcggt   2040

tagtggaagc atgattggtg cccagttagc ctctgcagga tgtggaaacc tccttccagg   2100

ggaggttcag tgaattgtgt aggagaggtt gtctgtggcc agaatttaaa cctatactca   2160

ctttcccaaa ttgaatcact gctcacactg ctgatgattt agagtgctgt ccggtggaga   2220

tcccacccga acgtcttatc taatcatgaa actccctagt tccttcatgt aacttccctg   2280

aaaaatctaa gtgtttcata aatttgagag tctgtgaccc acttaccttg catctcacag   2340

gtagacagta tataactaac aaccaaagac tacatattgt cactgacaca cacgttataa   2400

tcatttatca tatatataca tacatgcata cactctcaaa gcaaataatt tttcacttca   2460

aaacagtatt gacttgtata ccttgtaatt tgaaatattt tctttgttaa aatagaatgg   2520

tatcaataaa tagaccatta atcag                                         2545
```

<210> SEQ ID NO 46
<211> LENGTH: 125
<212> TYPE: PRT
<213> ORGANISM: Homo sapiens

<400> SEQUENCE: 46

```
Met Lys Lys Ser Gly Val Leu Phe Leu Leu Gly Ile Ile Leu Leu Val
1               5                   10                  15

Leu Ile Gly Val Gln Gly Thr Pro Val Val Arg Lys Gly Arg Cys Ser
            20                  25                  30
```

-continued

```
Cys Ile Ser Thr Asn Gln Gly Thr Ile His Leu Gln Ser Leu Lys Asp
        35                  40                  45

Leu Lys Gln Phe Ala Pro Ser Pro Ser Cys Glu Lys Ile Glu Ile Ile
    50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Lys Val Leu Lys
            100                 105                 110

Val Arg Lys Ser Gln Arg Ser Arg Gln Lys Lys Thr Thr
        115                 120                 125


<210> SEQ ID NO 47
<211> LENGTH: 1184
<212> TYPE: DNA
<213> ORGANISM: Homo sapiens

<400> SEQUENCE: 47

gggggagaca ttcctcaatt gcttagacat attctgagcc tacagcagag gaacctccag      60

tctcagcacc atgaatcaaa ctgccattct gatttgctgc cttatctttc tgactctaag     120

tggcattcaa ggagtacctc tctctagaac tgtacgctgt acctgcatca gcattagtaa     180

tcaacctgtt aatccaaggt ctttagaaaa acttgaaatt attcctgcaa gccaattttg     240

tccacgtgtt gagatcattg ctacaatgaa aaagaagggt gagaagagat gtctgaatcc     300

agaatcgaag gccatcaaga atttactgaa agcagttagc aaggaaaggt ctaaaagatc     360

tccttaaaac cagaggggag caaaatcgat gcagtgcttc caaggatgga ccacacagag     420

gctgcctctc ccatcacttc cctacatgga gtatatgtca agccataatt gttcttagtt     480

tgcagttaca ctaaaaggtg accaatgatg gtcaccaaat cagctgctac tactcctgta     540

ggaaggttaa tgttcatcat cctaagctat tcagtaataa ctctaccctg gcactataat     600

gtaagctcta ctgaggtgct atgttcttag tggatgttct gaccctgctt caaatatttc     660

cctcaccttt cccatcttcc aagggtacta aggaatcttt ctgctttggg gtttatcaga     720

attctcagaa tctcaaataa ctaaaaggta tgcaatcaaa tctgcttttt aaagaatgct     780

ctttacttca tggacttcca ctgccatcct cccaaggggc ccaaattctt tcagtggcta     840

cctacataca attccaaaca catacaggaa ggtagaaata tctgaaaatg tatgtgtaag     900

tattcttatt taatgaaaga ctgtacaaag tagaagtctt agatgtatat atttcctata     960

ttgttttcag tgtacatgga ataacatgta attaagtact atgtatcaat gagtaacagg    1020

aaaattttaa aaatacagat agatatatgc tctgcatgtt acataagata aatgtgctga    1080

atggttttca aaataaaaat gaggtactct cctggaaata ttaagaaaga ctatctaaat    1140

gttgaaagat caaaaggtta ataaagtaat tataactaaa aaaa                    1184


<210> SEQ ID NO 48
<211> LENGTH: 98
<212> TYPE: PRT
<213> ORGANISM: Homo sapiens

<400> SEQUENCE: 48

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30
```

```
Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro


<210> SEQ ID NO 49
<211> LENGTH: 1179
<212> TYPE: DNA
<213> ORGANISM: Homo sapiens

<400> SEQUENCE: 49

aaaacaaaac atttgagaaa cacggctcta aactcatgta aagagtgcat gaaggaaagc     60

aaaaacagaa atggaaagtg gcccagaagc attaagaaag tggaaatcag tatgttccct    120

atttaaggca tttgcaggaa gcaaggcctt cagagaacct agagcccaag gttcagagtc    180

acccatctca gcaagcccag aagtatctgc aatatctacg atggcctcgc cctttgcttt    240

actgatggtc ctggtggtgc tcagctgcaa gtcaagctgc tctctgggct gtgatctccc    300

tgagacccac agcctggata acaggaggac cttgatgctc ctggcacaaa tgagcagaat    360

ctctccttcc tcctgtctga tggacagaca tgactttgga tttccccagg aggagtttga    420

tggcaaccag ttccagaagg ctccagccat ctctgtcctc catgagctga tccagcagat    480

cttcaacctc tttaccacaa aagattcatc tgctgcttgg gatgaggacc tcctagacaa    540

attctgcacc gaactctacc agcagctgaa tgacttggaa gcctgtgtga tgcaggagga    600

gagggtggga gaaactcccc tgatgaatgc ggactccatc ttggctgtga agaaatactt    660

ccgaagaatc actctctatc tgacagagaa gaaatacagc ccttgtgcct gggaggttgt    720

cagagcagaa atcatgagat ccctctcttt atcaacaaac ttgcaagaaa gattaaggag    780

gaaggaataa catctggtcc aacatgaaaa caattcttat tgactcatac accaggtcac    840

gctttcatga attctgtcat ttcaaagact ctcacccctg ctataactat gaccatgctg    900

ataaactgat ttatctattt aaatatttat ttaactattc ataagattta aattattttt    960

gttcatataa cgtcatgtgc acctttacac tgtggttagt gtaataaaac atgttcctta   1020

tatttactca atccattatt ttgtgttgtt cattaaactt ttactatagg aacttcctgt   1080

atgtgttcat tctttaatat gaaattccta gcctgactgt gcaacctgat tagagaataa   1140

agggtatatt ttatttgctt atcattatta tatgtaaga                           1179


<210> SEQ ID NO 50
<211> LENGTH: 189
<212> TYPE: PRT
<213> ORGANISM: Homo sapiens

<400> SEQUENCE: 50

Met Ala Ser Pro Phe Ala Leu Leu Met Val Leu Val Val Leu Ser Cys
1               5                   10                  15

Lys Ser Ser Cys Ser Leu Gly Cys Asp Leu Pro Glu Thr His Ser Leu
            20                  25                  30

Asp Asn Arg Arg Thr Leu Met Leu Leu Ala Gln Met Ser Arg Ile Ser
        35                  40                  45
```

```
Pro Ser Ser Cys Leu Met Asp Arg His Asp Phe Gly Phe Pro Gln Glu
    50                  55                  60

Glu Phe Asp Gly Asn Gln Phe Gln Lys Ala Pro Ala Ile Ser Val Leu
65                  70                  75                  80

His Glu Leu Ile Gln Gln Ile Phe Asn Leu Phe Thr Thr Lys Asp Ser
                85                  90                  95

Ser Ala Ala Trp Asp Glu Asp Leu Leu Asp Lys Phe Cys Thr Glu Leu
            100                 105                 110

Tyr Gln Gln Leu Asn Asp Leu Glu Ala Cys Val Met Gln Glu Glu Arg
        115                 120                 125

Val Gly Glu Thr Pro Leu Met Asn Ala Asp Ser Ile Leu Ala Val Lys
    130                 135                 140

Lys Tyr Phe Arg Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Leu Ser Thr Asn Leu Gln Glu Arg Leu Arg Arg Lys Glu
            180                 185
```

<210> SEQ ID NO 51
<211> LENGTH: 985
<212> TYPE: DNA
<213> ORGANISM: Homo sapiens

<400> SEQUENCE: 51

```
gcggagctgg gtgcgagcgc cctaccgctt tcgctttccc ttcgcggtgc ccactccact      60

ccttgtgcgg cgctaggccc cccgtcccgg tcatggccat gctcagggtc cagcccgagg     120

cccaagccaa ggtggatgtg tttcgtgaag acctctgtac caagacagag aacctgctcg     180

ggagctattt ccccaagaag atttctgagc tggatgcatt tttaaaggag ccagctctca     240

atgaagccaa cttgagcaat ctgaaggccc cattggacat cccagtgcct gatccagtca     300

aggagaaaga gaaagaggag cggaagaaac agcaggagaa ggaagacaag gatgaaaaga     360

agaaggggga ggatgaagac aaaggtcctc cctgtggccc agtgaactgc aatgaaaaga     420

tcgtggtcct tctgcagcgc ttgaagcctg agatcaagga tgtcattgag cagctcaacc     480

tggtcaccac ctggttgcag ctgcagatac ctcggattga ggatggtaac aattttggag     540

tggctgtcca ggagaaggtg tttgagctga tgaccagcct ccacaccaag ctagaaggct     600

tccacactca aatctctaag tatttctctg agcgtggtga tgcagtgact aaagcagcca     660

agcagcccca tgtgggtgat tatcggcagc tggtgcacga gctggatgag gcagagtacc     720

gggacatccg gctgatggtc atggagatcc gcaatgctta tgctgtgtta tatgacatca     780

tcctgaagaa cttcgagaag ctcaagaagc ccaggggaga aacaaaggga atgatctatt     840

gagagccctc tctcccattc tgtgatgagt acagcagaga ccttcctgct ttttactggg     900

gactccagat tttccccaaa cttgcttctg ttgagatttt tccctcacct tgcctctcag     960

gcacaataaa tatagttata ccact                                           985
```

<210> SEQ ID NO 52
<211> LENGTH: 249
<212> TYPE: PRT
<213> ORGANISM: Homo sapiens

<400> SEQUENCE: 52

```
Met Ala Met Leu Arg Val Gln Pro Glu Ala Gln Ala Lys Val Asp Val
```

-continued

```
1               5                   10                  15

Phe Arg Glu Asp Leu Cys Thr Lys Thr Glu Asn Leu Leu Gly Ser Tyr
            20                  25                  30

Phe Pro Lys Lys Ile Ser Glu Leu Asp Ala Phe Leu Lys Glu Pro Ala
        35                  40                  45

Leu Asn Glu Ala Asn Leu Ser Asn Leu Lys Ala Pro Leu Asp Ile Pro
    50                  55                  60

Val Pro Asp Pro Val Lys Glu Lys Glu Lys Glu Glu Arg Lys Lys Gln
65                  70                  75                  80

Gln Glu Lys Glu Asp Lys Asp Glu Lys Lys Lys Gly Glu Asp Glu Asp
                85                  90                  95

Lys Gly Pro Pro Cys Gly Pro Val Asn Cys Asn Glu Lys Ile Val Val
            100                 105                 110

Leu Leu Gln Arg Leu Lys Pro Glu Ile Lys Asp Val Ile Glu Gln Leu
        115                 120                 125

Asn Leu Val Thr Thr Trp Leu Gln Leu Gln Ile Pro Arg Ile Glu Asp
    130                 135                 140

Gly Asn Asn Phe Gly Val Ala Val Gln Glu Lys Val Phe Glu Leu Met
145                 150                 155                 160

Thr Ser Leu His Thr Lys Leu Glu Gly Phe His Thr Gln Ile Ser Lys
                165                 170                 175

Tyr Phe Ser Glu Arg Gly Asp Ala Val Thr Lys Ala Ala Lys Gln Pro
            180                 185                 190

His Val Gly Asp Tyr Arg Gln Leu Val His Glu Leu Asp Glu Ala Glu
        195                 200                 205

Tyr Arg Asp Ile Arg Leu Met Val Met Glu Ile Arg Asn Ala Tyr Ala
    210                 215                 220

Val Leu Tyr Asp Ile Ile Leu Lys Asn Phe Glu Lys Leu Lys Lys Pro
225                 230                 235                 240

Arg Gly Glu Thr Lys Gly Met Ile Tyr
                245
```

<210> SEQ ID NO 53
<211> LENGTH: 694
<212> TYPE: DNA
<213> ORGANISM: Homo sapiens

<400> SEQUENCE: 53

```
catcactcac accttgcatt tcacccctgc atcccagtcg ccctgcagcc tcacacagat     60

cctgcacaca cccagacagc tggcgctcac acattcaccg ttggcctgcc tctgttcacc    120

ctccatggcc ctgctactgg ccctcagcct gctggttctc tggacttccc cagccccaac    180

tctgagtggc accaatgatg ctgaagactg ctgcctgtct gtgacccaga aacccatccc    240

tgggtacatc gtgaggaact tccactacct tctcatcaag gatggctgca gggtgcctgc    300

tgtagtgttc accacactga ggggccgcca gctctgtgca cccccagacc agccctgggt    360

agaacgcatc atccagagac tgcagaggac ctcagccaag atgaagcgcc gcagcagtta    420

acctatgacc gtgcagaggg agcccggagt ccgagtcaag cattgtgaat tattacctaa    480

cctggggaac cgaggaccag aaggaaggac caggcttcca gctcctctgc accagacctg    540

accagccagg acagggcctg ggtgtgtgt gagtgtgagt gtgagcgaga gggtgagtgt    600

ggtcagagta aagctgctcc acccccagat tgcaatgcta ccaataaagc cgcctggtgt    660

ttacaactaa aaaaaaaaaa aaaaaaaaaa aaaa                                694
```

<210> SEQ ID NO 54
<211> LENGTH: 97
<212> TYPE: PRT
<213> ORGANISM: Homo sapiens

<400> SEQUENCE: 54

```
Ala Leu Leu Leu Ala Leu Ser Leu Leu Val Leu Trp Thr Ser Pro Ala
1               5                   10                  15

Pro Thr Leu Ser Gly Thr Asn Asp Ala Glu Asp Cys Cys Leu Ser Val
            20                  25                  30

Thr Gln Lys Pro Ile Pro Gly Tyr Ile Val Arg Asn Phe His Tyr Leu
        35                  40                  45

Leu Ile Lys Asp Gly Cys Arg Val Pro Ala Val Val Phe Thr Thr Leu
    50                  55                  60

Arg Gly Arg Gln Leu Cys Ala Pro Pro Asp Gln Pro Trp Val Glu Arg
65                  70                  75                  80

Ile Ile Gln Arg Leu Gln Arg Thr Ser Ala Lys Met Lys Arg Arg Ser
                85                  90                  95

Ser
```

<210> SEQ ID NO 55
<211> LENGTH: 856
<212> TYPE: DNA
<213> ORGANISM: Homo sapiens

<400> SEQUENCE: 55

```
cacagacatg gctcagtcac tggctctgag cctccttatc ctggttctgg cctttggcat      60

ccccaggacc caaggcagtg atggaggggc tcaggactgt tgcctcaagt acagccaaag     120

gaagattccc gccaaggttg tccgcagcta ccggaagcag gaaccaagct taggctgctc     180

catcccagct atcctgttct tgccccgcaa gcgctctcag gcagagctat gtgcagaccc     240

aaaggagctc tgggtgcagc agctgatgca gcatctggac aagacaccat ccccacagaa     300

accagcccag ggctgcagga aggacagggg ggcctccaag actggcaaga aaggaaaggg     360

ctccaaaggc tgcaagagga ctgagcggtc acagacccct aaagggccat agcccagtga     420

gcagcctgga gccctggaga ccccaccagc ctcaccagcg cttgaagcct gaacccaaga     480

tgcaagaagg aggctatgct caggggccct ggagcagcca ccccatgctg gccttgccac     540

actctttctc ctgctttaac caccccatct gcattcccag ctctaccctg catggctgag     600

ctgcccacag caggccaggt ccagagagac cgaggaggga gagtctccca gggagcatga     660

gaggaggcag caggactgtc cccttgaagg agaatcatca ggaccctgga cctgatacgg     720

ctccccagta caccccacct cttccttgta aatatgattt atacctaact gaataaaaag     780

ctgttctgtc ttcccaccca aaaaaaaaaa aaaaaaaaaa aaaaaaaaaa aaaaaaaaaa     840

aaaaaaaaaa aaaaaa                                                     856
```

<210> SEQ ID NO 56
<211> LENGTH: 134
<212> TYPE: PRT
<213> ORGANISM: Homo sapiens

<400> SEQUENCE: 56

```
Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
            20                  25                  30
```

```
Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
    130


<210> SEQ ID NO 57
<211> LENGTH: 1669
<212> TYPE: DNA
<213> ORGANISM: Homo sapiens

<400> SEQUENCE: 57

ctccctcagc aaggacagca gaggaccagc taagagggag agaagcaact acagaccccc      60

cctgaaaaca accctcagac gccacatccc ctgacaagct gccaggcagg ttctcttcct     120

ctcacatact gacccacggc tccaccctct ctcccctgga aaggacacca tgagcactga     180

aagcatgatc cgggacgtgg agctggccga ggaggcgctc cccaagaaga caggggggcc     240

ccagggctcc aggcggtgct tgttcctcag cctcttctcc ttcctgatcg tggcaggcgc     300

caccacgctc ttctgcctgc tgcactttgg agtgatcggc ccccagaggg aagagttccc     360

cagggacctc tctctaatca gccctctggc ccaggcagtc agatcatctt ctcgaacccc     420

gagtgacaag cctgtagccc atgttgtagc aaaccctcaa gctgaggggc agctccagtg     480

gctgaaccgc cgggccaatg ccctcctggc caatggcgtg gagctgagag ataaccagct     540

ggtggtgcca tcagagggcc tgtacctcat ctactcccag gtcctcttca agggccaagg     600

ctgcccctcc acccatgtgc tcctcaccca caccatcagc cgcatcgccg tctcctacca     660

gaccaaggtc aacctcctct ctgccatcaa gagcccctgc cagagggaga ccccagaggg     720

ggctgaggcc aagccctggt atgagcccat ctatctggga ggggtcttcc agctggagaa     780

gggtgaccga ctcagcgctg agatcaatcg gcccgactat ctcgactttg ccgagtctgg     840

gcaggtctac tttgggatca ttgccctgtg aggaggacga acatccaacc ttcccaaacg     900

cctcccctgc cccaatccct ttattacccc ctccttcaga caccctcaac ctcttctggc     960

tcaaaaagag aattgggggc ttagggtcgg aacccaagct tagaacttta agcaacaaga    1020

ccaccacttc gaaacctggg attcaggaat gtgtggcctg cacagtgaag tgctggcaac    1080

cactaagaat tcaaactggg gcctccagaa ctcactgggg cctacagctt tgatccctga    1140

catctggaat ctggagacca gggagccttt ggttctggcc agaatgctgc aggacttgag    1200

aagacctcac ctagaaattg acacaagtgg accttaggcc ttcctctctc cagatgtttc    1260

cagacttcct tgagacacgg agcccagccc tccccatgga gccagctccc tctatttatg    1320

tttgcacttg tgattattta ttatttattt attatttatt tatttacaga tgaatgtatt    1380

tatttgggag accggggtat cctgggggac ccaatgtagg agctgccttg gctcagacat    1440

gttttccgtg aaaacggagc tgaacaatag gctgttccca tgtagccccc tggcctctgt    1500
```

gccttctttt gattatgttt tttaaaatat ttatctgatt aagttgtcta aacaatgctg 1560
atttggtgac caactgtcac tcattgctga gcctctgctc cccaggggag ttgtgtctgt 1620
aatcgcccta ctattcagtg gcgagaaata aagtttgctt agaaaagaa 1669

<210> SEQ ID NO 58
<211> LENGTH: 233
<212> TYPE: PRT
<213> ORGANISM: Homo sapiens

<400> SEQUENCE: 58

Met Ser Thr Glu Ser Met Ile Arg Asp Val Glu Leu Ala Glu Glu Ala
1 5 10 15

Leu Pro Lys Lys Thr Gly Gly Pro Gln Gly Ser Arg Arg Cys Leu Phe
20 25 30

Leu Ser Leu Phe Ser Phe Leu Ile Val Ala Gly Ala Thr Thr Leu Phe
35 40 45

Cys Leu Leu His Phe Gly Val Ile Gly Pro Gln Arg Glu Glu Phe Pro
50 55 60

Arg Asp Leu Ser Leu Ile Ser Pro Leu Ala Gln Ala Val Arg Ser Ser
65 70 75 80

Ser Arg Thr Pro Ser Asp Lys Pro Val Ala His Val Val Ala Asn Pro
85 90 95

Gln Ala Glu Gly Gln Leu Gln Trp Leu Asn Arg Arg Ala Asn Ala Leu
100 105 110

Leu Ala Asn Gly Val Glu Leu Arg Asp Asn Gln Leu Val Val Pro Ser
115 120 125

Glu Gly Leu Tyr Leu Ile Tyr Ser Gln Val Leu Phe Lys Gly Gln Gly
130 135 140

Cys Pro Ser Thr His Val Leu Leu Thr His Thr Ile Ser Arg Ile Ala
145 150 155 160

Val Ser Tyr Gln Thr Lys Val Asn Leu Leu Ser Ala Ile Lys Ser Pro
165 170 175

Cys Gln Arg Glu Thr Pro Glu Gly Ala Glu Ala Lys Pro Trp Tyr Glu
180 185 190

Pro Ile Tyr Leu Gly Gly Val Phe Gln Leu Glu Lys Gly Asp Arg Leu
195 200 205

Ser Ala Glu Ile Asn Arg Pro Asp Tyr Leu Asp Phe Ala Glu Ser Gly
210 215 220

Gln Val Tyr Phe Gly Ile Ile Ala Leu
225 230

<210> SEQ ID NO 59
<211> LENGTH: 1077
<212> TYPE: DNA
<213> ORGANISM: Homo sapiens

<400> SEQUENCE: 59
ggggaccaaa gaggctgggc cccgccatgg gccagacggc aggcgacctt ggctggcggc 60
tcagcctgtt gctgcttccc ttgctcctgg ttcaagctgg tgtctgggga ttcccaaggc 120
ccccagggag gccccagctg agcctgcagg agctgcggag ggagttcaca gtcagcctgc 180
atctcgccag gaagctgctc gccgaggttc ggggccaggc ccaccgcttt gcggaatctc 240
acctgccagg agtgaacctg tacctcctgc ccctgggaga gcagctccct gatgtttccc 300
tgaccttcca ggcctggcgc cgcctctctg acccggagcg tctctgcttc atctccacca 360

```
cgcttcagcc cttccatgcc ctgctgggag ggctggggac ccagggccgc tggaccaaca    420

tggagaggat gcagctgtgg gccatgaggc tggacctccg cgatctgcag cggcacctcc    480

gcttccaggt gctggctgca ggattcaacc tcccggagga ggaggaggag gaagaggagg    540

aggaggagga ggagaggaag ggctgctcc caggggcact gggcagcgcc ttacagggcc     600

cggcccaggt gtcctggccc cagctcctct ccacctaccg cctgctgcac tccttggagc    660

tcgtcttatc tcgggccgtg cgggagttgc tgctgctgtc caaggctggg cactcagtct    720

ggcccttggg gttcccaaca ttgagccccc agccctgatc ggtggcttct tagccccctg    780

ccccccaccc tttagaactt taggactgga gtcttggcat cagggcagcc ttcgcatcat    840

cagccttgga caagggaggg ctcttccagc cccctgcccc aggccctacc cagtaactga    900

aagcccctct ggtcctcgcc agctatttat ttcttggata tttatttatt gtttagggag    960

atgatggttt atttattgtc ttggggcccg atggtcctcc tcgggccaag cccccatgct   1020

gggtgcccaa taaagcactc tcatccataa aaaaaaaaaa aaaaaaaaaa aaaaaaa      1077


<210> SEQ ID NO 60
<211> LENGTH: 243
<212> TYPE: PRT
<213> ORGANISM: Homo sapiens

<400> SEQUENCE: 60

Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
            20                  25                  30

Pro Gly Arg Pro Gln Leu Ser Leu Gln Glu Leu Arg Arg Glu Phe Thr
        35                  40                  45

Val Ser Leu His Leu Ala Arg Lys Leu Leu Ala Glu Val Arg Gly Gln
    50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
                85                  90                  95

Trp Arg Arg Leu Ser Asp Pro Glu Arg Leu Cys Phe Ile Ser Thr Thr
            100                 105                 110

Leu Gln Pro Phe His Ala Leu Leu Gly Gly Leu Gly Thr Gln Gly Arg
        115                 120                 125

Trp Thr Asn Met Glu Arg Met Gln Leu Trp Ala Met Arg Leu Asp Leu
    130                 135                 140

Arg Asp Leu Gln Arg His Leu Arg Phe Gln Val Leu Ala Ala Gly Phe
145                 150                 155                 160

Asn Leu Pro Glu Glu Glu Glu Glu Glu Glu Glu Glu Glu Glu Glu Glu
                165                 170                 175

Arg Lys Gly Leu Leu Pro Gly Ala Leu Gly Ser Ala Leu Gln Gly Pro
            180                 185                 190

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
    210                 215                 220

Ser Lys Ala Gly His Ser Val Trp Pro Leu Gly Phe Pro Thr Leu Ser
225                 230                 235                 240

Pro Gln Pro
```

<210> SEQ ID NO 61
<211> LENGTH: 711
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 61
atggtgagca agggcgagga ggataacatg gccatcatca aggagttcat gcgcttcaag 60
gtgcacatgg agggctccgt gaacggccac gagttcgaga tcgagggcga gggcgagggc 120
cgcccctacg agggcaccca gaccgccaag ctgaaggtga ccaagggtgg cccccctgccc 180 ttcgcctggg acatcctgtc ccctcagttc atgtacggct ccaaggccta cgtgaagcac 240
cccgccgaca tccccgacta cttgaagctg tccttccccg agggcttcaa gtgggagcgc 300
gtgatgaact tcgaggacgg cggcgtggtg accgtgaccc aggactcctc cctgcaggac 360
ggcgagttca tctacaaggt gaagctgcgc ggcaccaact tcccctccga cggccccgta 420
atgcagaaga agaccatggg ctgggaggcc tcctccgagc ggatgtaccc cgaggacggc 480
gccctgaagg gcgagatcaa gcagaggctg aagctgaagg acggcggcca ctacgacgct 540
gaggtcaaga ccacctacaa ggccaagaag cccgtgcagc tgcccggcgc ctacaacgtc 600
aacatcaagt tggacatcac ctcccacaac gaggactaca ccatcgtgga acagtacgaa 660
cgcgccgagg gccgccactc caccggcggc atggacgagc tgtacaagta a 711

<210> SEQ ID NO 62
<211> LENGTH: 1605
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 62
atggctcaga tgatgactct gagcctcctt agcctggtcc tggctctctg catcccctgg 60
acccaaggca gtgatggagg gggtcaggac tgctgcctta agtacagcca gaagaaaatt 120
ccctacagta ttgtccgagg ctataggaag caagaaccaa gtttaggctg tcccatcccg 180
gcaatcctgt tctcaccccg gaagcactct aagcctgagc tatgtgcaaa ccctgaggaa 240
ggctgggtgc agaacctgat gcgccgcctg gaccagcctc cagccccagg gaaacaaagc 300
cccggctgca ggaagaaccg gggaacctct aagtctggaa agaaaggaaa gggctccaag 360
ggctgcaaga gaactgaaca gacacagccc tcaagaggaa gatccatggt gagcaagggc 420
gaggaggata acatggccat catcaaggag ttcatgcgct tcaaggtgca catggagggc 480
tccgtgaacg gccacgagtt cgagatcgag ggcgagggcg agggccgccc ctacgagggc 540
acccagaccg ccaagctgaa ggtgaccaag ggtggccccc tgcccttcgc ctgggacatc 600
ctgtcccctc agttcatgta cggctccaag gcctacgtga agcaccccgc cgacatcccc 660
gactacttga agctgtcctt ccccgagggc ttcaagtggg agcgcgtgat gaacttcgag 720
gacggcggcg tggtgaccgt gacccaggac tcctccctgc aggacggcga gttcatctac 780
aaggtgaagc tgcgcggcac caacttcccc tccgacggcc ccgtaatgca gaagaagacc 840
atgggctggg aggcctcctc cgagcggatg taccccgagg acggcgccct gaagggcgag 900
atcaagcaga ggctgaagct gaaggacggc ggccactacg acgctgaggt caagaccacc 960

-continued

```
tacaaggcca agaagcccgt gcagctgccc ggcgcctaca acgtcaacat caagttggac   1020

atcacctccc acaacgagga ctacaccatc gtggaacagt acgaacgcgc cgagggccgc   1080

cactccaccg gcggcatgga cgagctgtac aagtaatgca cacaacactg gcaggatgct   1140

gtgccttgga cagaactcct cagtctacag acagaggatg gcttctggaa acttacacca   1200

gaactgggac ttatattaaa tcttaataca aatggtttgc acagctttct taaacaaaaa   1260

ggcattcaat ctctaggtgt aaaaggaaga gaatgtctcc tggacctaat tgccacaatg   1320

ctggtactac agtttattcg caccaggttg gaaaaagagg gaatagtgtt caaatcactg   1380

atgaaaatgg atgacccttc tatttccagg aatattccct gggcttttga ggcaataaag   1440

caagcaagtg aatgggtaag aagaactgaa ggacagtacc catctatctg cccacggctt   1500

gaactgggga acgactggga ctctgccacc aagcagttgc tgggactcca gcccataagc   1560

actgtgtccc ctcttcatag agtcctccat tacagtcaag gctaa                   1605
```

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 63

```
gcgcggatcc ccatggctca gatgatg                                         27
```

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 64

```
gcgcagatct tcctcttgag ggctgtgtct g                                    31
```

<210> SEQ ID NO 65
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 65

```
ccccactagt ccagttctca gtcactggct ctg                                  33
```

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 66

```
ccccgctagc tggcccttta ggggtctgtg                                      30
```

<210> SEQ ID NO 67
<211> LENGTH: 30

<212> TYPE: DNA
<213> ORGANISM: Artificial Sequence
<220> FEATURE:
<223> OTHER INFORMATION: Description of Artificial Sequence: Synthetic
primer

<400> SEQUENCE: 67
ccccgctagc tgcacacaac actggcagga 30

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 68
ggggctcgag ttagccttga ctgtaatgga 30

<210> SEQ ID NO 69
<211> LENGTH: 252
<212> TYPE: PRT
<213> ORGANISM: Homo sapiens

<400> SEQUENCE: 69

```
Ala Asn Leu Arg Leu Pro Met Ala Ser Ala Leu Pro Glu Ala Leu Cys
1               5                   10                  15

Ser Gln Ser Arg Thr Thr Pro Val Asp Leu Cys Leu Leu Glu Glu Ser
            20                  25                  30

Val Gly Ser Leu Glu Gly Ser Arg Cys Pro Val Phe Ala Phe Gln Ser
        35                  40                  45

Ser Asp Thr Glu Ser Asp Glu Leu Ser Glu Val Leu Gln Asp Ser Cys
    50                  55                  60

Phe Leu Gln Ile Lys Cys Asp Thr Lys Asp Asp Ser Ile Pro Cys Phe
65                  70                  75                  80

Leu Glu Leu Lys Glu Glu Asp Glu Ile Val Cys Thr Gln His Trp Gln
                85                  90                  95

Asp Ala Val Pro Trp Thr Glu Leu Leu Ser Leu Gln Thr Glu Asp Gly
            100                 105                 110

Phe Trp Lys Leu Thr Pro Glu Leu Gly Leu Ile Leu Asn Leu Asn Thr
        115                 120                 125

Asn Gly Leu His Ser Phe Leu Lys Gln Lys Gly Ile Gln Ser Leu Gly
    130                 135                 140

Val Lys Gly Arg Glu Cys Leu Leu Asp Leu Ile Ala Thr Met Leu Val
145                 150                 155                 160

Leu Gln Phe Ile Arg Thr Arg Leu Glu Lys Glu Gly Ile Val Phe Lys
                165                 170                 175

Ser Leu Met Lys Met Asp Asp Pro Ser Ile Ser Arg Asn Ile Pro Trp
            180                 185                 190

Ala Phe Glu Ala Ile Lys Gln Ala Ser Glu Trp Val Arg Arg Thr Glu
        195                 200                 205

Gly Gln Tyr Pro Ser Ile Cys Pro Arg Leu Glu Leu Gly Asn Asp Trp
    210                 215                 220

Asp Ser Ala Thr Lys Gln Leu Leu Gly Leu Gln Pro Ile Ser Thr Val
225                 230                 235                 240

Ser Pro Leu His Arg Val Leu His Tyr Ser Gln Gly
                245                 250
```

VAULT COMPLEXES FOR CYTOKINE DELIVERY

CROSS REFERENCE TO RELATED APPLICATIONS

This application claims the benefit of U.S. Provisional Application No. 61/257,358, filed Nov. 2, 2009, the entire disclosure of which is hereby incorporated by reference in its entirety for all purposes.

STATEMENT REGARDING FEDERALLY SPONSORED RESEARCH OR DEVELOPMENT

This invention was made with Government support under Grant No. CA126944, awarded by the National Institutes of Health. This work was supported by the U.S. Department of Veterans Affairs, and the Federal Government has certain rights in the invention.

REFERENCE TO A SEQUENCE LISTING

This application includes a Sequence Listing submitted electronically as a text file named 11111US_sequencelisting.txt, created on May 1, 2012, with a size of 208,279 bytes. The sequence listing is incorporated by reference.

BACKGROUND OF THE INVENTION

1. Field of the Invention

The invention relates to compositions of vault complexes containing cytokines, such as the chemokine CCL-21, and use of vault complexes for delivering the cytokines to a cell. The vault complexes include a fusion protein of the cytokine of interest fused to major vault interaction domain. Also included in the invention is the use of the compositions as cancer immunotherapy agents for activating an immune response against a tumor and for treating cancers, including lung cancer.

2. Description of the Related Art

Vaults are cytoplasmic ubiquitous ribonucleoprotein particles first described in 1986 that are found in all eukaryotic cells [1]. Native vaults are 12.9±1 MDa ovoid spheres with overall dimensions of approximately 40 nm in width and 70 nm in length [2,3], present in nearly all-eukaryotic organisms with between $10^4$ and $10^7$ particles per cell [4]. Despite their cellular abundance, vault function remains elusive although they have been linked to many cellular processes, including the innate immune response, multidrug resistance in cancer cells, multifaceted signaling pathways, and intracellular transport [5].

Vaults are highly stable structures in vitro, and a number of studies indicate that the particles are non-immunogenic [6]. Vaults can be engineered and expressed using a baculovirus expression system and heterologous proteins can be encapsulated inside of these recombinant particles using a protein-targeting domain termed INT for vault INTeraction. Several heterologous proteins have been fused to the INT domain (e.g. fluorescent and enzymatic proteins) and these fusion proteins are expressed in the recombinant vaults and retain their native characteristics, thus conferring new properties onto these vaults [7,8].

CCL-21 has been identified as a lymphoid chemokine that is predominantly and constitutively expressed by high endothelial venules in lymph nodes and Peyer's patches and by lymphatic vessels, stromal cells in the spleen and appendix [9]. CCL-21 binds to the chemokine receptor CCR7 and is a chemoattractant for mature DCs, naive and memory T cells [10,11]. This chemokine, along with CCL-19, is required for normal lymphoid tissue organization that is ultimately essential for effective T cell-DC interactions. Natural killer (NK) and natural killer T (NKT) antitumor effectors express the CCR7 receptor and are chemo attracted by CCL-21. The use of chemokines that attract DC, lymphocyte, and NK and NKT effectors into tumors can serve as an effective antitumor strategy. Based on this concept, it has been previously shown that intratumoral administration of recombinant CCL-21 reduces tumor burden in murine lung cancer models [12]. The antitumor responses induced by recombinant CCL-21 however required high and frequent dosing because proteins administered intratumorally are not retained locally for prolonged periods. Although these studies delineated the role of CCL-21 as an effective antitumor agent, frequent high dose intratumoral administration is clinically limiting with the potential of unnecessary systemic toxicity. Based on the limitations of this approach, the use of autologous dendritic cells for intratumoral CCL-21 delivery was examined [13.14]. In preclinical studies, it was demonstrated that intratumoral administration of CCL-21 gene modified dendritic cells led to tumor eradication in murine lung cancer models. Following this initial description of the antitumor properties of CCL-21, several other research groups have reported that CCL-21 has potent antitumor properties in a variety of model systems [15-19]. In all models, CCL-21 demonstrated potent regression of tumors, which was shown to be dependent on host T cell immunity. Based on extensive pre-clinical evaluation, the intratumoral injection of DC transduced with an adenoviral vector expressing the secondary lymphoid chemokine gene (Ad-CCL-21-DC) was assessed in a phase I trial in advanced non-small cell lung cancer (NSCLC).

While clinical studies utilizing intratumoral administration of chemokine gene modified DC show promise as an effective therapy, the preparation of CCL-21 expressing autologous dendritic cells is cumbersome, expensive and time consuming. A reagent that is efficacious and works through a similar therapeutic mechanism is highly desired. Compositions and methods are needed to circumvent autologous DC preparation, minimize batch to batch variability and allow for comparability and standardization. There is a need for cytokine delivery, e.g., a non-DC based approach for intratumoral CCL-21 delivery for the purpose of initiating antitumor immune responses Vaults are generally described in U.S. Pat. No. 7,482,319, filed on Mar. 10, 2004; U.S. application Ser. No. 12/252,200, filed on Oct. 15, 2008; International Application No. PCT/US2004/007434, filed on Mar. 10, 2004; U.S. Provisional Application No. 60/453,800, filed on Mar. 20, 2003; U.S. Pat. No. 6,156,879, filed on Jun. 3, 1998; U.S. Pat. No. 6,555,347, filed on Jun. 28, 2000; U.S. Pat. No. 6,110,740, filed on Mar. 26, 1999; International Application No. PCT/US1999/06683, filed on Mar. 26, 1999; U.S. Provisional App. No. 60/079,634, filed on Mar. 27, 1998; and International Application No. PCT/US1998/011348, filed on Jun. 3, 1998. Vault compositions for immunization against chlamydia genital infection are described in U.S. application Ser. No. 12/467,255, filed on May 15, 2009. The entire contents of these applications are incorporated by reference in their entirety for all purposes.

SUMMARY OF THE INVENTION

Disclosed herein are compositions including a vault complex having a fusion protein of a cytokine and a vault targeting domain, e.g., mINT. In one embodiment, the vault complex includes a chemokine fusion protein having a chemokine (C-C motif) ligand 21 (CCL-21) consisting of SEQ ID NO:1 (mouse CCL21 amino acid sequence) and a major vault protein interaction domain (mINT) consisting of SEQ ID NO:9 (mouse mINT amino acid sequence). In another embodiment, the vault complex includes a chemokine fusion protein having a chemokine (C-C motif) ligand 21 (CCL-21) consisting of SEQ ID NO:2 (human CCL21 amino acid sequence) and a major vault protein interaction domain (mINT) consisting of SEQ ID NO:8 (human mINT amino acid sequence).

Accordingly, in one aspect of the invention, the cytokine is a chemokine. In one aspect, the cytokine is a cysteine-cysteine (CC) chemokine. In another aspect, the cytokine is a CCL-21 chemokine. The chemokine can include all or part of human or mouse CCL-21, e.g, SEQ ID NO:1 or SEQ ID NO:2. In some embodiments, the cytokine fusion protein includes a fluorescent protein, e.g., mCherry fluorescent protein.

In one embodiment, the vault targeting domain is a vault interaction domain from a vault poly ADP-ribose polymerase (VPARP). In one embodiment, the vault targeting domain is a major vault protein interaction (mINT) domain. In another embodiment, the vault targeting domain comprises or consists of SEQ ID NO:8 (a human amino acid sequence). In yet another embodiment, the vault targeting domain comprises SEQ ID NO:9 (a mouse amino acid sequence).

In some embodiments, the vault complex includes a MVP. The MVP can be a human MVP, e.g., SEQ ID NO:16.

Vault complexes of the invention can include a vault poly ADP-ribose polymerase (VPARP), and/or a telomerase vault associated protein 1 (TEP1), and/or an untranslated RNA molecule (vRNA).

In addition, the invention provides an isolated nucleic acid encoding a cytokine fusion protein that includes a cytokine encoding sequence and a mINT encoding sequence. In one embodiment, the mINT encoding sequence is SEQ ID NO:7 (a human sequence) or SEQ ID NO:6 (a mouse sequence). In another embodiment, the cytokine encoding sequence is SEQ ID NO:5 (human) and the mINT encoding sequence consists of SEQ ID NO:7 (human). In one embodiment, the cytokine encoding sequence is SEQ ID NO:3 (a mouse sequence) and the mINT encoding sequence is SEQ ID NO:6 (a mouse sequence).

In some embodiments, the cytokine fusion protein is SEQ ID NO:13 (human). In other embodiments, the cytokine fusion protein is SEQ ID NO:12 (mouse). Also included in the invention are vectors including an isolated nucleic acid described herein, cells having an isolated nucleic acid described herein, and cells having a vector described herein.

The invention also includes a method of delivering a cytokine to a cell, including introducing the vault complexes of the invention to the cell. In some embodiments, the method includes introducing the vault complexes into the extracellular environment surrounding the cell. The invention includes a method for stimulating an immune response in a cell by contacting the cell with the vault complexes of the invention. In some embodiments, the cell is a human cell. In other embodiments, the immune response induces migration of T cells and dendritic cells. In another embodiment, contacting the cell with the vault complexes of the invention increases T cell migration to the cell by at least 5% compared to administration of CCL-21 cytokine alone.

In addition, the invention provides a method for stimulating an immune response in a subject by administering the vault complexes the invention to the subject. In one embodiment, the subject is a human.

In another embodiment, the invention includes a method of treating or managing cancer in a subject in need of treatment or management of cancer including administering to a subject a therapeutically effective amount of the vault complexes described herein. In some embodiments, administering includes intra-tumoral injection of the composition to a tumor in the subject. In one embodiment, the cancer is lung cancer. In another embodiment, administering reduces tumor volume and/or reduces tumor growth. In some embodiments, administering increases interleukin-2 (IL-2) expression. In one embodiment, the method includes a subject that is a mammal or a human.

The invention includes a method of preparing the vault complexes of the invention including a) mixing a fusion protein comprising a cytokine fused to a mINT generated in Sf9 cells with a rat MVP generated in Sf9 cells to generate a mixture; b) incubating the mixture for a sufficient period of time to allow packaging of the fusion protein inside of vault complexes, thereby generating the vault complexes.

In yet another embodiment, the invention also provides method of preparing the vault complexes of the invention including a) mixing a fusion protein comprising a cytokine fused to a mINT generated in insect larvae cells with a rat MVP generated in insect larvae cells to generate a mixture; b) incubating the mixture for a sufficient period of time to allow packaging of the fusion protein inside of vault complexes, thereby generating the vault complexes described herein.

In another embodiment, the invention provides a method of preparing the composition of the invention including a) mixing a fusion protein comprising a cytokine fused to a mINT generated in Sf9 cells or insect larvae cells with a human MVP generated in Sf9 cells or insect larvae cells to generate a mixture; b) incubating the mixture for a sufficient period of time to allow packaging of the fusion protein inside of vault complexes, thereby generating the vault complexes described herein.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION OF THE INVENTION

Figure 1:
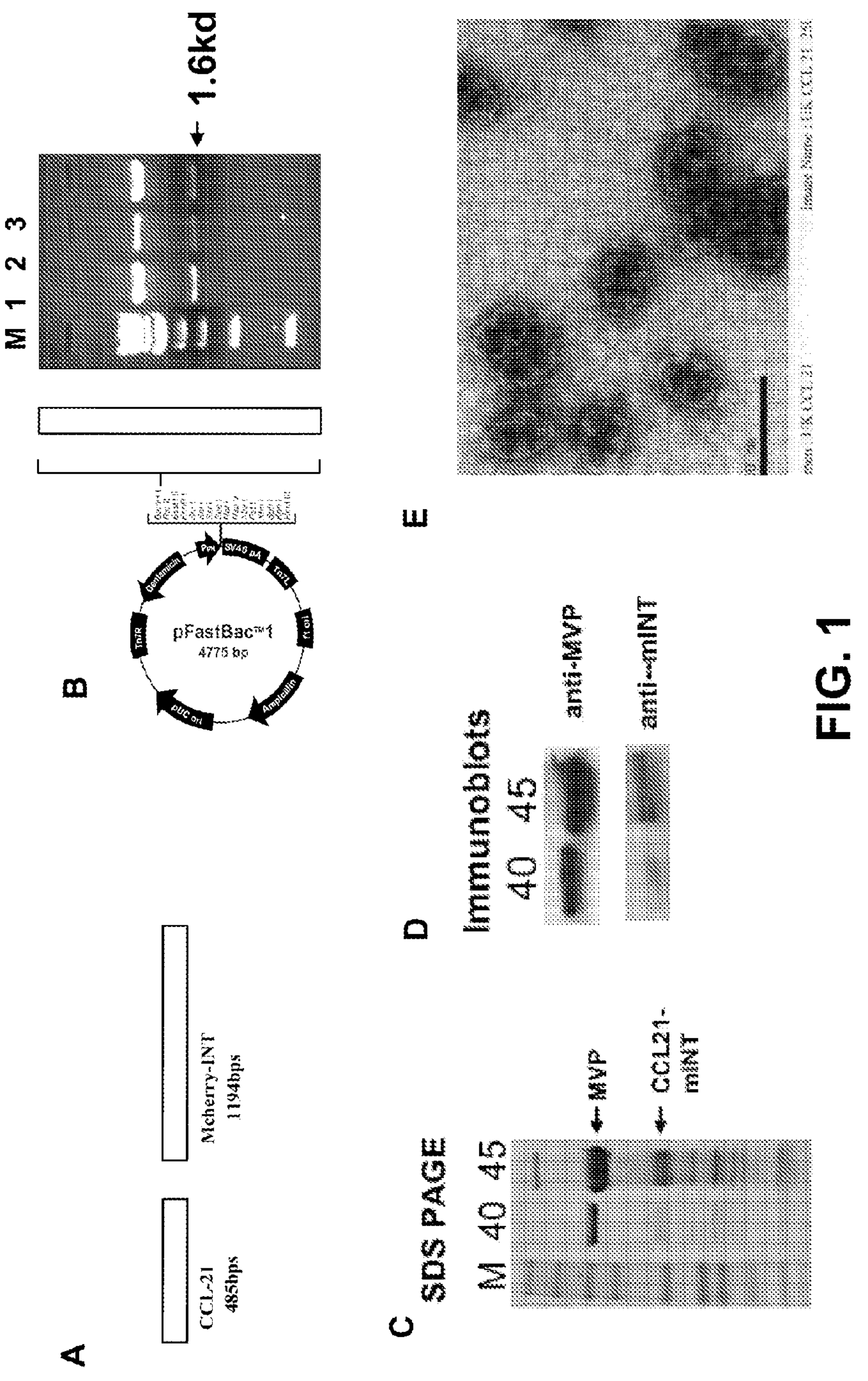
FIG. 1A shows a diagram of the CCL-21 and mCherry-INT constructs that were fused to create the CCL-21 fusion protein.
FIG. 1B shows the incorporation into a pFastBac expression vector by restriction digest and expression of CCL-21 fusion protein as analyzed by gel electrophoresis.
FIG. 1C shows the MVP recombinant vaults containing packaged CCL-21-mCherry-mINT purified on a sucrose gradient. The 40 and 45% fractions were analyzed by SDS-PAGE.
FIG. 1D shows the MVP recombinant vaults containing packaged CCL-21-mCherry-mINT purified on a sucrose gradient and analyzed by staining with Coomassie.
FIG. 1E shows purified vault complexes examined by negative stain transmission electron microscopy.

The descriptions of various aspects of the invention are presented for purposes of illustration, and are not intended to be exhaustive or to limit the invention to the forms disclosed. Persons skilled in the relevant art can appreciate that many modifications and variations are possible in light of the embodiment teachings.

It should be noted that the language used herein has been principally selected for readability and instructional purposes, and it may not have been selected to delineate or circumscribe the inventive subject matter. Accordingly, the disclosure is intended to be illustrative, but not limiting, of the scope of invention.

It must be noted that, as used in the specification, the singular forms "a", "an", and "the" include plural referents unless the context clearly dictates otherwise.

Any terms not directly defined herein shall be understood to have the meanings commonly associated with them as understood within the art of the invention. Certain terms are discussed herein to provide additional guidance to the practitioner in describing the compositions, devices, methods and the like of embodiments of the invention, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the embodiments of the invention herein.

Briefly, and as described in more detail below, described herein are compositions of vault complexes containing cytokines, such as CCL-21, and their use in delivering the cytokines to a cell. The vault particles include a fusion protein of the cytokine of interest fused to major vault interaction domain. Also included in the invention is the use of the compositions as cancer immunotherapy agents for activating an immune response against a tumor and for treating cancers, including lung cancer.

CCL-21 and other cytokines have been shown to be effective as cancer immunotherapy agents. However, conventional approaches for cancer therapy treatment with cytokines, such as CCL-21, involve use of modified dendritic cells. These preparations and treatments are cumbersome, expensive and time consuming. Difficulties with conventional methods include autologous DC preparation, batch to batch variability and lack of comparability and standardization. More convenient and efficacious options for delivery and treatment with cytokine reagents are required.

The invention supplies the deficiencies of the conventional DC-based methods. Vault complexes provide effective and efficient intratumoral cytokine, e.g., CCL-21 delivery for the purpose of initiating antitumor immune responses.

Definitions

Terms used in the claims and specification are defined as set forth below unless otherwise specified.

The term "cytokine" is a protein that is a member of a family of secreted cell-signaling proteins involved in immunoregulatory and inflammatory processes. A "chemokine" is a member of a family of cytokines defined by invariant cysteine residues that form disulfide bonds. One example of a chemokine is "CCL-21" referring to a chemokine (C-C motif) ligand 21. A C-C motif is a cysteine-cysteine motif.

As used herein, the term "vault" or "vault particle" refers to a large cytoplasmic ribonucleoprotein (RNP) particle found in eukaryotic cells. The vault or vault particle is composed of MVP, VPARP, and/or TEP1 proteins and one or more untranslated vRNA molecules.

As used herein, the term "vault complex" refers to a recombinant vault that encapsulates a small molecule or protein of interest. A vault complex of the invention includes a fusion protein, e.g., a cytokine fusion protein.

As used herein, the term "cytokine fusion protein" is a recombinant protein expressed from a nucleotide encoding a cytokine fused in frame to a vault targeting domain.

As used herein, the term "vault targeting domain" or "vault interaction domain" is a domain that is responsible for interaction or binding of a heterologous fusion protein with a vault protein, or interaction of a VPARP with a vault protein, such as a MVP. As used herein, the term "mINT domain" is a vault interaction domain from a vault poly ADP-ribose polymerase (VPARP) that is responsible for the interaction of VPARP with a major vault protein (MVP). The term "mINT domain" refers to a major vault protein (MVP) interaction domain.

As used herein, the term "MVP" is major vault protein. The term "cp-MVP" is a cysteine-rich peptide major vault protein.

The term "VPARP" refers to a vault poly ADP-ribose polymerase.

As used herein, the term "TEP-1" is a telomerase/vault associated protein 1.

As used herein, the term "vRNA" is an untranslated RNA molecule found in vaults.

As used herein, the term “fluorescent protein” is a protein that has the property of forming a visible wavelength chromophore from within its polypeptide sequence. Fluorescent proteins can be engineered to be expressed with other proteins, and include, but are not limited to, green fluorescent protein (GFP), red fluorescent protein (mCherry), blue fluorescent protein (EBFP, EBFP2, Azurite, mKalama1), cyan fluorescent protein (ECFP, Cerulean, CyPet) and yellow fluorescent protein derivatives (YFP, Citrine, Venus, YPet).

As used herein, the term “vector” is a DNA or RNA molecule used as a vehicle to transfer foreign genetic material into a cell. The four major types of vectors are plasmids, bacteriophages and other viruses, cosmids, and artificial chromosomes. Vectors can include an origin of replication, a multi-cloning site, and a selectable marker.

As used herein, a “cell” includes eukaryotic and prokaryotic cells.

As used herein, the terms “organism”, “tissue” and “cell” include naturally occurring organisms, tissues and cells, genetically modified organisms, tissues and cells, and pathological tissues and cells, such as tumor cell lines in vitro and tumors in vivo.

As used herein, the term “T cell” or T lymphocyte is a white blood cell known as a lymphocyte, and plays a central role in cell-mediated immunity.

As used herein, the term “extracellular environment” is the environment external to the cell.

As used herein, the term “in vivo” refers to processes that occur in a living organism.

A “subject” referred to herein can be any animal, including a mammal (e.g., a laboratory animal such as a rat, mouse, guinea pig, rabbit, primates, etc.), a farm or commercial animal (e.g., a cow, horse, goat, donkey, sheep, etc.), a domestic animal (e.g., cat, dog, ferret, etc.), an avian species, or a human.

The term “mammal” as used herein includes both humans and non-humans and include but is not limited to humans, non-human primates, canines, felines, murines, bovines, equines, and porcines.

As used herein, the term “human” refers to “*Homo sapiens.*”

As used herein, the term “sufficient amount” is an amount sufficient to produce a desired effect, e.g., an amount sufficient to modulate protein aggregation in a cell.

As used herein, the term “therapeutically effective amount” is an amount that is effective to ameliorate a symptom of a disease, such as cancer.

A “prophylactically effective amount” refers to an amount that is effective for prophylaxis.

An “immune response” is a response by a host against foreign immunogens or antigens. A “cell-mediated immune response” refers to a helper T cell response which involves the production of interferon-gamma (IFN-γ), leading to cell-mediated immunity.

As used herein, the term “stimulating” refers to activating, increasing, or triggering a molecular, cellular or enzymatic activity or response from within a cell or organism.

As used herein, the term “administering” includes any suitable route of administration, as will be appreciated by one of ordinary skill in the art with reference to this disclosure, including direct injection into a solid organ, direct injection into a cell mass such as a tumor, inhalation, intraperitoneal injection, intravenous injection, topical application on a mucous membrane, or application to or dispersion within an environmental medium, and a combination of the preceding.

As used in this disclosure, the term “modified” and variations of the term, such as “modification,” means one or more than one change to the naturally occurring sequence of MVP, VPARP or TEP1 selected from the group consisting of addition of a polypeptide sequence to the C-terminal, addition of a polypeptide sequence to the N-terminal, deletion of between about 1 and 100 amino acid residues from the C-terminal, deletion of between about 1 and 100 amino acid residues from the N-terminal, substitution of one or more than one amino acid residue that does not change the function of the polypeptide, as will be appreciated by one of ordinary skill in the art with reference to this disclosure, such as for example, an alanine to glycine substitution, and a combination of the preceding.

As used herein, the term percent “identity,” in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent “identity” can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

As used in this disclosure, the term “comprise” and variations of the term, such as “comprising” and “comprises,” are not intended to exclude other additives, components, integers or steps.

It must be noted that, as used in the specification and the appended claims, the singular forms “a,” “an” and “the” include plural referents unless the context clearly dictates otherwise.

Compositions of the Invention

As described in more detail below, the invention includes compositions and methods of using vault particles. The vault particles are recombinant particles having a MVP and a fusion protein and mINT and a protein of interest, e.g., a cytokine, e.g., CCL-21. The vault particle can be used for delivery of the protein of interest, e.g., the cytokine, to a cell or tumor or subject.

Vaults and Vault Complexes

The compositions of the invention comprise a vault complex. A vault complex is a recombinant particle that encapsulates a small molecule (drug, sensor, toxin, etc.), or a protein of interest, e.g., a peptide, or a protein, including an endogenous protein, a heterologous protein, a recombinant protein, or recombinant fusion protein. Vault complexes are of the invention include a cytokine recombinant fusion protein. Vault complexes are derived from vault particles.

Vaults, e.g., vault particles are ubiquitous, highly conserved ribonucleoprotein particles found in nearly all eukaryotic tissues and cells, including dendritic cells (DCs), endometrium, and lung, and in phylogeny as diverse as mammals, avians, amphibians, the slime mold *Dictyostelium discoideum*, and the protozoan *Trypanosoma brucei* (Izquierdo et al., *Am. J. Pathol.,* 148(3):877-87 (1996)). Vaults have a hollow, barrel-like structure with two protruding end caps, an invaginated waist, and regular small openings surround the vault cap. These openings are large enough to allow small molecules and ions to enter the interior of the vault. Vaults have a mass of about 12.9±1 MDa (Kedersha et al., *J. Cell Biol.,* 112(2):225-35 (1991)) and overall dimensions of about 42×42×75 nm (Kong et al., *Structure,* 7(4):371-9 (1999)). The volume of the internal vault cavity is approximately $50\times10^3$ $nm^3$, which is large enough to enclose an entire ribosomal protein.

Vaults comprise three different proteins, designated MVP, VPARP and TEP1, and comprise one or more different untranslated RNA molecules, designated vRNAs. The number of vRNA can vary. For example, the rat *Rattus norvegicus* has only one form of vRNA per vault, while humans have three forms of vRNA per vault. The most abundant protein, major vault protein (MVP), is a 95.8 kDa protein in *Rattus norvegicus* and a 99.3 kDa protein in humans which is present in 96 copies per vault and accounts for about 75% of the total protein mass of the vault particle. The two other proteins, the vault poly-ADP ribose polymerase, VPARP, a 193.3 kDa protein in humans, and the telomerase/vault associated protein 1, TEP1, a 292 kDa protein in *Rattus norvegicus* and a 290 kDa protein in humans, are each present in between about 2 and 16 copies per vault.

VPARP, mINT Domain, and mINT Fusion Proteins

A vault poly ADP-ribose polymerase (VPARP) includes a region of about 350 amino acids that shares 28% identity with the catalytic domain of poly ADP-ribosyl polymerase, PARP, a nuclear protein that catalyzes the formation of ADP-ribose polymers in response to DNA damage. VPARP catalyzes an NAD-dependent poly ADP-ribosylation reaction, and purified vaults have poly ADP-ribosylation activity that targets MVP, as well as VPARP itself. VPARP includes a mINT domain (major vault protein (MVP) interaction domain). The mINT domain is responsible for the interaction of VPARP with a major vault protein (MVP).

A vault complex of the invention includes a mINT domain. The mINT domain is responsible for interaction of a protein of interest, e.g., a cytokine, with a vault protein such as a MVP. In general, the mINT domain is expressed as a fusion protein with a protein of interest, e.g., a cytokine. The mINT of the vault complexes of the invention are derived from VPARP sequences. Exemplary VPARP sequences and mINT sequences can be found in Table 1. One of skill in the art understands that the mINT can have the entire naturally occurring sequence or portions of the sequence or fragments thereof. In other embodiments, the mINT has at least 50%, 60%, 70%, 80%, 90%, 95%, 96%, 97%, 98% or 99% sequence identity to any of the VPARP and/or mINT sequences disclosed in Table 1.

In one embodiment, the mINT is derived from a human VPARP, SEQ ID NO:14, GenBank accession number AAD47250, encoded by the cDNA, SEQ ID NO:15, GenBank accession number AF158255. In some embodiments, the vault targeting domain comprises or consists of the INT domain corresponding to residues 1473-1724 (SEQ ID NO:69) of human VPARP protein sequence (full human VPARP amino acid sequence is SEQ ID NO:14). In other embodiments, the vault targeting domain comprises or consists of the mINT domain comprising residues 1563-1724 (SEQ ID NO: 8) of the human VPARP protein sequence. In certain embodiments, the vault targeting domain comprises or consists of a mINT domain (SEQ ID NO: 6) (mouse mINT). In some embodiments, the vault targeting domain comprises or consists of SEQ ID NO: 7 (human mINT). In certain embodiments, the vault targeting domain is at least 90%, 91%, 92%, 93%, 94%, 95%, 96%, 97%, 98%, or 99% identical to SEQ ID NOs: 6 or 7.

In alternative embodiments, the mINT domain is derived from TEP1 sequences. One of skill in the art understands that the mINT can have the entire naturally occurring sequence of the vault interaction domain in TEP1 or portions of the sequence or fragments thereof.

MVP

A vault complex of the invention generally includes an MVP. Exemplary MVP sequences can be found in Table 1. One of skill in the art understands that the MVP can have the entire naturally occurring sequence or portions of the sequence or fragments thereof. In other embodiments, the MVP has at least 50%, 60%, 70%, 80%, 90%, 95%, 96%, 97%, 98% or 99% sequence identity to any of the MVP sequences disclosed in Table 1.

In one embodiment, the MVP is human MVP, SEQ ID NO:16, GenBank accession number CAA56256, encoded by the cDNA, SEQ ID NO:17, GenBank accession number X79882. In another embodiment, the MVP is *Rattus norvegicus* MVP, SEQ ID NO:18, GenBank accession number AAC52161, encoded by the cDNA, SEQ ID NO:19, GenBank accession number U09870. In other embodiments, the MVP is at least 90%, 91%, 92%, 93%, 94%, 95%, 96%, 97%, 98%, or 99% identical to the MVP sequences described herein.

In one embodiment, there is provided a vault complex comprising, consisting essentially of, or consisting of an MVP modified by adding a peptide to the N-terminal to create a one or more than one of heavy metal binding domains. In a preferred embodiment, the heavy metal binding domains bind a heavy metal selected from the group consisting of cadmium, copper, gold and mercury. In a preferred embodiment, the peptide added to the N-terminal is a cysteine-rich peptide (CP), such as for example, SEQ ID NO:20, the MVP is human MVP, SEQ ID NO:16, and the modification results in CP-MVP, SEQ ID NO:21, encoded by the cDNA, SEQ ID NO:22. In another preferred embodiment, the cysteine-rich peptide is SEQ ID NO:20, the MVP is *Rattus norvegicus* MVP, SEQ ID NO:18, and the modification results in CP-MVP, SEQ ID NO:23, encoded by the cDNA, SEQ ID NO:24. These embodiments are particularly useful because vault particles consisting of CP-MVP, SEQ ID NO:21 or SEQ ID NO:23, are stable without the presence of other vault proteins.

Any of the vault complexes described herein can include MVPs or modified MVPs disclosed herein.

TEP1

In some embodiments, a vault particle of the invention includes a TEP1 protein. Exemplary TEP1 sequences can be found in Table 1. One of skill in the art understands that the TEP1 can have the entire naturally occurring sequence or portions of the sequence or fragments thereof. In other embodiments, the TEP1 has at least 50%, 60%, 70%, 80%, 90%, 95%, 96%, 97%, 98% or 99% sequence identity to any of the TEP1 sequences disclosed in Table 1.

The TEP1 can be human TEP1, SEQ ID NO:25, GenBank accession number AAC51107, encoded by the cDNA, SEQ ID NO:26, GenBank accession number U86136. In another embodiment, the TEP1 is *Rattus norvegicus* TEP1, SEQ ID NO:27, GenBank accession number AAB51690, encoded by the cDNA, SEQ ID NO:28, GenBank accession number U89282. Any of the vault complexes described herein can include TEP1 or modifications thereof.

vRNA

A vault complex of the invention can include a vRNA. Exemplary vRNA sequences can be found in Table 1. One of skill in the art understands that the vRNA can have the entire naturally occurring sequence or portions of the sequence or fragments thereof. In other embodiments, the vRNA has at least 50%, 60%, 70%, 80%, 90%, 95%, 96%, 97%, 98% or 99% sequence identity to any of the vRNA sequences disclosed in Table 1.

In one embodiment, the vRNA can be a human vRNA, SEQ ID NO:29, GenBank accession number AF045143, SEQ ID NO:30, GenBank accession number AF045144, or SEQ ID NO:31, GenBank accession number AF045145, or a combination of the preceding. In another embodiment, the vRNA is *Rattus norvegicus* vRNA, SEQ ID NO:32, GenBank accession number Z1171.

As will be appreciated by one of ordinary skill in the art with reference to this disclosure, the actual sequence of any of MVP, VPARP, TEP1 and vRNAs can be from any species suitable for the purposes disclosed in this disclosure, even though reference or examples are made to sequences from specific species. For example, when delivering chemokines or cytokines to human organs or tissues, it is preferred to use human vaults or vault-like particles comprising human sequences for MVP, VPARP, TEP1 and vRNAs. Further, as will be appreciated by one of ordinary skill in the art with reference to this disclosure, there are some intraspecies variations in the sequences of MVP, VPARP, TEP1 and vRNAs that are not relevant to the purposes of the present invention. Therefore, references to MVP, VPARP, TEP1 and vRNAs are intended to include such intraspecies variants.

Cytokines

The compositions of the invention include a vault complex including a cytokine. In general, the vault complex includes a cytokine fusion protein.

Cytokines are a family of secreted cell-signaling proteins involved in immunoregulatory and inflammatory processes, which are secreted by the glial cells of the nervous system and by numerous cells of the immune system. Cytokines can be classified as proteins, peptides or glycoproteins, and encompass a large and diverse family of regulators. Cytokines bind to cell surface receptors to trigger intracellular signaling, which can result in upregulation or downregulation of several genes and their transcription factors, or feedback inhibition.

In certain embodiments, the cytokines of the invention include immunomodulating agents, such as interleukins (IL) and interferons (IFN). Suitable cytokines can include proteins from one or more of the following types: the four α-helix bundle family (which includes the IL-2 subfamily, the IFN subfamily, and the IL-10 subfamily); the IL-1 family (which includes IL-1 and IL-8), and the IL-17 family. Cytokines can also include those classified as type 1 cytokines, which enhance cellular immune responses (e.g., IFN-γ, TGF-β, etc.), or type 2 cytokines, which favor antibody responses (e.g., IL-4, IL-10, IL-13, etc.).

In one embodiment, the cytokine is a chemokine Chemokines are the largest family of cytokines and are defined by four invariant cysteine residues that form disulfide bonds. Chemokines function by activating specific G protein-coupled receptors, which results in the migration of inflammatory and noninflammatory cells to the appropriate tissues or compartments within tissues. The role of chemokines is to act as a chemoattractant to guide the migration of cells and to promote accumulation of cells at the source of chemokine production.

In some embodiments, the cytokines of the invention include homeostatic chemokines, which are constitutively produced and secreted. Homeostatic chemokines direct trafficking of lymphocytes to lymphoid tissues and are involved in immune surveillance and function to localize T cells or B cells with an antigen in the lymphatic system. In other embodiments, the chemokines of the invention include inflammatory chemokines that promote recruitment and localization of dendritic cells to sites of inflammation and infection. Several chemokines are involved in migration of monocytes and immature dendritic cells, which express chemokine receptors such as CCR1, CCR2, CCR5, CCR6, CCR7 and CXCR2. Chemokine receptor expression is regulated on these dendritic cells. Upon exposure to maturation signals, dendritic cells undergo a chemokine receptor switch, with downregulation of inflammatory chemokine receptors followed by induction of CCR7. This allows immature dendritic cells to leave tissues and to localize in lymphoid organs (due to CCR7 agonists), where antigen presentation takes place.

In certain embodiments, the cytokine comprises CC or β-chemokines, which have the first two cysteines adjacent to each other. In other embodiments, the chemokine comprises CXC or α chemokines, which have an intervening amino acid between the first two cysteines. In other embodiments, the chemokine comprises a CX3C or γ-chemokine, which possess only one protein in its category and is defined by three intervening residues between the first two cysteines. One of two exceptions to the four-cysteine paradigm is the C or 6-chemokine, in which the polypeptide has only two of the four cysteines.

In some embodiments, the cytokine comprises a CC chemokine. The CC chemokine is characterized by two adjacent cysteines near the amino terminus and is also called a β-chemokine or 17q chemokine. The CC subfamily includes at least 27 distinct members of the subfamily in mammals. These include, but are not limited to the following CC chemokines: CCL-1, CCL-2, CCL-3, CCL-4, CCL-5, CCL-7, CCL-8, CCL-9/CCL-10, CCL-11, CCL-12, CCL-13, CCL-14, CCL-15, CCL-16, CCL-17, CCL-18, CCL-19, CCL-20, CCL-21, CCL-22, CCL-23, CCL-24, CCL-25, CCL-26, CCL-27 and CCL-28. Chemokines of this subfamily usually contain four cysteines (C4-CC chemokines), but a small number of CC chemokines possess six cysteines (C6-CC chemokines). C6-CC chemokines include CCL1, CCL15, CCL21, CCL23 and CCL28. CC chemokines inhibit hemopoiesis and induce the migration of monocytes and other cell types such as natural killer (NK) cells and dendritic cells. CC Chemokines are chemotactic in vitro for thymocytes and activated T cells, but not for B cells, macrophages, or neutrophils. CC Chemokines may also play a role in mediating homing of lymphocytes to secondary lymphoid organs.

In other embodiments, the cytokine comprises a CXC chemokine CXC chemokines have two N-terminal cysteines separated by an amino acid "X". There are 17 different CXC chemokines in mammals and are separated in two categories, those with a specific amino acid sequence (or motif) of glutamic acid-leucine-arginine (or ELR for short) immediately before the first cysteine of the CXC motif (ELR-positive), and those without an ELR motif (ELR-negative). Other CXC chemokines that lack the ELR motif, such as CXCL13, tend to be chemoattractant for lymphocytes. CXC chemokines bind to CXC chemokine receptors, of which seven have been discovered to date, designated CXCR1-7.

In another embodiment, the cytokine comprises a C chemokine (also called γ chemokine), which has only two cysteines (one N-terminal cysteine and one cysteine downstream). Two chemokines are included in this subgroup (XCL1 (lymphotactin-α) and XCL2 (lymphotactin-β)). These chemokines attract T cell precursors to the thymus.

In yet another embodiment, the cytokine comprises a $CX_3C$ chemokine (or d-chemokines). The $CX_3C$ chemokine has three amino acids between the two cysteines. The only $CX_3C$ chemokine discovered to date is called fractalkine (or $CX_3CL1$).

In some embodiments, the cytokine comprises a CCL-21 protein. CCL-21 stands for chemokine (C-C motif) ligand 21 and is a member of the CC chemokine family. CCL-21 is encoded by the Scya21 gene and is also called secondary lymphoid-tissue chemokine (SLC), 6Ckine, Exodus-2, Ckβ9, and TCA-4. The CCL-21 binds to the CCR7 receptor, a cell surface chemokine receptor. The human CCL-21 gene is found on the p-arm of chromosome 9 and has the Genbank Accession No. NP_002980.

Exemplary cytokine sequences can be found in Table 1. One of skill in the art understands that the cytokine can have the entire naturally occurring sequence or portions of the sequence or fragments thereof. In other embodiments, the cytokine has at least 50%, 60%, 70%, 80%, 90%, 95%, 96%, 97%, 98% or 99% sequence identity to any of the cytokine sequences disclosed in Table 1.

In some embodiments, the cytokine comprises or consists of SEQ ID NO: 1 (mouse CCL-21 protein sequence). In other embodiments, the cytokine comprises or consists of SEQ ID NO:2 (human CCL-21 protein sequence). In other embodiments, the cytokine has at least 50%, 60%, 70%, 80%, 90%, 95%, 96%, 97%, 98% or 99% sequence identity to SEQ ID NOs:1 or 2. In another embodiment, the cytokine of the invention is encoded by a nucleic acid comprising SEQ ID NO:3 (mouse CCL-21 DNA sequence minus 3 amino acids for stop codon) or SEQ ID NO:4 (full mouse CCL-21 DNA sequence). In yet another embodiment, the cytokine of the invention is encoded by a nucleic acid comprising SEQ ID NO:5 (human CCL-21 DNA sequence). In certain embodiments, the cytokine of the invention comprises the entire naturally occurring DNA sequence, portions of the DNA sequence or fragments thereof. In some embodiments, the cytokine of the invention is encoded by a nucleic acid comprising 50%, 60%, 70%, 80%, 85%, 90%, 95%, 96%, 97%, 98%, or 99% sequence identity to SEQ ID NOs:3, 4 or 5.

In yet another embodiment, the cytokine comprises one of any of the sequences of cytokines or chemokines in Table 1, shown below. Suitable cytokines from humans for use in compositions and methods of the invention include, but are not limited to, interleukin-2 (IL-2) (DNA sequence is SEQ ID NO:33 and protein sequence is SEQ ID NO:34), interleukin-7 (IL-7) (DNA sequence is SEQ ID NO:35 and protein sequence is SEQ ID NO:36), interleukin 15 (IL-15) (DNA sequence is SEQ ID NO:37 and protein sequence is SEQ ID NO:38), interleukin 12B (IL-12B) (DNA sequence is SEQ ID NO:39 and protein sequence is SEQ ID NO:40), interleukin 12A (IL-12A) (DNA sequence is SEQ ID NO:41 and protein sequence is SEQ ID NO:42), colony stimulating factor 2 (DNA sequence is SEQ ID NO:43 and protein sequence is SEQ ID NO:44), chemokine (C-X-C motif) ligand 9 (CXCL9) (DNA sequence is SEQ ID NO:45 and protein sequence is SEQ ID NO:46), chemokine (C-X-C motif) ligand 10 (CXCL10) (DNA sequence is SEQ ID NO:47 and protein sequence is SEQ ID NO:48), interferon alpha-d (IFN-alpha) (DNA sequence is SEQ ID NO:49 and protein sequence is SEQ ID NO:50), interferon-gamma IEF SSP 5111 (DNA sequence is SEQ ID NO:51 and protein sequence is SEQ ID NO:52), chemokine (C-C motif) ligand 19 (CCL-19) (DNA sequence is SEQ ID NO:53 and protein sequence is SEQ ID NO:54), chemokine (C-C motif) ligand 21 (CCL-21) (DNA sequence is SEQ ID NO:55 and protein sequence is SEQ ID NO:56), tumor necrosis factor (TNF) (DNA sequence is SEQ ID NO:57 and protein sequence is SEQ ID NO:58), and interleukin 27 (IL-27) (DNA sequence is SEQ ID NO:59 and protein sequence is SEQ ID NO:60).

As will be appreciated by one of ordinary skill in the art with reference to this disclosure, the actual sequence of any of cytokine can be from any species suitable for the purposes disclosed in this disclosure, even though reference or examples are made to sequences from specific species. For example, when delivering chemokines or cytokines to human organs or tissues, it is preferred to use human cytokines. Further, as will be appreciated by one of ordinary skill in the art with reference to this disclosure, there are some intraspecies variations in the sequences of cytokine that are not relevant to the purposes of the present invention. Therefore, references to cytokine are intended to include such intraspecies variants.

Fusion Proteins

In general, the vault complexes of the invention include a fusion protein, e.g., a cytokine fusion protein. The cytokine fusion protein is a recombinant protein expressed from a nucleotide encoding a chemokine or cytokine fused in frame to a vault targeting domain, e.g., mINT. In some embodiments, the cytokine fusion protein comprises a mINT domain fused to a chemokine protein sequence. In other embodiments, the cytokine fusion protein comprises a mINT domain fused to a CCL-21 protein. In another embodiment, the cytokine is fused to the N-terminus of an MVP protein. In one embodiment, the cytokine is fused to the C-terminus of the MVP protein.

Exemplary cytokine fusion sequences can be found in Table 1. One of skill in the art understands that the cytokine fusion sequences can have the entire naturally occurring sequence or portions of the sequence or fragments thereof. In other embodiments, the cytokine fusion sequence has at least 50%, 60%, 70%, 80%, 90%, 95%, 96%, 97%, 98% or 99% sequence identity to any of the cytokine fusion sequences disclosed in Table 1.

In certain embodiments, the cytokine fusion protein is encoded by the nucleic acid sequence of SEQ ID NO: 10 (mouse CCL21-mINT fusion DNA sequence). In other embodiments, the cytokine fusion protein is encoded by the nucleic acid sequence of SEQ ID NO: 11 (human CCL21-mINT fusion DNA sequence). In some embodiments, the cytokine fusion protein comprises or consists of SEQ ID NO:12 (mouse CCL-21-mINT fusion protein sequence). In some embodiments, the cytokine fusion protein comprises or consists of SEQ ID NO: 13 (human CCL-21-mINT fusion protein sequence).

In one embodiment, the cytokine fusion protein includes the entire naturally occurring cytokine protein sequence, a portion of the cytokine protein sequence, or fragments thereof. In other embodiments, the cytokine fusion protein is at least 90%, 91%, 92%, 93%, 94%, 95%, 96%, 97%, 98%, or 99% identical to SEQ ID NOs: 12 or 13. In another embodiment, the cytokine fusion recombinant DNA sequence includes the entire naturally occurring cytokine DNA sequence, a portion of the cytokine DNA sequence, or fragments thereof.

Any of the cytokines described herein can be expressed as a fusion protein with any of the mINT domain disclosed herein.

Fluorescent Proteins

In certain embodiments, the vault complex of the invention includes a fluorescent protein. In some embodiments, the cytokine fusion protein comprises a fluorescent protein. Fluorescent proteins can be engineered to be expressed with other proteins, and include, but are not limited to, green fluorescent protein (GFP), red fluorescent protein (mCherry), blue fluorescent protein (EBFP, EBFP2, Azurite, mKalama1), cyan fluorescent protein (ECFP, Cerulean, CyPet) and yellow fluorescent protein derivatives (YFP, Citrine, Venus, YPet). In one embodiment, the cytokine fusion protein comprises a mCherry fluorescent protein or a portion of a mCherry fluorescent protein.

Isolated Nucleic Acids and Vectors

The invention also includes isolated nucleic acid encoding a cytokine fusion protein comprising a cytokine encoding sequence and a vault targeting domain encoding sequence. In one embodiment, the isolated nucleic acid encodes a chemokine fusion protein comprising a CCL-21 encoding sequence and a mINT encoding sequence. In another embodiment, the chemokine encoding sequence comprises or consists of SEQ ID NO:5 (human) and the mINT encoding sequence consists of SEQ ID NO:7 (human). In another embodiment, the chemokine encoding sequence comprises or consists of SEQ ID NO:3 (mouse) and the mINT encoding sequence consists of SEQ ID NO:6 (mouse). In one embodiment, the isolated nucleic acid is a cDNA plasmid construct encoding the full length cytokine protein and a mINT domain comprising or consisting of SEQ ID NO: 6 or 7 (human and mouse mINT). Table 1 lists nucleic acid sequences encoding some exemplary chemokine or cytokine fusion proteins.

The nucleic acid molecules encoding a cytokine fusion protein of the invention can be expressed from a vector, such as a recombinant viral vector. The recombinant viral vectors of the invention comprise sequences encoding the cytokine fusion protein of the invention and any suitable promoter for expressing the cytokine fusion sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the cytokine fusion recombinant genes in a particular tissue or in a particular intracellular environment. In one embodiment, recombinant baculoviruses and promoters can be used from pFastBac plasmid and the Bac-to-Bac protocol (Invitrogen, Gaithersburg, Md., Cat. No. 13459-016 or 10608-016).

Suitable expression vectors generally include DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of expression vectors can be systemic, such as by intravenous or intramuscular administration, by administration to target cells ex-planted from the patient followed by reintroduction into the patient, or by any other means that allows for introduction into a desired target cell.

Plasmids expressing a nucleic acid sequence encoding a cytokine fusion protein can be transfected into target cells as a complex with cationic lipid carriers (e.g., Oligofectamine) or non-cationic lipid-based carriers (e.g., Transit-TKO™). Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct may be incorporated into vectors capable of episomal replication, e.g., EPV and EBV vectors. Constructs for the recombinant expression of a nucleic acid encoding a cytokine fusion protein will generally require regulatory elements, e.g., promoters, enhancers, etc., to ensure the expression of the cytokine fusion nucleic acid in target cells. Other aspects to consider for vectors and constructs are further described below.

Vectors useful for the delivery of a cytokine fusion nucleic acid can include regulatory elements (promoter, enhancer, etc.) sufficient for expression of the cytokine fusion nucleic acid in the desired target cell or tissue. The regulatory elements can be chosen to provide either constitutive or regulated/inducible expression. A person skilled in the art would be able to choose the appropriate regulatory/promoter sequence based on the intended use of the transgene.

In a specific embodiment, viral vectors that contain the recombinant gene can be used. For example, a retroviral vector can be used (see Miller et al., Meth. Enzymol. 217: 581-599 (1993)). These retroviral vectors contain the components necessary for the correct packaging of the viral genome and integration into the host cell DNA. The nucleic acid sequences encoding a cytokine fusion protein are cloned into one or more vectors, which facilitates delivery of the nucleic acid into a patient. More detail about retroviral vectors can be found, for example, in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of isolated nucleic acids encoding cytokine fusion proteins into a cell. Adenoviruses are especially attractive vehicles for delivering genes to respiratory epithelia or for use in adenovirus-based delivery systems such as delivery to the liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252: 431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). A suitable AV vector for expressing a nucleic acid molecule featured in the invention, a method for constructing the recombinant AV vector, and a method for delivering the vector into target cells, are described in Xia H et al. (2002), *Nat. Biotech.* 20: 1006-1010.

Use of Adeno-associated virus (AAV) vectors is also contemplated (Walsh et al., Proc. Soc. Exp. Biol. Med. 204:289-300 (1993); U.S. Pat. No. 5,436,146). Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Another preferred viral vector is a pox virus such as a vaccinia virus, for example an attenuated vaccinia such as Modified Virus Ankara (MVA) or NYVAC, an avipox such as fowl pox or canary pox.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Examples of additional expression vectors that can be used in the invention include pFASTBAC expression vectors and *E. coli* pET28a expression vectors.

Generally, recombinant vectors capable of expressing genes for recombinant cytokine fusion proteins are delivered into and persist in target cells. The vectors or plasmids can be transfected into target cells by a transfection agent, such as Lipofectamine. Examples of cells useful for expressing the nucleic acids encoding the cytokine fusion proteins of the invention include Sf9 cells or insect larvae cells. Recombinant vaults based on expression of the MVP protein alone can be produced in insect cells. Stephen, A. G. et al. (2001). *J. Biol. Chem.* 276:23217:23220; Poderycki, M. J., et al. (2006). *Biochemistry* (Mosc). 45: 12184-12193.

Pharmaceutical Compositions of the Invention

In one embodiment, the invention provides methods using pharmaceutical compositions comprising the vault complexes of the invention. These compositions can comprise, in addition to one or more of the vault complexes, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

In certain embodiments, the pharmaceutical compositions that are injected intratumorally comprise an isotonic or other suitable carrier fluid or solution.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

In other embodiments, pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

In some embodiments, administration of the pharmaceutical compositions may be topical, pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g., intraparenchymal, intrathecal or intraventricular, administration. Formulations for parenteral administration may include sterile aqueous solutions which may also contain buffers, diluents and other suitable additives. For intravenous use, the total concentration of solutes should be controlled to render the preparation isotonic.

Methods of Use

Vault complexes described herein can be used to deliver a protein of interest, e.g., cytokines, to a cell, a tissue, an environment outside a cell, a tumor, an organism or a subject. In one embodiment, the vault complex comprises a cytokine described herein, e.g., CCL-21, and the vault complex is introduced to the cell, tissue, or tumor. In some embodiments, the vault complex is introduced into the extracellular environment surrounding the cell. In other embodiments, the vault complex is introduced into an organism or subject. Delivery of the vault complex of the invention can include administering the vault complex to a specific tissue, specific cells, an environmental medium, or to the organism. In some embodiments, delivery of the vault complex can be detected by a sensor within the cell, tissue, or organism. For example, detection can be performed using standard techniques, such as fluorometry or spectrophotometry. This method can be used, for example, to determine the pH within cells, where the sensor is a pH dependent fluorescent sensor, as will be appreciated by one of ordinary skill in the art with reference to this disclosure.

The methods of the invention comprise stimulating an immune response to a cell by contacting the cell with any of the vault complexes described herein. Cells of the invention can include, but are not limited to, any eukaryotic cell, mammalian cell, or human cells, including tumor cells. In some embodiments, contacting the cell with a vault complex induces migration of T cells and/or dendritic cells to the cell.

Methods of the invention include delivery of the vault complex to a subject. The delivery of a vault complex to a subject in need thereof can be achieved in a number of different ways. In vivo delivery can be performed directly by administering a vault complex to a subject. Alternatively, delivery can be performed indirectly by administering one or more vectors that encode and direct the expression of the vault complex or components of the vault complex. In one embodiment, the vault complex is administered to a mammal, such as a mouse or rat. In another embodiment, the vault complex is administered to a human.

In one embodiment, the methods of delivery of the invention include systemic injection of vault complexes to tumors, producing the enhanced permeability and retention (EPR) effect. See Maeda et al., *J. of Controlled Release* 2000, 65: 271-284; Griesh, K., *J. of Drug Targeting* 2007, 15(7-8): 457-464; Allen et al., *Science* 2004, 303:1818-1822. Solid tumors possess extensive angiogenesis and hence hypervasculature, defective vascular architecture, impaired lymphatic drainage/recovery systems, and greatly increased production of a number of permeability mediators. Due to the biology of solid tumors, macromolecular anticancer drugs and agents, including vault complexes, administered intravenously can accumulate and are retained in the tumor due to the lack of efficient lymphatic drainage in the solid tumor. The invention includes methods of systemic or targeted delivery of vault complexes described herein to solid tumors, such as those found in lung cancer.

Other methods of the invention include stimulating an immune response in a subject. The method comprises administering the vault complex to a subject. Administering can include intra-tumoral injection of the vault complex in a subject, which is described in detail herein.

Methods of Treatment

The invention features a method of treating or managing disease, such as cancer, by administering the vault complex of the invention to a subject (e.g., patient). In some embodiments, the vault complexes of the invention can be used for treating or managing lung cancer. In another embodiment, the method of the invention comprises treating or managing cancer in a subject in need of such treatment or management, comprising administering to the subject a therapeutically effective amount of the vault complexes described herein. In one embodiment, the method involves treating a human by identifying a human diagnosed as having lung cancer or at risk for developing lung cancer and administering to the human a therapeutically or prophylactically effective amount of the CCL-21 vault complex to the human. In another embodiment, the method comprises administering to the human to therapeutically or prophylactically effective amount of the CCL-21 vault complex by intra-tumoral injection.

Vault complexes of the invention can be used to treat any solid cancer, e.g., lung cancer, breast cancer, head and neck cancer, prostate cancer, etc. Advances in mouse genetics have generated a number of mouse models for the study of various human diseases, such as treatment of lung cancer. Such models are used for in vivo testing of vault complexes, as well as for determining a therapeutically effective dose. A suitable mouse model is, for example, a tumor-bearing mouse that is administered an intra-tumoral injection of a CCL-21 vault complex.

The data obtained from cell culture assays and animal studies can be used in formulating a range of dosage for use in humans. For any compound used in the methods featured in the invention, the therapeutically effective dose can be estimated initially from cell culture assays. A dose may be formulated in animal models to achieve a circulating plasma concentration range of the vault complex. Such information can be used to more accurately determine useful doses in humans. Analysis of tumor cell samples of mice administered a vault complex can also indicate a therapeutically effective dose.

The pharmaceutical composition according to the present invention to be given to a subject, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980. A composition can be administered alone or in combination with other treatments, either simultaneously or sequentially dependent upon the condition to be treated.

In certain embodiments, the dosage of vault complexes is between about 0.1 and 10,000 micrograms per kilogram of body weight or environmental medium. In another embodiment, the dosage of vault complexes is between about 1 and 1,000 micrograms per kilogram of body weight or environmental medium. In another embodiment, the dosage of vault complexes is between about 10 and 1,000 micrograms per kilogram of body weight or environmental medium. For intravenous injection and intraperitoneal injection, the dosage is preferably administered in a final volume of between about 0.1 and 10 ml. For inhalation the dosage is preferably administered in a final volume of between about 0.01 and 1 ml. As will be appreciated by one of ordinary skill in the art with reference to this disclosure, the dose can be repeated a one or multiple times as needed using the same parameters to effect the purposes disclosed in this disclosure.

For instance, the pharmaceutical composition may be administered once for each tumor in a subject, or the vault complex may be administered as two, three, or more sub-doses or injections at appropriate intervals. In that case, the vault complexes can be injected in sub-doses in order to achieve the total required dosage.

The vault complexes featured in the invention can be administered in combination with other known agents effective in treatment of cancers, including lung cancer. An administering physician can adjust the amount and timing of vault complex administration or injection on the basis of results observed using standard measures of efficacy known in the art or described herein. The skilled artisan will also appreciate that certain factors may influence the dosage and timing required to effectively treat a subject, including but not limited to the severity of the disease or disorder, previous treatments, the general health and/or age of the subject, and other diseases present.

Methods of Preparing Vault Complexes

The methods of the invention include preparing the vault complexes described herein.

In one embodiment, the vault complexes are derived or purified from natural sources, such as mammalian liver or spleen tissue, using methods known to those with skill in the art, such as for example tissue homogenization, differential centrifugation, discontinuous sucrose gradient fractionation and cesium chloride gradient fractionation. In another embodiment, the vault complexes are made using recombinant technology. Details about the methods for recombinant vault complexes are described below.

In some embodiments, a target of interest, i.e., protein of interest, is selected for packaging in the vault complexes. The target of interest may be selected from the group consisting of an enzyme, a pharmaceutical agent, a plasmid, a polynucleotide, a polypeptide, a sensor and a combination of the preceding. In a preferred embodiment, the target of interest is a recombinant protein, e.g., a cytokine fusion protein, e.g., a CCL-21 fusion protein.

Preferably, if the target of interest is a recombinant protein, the polynucleotide sequences encoding the recombinant protein are used to generate a bacmid DNA, which is used to generate a baculovirus comprising the sequence. The baculovirus is then used to infect insect cells for protein production using an in situ assembly system, such as the baculovirus protein expression system, according to standard techniques, as will be appreciated by one of ordinary skill in the art with reference to this disclosure. Advantageously, the baculovirus protein expression system can be used to produce milligram quantities of vault complexes, and this system can be scaled up to allow production of gram quantities of vault complexes according to the present invention.

In another embodiment, the target of interest is incorporated into the provided vaults. In a preferred embodiment, incorporation is accomplished by incubating the vaults with the target of interest at an appropriate temperature and for an appropriate time, as will be appreciated by one of ordinary skill in the art with reference to this disclosure. The vaults containing the protein of interest are then purified, such as, for example sucrose gradient fractionation, as will be appreciated by one of ordinary skill in the art with reference to this disclosure.

In other embodiments, the vaults comprising the target of interest are administered to an organism, to a specific tissue, to specific cells, or to an environmental medium. Administration is accomplished using any suitable route, as will be appreciated by one of ordinary skill in the art with reference to this disclosure.

In one embodiment, the method comprises preparing the composition of the invention by a) mixing a fusion protein comprising a chemokine fused to a mINT generated in Sf9 cells with a rat MVP generated in Sf9 cells to generate a mixture; b) incubating the mixture for a sufficient period of time to allow packaging of the fusion protein inside of vault complexes, thereby generating the composition. Sf9 cells are infected with CCL-21-mCherry-mINT or CP-MVP encoding recombinant baculoviruses. Lysates containing recombinant CCL-21-mINT and rat MVP generated in Sf-9 cells can be mixed to allow the formation of a macromolecular vault complex containing the CCL-21 fusion protein.

In another embodiment, the composition is prepared by a) mixing a fusion protein comprising a chemokine fused to a mINT generated in insect larvae cells with a rat MVP generated in insect larvae cells to generate a mixture; b) incubating the mixture for a sufficient period of time to allow packaging of the fusion protein inside of vault complexes.

Details about methods of preparing vault complexes are further described in the Examples.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* 3$^{rd}$ *Ed.* (Plenum Press) Vols A and B (1992).

Methods

Cloning, Expression, and Purification of Vault Complexes

A cDNA encoding CCL-21 was fused in frame to either mINT or mCherry-mINT [21]. Murine CCL-21 was PCR amplified using the following primers: CCL21-forward GCGCGGATCCCCATGGCTCAGATGATG (SEQ ID NO:63) and CCL-21-reverse GCGCAGATCTTCCTCTTGAGGGCTGTGTCTG (SEQ ID NO:64). To form mCCL-21-mCherry-mINT in pFastBac, the CCL21 PCR product was purified on a Qiagen column, digested with BamH1 and Bgl I, gel purified, and ligated to BamH1 phosphatase treated mCherry-mINT pFastBac. Human CCL21 was PCR amplified with the following primers: CCL-21 F-SpeI CCCCACTAGTCCAGTTCTCAGTCACTGGCTCTG (SEQ ID NO: 65), CCL-21-NheI CCCCGCTAGCTGGCCCTTTAGGGGTCTGTG (SEQ ID NO:66), mINT with NheI CCCCGCTAGCTGCACACAACACTGGCAGGA (SEQ ID NO:67), mINT with XhoI GGGGCTCGAGTTAGCCTTGACTGTAATGGA (SEQ ID NO:68) to form hCCL-21-mINT.

Recombinant baculoviruses were generated using the Bac-to-Bac protocol (Invitrogen, Gaithersburg, Md.). Sf9 cells were infected with CCL-21-mCherry-mINT or CP-MVP encoding recombinant baculoviruses at a multiplicity of infection (MOI) of 0.01 for 65 h. The infected cells were pelleted, and lysed on ice in buffer A [50 mM Tris-HCl (pH 7.4), 75 mM NaCl, and 0.5 mM $MgCl_2$] with 1% Triton X-100, 1 mM dithiotreitol, 0.5 mM PMSF, and protease inhibitor cocktail (Sigma P8849). Lysates containing CP-MVP vaults were mixed with lysates containing mCCL-21-mCherry-mINT, hCCL-21-mINT and were incubated on ice for 30 min to allow the INT fusion proteins to package inside of vaults. Recombinant vault complexes were purified as previously described [7]. Purified recombinant vault complexes were resuspended in 100-200 μl of sterile phosphate buffered saline. Protein concentration was determined using the BCA assay (Bio-Rad Laboratories, Hercules, Calif.) and sample integrity was analyzed by negative stain electron microscopy and SDS-PAGE followed by Coomassie staining and Western blot analysis.

Antibodies

Primary antibodies for Western blot analyses were rabbit anti-MVP polyclonal antibody (1/1000 dilution) or rabbit anti-VPARP polyclonal antibody (1/500 dilution, overnight) and secondary goat anti-rabbit HRP-conjugated antibodies (1:2000 dilution) (Amersham). The anti-CCL-21 antibodies were purchased from R&D Systems, (Minneapolis, Minn.). Primary antibody for immunostaining for CD3 was purchased from DAKO. Fluorescein isothiocyanate-, phycoerythrin-, allophycocyanin-, PerCP- or PerCP-Cy7-conjugated anti-mouse mAbs to CD3 (145-2C11), CD4 (RM4-5), CD8a (53-6.7) and subclass control antibody, were purchased from BD Biosciences (San Diego, Calif.). Anti-mouse mAbs to detect Tregs with cell surface CD4 (GK1.5), CD25 (PC61), intranuclear Foxp3 (FJK-16s) IL-10 (JES5-16E3), and IFNγ (XMG1.2) were purchased from eBioScience (San Diego, Calif.) were purchased from eBioScience (San Diego, Calif.). Antibodies to DEC205 (205yekta), CCR7 (4B12) and EpCam (G8.8) were from eBioScience. Antibody to mouse CD11b (M1/70), Gr1 (RB6-8C5), were purchased from BioLegend (San Diego). Anti-mouse mAb to CXCR3 (220803), was purchased from R&D Systems (Minneapolis, Minn.). Ovalbumin protein and Bradford protein quantification dye was obtained from Sigma (St. Louis, Mo.). Tissue digestion buffer consisted of [0.2 mg/ml of Collagenase A (Boehringer Mannheim/Roche, Indianapolis, Ind.), DNase 25 U/ml (Sigma), and 0.3 U/ml of Dispase (Invitrogen, Carlsbad, Calif.)] in RPMI.

Chemotaxis Assay

Dual-chamber chemotaxis assays were performed using 24-well plates with 3 μm pore size inserts (Costar/Corning, Corning, N.Y., United States) according to the manufacturer's instructions. Briefly, $2.0\times10^5$ T2 cells were resuspended in serum-free medium and loaded in the upper chamber. 200 ng/ml of CCL-21-mcherry-vault, 600 ng/ml recombinant CCL-21 (R&D Systems), 200 ng/ml CCL-21-mcherry-vault with neutralizing anti-CCL-21 recombinant antibody (5 μg/ml), 600 ng/ml CCL-21 with neutralizing anti-CCL-21 antibody (5 μg/ml) were added to the lower chamber of the wells (in triplicate). The neutralizing concentration of anti-CCL-21 antibody (R&D) used in these studies (5 μg/ml) was based on the ND50 (50% maximum inhibition of cytokine activity when CCL-21 is present at a concentration high enough to elicit maximum response). After 2 hours incubation at 37° C., migrated cells were recovered from the lower chamber and the inserts according to the manufacturer's instructions. Migrated T2 cells were resuspended in FACS buffer and evaluated by counting the number of lymphocytes.

Antigen Processing and Presentation Assay

Cells (DC2.4 ($5\times10^4$ c/well)) were plated in triplicates in 96-well plates with OVA protein (350 μg/ml), MHC Class I restricted CD8 T cell line B3Z ($10^5$ c/well), in the presence of control vaults (200 ng/ml), or CCL-21 vault complex (200 ng/ml) or rCCL-21 (200 ng/ml) for 24 hrs. To determine the impact of CCL-21 on APC activity, CCL-21 was neutralized with anti-CCL-21 Ab (5 μg/ml) (R&D). IL-2 secreted by the activated CD8 T cells in the supernatant was quantified by ELISA (eBioScience).

Cell Culture

The murine Lewis lung carcinoma cell line (3LL, $H2^b$) was obtained from American Type Culture Collection (ATCC, Manassas, Va.). The cells were routinely cultured as monolayers in 25-$cm^2$ tissue culture flasks containing RPMI 1640 medium (Irvine Scientific, Santa Ana, Calif.) supplemented with 10% FBS (Gemini Bioproducts, Calabasas, Calif.), penicillin (100 U/ml), streptomycin (0.1 mg/ml), and 2 mM glutamine (JRH Biosciences, Lenexa, Kans.), and maintained at 37° C. in humidified atmosphere containing 5% $CO_2$ in air. The cell line was mycoplasma free, and cells were utilized before the tenth passage.

Tumorigenesis Model

Pathogen-free C57BL/6 mice and UBC-GFP/BL6 (6-8 wk old; Jackson Laboratory) were maintained in the West Los Angeles Veterans Affairs Animal Research vivarium. For tumorigenesis experiments, $1.5\times10^5$ 3LL tumor cells were injected s.c. in the right suprascapular area of C57BL/6 mice. Mice bearing 9-day-old established tumors were treated with a single intratumoral injection of mCCL-21-mCherry-CP-MVP vaults (200 ng), CP-MVP vaults (200 ng) in 200 μl or normal saline diluents. Tumor volumes were monitored by measuring two bisecting diameters of each tumor with calipers. Tumor volumes were calculated using the formula: $V=0.4\ ab^2$, with "a" as the larger diameter and "b" as the smaller diameter. To determine the extent of lymphocytes infiltrating the tumors, UBC-GFP/BL6 mice bearing 9-day tumors were treated as described and 7 days post treatment, non-necrotic tumors were isolated and frozen in OCT. The frozen tissue was sectioned to 5-μm thickness, fixed onto slides, and counterstained with 4',6-diamidino-2-phenylindole (DAPI) fixative. The slides were observed under a 1X71 Olympus fluorescence microscope attached to a charge-coupled device camera. The images were acquired under ×10 and ×40 objectives using the Image Pro software.

Orthotopic Model

Implantation of the tumors in the lung was performed as previously described in Andersson, A. et al. *J Immunol* 2009, 182(11):6951-6958 [24]. Briefly, $5\times10^3$ 3LL-GFP cells in 25 μl NS diluent were injected by the transthoracic route of C57BL/6 mice utilizing a tuberculin syringe with a 30-gauge needle in the left lung under ketamine/xylazine anesthesia. One week following tumor inoculation, mice were treated with diluent, control vault or CCL-21 vault complex via transthoracic injection. Four weeks after tumor implantation, lungs were harvested for evaluation of tumor burden and leukocytic infiltrates. Tumor burden was quantified by gating on the GFP and EpCam expressing 3LL tumor cells in single cell suspension of lung-tumor digests.

Immunostaining

Immunohistochemical staining was performed to determine and characterize the infiltrating cells. Specifically, paraffin sections of 5 μm were deparaffinized in xylene and rehydrated in decreasing concentrations of ethanol according to standard protocol [25]. Heat-induced antigen retrieval in citrate buffer (3 min in a steamer) was followed by blockade of endogenous peroxidase activity with 3% hydrogen peroxide in TBS for 10 min. All tissue was blocked (4% BSA, 10% sucrose, 1% normal swine serum in TBS) for 20 min at room temperature (RT). Primary antibody (DAKO, Cytomation, Carpinteria, Calif., USA) was diluted in the blocking solution to the following concentrations: CD3 1:200. Sections were incubated with the antibodies overnight at 4° C. On the second day, the slides were washed with Tris-buffered saline containing 0.02% Tween. This was followed by incubation with secondary biotinylated goat anti-mouse antibody at room temperature, streptavidin-conjugated alkaline phosphatase (Vectastain ABC-AP kit; Vector Laboratories, Burlingame, Calif.), and chromagen development with Vector Red substrate solution (Vector Laboratories). Slides were counterstained with hematoxylin, dehydrated, and mounted for analysis and photography.

Flow Cytometry

Flow cytometry was performed for the following leukocytic markers CD3, CD4, CD8, CCR7, CD11b, Gr1, DEC205, CD25, FOXP3 and CXCR3 on single cell suspension of tumors following treatment as described above. T cells were stained for intracytoplasmic IFNγ and IL-10. For analyses in the tumor tissue, tumors were mechanically dissociated on a wire mesh by crushing with a 10 ml syringe and incubated in tissue digestion buffer at 37° C. for 25 min. The cells were filtered through 70 μm nylon strainers (BD Biosciences, Bedford, Mass.) and stained with specific markers and analyzed by flow cytometry. Samples were acquired on a FACSCanto (BD Biosciences/FACSCalibur flow cytometer (Becton Dickinson, San Jose, Calif.) in the University of California, Los Angeles, Jonsson Cancer Center Flow Cytometry Core Facility. A total of 10,000 to 25,000 gated events were analyzed using FCS Express 3 (De Novo Software, Canada). Cells incubated with irrelevant isotype-matched antibodies and unstained cells served as controls. The cutoffs were set according to control staining.

T Cell Cytolysis

T lymphocyte lytic responses were evaluated following therapy. T cells were purified from spleens by negative selection using Miltenyi Biotec beads, and cytolytic activities were evaluated against autologous 3LL tumor cell line and the syngeneic control B16 melanoma tumor cell line. The T cell effectors were co-cultured with tumor cell targets (E:T of 20:1 and 40:1) in quadruplet wells in a 96-well plate, and 20 μl alamar blue was added to each well after 18 hours of incubation. Three hours after alamar blue addition, the plate was read with the Wallac 1420 fluorescence plate reader (Perkin-Elmer Life Science, Turku, Finland) with the excitation/emission set at 530/590 nm.

Example 1

Packaging CCL-21 into the Recombinant Vaults

A mouse chemokine CCL-21 was fused to a mouse mINT to create a CCL-21 fusion protein that was packaged into vault complexes. FIG. 1A shows a diagram of the CCL-21 and mCherry-INT constructs (SEQ ID NO:60) that were fused to create the mouse CCL-21-mCherry-mINT fusion protein (SEQ ID NO: 61). Mixing of lysates containing recombinant CCL-21-mINT and rat MVP generated in Sf-9 cells allowed the formation of a macromolecular vault complex containing the CCL-21 fusion protein that could be isolated by density gradient ultracentrifugation. The purified vault complexes contained both MVP as well as CCL-21-mINT (henceforth referred to as CCL-21 vault complex). FIG. 1B shows the incorporation of the recombinant CCL-21-mINT into a pFastBac expression vector by restriction digest and expression of CCL-21 fusion protein as analyzed on an electrophoresis gel. The MVP recombinant vaults containing packaged CCL-21-mCherry-mINT were purified on a sucrose gradient and the 40 and 45% fractions were analyzed by SDS-PAGE (FIG. 1C) and followed by staining with Coomassie (FIG. 1D). FIG. 1E shows a negative stain TEM image of vaults containing CCL-21-mCherry-mINT.

There was an estimated 20-30 molecules of the CCL-21-mINT protein in each vault complex is based on extrapolation from densitometric analysis of the Coomassie stained SDS-PAGE gels. This is consistent with previous studies in packaging multiple copies of other mINT fusion proteins into recombinant vault complexes [21]. With an estimate of 20-30 CCL-21-mINT proteins per vault, it is likely that this is at or near a saturating level for the packaging of this size protein. The CCL-21 vault complex also exhibited a very similar sedimentation profile on sucrose gradients as vault particles containing the INT domain fused to luciferase [6, 8, 21], suggesting that incorporation of CCL-21-mINT did not impact the normal structure of recombinant vault complexes. FIG. 1E shows purified vault complexes examined by negative stain transmission electron microscopy.

These results demonstrate that CCL-21 vaults complexes exhibit the characteristic barrel shaped morphology of vaults, consistent with the previously established morphology of vaults containing recombinant-INT fusion proteins [8, 26].

Example 2

CCL-21-Vault Complexes are Biologically Active and Induce the Migration of T2 Cells In Vitro To determine whether CCL-21 retains its biological function when packaged inside the vault, a chemotaxis assay was used. The chemotactic activity of CCL-21 is mediated through its receptor CCR7 to induce the migration of T cells and dendritic cells. To evaluate the biological activity of CCL-21 in the vault, T2 hybridoma cells were used that constitutively express CCR7. Two different concentrations of CCL-21 vault complexes (200 ng and 600 ng), empty vaults (600 ng), and recombinant CCL-21 (600 ng) were placed in the bottom chamber of a 24-well transwell plates and $2\times10^5$ T2 cells were loaded in the upper chamber.

Figure 2:
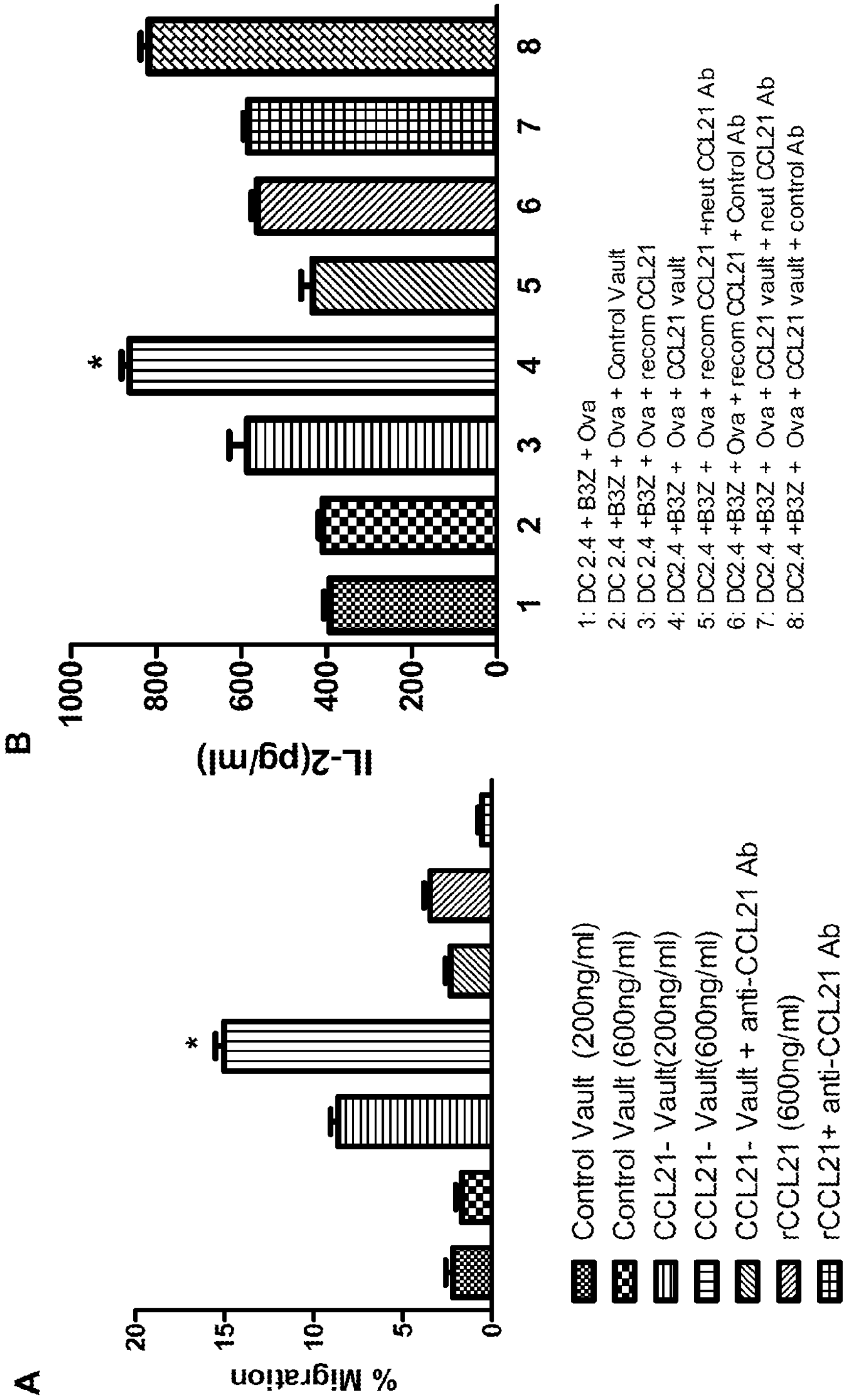
FIG. 2A is a graph that shows CCL-21 vault complexes increases the migration of T2 cells.
FIG. 2B is a graph showing T cell activation by CCL-21 vault complexes measured by IL-2 production.

In FIG. 2A, the number of cells that migrated to the lower chamber following incubation was determined by flow cytometry and represented as the % migration. $2.0\times10^5$ T2 cells were plated in serum-free medium in the upper chamber. CCL-21-mCherry-vault complexes (200 ng/ml or 600 ng/ml), recombinant CCL-21 (600 ng/ml), control vaults (600 ng/ml) or neutralizing anti-CCL-21 recombinant antibody (5 μg/ml) were added to the lower chamber of the wells. Following a two hour incubation, migration of T2 cells were analyzed by flow cytometry. CCL-21 vault complexes effectively increased the T2 migration as compared with control, and anti-CCL-21 neutralizing Ab. abrogated the increase in migration suggesting that CCL-21 vault complexes are biological active and can mediate the chemotatic migration of T cells. Data in the panel are representative of 2 independent experiments. (Bars; Mean±SEM, *$p<0.05$ between the CCL-21 vault complexes and control vault or anti-CCL-21 antibody treatment groups.)

More than 7.5% of the T2 cells responded to 200 ng of CCL-21 vault complexes compared with ≤2.5% of the T2 cells incubated with 600 ng of recombinant CCL-21. This is a phenomenal response considering that the given concentration is of CCL-vault complexes and the actual concentration of CCL-21 inside of the vaults would be estimated to be ≤20 ng. It is possible that the increased bioactivity of CCL-21 vault complexes results from increased stabilization of CCL-21 resulting from packaging of the protein into the protective environment of the vault lumen. As the fusion protein non-covalently associates within vaults, it is plausible that vault breathing in solution releases CCL-21 in a gradient fashion and the number of cells migrated was higher than the recombinant CCL-21 because a steeper gradient is formed. To demonstrate that the migration of T2 cells was CCL-21 dependent, a neutralizing antibody (against CCL-21) was shown to efficiently block the chemotactic activity of both recombinant CCL-21 and CCL-21 vault complexes. This led to the conclusion that CCL-21 vault complexes were functionally active at inducing the migration of T2 cells in vitro.

These results demonstrate that CCL-21 cytokines retain their biological function when packaged inside the vault complex.

Example 3

CCL-21 Vault Complexes Enhance DC APC Activity

In order to determine the effect of CCL-21 vault complexes on dendritic cell (DC) antigen presenting cell (APC) activity, the impact of CCL-21-vault complexes on DC APC activity was studied in vitro. In comparison to control vaults, CCL-21-vault complexes augmented DC capacity to process and present ovalbumin and activate CD8 T cells to secrete IL-2 (FIG. 2B).

FIG. 2B shows CCL-21 vault complexes enhanced DC APC activity, and blocking CCL-21 reversed the increase in APC activity. B3Z cells ($1\times10^5$ cells/200 ul/well) were co-cultured with DC 2.4 ($5\times10^4$ cells/200 ul/well) and ovalbumin (350 ug/ml) in the presence or absence of CCL21 vaults (200 ng/ml) and anti-CCL-21 antibody (5 ug/ml) or control antibody (5 ug/ml goat IgG) for 24 hrs. Control vaults were used at concentration of 200 ng/ml. T cell activation was analyzed by measuring IL-2 production by ELISA. Data are representative of 2 independent experiments. (Bars; Mean±SEM, *$p<0.05$ between the CCL21 vault and control vault or anti-CCL21 antibody treatment groups.) Neutralization of CCL-21 abrogated the increase in DC APC activity to control levels.

These results demonstrate that CCL-21 vault complexes enhance DC APC activity in vitro.

Example 4

CCL-21 Vault Complexes Enhance the Recruitment of Antitumor Leukocytic Infiltrates and Reduce 3LL Tumor Burden In Vivo To determine the anti-tumor activity of CCL-21 vault complexes in vivo, CCL-21 vault complexes were tested for effects on established tumor burden in 3LL tumor-bearing mice.

Figure 3:
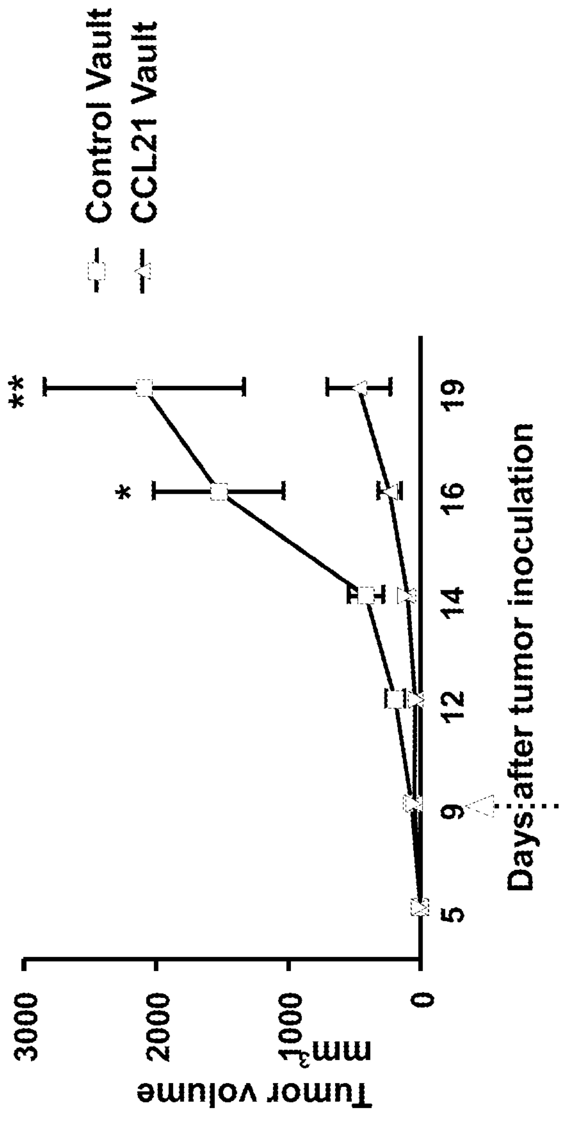
FIG. 3 is a graph showing a decrease in tumor burden by intratumoral injection of CCL-21 vault complexes (200 ng) compared to empty vaults.

As shown in FIG. 3, a single intratumoral injection of CCL-21 vault complexes (200 ng) led to significant decrease in tumor burden compared to empty vaults. C57BL/6 mice (n=5) were injected s.c. with $1.5\times10^5$ 3LL tumor cells and tumor growth was monitored daily. After 5 days following tumor implantation, mice were treated with vaults containing CCL-21-mCherry-mINT (200 ng), vaults alone (200 ng) or normal saline (diluent) via intra tumoral injection and tumor growth was monitored for the duration of the experiment. Tumor size was measured and tumor volume calculated as described herein. Bisecting tumor diameters were measured with calipers. Intra-tumoral administration of vaults containing CCL-21-mCherry-mINT led to significant reduction in tumor volume compared with untreated tumor bearing mice ($p<0.001$).

Figure 4:
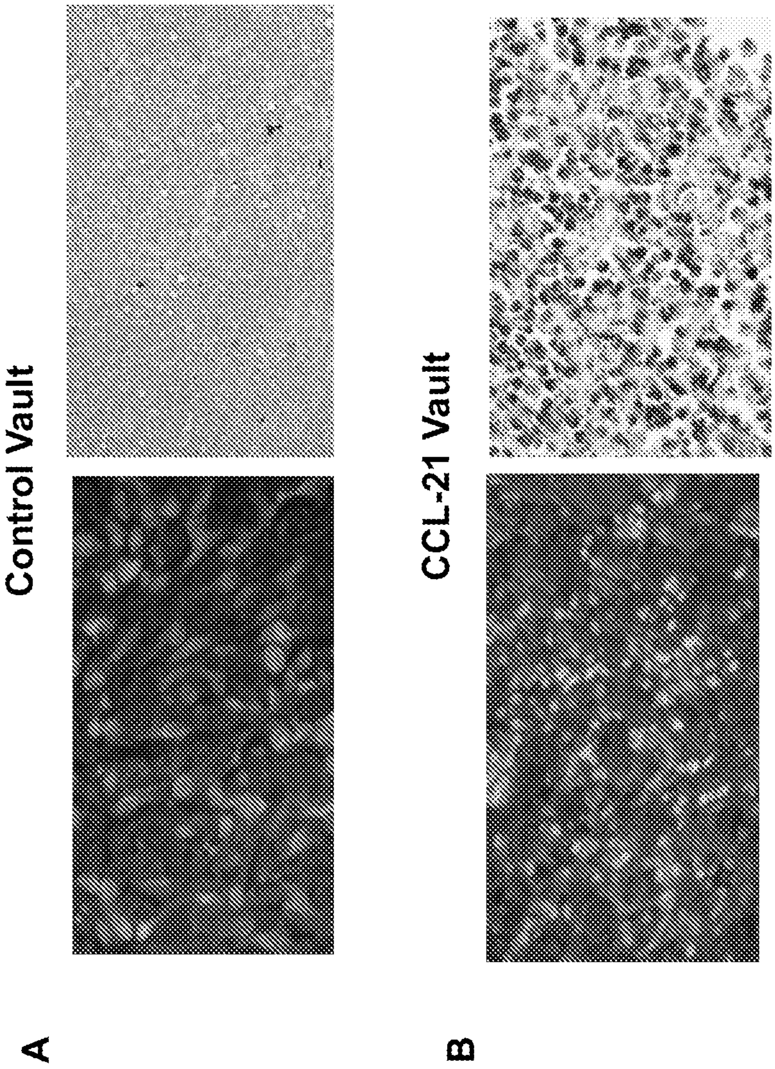
FIG. 4A shows the leukocytic infiltrates in cells treated with a control vault.
FIG. 4B shows the leukocytic infiltrates in cells treated with CCL-21 vault complexes.

FIGS. 4A-4B show that the CCL-21-vault complex treatment group (FIG. 4B) had enhanced leukocytic infiltrates compared to control vault (FIG. 4A), and immune staining showed that the infiltrates were mostly CD3 expressing T cells (FIG. 4B, bottom right panel). Sections from paraffin-embedded tissue were stained by hematoxylin-eosin (H&E) and CD3, CD4, CD8 and S-100 by immunohistochemistry using commercially available antibodies. Each panel of FIGS. 4A and 4B show photographs taken at 400× of representative areas within distinct primary tumors and Lymph nodes. Thus, CCL-21 vaults reduced tumor burden and increased the influx of CD3 expressing T cells in the tumor as compared to control vaults. (Data; Mean±SEM, *$p<0.05$ between CCL-21 vaults and control group, n=8 mice/group.)

Figure 5:
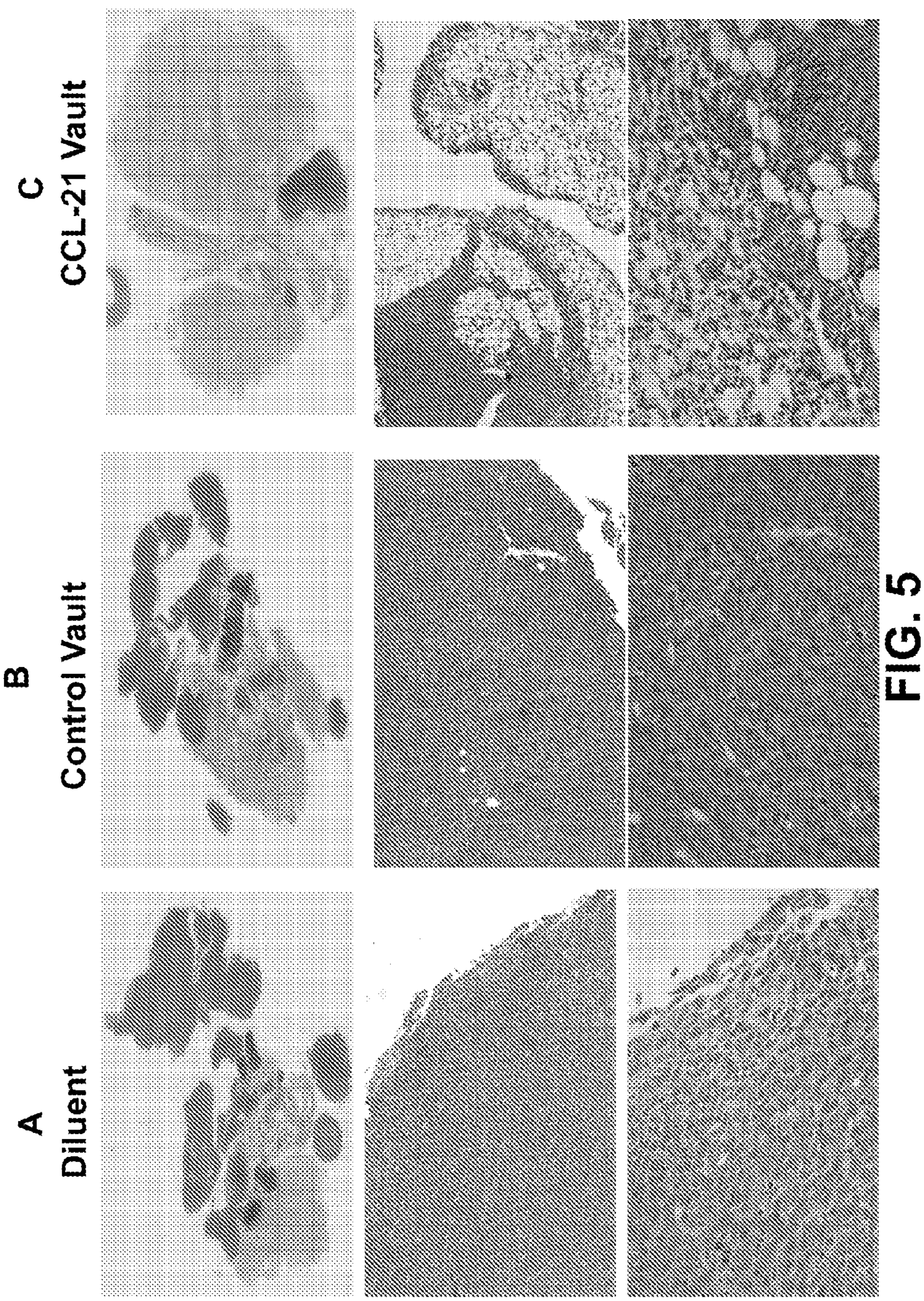
FIG. 5A is a photo showing the effects of treatment of 3LL lung cancer cells with diluent.
FIG. 5B is a photo showing the effects of treatment of 3LL lung cancer cells with control vault.
FIG. 5C is a photo showing the effects of treatment of 3LL lung cancer cells with CCL-21 vault complex.

In additional experiments, the antitumor efficacy of CCL-21-vault complexes was determined in a 7-day established orthotopic 3LL lung cancer model. CCL-21-vault complexes reduced tumor burden by 7-fold compared to controls. In FIGS. 5A-5C, H&E staining of lung tumor sections from diluent or control vaults showed increased tumor masses as compared to reduced tumor mass in the CCL-21 vault complex treatment group. FIG. 5A illustrates the effects of treatment of 3LL lung cancer cells with diluents only. FIG. 5B shows treatment with control vault, and FIG. 5C shows treatment with CCL-21 vault.

Figure 6:
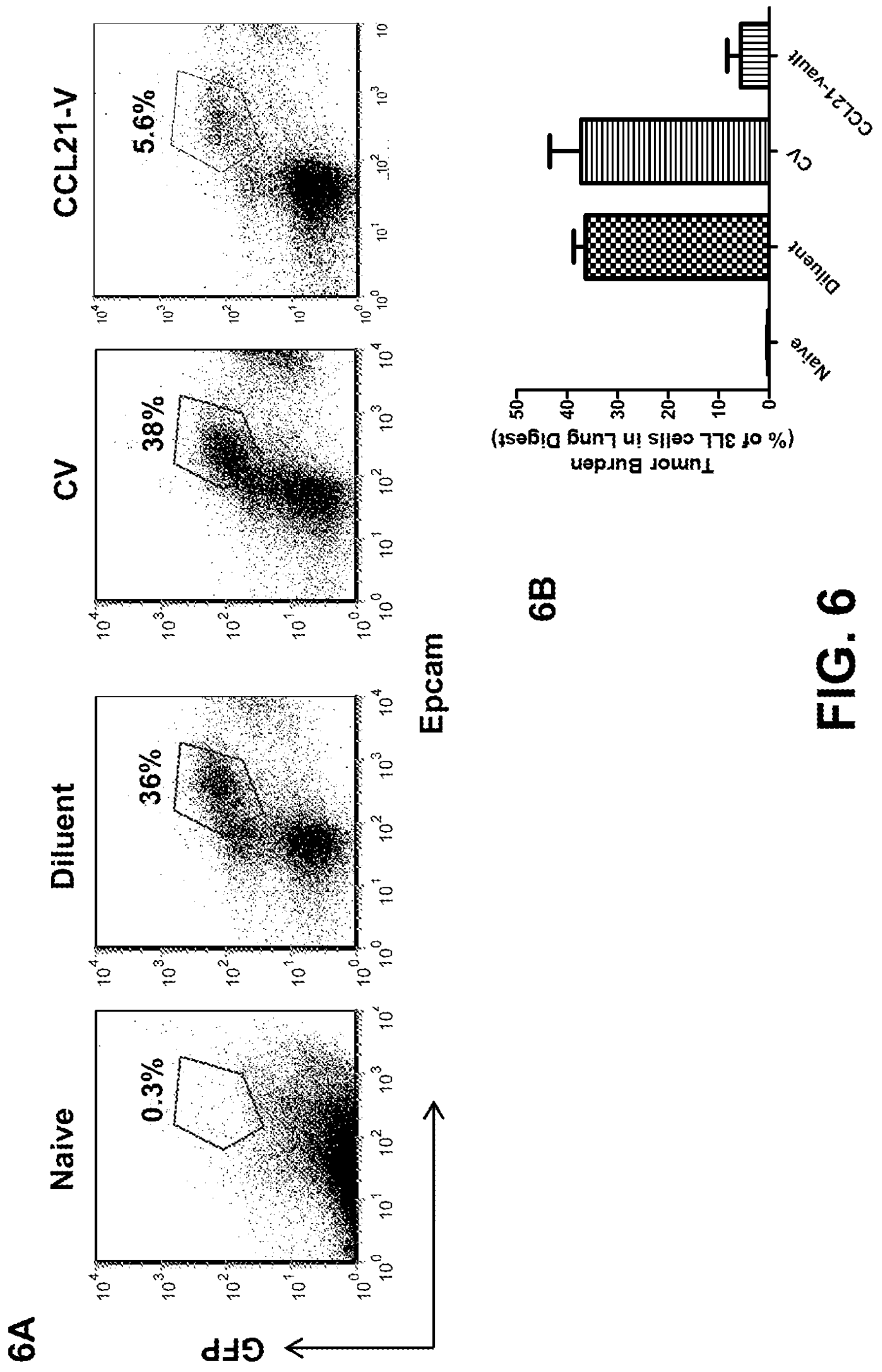
FIG. 6A is a set of graphs showing the percentage tumor burden in naïve 3LL cells, and 3LL cells treated with diluents, control vault (VC), or CCL-21 vault complexes as measured in a flow cytometry assay. Tumor burden was calculated on total percentage of GFP and Epcam expressing tumor cells in total lung digest.
FIG. 6B is a bar graph showing percentage tumor burden in 3LL cells after treatment with diluents, control vault, or CCL-21 vault complexes.

FIG. 6A shows the percentage tumor burden in naïve cells, and 3LL cells treated with diluents, control vault (CV), or CCL-21 vault complexes in a flow cytometry assay. Tumor burden was calculated on total percentage of GFP and Epcam expressing tumor cells in total lung digest. Naïve lung was used as control to set up the gate. CCL-21 vault complex treatment reduced tumor burden. FIG. 6B is a graph illustrating the percentage tumor burden in 3LL cells after treatment with diluents, control vault, or CCL-21 vault complexes.

Example 5

CCL-21-Vault Complexes Induce Tumor Infiltrating T Cell IFNγ but Reduce IL-10 and Augment Systemic T Cell Cytolytic Activity The effect of CCL-21 vault complexes on inducing tumor infiltrates and IL-10 expression was studied in vivo.

Figure 7:
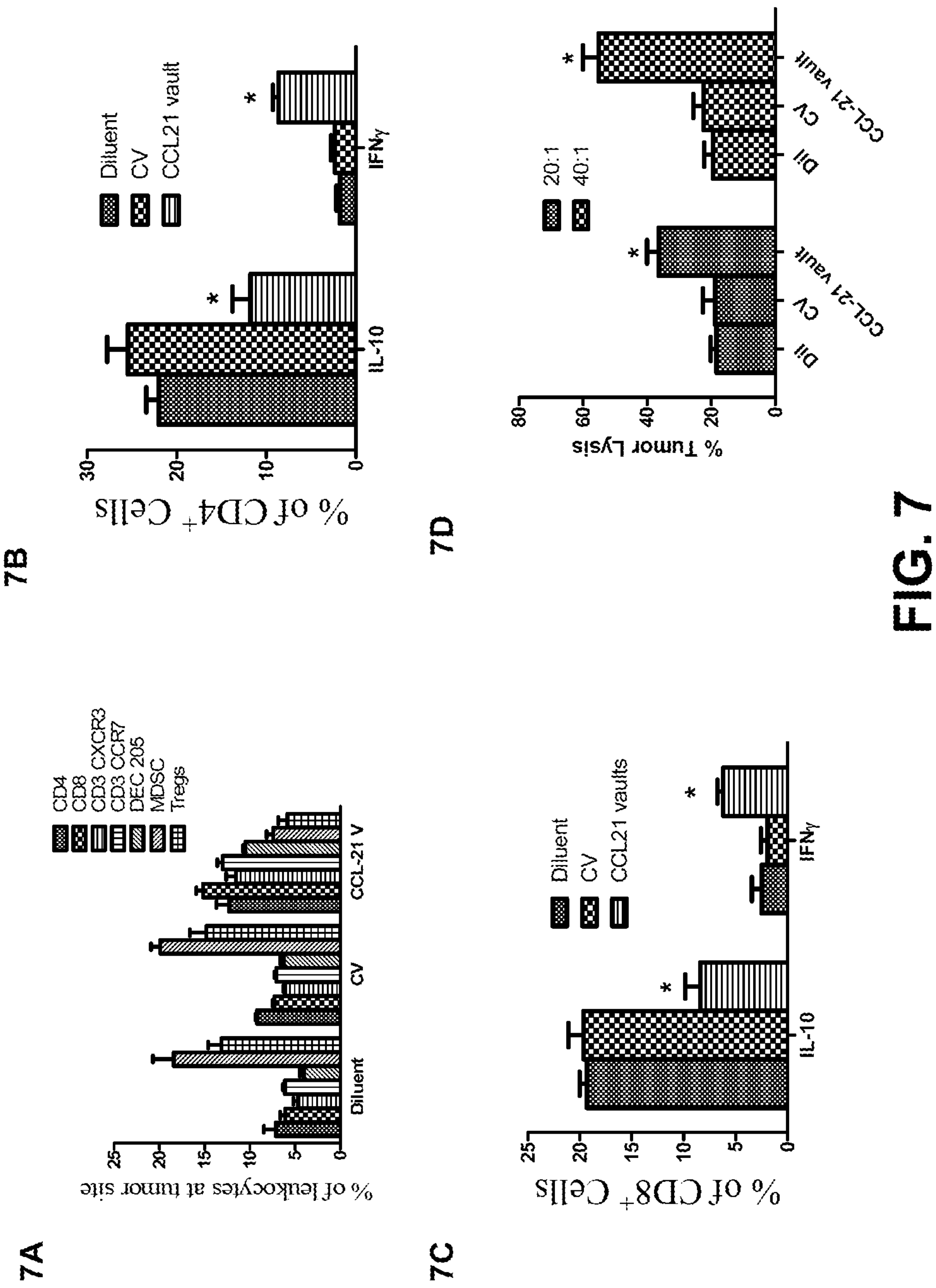
FIG. 7A is a graph showing percentage of intratumoral leukocytic populations (CD4, CD8, CD3 CXCR3, CD3 CCR7, DEC205, MDSC and Tregs) at the tumor site after injection with diluent, control vault, or CCL-21 vault complexes. CCL-21 vault complex augmented CD4, CD8, $CXCR3^+CD3^+T$, $CCR7^+CD3^+T$ and $DEC205^+DC$ infiltrates and reduced MDSC and Tregs.
FIG. 7B is a graph of the percentage of CD4+ cells with IFNγ and IL-10 expression after treatment with diluent, control vault, or CCL-21 vault complexes. Tumor T lymphocytic infiltrates from CCL-21 vault complex treated mice had increased intracytoplasmic IFNγ and reduced IL-10 expression.
FIG. 7C is a graph of the percentage of CD8+ cells with IFNγ and IL-10 expression after treatment with diluent, control vault, or CCL-21 vault complexes.
FIG. 7D is a graph of percentage tumor lysis of splenic T cells after intratumoral injection with diluent, control vault, or CCL-21 vault complexes.

Accompanying the reduced tumor burden, an evaluation of intratumoral leukocytic populations showed enhanced frequency of CD4, CD8, CD3 CXCR3, CD3 CCR7 and DEC205 but reduced levels of MDSC and Tregs (FIG. 7A-7D). In FIG. 7A, CCL-21 vault complexes augmented CD4, CD8, $CXCR3^+CD3^+T$, CCR7'$CD3^+T$ and $DEC205^+$ DC infiltrates and reduced MDSC and Tregs compared with treatment with diluents or control vault alone. FIGS. 7B and 7C show T cell infiltrates of CCL-21 vault complex treatment mice increased IFNγ and reduced IL-10 expression compared to controls. FIG. 7D illustrates that CCL-21 vault treatment enhanced the cytolytic activity of purified splenic T cells against parental 3LL tumors in vitro (E:T of 20:1 and 40:1).

FIGS. 6A-7D demonstrate that CCL-21 vaults reduced tumor burden and immune suppressors, increased T and DC infiltrates and induced systemic T cell antitumor activity. Specifically, CCL-21 vaults reduced tumor burden and immune suppressors (MDSC and Tregs) and enhanced intratumoral immune cell infiltrates in a 3LL orthotropic lung cancer model. For experiments shown in FIGS. 6A-7D, $5\times10^3$ 3LL-GFP tumor cells were injected in the left lung via transthoracic route. One week after tumor injections, mice were treated with diluent (NS), control vaults (2 ug) or CCL-21 vaults (2 ug) via transthoracic route in the left lung. Day 28 post tumor implantation, lung tumors were harvested for the analysis of tumor burden and tumor leukocytic infiltrates. (Data bars, mean±SEM, *$p<0.05$ between CCL-21 vaults and control vault groups, n=8 mice/group.).

These results demonstrate that CCL-21 vault complexes induce tumor infiltrating T cell IFNγ but reduce IL-10 and augment systemic T cell cytolytic activity.

Example 6

Use of CCL-21 Vault Complexes for Treatment of Cancer in Humans

For treatment of cancer in humans, the pharmaceutical compositions used in the present invention may be administered in a number of ways depending upon the invasiveness of treatment and based on whether local or systemic treatment is desired. The preferred initial treatment may be performed by intra-tumoral injection of the CCL-21 vault complex into a tumor of the patient. In some embodiments, intra-tumoral injection of a CCL-21 vault complex is performed on a tumor in the lung of the patient in need of treatment of lung cancer.

In certain embodiments, various dosages of the pharmaceutical composition comprising CCL-21 vault complexes can be administered to the patient.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

TABLE 1

| Sequences |
|---|
| Mouse CCL-21 Protein sequence<br>SEQ ID NO: 1<br>MAQMMTLSLLSLVLALCIPWTQGSDGGGQDCCLKYSQKKIPYSIVRGYRKQEPSLGCPIP<br>AILFSPRKHSKPELCANPEEGWVQNLMRRLDQFPAPGKQSPGCRKNRGTSKSGKKGKGSK<br>GCKRTEQTQPSRG |
| Human CCL-21 Protein sequence<br>SEQ ID NO: 2<br>MAQSLALSLLILVLAFGIPRTQGSDGGAQDCCLKYSQRKIPAKVVRSYRKQEPSLGCSIP<br>AILFLPRKRSQAELCADPKELWVQQLMQHLDKTPSPQKPAQGCRKDRGASKTGKKGKGSK<br>GCKRTERSQTPKGP |
| Mouse CCL-21 DNA cloned sequence<br>SEQ ID NO: 3<br>ATGGCTCAGATGATGACTCTGAGCCTCCTTAGCCTGGTCCTGGCTCTCTGCATCCCCTGGACCCAAGGCA<br>GTGATGGAGGGGGTCAGGACTGCTGCCTTAAGTACAGCCAGAAGAAAATTCCCTACAGTATTGTCCGAGG<br>CTATAGGAAGCAAGAACCAAGTTTAGGCTGTCCCATCCCGGCAATCCTGTTCTCACCCCGGAAGCACTCT<br>AAGCCTGAGCTATGTGCAAACCCTGAGGAAGGCTGGGTGCAGAACCTGATGCGCCGCCTGGACCAGCCTC<br>CAGCCCCAGGGAAACAAAGCCCCGGCTGCAGGAAGAACCGGGGAACCTCTAAGTCTGGAAAGAAAGGAAA<br>GGGCTCCAAGGGCTGCAAGAGAACTGAACAGACACAGCCCTCAAGAGGA |
| Mouse CCL-21 DNA full sequence<br>SEQ ID NO: 4<br>ATGGCTCAGATGATGACTCTGAGCCTCCTTAGCCTGGTCCTGGCTCTCTGCATCCCCTGGACCCAAGGCA<br>GTGATGGAGGGGGTCAGGACTGCTGCCTTAAGTACAGCCAGAAGAAAATTCCCTACAGTATTGTCCGAGG<br>CTATAGGAAGCAAGAACCAAGTTTAGGCTGTCCCATCCCGGCAATCCTGTTCTCACCCCGGAAGCACTCT<br>AAGCCTGAGCTATGTGCAAACCCTGAGGAAGGCTGGGTGCAGAACCTGATGCGCCGCCTGGACCAGCCTC<br>CAGCCCCAGGGAAACAAAGCCCCGGCTGCAGGAAGAACCGGGGAACCTCTAAGTCTGGAAAGAAAGGAAA<br>GGGCTCCAAGGGCTGCAAGAGAACTGAACAGACACAGCCCTCAAGAGGATAG |
| Human CCL-21 DNA sequence, Genbank #NP_002980<br>SEQ ID NO: 5<br>ATGGCTCAGTCACTGGCTCTGAGCCTCCTTATCCTGGTTCTGGCCTTTGGCATCCCCAGGACCCAAGGCA<br>GTGATGGAGGGGCTCAGGACTGTTGCCTCAAGTACAGCCAAAGGAAGATTCCCGCCAAGGTTGTCCGCAG<br>CTACCGGAAGCAGGAACCAAGCTTAGGCTGCTCCATCCCAGCTATCCTGTTCTTGCCCCGCAAGCGCTCT<br>CAGGCAGAGCTATGTGCAGACCCAAAGGAGCTCTGGGTGCAGCAGCTGATGCAGCATCTGGACAAGACAC<br>CATCCCCACAGAAACCAGCCCAGGGCTGCAGGAAGGACAGGGGGGCCTCCAAGACTGGCAAGAAAGGAAA<br>GGGCTCCAAAGGCTGCAAGAGGACTGAGCGGTCACAGACCCCTAAAGGGCCATAG |
| Mouse mINT DNA sequence<br>SEQ ID NO: 6<br>TGC ACA CAA CAC TGG CAG GAT GCT GTG CCT TGG ACA GAA CTC CTC AGT CTA CAG ACA GAG GAT<br>GGC TTC TGG AAA CTT ACA CCA GAA CTG GGA CTT ATA TTA AAT CTT AAT ACA AAT GGT TTG CAC<br>AGC TTT CTT AAA CAA AAA GGC ATT CAA TCT CTA GGT GTA AAA GGA AGA GAA TGT CTC CTG GAC<br>CTA ATT GCC ACA ATG CTG GTA CTA CAG TTT ATT CGC ACC AGG TTG GAA AAA GAG GGA ATA GTG<br>TTC AAA TCA CTG ATG AAA ATG GAT GAC CCT TCT ATT TCC AGG AAT ATT CCC TGG GCT TTT GAG<br>GCA ATA AAG CAA GCA AGT GAA TGG GTA AGA AGA ACT GAA GGA CAG TAC CCA TCT ATC TGC CCA<br>CGG CTT GAA CTG GGG AAC GAC TGG GAC TCT GCC ACC AAG CAG TTG CTG GGA CTC CAG CCC ATA<br>AGC ACT GTG TCC CCT CTT CAT AGA GTC CTC CAT TAC AGT CAA GGC TAA |
| Human mINT DNA sequence<br>SEQ ID NO: 7<br>TGC ACA CAA CAC TGG CAG GAT GCT GTG CCT TGG ACA GAA CTC CTC AGT CTA CAG ACA GAG GAT<br>GGC TTC TGG AAA CTT ACA CCA GAA CTG GGA CTT ATA TTA AAT CTT AAT ACA AAT GGT TTG CAC<br>AGC TTT CTT AAA CAA AAA GGC ATT CAA TCT CTA GGT GTA AAA GGA AGA GAA TGT CTC CTG GAC<br>CTA ATT GCC ACA ATG CTG GTA CTA CAG TTT ATT CGC ACC AGG TTG GAA AAA GAG GGA ATA GTG<br>TTC AAA TCA CTG ATG AAA ATG GAT GAC CCT TCT ATT TCC AGG AAT ATT CCC TGG GCT TTT GAG<br>GCA ATA AAG CAA GCA AGT GAA TGG GTA AGA AGA ACT GAA GGA CAG TAC CCA TCT ATC TGC CCA<br>CGG CTT GAA CTG GGG AAC GAC TGG GAC TCT GCC ACC AAG CAG TTG CTG GGA CTC CAG CCC ATA<br>AGC ACT GTG TCC CCT CTT CAT AGA GTC CTC CAT TAC AGT CAA GGC TAA |
| Human mINT protein sequence (residues 1563-1724 of the human VPARP protein sequence)<br>SEQ ID NO: 8<br>ctqhwqdavpwtells1qtedgfwkltpelglilnlntnglhsflkqkgicislgvkgreclldliatmlvlqfirtrlekegi<br>vfkslmkmddpsisrnipwafeaikqasewvrrtegqypsicprlelgndwdsatkqllglqpistvsplhrylhysqg<br>Mouse mINT protein sequence |

TABLE 1-continued

| Sequences |
|---|

SEQ ID NO: 9
CTQHWQDAVPWTELLSLQTEDGFWKLTPELGLILNLNTNGLHSFLKQKGIQSLGVKGRECLLDLIATMLVLQFIRTRLEKEGI
VFKSLMKMDDPSISRNIPWAFEAIKQASEWVRRTEGQYPSICPRLELGNDWDSATKQLLGLQPISTVSPLHRVLHYSQG

Mouse CCL-21-mINT fusion DNA sequence

SEQ ID NO: 10
ATGGCTCAGATGATGACTCTGAGCCTCCTTAGCCTGGTCCTGGCTCTCTGCATCCCCTGGACCCAAGGCA
GTGATGGAGGGGGTCAGGACTGCTGCCTTAAGTACAGCCAGAAGAAAATTCCCTACAGTATTGTCCGAGG
CTATAGGAAGCAAGAACCAAGTTTAGGCTGTCCCATCCCGGCAATCCTGTTCTCACCCCGGAAGCACTCT
AAGCCTGAGCTATGTGCAAACCCTGAGGAAGGCTGGGTGCAGAACCTGATGCGCCGCCTGGACCAGCCTC
CAGCCCCAGGGAAACAAAGCCCCGGCTGCAGGAAGAACCGGGGAACCTCTAAGTCTGGAAAGAAAGGAAA
GGGCTCCAAGGGCTGCAAGAGAACTGAACAGACACAGCCCTCAAGAGGA TGC ACA CAA CAC TGG CAG GAT GCT
GTG CCT TGG ACA GAA CTC CTC AGT CTA CAG ACA GAG GAT GGC TTC TGG AAA CTT ACA CCA GAA
CTG GGA CTT ATA TTA AAT CTT AAT ACA AAT GGT TTG CAC AGC TTT CTT AAA CAA AAA GGC ATT
CAA TCT CTA GGT GTA AAA GGA AGA GAA TGT CTC CTG GAC CTA ATT GCC ACA ATG CTG GTA CTA
CAG TTT ATT CGC ACC AGG TTG GAA AAA GAG GGA ATA GTG TTC AAA TCA CTG ATG AAA ATG GAT
GAC CCT TCT ATT TCC AGG AAT ATT CCC TGG GCT TTT GAG GCA ATA AAG CAA GCA AGT GAA TGG
GTA AGA AGA ACT GAA GGA CAG TAC CCA TCT ATC TGC CCA CGG CTT GAA CTG GGG AAC GAC TGG
GAC TCT GCC ACC AAG CAG TTG CTG GGA CTC CAG CCC ATA AGC ACT GTG TCC CCT CTT CAT AGA
GTC CTC CAT TAC AGT CAA GGC TAA

Human CCL-21-mINT fusion DNA sequence

SEQ ID NO: 11
ATGGCTCAGTCACTGGCTCTGAGCCTCCTTATCCTGGTTCTGGCCTTTGGCATCCCCAGGACCCAAGGCA
GTGATGGAGGGGCTCAGGACTGTTGCCTCAAGTACAGCCAAAGGAAGATTCCCGCCAAGGTTGTCCGCAG
CTACCGGAAGCAGGAACCAAGCTTAGGCTGCTCCATCCCAGCTATCCTGTTCTTGCCCCGCAAGCGCTCT
CAGGCAGAGCTATGTGCAGACCCAAAGGAGCTCTGGGTGCAGCAGCTGATGCAGCATCTGGACAAGACAC
CATCCCCACAGAAACCAGCCCAGGGCTGCAGGAAGGACAGGGGGGCCTCCAAGACTGGCAAGAAAGGAAA
GGGCTCCAAAGGCTGCAAGAGGACTGAGCGGTCACAGACCCCTAAAGGGCCAGCTAGCTGC ACA CAA CAC TGG CAG
GAT GCT GTG CCT TGG ACA GAA CTC CTC AGT CTA CAG ACA GAG GAT GGC TTC TGG AAA CTT ACA
CCA GAA CTG GGA CTT ATA TTA AAT CTT AAT ACA AAT GGT TTG CAC AGC TTT CTT AAA CAA AAA
GGC ATT CAA TCT CTA GGT GTA AAA GGA AGA GAA TGT CTC CTG GAC CTA ATT GCC ACA ATG CTG
GTA CTA CAG TTT ATT CGC ACC AGG TTG GAA AAA GAG GGA ATA GTG TTC AAA TCA CTG ATG AAA
ATG GAT GAC CCT TCT ATT TCC AGG AAT ATT CCC TGG GCT TTT GAG GCA ATA AAG CAA GCA AGT
GAA TGG GTA AGA AGA ACT GAA GGA CAG TAC CCA TCT ATC TGC CCA CGG CTT GAA CTG GGG AAC
GAC TGG GAC TCT GCC ACC AAG CAG TTG CTG GGA CTC CAG CCC ATA AGC ACT GTG TCC CCT CTT
CAT AGA GTC CTC CAT TAC AGT CAA GGC TAA

Mouse CCL-21-INT fusion Protein Sequence

SEQ ID NO: 12
MAQMMTLSLLSLVLALCIPWTQGSDGGGQDCCLKYSQKKIPYSIVRGYRKQEPSLGCPIPAILFSPRKHSKPELCANPEEGWV
QNLMRRLDQPPAPGKQSPGCRKNRGTSKSGKKGKGSKGCKRTEQTQPSRGCTQHWQDAVPWTELLSLQTEDGFWKLTPELGLI
LNLNTNGLHSFLKQKGIQSLGVKGRECLLDLIATMLVLQFIRTRLEKEGIVFKSLMKMDDPSISRNIPWAFEAIKQASEWVRR
TEGQYPSICPRLELGNDWDSATKQLLGLQPISTVSPLHRVLHYSQG

Human CCL-21-INT fusion Protein Sequence

SEQ ID NO: 13
MAQSLALSLLILVLAFGIPRTQGSDGGAQDCCLKYSQRKIPAKVVRSYRKQEPSLGCSIPAILFLPRKRSQAELCADPKELWV
QQLMQHLDKTPSPQKPAQGCRKDRGASKTGKKGKGSKGCKRTERSQTPKGPASCTQHWQDAVPWTELLSLQTEDGFWKLTPEL
GLILNLNTNGLHSFLKQKGIQSLGVKGRECLLDLIATMLVLQFIRTRLEKEGIVFKSLMKMDDPSISRNIPWAFEAIKQASEW
VRRTEGQYPSICPRLELGNDWDSATKQLLGLQPISTVSPLHRVLHYSQG

Human VPARP protein sequence Genbank #AAD47250

SEQ ID NO: 14
Met Val Met Gly Ile Phe Ala Asn Cys Ile Phe Cys Leu Lys Val Lys
Tyr Leu Pro Gln Gln Gln Lys Lys Lys Leu Gln Thr Asp Ile Lys Glu
Asn Gly Gly Lys Phe Ser Phe Ser Leu Asn Pro Gln Cys Thr His Ile
Ile Leu Asp Asn Ala Asp Val Leu Ser Gln Tyr Gln Leu Asn Ser Ile
Gln Lys Asn His Val His Ile Ala Asn Pro Asp Phe Ile Trp Lys Ser
Ile Arg Glu Lys Arg Leu Leu Asp Val Lys Asn Tyr Asp Pro Tyr Lys
Pro Leu Asp Ile Thr Pro Pro Pro Asp Gln Lys Ala Ser Ser Ser Glu
Val Lys Thr Glu Gly Leu Cys Pro Asp Ser Ala Thr Glu Glu Glu Asp
Thr Val Glu Leu Thr Glu Phe Gly Met Gln Asn Val Glu Ile Pro His
Leu Pro Gln Asp Phe Glu Val Ala Lys Tyr Asn Thr Leu Glu Lys Val
Gly Met Glu Gly Gly Gln Glu Ala Val Val Val Glu Leu Gln Cys Ser
Arg Asp Ser Arg Asp Cys Pro Phe Leu Ile Ser Ser His Phe Leu Leu
Asp Asp Gly Met Glu Thr Arg Arg Gln Phe Ala Ile Lys Lys Thr Ser
Glu Asp Ala Ser Glu Tyr Phe Glu Asn Tyr Ile Glu Glu Leu Lys Lys
Gln Gly Phe Leu Leu Arg Glu His Phe Thr Pro Glu Ala Thr Gln Leu
Ala Ser Glu Gln Leu Gln Ala Leu Leu Leu Glu Glu Val Met Asn Ser
Ser Thr Leu Ser Gln Glu Val Ser Asp Leu Val Glu Met Ile Trp Ala
Glu Ala Leu Gly His Leu Glu His Met Leu Leu Lys Pro Val Asn Arg
Ile Ser Leu Asn Asp Val Ser Lys Ala Glu Gly Ile Leu Leu Leu Val
Lys Ala Ala Leu Lys Asn Gly Glu Thr Ala Glu Gln Leu Gln Lys Met
Met Thr Glu Phe Tyr Arg Leu Ile Pro His Lys Gly Thr Met Pro Lys
Glu Val Asn Leu Gly Leu Leu Ala Lys Lys Ala Asp Leu Cys Gln Leu

TABLE 1-continued

| Sequences |
| --- |
| Ile Arg Asp Met Val Asn Val Cys Glu Thr Asn Leu Ser Lys Pro Asn<br>Pro Pro Ser Leu Ala Lys Tyr Arg Ala Leu Arg Cys Lys Ile Glu His<br>Val Glu Gln Asn Thr Glu Glu Phe Leu Arg Val Arg Lys Glu Val Leu<br>Gln Asn His His Ser Lys Ser Pro Val Asp Val Leu Gln Ile Phe Arg<br>Val Gly Arg Val Asn Glu Thr Thr Glu Phe Leu Ser Lys Leu Gly Asn<br>Val Arg Pro Leu Leu His Gly Ser Pro Val Gln Asn Ile Val Gly Ile<br>Leu Cys Arg Gly Leu Leu Leu Pro Lys Val Val Glu Asp Arg Gly Val<br>Gln Arg Thr Asp Val Gly Asn Leu Gly Ser Gly Ile Tyr Phe Ser Asp<br>Ser Leu Ser Thr Ser Ile Lys Tyr Ser His Pro Gly Glu Thr Asp Gly<br>Thr Arg Leu Leu Leu Ile Cys Asp Val Ala Leu Gly Lys Cys Met Asp<br>Leu His Glu Lys Asp Phe Pro Leu Thr Glu Ala Pro Pro Gly Tyr Asp<br>Ser Val His Gly Val Ser Gln Thr Ala Ser Val Thr Thr Asp Phe Glu<br>Asp Asp Glu Phe Val Val Tyr Lys Thr Asn Gln Val Lys Met Lys Tyr<br>Ile Ile Lys Phe Ser Met Pro Gly Asp Gln Ile Lys Asp Phe His Pro<br>Ser Asp His Thr Glu Leu Glu Glu Tyr Arg Pro Glu Phe Ser Asn Phe<br>Ser Lys Val Glu Asp Tyr Gln Leu Pro Asp Ala Lys Thr Ser Ser Ser<br>Thr Lys Ala Gly Leu Gln Asp Ala Ser Gly Asn Leu Val Pro Leu Glu<br>Asp Val His Ile Lys Gly Arg Ile Ile Asp Thr Val Ala Gln Val Ile<br>Val Phe Gln Thr Tyr Thr Asn Lys Ser His Val Pro Ile Glu Ala Lys<br>Tyr Ile Phe Pro Leu Asp Asp Lys Ala Ala Val Cys Gly Phe Glu Ala<br>Phe Ile Asn Gly Lys His Ile Val Gly Glu Ile Lys Glu Lys Glu Glu<br>Ala Gln Gln Glu Tyr Leu Glu Ala Val Thr Gln Gly His Gly Ala Tyr<br>Leu Met Ser Gln Asp Ala Pro Asp Val Phe Thr Val Ser Val Gly Asn<br>Leu Pro Pro Lys Ala Lys Val Leu Ile Lys Ile Thr Tyr Ile Thr Glu<br>Leu Ser Ile Leu Gly Thr Val Gly Val Phe Phe Met Pro Ala Thr Val<br>Ala Pro Trp Gln Gln Asp Lys Ala Leu Asn Glu Asn Leu Gln Asp Thr<br>Val Glu Lys Ile Cys Ile Lys Glu Ile Gly Thr Lys Gln Ser Phe Ser<br>Leu Thr Met Ser Ile Glu Met Pro Tyr Val Ile Glu Phe Ile Phe Ser<br>Asp Thr His Glu Leu Lys Gln Lys Arg Thr Asp Cys Lys Ala Val Ile<br>Ser Thr Met Glu Gly Ser Ser Leu Asp Ser Ser Gly Phe Ser Leu His<br>Ile Gly Leu Ser Ala Ala Tyr Leu Pro Arg Met Trp Val Glu Lys His<br>Pro Glu Lys Glu Ser Glu Ala Cys Met Leu Val Phe Gln Pro Asp Leu<br>Asp Val Asp Leu Pro Asp Leu Ala Ser Glu Ser Glu Val Ile Ile Cys<br>Leu Asp Cys Ser Ser Ser Met Glu Gly Val Thr Phe Leu Gln Ala Lys<br>Gln Ile Thr Leu His Ala Leu Ser Leu Val Gly Glu Lys Gln Lys Val<br>Asn Ile Ile Gln Phe Gly Thr Gly Tyr Lys Glu Leu Phe Ser Tyr Pro<br>Lys His Ile Thr Ser Asn Thr Thr Ala Ala Glu Phe Ile Met Ser Ala<br>Thr Pro Thr Met Gly Asn Thr Asp Phe Trp Lys Thr Leu Arg Tyr Leu<br>Ser Leu Leu Tyr Pro Ala Arg Gly Ser Arg Asn Ile Leu Leu Val Ser<br>Asp Gly His Leu Gln Asp Glu Ser Leu Thr Leu Gln Leu Val Lys Arg<br>Ser Arg Pro His Thr Arg Leu Phe Ala Cys Gly Ile Gly Ser Thr Ala<br>Asn Arg His Val Leu Arg Ile Leu Ser Gln Cys Gly Ala Gly Val<br>Phe Glu Tyr Phe Asn Ala Lys Ser Lys His Ser Trp Arg Lys Gln<br>Ile Glu Asp Gln Met Thr Arg Leu Cys Ser Pro Ser Cys His Ser<br>Val Ser Val Lys Trp Gln Gln Leu Asn Pro Asp Ala Pro Glu Ala<br>Leu Gln Ala Pro Ala Gln Val Pro Ser Leu Phe Arg Asn Asp Arg<br>Leu Leu Val Tyr Gly Phe Ile Pro His Cys Thr Gln Ala Thr Leu<br>Cys Ala Leu Ile Gln Glu Lys Glu Phe Cys Thr Met Val Ser Thr<br>Thr Glu Leu Gln Lys Thr Thr Gly Thr Met Ile His Lys Leu Ala<br>Ala Arg Ala Leu Ile Arg Asp Tyr Glu Asp Gly Ile Leu His Glu<br>Asn Glu Thr Ser His Glu Met Lys Lys Gln Thr Leu Lys Ser Leu<br>Ile Ile Lys Leu Ser Lys Glu Asn Ser Leu Ile Thr Gln Phe Thr<br>Ser Phe Val Ala Val Glu Lys Arg Asp Glu Asn Glu Ser Pro Phe<br>Pro Asp Ile Pro Lys Val Ser Glu Leu Ile Ala Lys Glu Asp Val<br>Asp Phe Leu Pro Tyr Met Ser Trp Gln Gly Glu Pro Gln Glu Ala<br>Val Arg Asn Gln Ser Leu Leu Ala Ser Ser Glu Trp Pro Glu Leu<br>Arg Leu Ser Lys Arg Lys His Arg Lys Ile Pro Phe Ser Lys Arg<br>Lys Met Glu Leu Ser Gln Pro Glu Val Ser Glu Asp Phe Glu Glu<br>Asp Gly Leu Gly Val Leu Pro Ala Phe Thr Ser Asn Leu Glu Arg<br>Gly Gly Val Glu Lys Leu Leu Asp Leu Ser Trp Thr Glu Ser Cys<br>Lys Pro Thr Ala Thr Glu Pro Leu Phe Lys Lys Val Ser Pro Trp<br>Glu Thr Ser Thr Ser Ser Phe Phe Pro Ile Leu Ala Pro Ala Val<br>Gly Ser Tyr Leu Thr Pro Thr Thr Arg Ala His Ser Pro Ala Ser<br>Leu Ser Phe Ala Ser Tyr Arg Gln Val Ala Ser Phe Gly Ser Ala<br>Ala Pro Pro Arg Gln Phe Asp Ala Ser Gln Phe Ser Gln Gly Pro<br>Val Pro Gly Thr Cys Ala Asp Trp Ile Pro Gln Ser Ala Ser Cys<br>Pro Thr Gly Pro Pro Gln Asn Pro Pro Ser Ala Pro Tyr Cys Gly<br>Ile Val Phe Ser Gly Ser Ser Leu Ser Ser Ala Gln Ser Ala Pro<br>Leu Gln His Pro Gly Gly Phe Thr Thr Arg Pro Ser Ala Gly Thr<br>Phe Pro Glu Leu Asp Ser Pro Gln Leu His Phe Ser Leu Pro Thr<br>Asp Pro Asp Pro Ile Arg Gly Phe Gly Ser Tyr His Pro Ser Ala<br>Tyr Ser Pro Phe His Phe Gln Pro Ser Ala Ala Ser Leu Thr Ala<br>Asn Leu Arg Leu Pro Met Ala Ser Ala Leu Pro Glu Ala Leu Cys<br>Ser Gln Ser Arg Thr Thr Pro Val Asp Leu Cys Leu Leu Glu Glu<br>Ser Val Gly Ser Leu Glu Gly Ser Arg Cys Pro Val Phe Ala Phe<br>Gln Ser Ser Asp Thr Glu Ser Asp Glu Leu Ser Glu Val Leu Gln<br>Asp Ser Cys Phe Leu Gln Ile Lys Cys Asp Thr Lys Asp Asp Ser<br>Ile Pro Cys Phe Leu Glu Leu Lys Glu Glu Asp Glu Ile Val Cys |

TABLE 1-continued

Sequences

```
Thr Gln His Trp Gln Asp Ala Val Pro Trp Thr Glu Leu Leu Ser
Leu Gln Thr Glu Asp Gly Phe Trp Lys Leu Thr Pro Glu Leu Gly
Leu Ile Leu Asn Leu Asn Thr Asn Gly Leu His Ser Phe Leu Lys
Gln Lys Gly Ile Gln Ser Leu Gly Val Lys Gly Arg Glu Cys Leu
Leu Asp Leu Ile Ala Thr Met Leu Val Leu Gln Phe Ile Arg Thr
Arg Leu Glu Lys Glu Gly Ile Val Phe Lys Ser Leu Met Lys Met
Asp Asp Pro Ser Ile Ser Arg Asn Ile Pro Trp Ala Phe Glu Ala
Ile Lys Gln Ala Ser Glu Trp Val Arg Arg Thr Glu Gly Gln Tyr
Pro Ser Ile Cys Pro Arg Leu Glu Leu Gly Asn Asp Trp Asp Ser
Ala Thr Lys Gln Leu Leu Gly Leu Gln Pro Ile Ser Thr Val Ser
Pro Leu His Arg Val Leu His Tyr Ser Gln Gly
```

Human VPARP cDNA, Genbank #AF158255

SEQ ID NO: 15

```
atggtgatgg gaatctttgc aaattgtatc ttctgtttga aagtgaagta cttacctcag
cagcagaaga aaaagctaca aactgacatt aaggaaaatg gcggaaagtt ttccttttcg
ttaaatcctc agtgcacaca tataatctta gataatgctg atgttctgag tcagtaccaa
ctgaattcta tccaaaagaa ccacgttcat attgcaaacc cagattttat atggaaatct
atcagagaaa agagactctt ggatgtaaag aattatgatc cttataagcc cctggacatc
acaccacctc ctgatcagaa ggcgagcagt tctgaagtga aaacagaagg tctatgcccg
gacagtgcca cagaggagga agacactgtg gaactcactg agtttggtat gcagaatgtt
gaaattcctc atcttcctca agattttgaa gttgcaaaat ataacacctt ggagaaagtg
ggaatggagg gaggccagga agctgtggtg gtggagcttc agtgttcgcg ggactccagg
gactgtcctt tcctgatatc ctcacacttc ctcctggatg atggcatgga gactagaaga
cagtttgcta taaagaaaac ctctgaagat gcaagtgaat actttgaaaa ttacattgaa
gaactgaaga aacaaggatt tctactaaga gaacatttca cacctgaagc aacccaatta
gcatctgaac aattgcaagc attgcttttg gaggaagtca tgaattcaag cactctgagc
caagaggtga gcgatttagt agagatgatt tgggcagagg ccctgggcca cctggaacac
atgcttctca agccagtgaa caggattagc ctcaacgatg tgagcaaggc agaggggatt
ctccttctag taaaggcagc actgaaaaat ggagaaacag cagagcaatt gcaaaagatg
atgacagagt tttacagact gatacctcac aaaggcacaa tgcccaaaga agtgaacctg
ggactattgg ctaagaaagc agacctctgc cagctaataa gagacatggt taatgtctgt
gaaactaatt tgtccaaacc caacccacca tccctggcca aataccgagc tttgaggtgc
aaaattgagc atgttgaaca gaatactgaa gaatttctca gggttagaaa agaggttttg
cagaatcatc acagtaagag cccagtggat gtcttgcaga tatttagagt tggcagagtg
aatgaaacca cagagttttt gagcaaactt ggtaatgtga ggcccttgtt gcatggttct
cctgtacaaa acatcgtggg aatcttgtgt cgagggttgc ttttacccaa agtagtggaa
gatcgtggtg tgcaaagaac agacgtcgga aaccttggaa gtgggattta tttcagtgat
tcgctcagta caagtatcaa gtactcacac ccgggagaga cagatggcac cagactcctg
ctcatttgtg acgtagccct cggaaagtgt atggacttac atgagaagga ctttccctta
actgaagcac caccaggcta cgacagtgtg catggagttt cacaaacagc ctctgtcacc
acagactttg aggatgatga atttgttgtc tataaaacca atcaggttaa aatgaaatat
attattaaat tttccatgcc tggagatcag ataaaggact ttcatcctag tgatcatact
gaattagagg aatacagacc tgagttttca aatttttcaa aggttgaaga ttaccagtta
ccagatgcca aaacttccag cagcaccaag gccggcctcc aggatgcctc tgggaacttg
gttcctctgg aggatgtcca catcaaaggg agaatcatag acactgtagc ccaggtcatt
gtttttcaga catacacaaa taaaagtcac gtgcccattg aggcaaaata tatctttcct
ttggatgaca aggccgctgt gtgtggcttc gaagccttca tcaatgggaa gcacatagtt
ggagagatta aagagaagga agaagcccag caagagtacc tagaagccgt gacccagggc
catggcgctt acctgatgag tcaggatgct ccggacgttt ttactgtaag tgttggaaac
ttacccccta aggctaaggt tcttataaaa attacctaca tcacagaact cagcatcctg
ggcactgttg gtgtcttttt catgcccgcc accgtagcac cctggcaaca ggacaaggct
ttgaatgaaa accttcagga tacagtagag aagatttgta taaaagaaat aggaacaaag
caaagcttct ctttgactat gtctattgag atgccgtatg tgattgaatt cattttcagt
gatacacatg aactgaaaca aaagcgcaca gactgcaaag ctgtcattag caccatggaa
ggcagctcct tagacagcag tggattttct ctccacatcg gtttgtctgc tgcctatctc
ccaagaatgt gggttgaaaa acatccagaa aaagaaagcg aggcttgcat gcttgtcttt
caacccgatc tcgatgtcga cctccctgac ctagccagtg agagcgaagt gattatttgt
cttgactgct ccagttccat ggagggtgtg acattcttgc aagccaagca aatcaccttg
catgcgctgt ccttggtggg tgagaagcag aaagtaaata ttatccagtt cggcacaggt
tacaaggagc tattttcgta tcctaagcat atcacaagca ataccacggc agcagagttc
atcatgtctg ccacacctac catggggaac acagacttct ggaaaacact ccgatatctt
agcttattgt accctgctcg agggtcacgg aacatcctcc tggtgtctga tgggcacctc
caggatgaga gcctgacatt acagctcgtg aagaggagcc gcccgcacac caggttattc
gcctgcggta tcggttctac agcaaatcgt cacgtcttaa ggattttgtc ccagtgtggt
gccggagtat ttgaatattt taatgcaaaa tccaagcata gttggagaaa acagatagaa
gaccaaatga ccaggctatg ttctccgagt tgccactctg tctccgtcaa atggcagcaa
ctcaatccag atgcgcccga ggccctgcag gccccagccc aggtgccatc cttgtttcgc
aatgatcgac tccttgtcta tggattcatt cctcactgca cacaagcaac tctgtgtgca
ctaattcaag agaaagaatt ttgtacaatg gtgtcgacta ctgagcttca gaagacaact
ggaactatga tccacaagct ggcagcccga gctctaatca gagattatga agatggcatt
cttcacgaaa atgaaaccag tcatgagatg aaaaaacaaa ccttgaaatc tctgattatt
aaactcagta aagaaaactc tctcataaca caatttacaa gctttgtggc agttgagaaa
agggatgaga atgagtcgcc ttttcctgat attccaaaag tttctgaact tattgccaaa
gaagatgtag acttcctgcc ctacatgagc tggcaggggg agccccaaga agccgtcagg
aaccagtctc ttttagcatc ctctgagtgg ccagaattac gtttatccaa acgaaaacat
aggaaaattc cattttccaa aagaaaaatg gaattatctc agccagaagt ttctgaagat
tttgaagagg atggcttagg tgtactacca gctttcacat caaatttgga acgtggaggt
```

TABLE 1-continued

| Sequences |
|---|
| gtggaaaagc tattggattt aagttggaca gagtcatgta aaccaacagc aactgaacca<br>ctatttaaga aagtcagtcc atgggaaaca tctacttcta gctttttcc tattttggct<br>ccggccgttg gttcctatct taccccgact acccgcgctc acagtcctgc ttccttgtct<br>tttgcctcat atcgtcaggt agctagtttc ggttcagctg ctcctcccag acagtttgat<br>gcatctcaat tcagccaagg ccctgtgcct ggcacttgtg ctgactggat cccacagtcg<br>gcgtcttgtc ccacaggacc tccccagaac ccaccttctg caccctattg tggcattgtt<br>ttttcaggga gctcattaag ctctgcacag tctgctccac tgcaacatcc tggaggcttt<br>actaccaggc cttctgctgg caccttccct gagctggatt ctccccagct tcatttctct<br>cttcctacag accctgatcc catcagaggt tttgggtctt atcatccctc tgcttactct<br>ccttttcatt ttcaaccttc cgcagcctct ttgactgcca accttaggct gccaatggcc<br>tctgctttac ctgaggctct ttgcagtcag tcccggacta ccccagtaga tctctgtctt<br>ctagaagaat cagtaggcag tctcgaagga agtcgatgtc ctgtctttgc ttttcaaagt<br>tctgacacag aaagtgatga gctatcagaa gtacttcaag acagctgctt tttacaaata<br>aagtgtgata caaaagatga cagtatcccg tgctttctgg aattaaaaga agaggatgaa<br>atagtgtgca cacaacactg gcaggatgct gtgccttgga cagaactcct cagtctacag<br>acagaggatg gcttctggaa acttacacca gaactgggac ttatattaaa tcttaataca<br>aatggtttgc acagctttct taaacaaaaa ggcattcaat ctctaggtgt aaaaggaaga<br>gaatgtctcc tggacctaat tgccacaatg ctggtactac agtttattcg caccaggttg<br>gaaaaagagg gaatagtgtt caaatcactg atgaaaatgg atgacccttc tatttccagg<br>aatattccct gggcttttga ggcaataaag caagcaagtg aatgggtaag aagaactgaa<br>ggacagtacc catctatctg cccacggctt gaactgggga acgactggga ctctgccacc<br>aagcagttgc tgggactcca gcccataagc actgtgtccc ctcttcatag agtcctccat<br>tacagtcaag gctaa<br><br>Human MVP, Genbank #CAA56256<br>SEQ ID NO: 16<br>Met Ala Thr Glu Glu Phe Ile Ile Arg Ile Pro Pro Tyr His Tyr Ile<br>His Val Leu Asp Gln Asn Ser Asn Val Ser Arg Val Glu Val Gly Pro<br>Lys Thr Tyr Ile Arg Gln Asp Asn Glu Arg Val Leu Phe Ala Pro Met<br>Arg Met Val Thr Val Pro Pro Arg His Tyr Cys Thr Val Ala Asn Pro<br>Val Ser Arg Asp Ala Gln Gly Leu Val Leu Phe Asp Val Thr Gly Gln<br>Val Arg Leu Arg His Ala Asp Leu Glu Ile Arg Leu Ala Gln Asp Pro<br>Phe Pro Leu Tyr Pro Gly Glu Val Leu Glu Lys Asp Ile Thr Pro Leu<br>Gln Val Val Leu Pro Asn Thr Ala Leu His Leu Lys Ala Leu Leu Asp<br>Phe Glu Asp Lys Asp Gly Asp Lys Val Val Ala Gly Asp Glu Trp Leu<br>Phe Glu Gly Pro Gly Thr Tyr Ile Pro Arg Lys Glu Val Glu Val Val<br>Glu Ile Ile Gln Ala Thr Ile Ile Arg Gln Asn Gln Ala Leu Arg Leu<br>Arg Ala Arg Lys Glu Cys Trp Asp Arg Asp Gly Lys Glu Arg Val Thr<br>Gly Glu Glu Trp Leu Val Thr Thr Val Gly Ala Tyr Leu Pro Ala Val<br>Phe Glu Glu Val Leu Asp Leu Val Asp Ala Val Ile Leu Thr Glu Lys<br>Thr Ala Leu His Leu Arg Ala Arg Arg Asn Phe Arg Asp Phe Arg Gly<br>Val Ser Arg Arg Thr Gly Glu Glu Trp Leu Val Thr Val Gln Asp Thr<br>Glu Ala His Val Pro Asp Val His Glu Glu Val Leu Gly Val Val Pro<br>Ile Thr Thr Leu Gly Pro His Asn Tyr Cys Val Ile Leu Asp Pro Val<br>Gly Pro Asp Gly Lys Asn Gln Leu Gly Gln Lys Arg Val Val Lys Gly<br>Glu Lys Ser Phe Phe Leu Gln Pro Gly Glu Gln Leu Glu Gln Gly Ile<br>Gln Asp Val Tyr Val Leu Ser Glu Gln Gln Gly Leu Leu Leu Arg Ala<br>Leu Gln Pro Leu Glu Glu Gly Glu Asp Glu Glu Lys Val Ser His Gln<br>Ala Gly Asp His Trp Leu Ile Arg Gly Pro Leu Glu Tyr Val Pro Ser<br>Ala Lys Val Glu Val Val Glu Glu Arg Gln Ala Ile Pro Leu Asp Glu<br>Asn Glu Gly Ile Tyr Val Gln Asp Val Lys Thr Gly Lys Val Arg Ala<br>Val Ile Gly Ser Thr Tyr Met Leu Thr Gln Asp Glu Val Leu Trp Glu<br>Lys Glu Leu Pro Pro Gly Val Glu Glu Leu Leu Asn Lys Gly Gln Asp<br>Pro Leu Ala Asp Arg Gly Glu Lys Asp Thr Ala Lys Ser Leu Gln Pro<br>Leu Ala Pro Arg Asn Lys Thr Arg Val Val Ser Tyr Arg Val Pro His<br>Asn Ala Ala Val Gln Val Tyr Asp Tyr Arg Glu Lys Arg Ala Arg Val<br>Val Phe Gly Pro Glu Leu Val Ser Leu Gly Pro Glu Glu Gln Phe Thr<br>Val Leu Ser Leu Ser Ala Gly Arg Pro Lys Arg Pro His Ala Arg Arg<br>Ala Leu Cys Leu Leu Leu Gly Pro Asp Phe Phe Thr Asp Val Ile Thr<br>Ile Glu Thr Ala Asp His Ala Arg Leu Gln Leu Gln Leu Ala Tyr Asn<br>Trp His Phe Glu Val Asn Asp Arg Lys Asp Pro Gln Glu Thr Ala Lys<br>Leu Phe Ser Val Pro Asp Phe Val Gly Asp Ala Cys Lys Ala Ile Ala<br>Ser Arg Val Arg Gly Ala Val Ala Ser Val Thr Phe Asp Asp Phe His<br>Lys Asn Ser Ala Arg Ile Ile Arg Thr Ala Val Phe Gly Phe Glu Thr<br>Ser Glu Ala Lys Gly Pro Asp Gly Met Ala Leu Pro Arg Pro Arg Asp<br>Gln Ala Val Phe Pro Gln Asn Gly Leu Val Val Ser Ser Val Asp Val<br>Gln Ser Val Glu Pro Val Asp Gln Arg Thr Arg Asp Ala Leu Gln Arg<br>Ser Val Gln Leu Ala Ile Glu Ile Thr Thr Asn Ser Gln Glu Ala Ala<br>Ala Lys His Glu Ala Gln Arg Leu Glu Gln Glu Ala Arg Gly Arg Leu<br>Glu Arg Gln Lys Ile Leu Asp Gln Ser Glu Ala Glu Lys Ala Arg Lys<br>Glu Leu Leu glu Leu Glu Ala Leu Ser Met Ala Val Glu Ser Thr Gly<br>Thr Ala Lys Ala Glu Ala Glu Ser Arg Ala Glu Ala Ala Arg Ile Glu<br>Gly Glu Gly Ser Val Leu Gln Ala Lys Leu Lys Ala Gln Ala Leu Ala<br>Ile Glu Thr Glu Ala Glu Leu Gln Arg Val Gln Lys Val Arg Glu Leu<br>Glu Leu Val Tyr Ala Arg Ala Gln Leu Glu Leu Glu Val Ser Lys Ala<br>Gln Gln Leu Ala Glu Val Glu Val Lys Lys Phe Lys Gln Met Thr Glu<br>Ala Ile Gly Pro Ser Thr Ile Arg Asp Leu Ala Val Ala Gly Pro Glu<br>Met Gln Val Lys Leu Leu Gln Ser Leu Gly Leu Lys Ser Thr Leu Ile |

TABLE 1-continued

| Sequences |
|---|
| Thr Asp Gly Ser Thr Pro Ile Asn Leu Phe Asn Thr Ala Phe Gly Leu<br>Leu Gly Met Gly Pro Glu Gly Gln Pro Leu Gly Arg Arg Val Ala Ser<br>Gly Pro Ser Pro Gly Glu Gly Ile Ser Pro Gln Ser Ala Gln Ala Pro<br>Gln Ala Pro Gly Asp Asn His Val Val Pro Val Leu Arg |
| Human MVP cDNA, Genbank #X79882<br>SEQ ID NO: 17<br>atggcaactg aagagttcat catccgcatc cccccatacc actatatcca tgtgctggac<br>cagaacagca acgtgtcccg tgtggaggtc gggccaaaga cctacatccg gcaggacaat<br>gagagggtac tgtttgcccc catgcgcatg gtgaccgtcc ccccacgtca ctactgcaca<br>gtggccaacc ctgtgtctcg ggatgcccag ggcttggtgc tgtttgatgt cacagggcaa<br>gttcggcttc gccacgctga cctcgagatc cggctggccc aggacccctt ccccctgtac<br>ccaggggagg tgctggaaaa ggacatcaca cccctgcagg tggttctgcc caacactgcc<br>ctccatctaa aggcgctgct tgattttgag gataaagatg gagacaaggt ggtggcagga<br>gatgagtggc ttttcgaggg acctggcacg tacatccccc ggaaggaagt ggaggtcgtg<br>gagatcattc aggccaccat catcaggcag aaccaggcgc tgcggctcag ggcccgcaag<br>gagtgctggg accgggacgg caaggagagg gtgacagggg aagaatggct ggtcaccaca<br>gtagggggcgt acctcccagc ggtgtttgag gaggttctgg atttggtgga cgccgtcatc<br>cttacggaaa agacagccct gcacctccgg gctcggcgga acttccggga cttcagggga<br>gtgtcccgcc gcactgggga ggagtggctg gtaacagtgc aggacacaga ggcccacgtg<br>ccagatgtcc acgaggaggt gctgggggtt gtgcccatca ccaccctggg cccccacaac<br>tactgcgtga ttctcgaccc tgtcggaccg gatggcaaga atcagctggg gcagaagcgc<br>gtggtcaagg gagagaagtc ttttttcctc cagccaggag agcagctgga acaaggcatc<br>caggatgtgt atgtgctgtc ggagcagcag gggctgctgc tgagggccct gcagcccctg<br>gaggaggggg aggatgagga gaaggtctca caccaggctg gggaccactg gctcatccgc<br>ggacccctgg agtatgtgcc atctgccaaa gtggaggtgg tggaggagcg ccaggccatc<br>cctctagacg agaacgaggg catctatgtg caggatgtca agaccggaaa ggtgcgcgct<br>gtgattggaa gcacctacat gctgacccag gacgaagtcc tgtgggagaa agagctgcct<br>cccggggtgg aggagctgct gaacaagggg caggaccctc tggcagacag gggtgagaag<br>gacacagcta agagcctcca gcccttggcg ccccggaaca agacccgtgt ggtcagctac<br>cgcgtgcccc acaacgctgc ggtgcaggtg tacgactacc gagagaagcg agcccgcgtg<br>gtcttcgggc ctgagctggt gtcgctgggt cctgaggagc agttcacagt gttgtccctc<br>tcagctgggc ggcccaagcg tccccatgcc cgccgtgcgc tctgcctgct gctggggcct<br>gacttcttca cagacgtcat caccatcgaa acggcggatc atgccaggct gcaactgcag<br>ctggcctaca actggcactt tgaggtgaat gaccggaagg acccccaaga gacggccaag<br>ctcttttcag tgccagactt tgtaggtgat gcctgcaaag ccatcgcatc ccgggtgcgg<br>ggggccgtgg cctctgtcac tttcgatgac ttccataaga actcagcccg catcattcgc<br>actgctgtct ttggctttga gacctcggaa gcgaagggcc ccgatggcat ggccctgccc<br>aggccccggg accaggctgt cttcccccaa aacgggctgg tggtcagcag tgtggacgtg<br>cagtcagtgg agcctgtgga tcagaggacc cgggacgccc tgcaacgcag cgtccagctg<br>gccatcgaga tcaccaccaa ctcccaggaa gcggcggcca agcatgaggc tcagagactg<br>gagcaggaag cccgcggccg gcttgagcgg cagaagatcc tggaccagtc agaagccgag<br>aaagctcgca aggaactttt ggagctggag gctctgagca tggccgtgga gagcaccggg<br>actgccaagg cggaggccga gtcccgtgcg gaggcagccc ggattgaggg agaagggtcc<br>gtgctgcagg ccaagctaaa agcacaggcc ttggccattg aaacggaggc tgagctccag<br>agggtccaga aggtccgaga gctggaactg gtctatgccc gggcccagct ggagctggag<br>gtgagcaagg ctcagcagct ggctgaggtg gaggtgaaga agttcaagca gatgacagag<br>gccataggcc ccagcaccat cagggacctt gctgtggctg ggcctgagat gcaggtaaaa<br>ctgctccagt ccctgggcct gaaatcaacc ctcatcaccg atggctccac tcccatcaac<br>ctcttcaaca cagcctttgg gctgctgggg atggggcccg agggtcagcc cctgggcaga<br>agggtggcca gtgggcccag ccctggggag gggatatccc cccagtctgc tcaggcccct<br>caagctcctg gagacaacca cgtggtgcct gtactgcgct aa |
| Rat MVP, Genbank #AAC52161<br>SEQ ID NO: 18<br>Met Ala Thr Glu Glu Ala Ile Ile Arg Ile Pro Pro Tyr His Tyr Ile<br>His Val Leu Asp Gln Asn Ser Asn Val Ser Arg Val Glu Val Gly Pro<br>Lys Thr Tyr Ile Arg Gln Asp Asn Glu Arg Val Leu Phe Ala Pro Val<br>Arg Met Val Thr Val Pro Pro Arg His Tyr Cys Ile Val Ala Asn Pro<br>Val Ser Arg Asp Thr Gln Ser Ser Val Leu Phe Asp Ile Thr Gly Gln<br>Val Arg Leu Arg His Ala Asp Gln Glu Ile Arg Leu Ala Gln Asp Pro<br>Phe Pro Leu Tyr Prl Gly Glu Val Leu Glu Lys Asp Ile Thr Pro Leu<br>Gln Val Val Leu Pro Asn Thr Ala Leu His Leu Lys Ala Leu Leu Asp<br>Phe Glu Asp Lys Asn Gly Asp Lys Val Met Ala Gly Asp Glu Trp Leu<br>Phe Glu Gly Pro Gly Thr Tyr Ile Pro Gln Lys Glu Val Glu Val Val<br>Glu Ile Ile Gln Ala Thr Val Ile Lys Gln Asn Gln Ala Leu Arg Leu<br>Arg Ala Arg Lys Glu Cys Phe Asp Arg Glu Gly Lys Gly Arg Val Thr<br>Gly Glu Glu Trp Leu Val Arg Ser Val Gly Ala Tyr Leu Pro Ala Val<br>Phe Glu Glu Val Leu Asp Leu Val Asp Ala Val Ile Leu Thr Glu Lys<br>Thr Ala Leu His Leu Arg Ala Leu Gln Asn Phe Arg Asp Leu Arg Gly<br>Val Leu His Arg Thr Gly Glu Glu Trp Leu Val Thr Val Gln Asp Thr<br>Glu Ala His Val Pro Asp Val Tyr Glu Glu Val Leu Gly Val Val Pro<br>Ile Thr Thr Leu Gly Pro Arg His Tyr Cys Val Ile Leu Asp Pro Met<br>Gly Pro Asp Gly Lys Asn Gln Leu Gly Gln Lys Arg Val Val Lys Gly<br>Glu Lys Ser Phe Phe Leu Gln Pro Gly Glu Arg Leu Glu Arg Gly Ile<br>Gln Asp Val Tyr Val Leu Ser Glu Gln Gln Gly Leu Leu Leu Lys Ala<br>Leu Gln Pro Leu Glu Glu Gly Glu Ser Glu Glu Lys Val Ser His Gln<br>Ala Gly Asp Cys Trp Leu Ile Arg Gly Pro Leu Glu Tyr Val Pro Ser |

TABLE 1-continued

Sequences

Ala Lys Val Glu Val Val Glu Glu Arg Gln Ala Ile Pro Leu Asp Gln
Asn Glu Gly Ile Tyr Val Gln Asp Val Lys Thr Gly Lys Val Arg Ala
Val Ile Gly Ser Thr Tyr Met Leu Thr Gln Asp Glu Val Leu Trp Glu
Lys Glu Leu Pro Ser Gly Val Glu Glu Leu Leu Asn Leu Gly His Asp
Pro Leu Ala Asp Arg Gly Gln Lys Gly Thr Ala Lys Pro Leu Gln Pro
Ser Ala Pro Arg Asn Lys Thr Arg Val Val Ser Tyr Arg Val Pro His
Asn Ala Ala Val Gln Val Tyr Asp Tyr Arg Ala Lys Arg Ala Arg Val
Val Phe Gly Pro Glu Leu Val Thr Leu Asp Pro Glu Glu Gln Phe Thr
Val Leu Ser Leu Ser Ala Gly Arg Pro Lys Arg Pro His Ala Arg Arg
Ala Leu Cys Leu Leu Leu Gly Pro Asp Phe Phe Thr Asp Val Ile Thr
Ile Glu Thr Ala Asp His Ala Arg Leu Gln Leu Gln Leu Ala Tyr Asn
Trp His Phe Glu Leu Lys Asn Arg Asn Asp Pro Ala Glu Ala Ala Lys
Leu Phe Ser Val Pro Asp Phe Val Gly Asp Ala Cys Lys Ala Ile Ala
Ser Arg Val Arg Gly Ala Val Ala Ser Val Thr Phe Asp Asp Phe His
Lys Asn Ser Ala Arg Ile Ile Arg Met Ala Val Phe Gly Phe Glu Met
Ser Glu Asp Thr Gly Pro Asp Gly Thr Leu Leu Pro Lys Ala Arg Asp
Gln Ala Val Phe Pro Gln Asn Gly Leu Val Val Ser Ser Val Asp Val
Gln Ser Val Glu Pro Val Asp Gln Arg Thr Arg Asp Ala Leu Gln Arg
Ser Val Gln Leu Ala Ile Glu Ile Thr Thr Asn Ser Gln Glu Ala Ala
Ala Lys His Glu Ala Gln Arg Leu Glu Gln Glu Ala Arg Gly Arg Leu
Glu Arg Gln Lys Ile Leu Asp Gln Ser Glu Ala Glu Lys Ala Arg Lys
Glu Leu Leu Glu Leu Glu Ala Met Ser Met Ala Val Glu Ser Thr Gly
Asn Ala Lys Ala Glu Ala Glu Ser Arg Ala Glu Ala Ala Arg Ile Glu
Gly Glu Gly Ser Val Leu Gln Ala Lys Leu Lys Ala Gln Ala Leu Ala
Ile Glu Thr Glu Ala Glu Leu Glu Arg Val Lys Lys Val Arg Glu Met
Glu Leu Ile Tyr Ala Arg Ala Gln Leu Glu Leu Glu Val Ser Lys Ala
Gln Gln Leu Ala Asn Val Glu Ala Lys Lys Phe Lys Glu Met Thr Glu
Ala Leu Gly Pro Gly Thr Ile Arg Asp Leu Ala Val Ala Gly Pro Glu
Met Gln Val Lys Leu Leu Gln Ser Leu Gly Leu Lys Ser Thr Leu Ile
Thr Asp Gly Ser Ser Pro Ile Asn Leu Phe Ser Thr Ala Phe Gly Leu
Leu Gly Leu Gly Ser Asp Gly Gln Pro Pro Ala Gln Lys

Rat MVP cDNA, Genbank #U09870

SEQ ID NO: 19 atggcaactg aagaggccat catccgcatc cccccatacc actacatcca tgtgctggac
cagaacagta atgtgtcccg tgtggaggtt ggaccaaaga cctacatccg gcaggacaat
gagagggtac tgtttgcccc agttcgcatg gtgaccgtcc ccccacgcca ctactgcata
gtggccaacc ctgtgtcccg ggacacccag agttctgtgt tatttgacat cacaggacaa
gtccgactcc ggcacgctga ccaggagatc cgactagccc aggacccctt ccccctgtat
ccaggggagg tgctggaaaa ggacatcacc ccactgcagg tggttctgcc caacacagca
ctgcatctta aggcgttgct ggactttgag gataagaatg gagacaaggt catggcagga
gacgagtggc tatttgaggg acctggcacc tacatcccac agaaggaagt ggaagtcgtg
gagatcattc aggccacagt catcaaacag aaccaagcac tgcggctaag ggcccgaaag
gagtgctttg accgggaggg caaggggcgc gtgacaggtg aggagtggct ggtccgatcc
gtgggggctt acctcccagc tgtctttgaa gaggtgctgg atctggtgga tgctgtgatc
cttacagaaa agactgccct gcacctccgg gctctgcaga acttcaggga ccttcgggga
gtgctccacc gcaccgggga ggaatggtta gtgacagtgc aggacacaga agcccatgtt
ccagatgtct atgaggaggt gcttggggta gtacccatca ccaccctggg acctcgacac
tactgtgtca ttcttgaccc aatgggacca gacggcaaga accagctggg acaaaagcgt
gttgtcaagg gagagaagtc ctttttcctc cagccaggag agaggctgga gcgaggcatc
caggatgtgt atgtgctgtc agagcagcag gggctgctac tgaaggcact gcagcccctg
gaggagggag agagcgagga gaaggtctcc catcaggccg gagactgctg gctcatccgt
gggcccctgg agtatgtgcc atctgcaaaa gtggaggtgg tggaggagcg tcaggctatc
cctctggacc aaaatgaggg catctatgtg caggatgtca agacggggaa ggtgcgggct
gtgattggaa gcacctacat gctgactcag gatgaagtcc tgtgggaaaa ggagctgcct
tctggggtgg aggagctgct gaacttgggg catgaccctc tggcagacag gggtcagaag
ggcacagcca agccccttca gccctcagct ccaaggaaca agacccgagt ggtcagctac
cgtgtcccgc acaatgcagc ggtgcaggtc tatgactaca gagccaagag agcccgtgtg
gtctttgggc ccgagctagt gacactggat cctgaggagc agttcacagt attgtccctt
tctgccgggc gacccaagcg tcctcatgcc cgccgtgcac tctgcctact gctgggacct
gatttcttta ctgatgtcat caccatcgaa actgcagatc atgccaggtt gcagctgcag
cttgcctaca actggcactt tgaactgaag aaccggaatg accctgcaga ggcagccaag
cttttctccg tgcctgactt cgtgggtgac gcctgcaagg ccattgcatc ccgagtccgg
ggggctgtag cctctgtcac ctttgatgac ttccataaaa actcagcccg gatcattcga
atggctgttt ttggctttga gatgtctgaa gacacaggtc ctgatggcac actcctgccc
aaggctcgag accaggcagt ctttccccaa aacgggctgg tagtcagcag tgtggatgtg
cagtcagtgg agcccgtgga ccagaggacc cgggatgccc ttcagcgcag cgttcagctg
gccatcgaaa ttaccaccaa ctcccaggag gcagcagcca agcacgaggc tcagagactg
gaacaggaag cccgtggtcg gcttgagagg cagaagatct tggaccagtc agaagctgaa
aaagcccgca aggaactctt ggagcttgag gctatgagca tggctgtgga gagcacgggt
aatgccaaag cagaggctga gtcccgtgca gaggcagcga ggatcgaagg agaaggctct
gtgctgcagg ccaagctcaa ggcacaggcg ctagccattg agacggaggc tgagttggag
cgagtaaaga aagtacgaga gatggaactg atctatgccc gggcccagtt ggagctggag
gtgagcaagg cgcagcagct tgccaatgtg gaggcaaaga agttcaagga gatgacagag
gcactgggcc ccggcaccat cagggacctg gctgtggccg ggccagagat gcaggtgaaa
cttctccagt ccctgggcct gaaatccact ctcatcaccg atggctcgtc tcccatcaac
ctcttcagca cagccttcgg gttgctgggg ctggggtctg atggtcagcc gccagcacag
aagtga TABLE 1-continued

| Sequences |
| --- |

CP Peptide

SEQ ID NO: 20

Met Ala Gly Cys Gly Cys Pro Cys Gly Cys Gly Ala

Human CP-MVP

SEQ ID NO: 21

Met Ala Gly Cys Gly Cys Pro Cys Gly Cys Gly Ala Met Ala Thr Glu
Glu Phe Ile Ile Arg Ile Pro Pro Tyr His Tyr Ile His Val Leu Asp
Gln Asn Ser Asn Val Ser Arg Val Glu Val Gly Pro Lys Thr Tyr Ile
Arg Gln Asp Asn Glu Arg Val Leu Phe Ala Pro Met Arg Met Val Thr
Val Pro Pro Arg His Tyr Cys Thr Val Ala Asn Pro Val Ser Arg Asp
Ala Gln Gly Leu Val Leu Phe Asp Val Thr Gly Gln Val Arg Leu Arg
His Ala Asp Leu Glu Ile Arg Leu Ala Gln Asp Pro Phe Pro Leu Tyr
Pro Gly Glu Val Leu Glu Lys Asp Ile Thr Pro Leu Gln Val Val Leu
Pro Asn Thr Ala Leu His Leu Lys Ala Leu Leu Asp Phe Glu Asp Lys
Asp Gly Asp Lys Val Val Ala Gly Asp Glu Trp Leu Phe Glu Gly Pro
Gly Thr Tyr Ile Pro Arg Lys Glu Val Glu Val Val Glu Ile Ile Gln
Ala Thr Ile Ile Arg Gln Asn Gln Ala Leu Arg Leu Arg Ala Arg Lys
Glu Cys Trp Asp Arg Asp Gly Lys Glu Arg Val Thr Gly Glu Glu Trp
Leu Val Thr Thr Val Gly Ala Tyr Leu Pro Ala Val Phe Glu Glu Val
Leu Asp Leu Val Asp Ala Val Ile Leu Thr Glu Lys Thr Ala Leu His
Leu Arg Ala Arg Arg Asn Phe Arg Asp Phe Arg Gly Val Ser Arg Arg
Thr Gly Glu Glu Trp Leu Val Thr Val Gln Asp Thr Glu Ala His Val
Pro Asp Val His Glu Glu Val Leu Gly Val Val Pro Ile Thr Thr Leu
Gly Pro His Asn Tyr Cys Val Ile Leu Asp Pro Val Gly Pro Asp Gly
Lys Asn Gln Leu Gly Gln Lys Arg Val Val Lys Gly Glu Lys Ser Phe
Phe Leu Gln Pro Gly Glu Gln Leu Glu Gln Gly Ile Gln Asp Val Tyr
Val Leu Ser Glu Gln Gln Gly Leu Leu Leu Arg Ala Leu Gln Pro Leu
Glu Glu Gly Glu Asp Glu Glu Lys Val Ser His Gln Ala Gly Asp His
Trp Leu Ile Arg Gly Pro Leu Glu Tyr Val Pro Ser Ala Lys Val Glu
Val Val Glu Glu Arg Gln Ala Ile Pro Leu Asp Glu Asn Glu Gly Ile
Tyr Val Gln Asp Val Lys Thr Gly Lys Val Arg Ala Val Ile Gly Ser
Thr Tyr Met Leu Thr Gln Asp Glu Val Leu Trp Glu Lys Glu Leu Pro
Pro Gly Val Glu Glu Leu Leu Asn Lys Gly Gln Asp Pro Leu Ala Asp
Arg Gly Glu Lys Asp Thr Ala Lys Ser Leu Gln Pro Leu Ala Pro Arg
Asn Lys Thr Arg Val Val Ser Tyr Arg Val Pro His Asn Ala Ala Val
Gln Val Tyr Asp Tyr Arg Glu Lys Arg Ala Arg Val Val Phe Gly Pro
Glu Leu Val Ser Leu Gly Pro Glu Glu Gln Phe Thr Val Leu Ser Leu
Ser Ala Gly Arg Pro Lys Arg Pro His Ala Arg Arg Ala Leu Cys Leu
Leu Leu Gly Pro Asp Phe Phe Thr Asp Val Ile Thr Ile Glu Thr Ala
Asp His Ala Arg Leu Gln Leu Gln Leu Ala Tyr Asn Trp His Phe Glu
Val Asn Asp Arg Lys Asp Pro Gln Glu Thr Ala Lys Leu Phe Ser Val
Pro Asp Phe Val Gly Asp Ala Cys Lys Ala Ile Ala Ser Arg Val Arg
Gly Ala Val Ala Ser Val Thr Phe Asp Asp Phe His Lys Asn Ser Ala
Arg Ile Ile Arg Thr Ala Val Phe Gly Phe Glu Thr Ser Glu Ala Lys
Gly Pro Asp Gly Met Ala Leu Pro Arg Pro Arg Asp Gln Ala Val Phe
Pro Gln Asn Gly Leu Val Val Ser Ser Val Asp Val Gln Ser Val Glu
Pro Val Asp Gln Arg Thr Arg Asp Ala Leu Gln Arg Ser Val Gln Leu
Ala Ile Glu Ile Thr Thr Asn Ser Gln Glu Ala Ala Ala Lys His Glu
Ala Gln Arg Leu Glu Gln Glu Ala Arg Gly Arg Leu Glu Arg Gln Lys
Ile Leu Asp Gln Ser Glu Ala Glu Lys Ala Arg Lys Glu Leu Leu Glu
Leu Glu Ala Leu Ser Met Ala Val Glu Ser Thr Gly Thr Ala Lys Ala
Glu Ala Glu Ser Arg Ala Glu Ala Ala Arg Ile Glu Gly Glu Gly Ser
Val Leu Gln Ala Lys Leu Lys Ala Gln Ala Leu Ala Ile Glu Thr Glu
Ala Glu Leu Gln Arg Val Gln Lys Val Arg Glu Leu Glu Leu Val Tyr
Ala Arg Ala Gln Leu Glu Leu Glu Val Ser Lys Ala Gln Gln Leu Ala
Glu Val Glu Val Lys Lys Phe Lys Gln Met Thr Glu Ala Ile Gly Pro
Ser Thr Ile Arg Asp Leu Ala Val Ala Gly Pro Glu Met Gln Val Lys
Leu Leu Gln Ser Leu Gly Leu Lys Ser Thr Leu Ile Thr Asp Gly Ser
Thr Pro Ile Asn Leu Phe Asn Thr Ala Phe Gly Leu Leu Gly Met Gly
Pro Glu Gly Gln Pro Leu Gly Arg Arg Val Ala Ser Gly Pro Ser Pro
Gly Glu gly Ile Ser Pro Gln Ser Ala Gln Ala Pro Gln Ala Pro Gly
Asp Asn His Val Val Pro Val Leu Arg Human CP-MVP cDNA

SEQ ID NO: 22 atggcaggct gcggttgtcc atgcggttgt ggcgccatgg caactgaaga gttcatcatc
cgcatccccc cataccacta tatccatgtg ctggaccaga acagcaacgt gtcccgtgtg
gaggtcgggc caaagaccta catccggcag gacaatgaga gggtactgtt tgcccccatg
cgcatggtga ccgtcccccc acgtcactac tgcacagtgg ccaaccctgt gtctcgggat
gcccagggct tggtgctgtt tgatgtcaca gggcaagttc ggcttcgcca cgctgacctc
gagatccggc tggcccagga ccccttcccc ctgtacccag gggaggtgct ggaaaaggac
atcacacccc tgcaggtggt tctggggaac actgccctcc atctaaaggc gctgcttgat
tttgaggata aagatggaga caaggtggtg gcaggagatg agtggctttt cgagggacct
ggcacgtaca tcccccggaa ggaagtggag gtcgtggaga tcattcaggc caccatcatc
aggcagaacc aggctctgcg gctcagggcc cgcaaggagt gctgggaccg ggacggcaag
gagagggtga caggggaaga atggctggtc accacagtag ggcgtacct cccagcggtg TABLE 1-continued

| Sequences |
|---|
| tttgaggagg ttctggattt ggtggacgcc gtcatcctta cggaaaagac agccctgcac<br>ctccgggctc ggcggaactt ccgggacttc aggggagtgt cccgccgcac tggggaggag<br>tggctggtaa cagtgcagga cacagaggcc cacgtgccag atgtccacga ggaggtgctg<br>ggggttgtgc ccatcaccac cctgggcccc cacaactact gcgtgattct cgaccctgtc<br>ggaccggatg gcaagaatca gctggggcag aagcgcgtgg tcaagggaga gaagtctttt<br>ttcctccagc caggagagca gctggaacaa ggcatccagg atgtgtatgt gctgtcggag<br>cagcaggggc tgctgctgag ggccctgcag cccctggagg agggggagga tgaggagaag<br>gtctcacacc aggctgggga ccactggctc atccgcggac ccctggagta tgtgccatct<br>gccaaagtgg aggtggtgga ggagcgccag gccatccctc tagacgagaa cgagggcatc<br>tatgtgcagg atgtcaagac cggaaaggtg cgcgctgtga ttggaagcac ctacatgctg<br>acccaggacg aagtcctgtg ggagaaagag ctgcctcccg ggtggaggga gctgctgaac<br>aaggggcagg accctctggc agacagggt gagaaggaca cagctaagag cctccagccc<br>ttggcgcccc ggaacaagac ccgtgtggtc agctaccgcg tgccccacaa cgctgcggtg<br>caggtgtacg actaccgaga gaagcgagcc cgcgtggtct tcgggcctga gctggtgtcg<br>ctgggtcctg aggagcagtt cacagtgttg tccctctcag ctgggcggcc caagcgtccc<br>catgcccgcc gtgcgctctg cctgctgctg gggcctgact tcttcacaga cgtcatcacc<br>atcgaaacgg cggatcatgc caggctgcaa ctgcagctgg cctacaactg gcactttgag<br>gtgaatgacc ggaaggaccc ccaagagacg gccaagctct tttcagtgcc agactttgta<br>ggtgatgcct gcaaagccat cgcatcccgg gtgcgggggg ccgtggcctc tgtcactttc<br>gatgacttcc ataagaactc agcccgcatc attcgcactg ctgtctttgg ctttgagacc<br>tcggaagcga agggccccga tggcatggcc ctgcccaggc cccgggacca ggctgtcttc<br>ccccaaaacg ggctggtggt cagcagtgtg gacgtgcagt cagtggagcc tgtggatcag<br>aggacccggg acgccctgca acgcagcgtc cagctggcca tcgagatcac caccaactcc<br>caggaagcgg cggccaagca tgaggctcag agactggagc aggaagcccg cggccggctt<br>gagcggcaga agatcctgga ccagtcagaa gccgagaaag ctcgcaagga actttttggag<br>ctggaggctc tgagcatggc cgtggagagc accgggactg ccaaggcgga ggccgagtcc<br>cgtgcggagg cagcccggat tgagggagaa gggtccgtgc tgcaggccaa gctaaaagca<br>caggccttgg ccattgaaac ggaggctgag ctccagaggg tccagaaggt ccgagagctg<br>gaactggtct atgcccgggc ccagctggag ctggaggtga gcaaggctca gcagctggct<br>gaggtggagg tgaagaagtt caagcagatg acagaggcca taggccccag caccatcagg<br>gaccttgctg tggctgggcc tgagatgcag gtaaaactgc tccagtccct gggcctgaaa<br>tcaaccctca tcaccgatgg ctccactccc atcaacctct tcaacacagc ctttgggctg<br>ctggggatgg ggcccgaggg tcagcccctg ggcagaaggg tggccagtgg gcccagcctc<br>ggggagggga tatcccccca gtctgctcag gcccctcaag ctcctggaga caaccacgtg<br>gtgcctgtac tgcgctaa |
| Rat CP-MVP<br>SEQ ID NO: 23 |
| Met Ala Gly Cys Gly Cys Pro Cys Gly Cys Gly Ala Met Ala Thr Glu<br>Glu Ala Ile Ile Arg Ile Pro Pro Tyr His Tyr Ile His Val Leu Asp<br>Gln Asn Ser Asn Val Ser Arg Val Glu Val Gly Pro Lys Thr Tyr Ile<br>Arg Gln Asp Asn Glu Arg Val Leu Phe Ala Pro Val Arg Met Val Thr<br>Val Pro Pro Arg His Tyr Cys Ile Val Ala Asn Pro Val Ser Arg Asp<br>Thr Gln Ser Ser Val Leu Phe Asp Ile Thr Gly Gln Val Arg Leu Arg<br>His Ala Asp Gln Glu Ile Arg Leu Ala Gln Asp Pro Phe Pro Leu Tyr<br>Pro Gly Glu Val Leu Glu Lys Asp Ile Thr Pro Leu Gln Val Val Leu<br>Pro Asn Thr Ala Leu His Leu Lys Ala Leu Leu Asp Phe Glu Asp Lys<br>Asn Gly Asp Lys Val Met Ala Gly Asp Glu Trp Leu Phe Glu Gly Pro<br>Gly Thr Tyr Ile Pro Gln Lys Glu Val Glu Val Val Glu Ile Ile Gln<br>Ala Thr Val Ile Lys Gln Asn Gln Ala Leu Arg Leu Arg Ala Arg Lys<br>Glu Cys Phe Asp Arg Glu Gly Lys Gly Arg Val Thr Gly Glu Glu Trp<br>Leu Val Arg Ser Val Gly Ala Tyr Leu Pro Ala Val Phe Glu Glu Val<br>Lue Asp Leu Val Asp Ala Val Ile Leu Thr Glu Lys Thr Ala Leu His<br>Leu Arg Ala Leu Gln Asn Phe Arg Asp Leu Arg Gly Val Leu His Arg<br>Thr Gly Glu Glu Trp Leu Val Thr Val Gln Asp Thr Glu Ala His Val<br>Pro Asp Val Tyr Glu Glu Val Leu Gly Val Val Pro Ile Thr Thr Leu<br>Gly Pro Arg His Tyr Cys Val Ile Leu Asp Pro Met Gly Pro Asp Gly<br>Lys Asn Gln Leu Gly Gln Lys Arg Val Val Lys Gly Glu Lys Ser Phe<br>Phe Leu Gln Pro Gly Glu Arg Leu Glu Arg Gly Ile Gln Asp Val Tyr<br>Val Leu Ser Glu Gln Gln Gly Leu Leu Leu Lys Ala Leu Gln Pro Leu<br>Glu Glu Gly Glu Ser Glu Glu Lys Val Ser His Gln Ala Gly Asp Cys<br>Trp Leu Ile Arg Gly Pro Leu Glu Tyr Val Pro Ser Ala Lys Val Glu<br>Val Val Glu Glu Arg Gln Ala Ile Pro Leu Asp Gln Asn Glu Gly Ile<br>Tyr Val Gln Asp Val Lys Thr Gly Lys Val Arg Ala Val Ile Gly Ser<br>Thr Tyr Met Leu Thr Gln Asp Glu Val Leu Trp Glu Lys Glu Leu Pro<br>Ser Gly Val Glu Glu Leu Leu Asn Leu Gly His Asp Pro Leu Ala Asp<br>Arg Gly Gln Lys Gly Thr Ala Lys Pro Leu Gln Pro Ser Ala Pro Arg<br>Asn Lys Thr Arg Val Val Ser Tyr Arg Val Pro His Asn Ala Ala Val<br>Gln Val Tyr Asp Tyr Arg Ala Lys Arg Ala Arg Val Val Phe Gly Pro<br>Glu Leu Val Thr Leu Asp Pro Glu Glu Gln Phe Thr Val Leu Ser Leu<br>Ser Ala Gly Arg Pro Lys Arg Pro His Ala Arg Arg Ala Leu Cys Leu<br>Leu Leu Gly Pro Asp Phe Phe Thr Asp Val Ile Thr Ile Glu Thr Ala<br>Asp His Ala Arg Leu Gln Leu Gln Leu Ala Tyr Asn Trp His Phe Glu<br>Leu Lys Asn Arg Asn Asp Pro Ala Glu Ala Ala Lys Leu Phe Ser Val<br>Pro Asp Phe Val Gly Asp Ala Cys Lys Ala Ile Ala Ser Arg Val Arg<br>Gly Ala Val Ala Ser Val Thr Phe Asp Asp Phe His Lys Asn Ser Ala<br>Arg Ile Ile Arg Met Ala Val Phe Gly Phe Glu Met Ser Glu Asp Thr<br>Gly Pro Asp Gly Thr Leu Leu Pro Lys Ala Arg Asp Gln Ala Val Phe |

TABLE 1-continued

| Sequences |
| --- |

Pro Gln Asn Gly Leu Val Val Ser Ser Val Asp Val Gln Ser Val Glu
Pro Val Asp Gln Arg Thr Arg Asp Ala Leu Gln Arg Ser Val Gln Leu
Ala Ile Glu Ile Thr Thr Asn Ser Gln Glu Ala Ala Ala Lys His Glu
Ala Gln Arg Leu Glu Gln Glu Ala Arg Gly Arg Leu Glu Arg Gln Lys
Ile Leu Asp Gln Ser Glu Ala Glu Lys Ala Arg Lys Glu Leu Leu Glu
Leu Glu Ala Met Ser Met Ala Val Glu Ser Thr Gly Asn Ala Lys Ala
Glu Ala Glu Ser Arg Ala Glu Ala Ala Arg Ile Glu Gly Glu Gly Ser
Val Leu Gln Ala Lys Leu Lys Ala Gln Ala Leu Ala Ile Glu Thr Glu
Ala Glu Leu Glu Arg Val Lys Lys Val Arg Glu Met Glu Leu Ile Tyr
Ala Arg Ala Gln Leu Glu Leu Glu Val Ser Lys Ala Gln Gln Leu Ala
Asn Val Glu Ala Lys Lys Phe Lys Glu Met Thr Glu Ala Leu Gly Pro
Gly Thr Ile Arg Asp Leu Ala Val Ala Gly Pro Glu Met Gln Val Lys
Leu Leu Gln Ser Leu Gly Leu Lys Ser Thr Leu Ile Thr Asp Gly Ser
Ser Pro Ile Asn Leu Phe Ser Thr Ala Phe Gly Leu Leu Gly Leu Gly
Ser Asp Gly Gln Pro Pro Ala Gln Lys

Rat CP-MVP cDNA

SEQ ID NO: 24 atggcaggct gcggttgtcc atgcggttgt ggcgccatgg caactgaaga ggccatcatc
cgcatccccc cataccacta catccatgtg ctggaccaga acagtaatgt gtcccgtgtg
gaggttggac caaagaccta catccggcag gacaatgaga gggtactgtt tgccccagtt
cgcatggtga ccgtcccccc acgccactac tgcatagtgg ccaaccctgt gtcccgggac
acccagagtt ctgtgttatt tgacatcaca ggacaagtcc gactccggca cgctgaccag
gagatccgac tagcccagga ccccttcccc ctgtatccag ggggaggtgct ggaaaaggac
atcaccccac tgcaggtggt tctgcccaac acagcactgc atcttaaggc gttgctggac
tttgaggata agaatggaga caaggtcatg gcaggagacg agtggctatt tgagggacct
ggcacctaca tcccacagaa ggaagtggaa gtcgtggaga tcattcaggc cacagtcatc
aaacagaacc aagcactgcg gctaagggcc cgaaaggagt gctttgaccg ggagggcaag
gggcgcgtga caggtgagga gtggctggtc cgatccgtgg gggcttacct cccagctgtc
tttgaagagg tgctggatct ggtggatgct gtgatcctta cagaaaagac tgccctgcac
ctccgggctc tgcagaactt cagggacctt cggggagtgc tccaccgcac cggggaggaa
tggttagtga cagtgcagga cacagaagcc catgttccag atgtctatga ggaggtgctt
ggggtagtac ccatcaccac cctgggacct cgacactact gtgtcattct tgacccaatg
ggaccagacg gcaagaacca gctgggacaa aagcgtgttg tcaagggaga gaagtccttt
ttcctccagc caggagagag gctggagcga ggcatccagg atgtgtatgt gctgtcagag
cagcaggggc tgctactgaa ggcactgcag cccctggagg agggagagag cgaggagaag
gtctcccatc aggccggaga ctgctggctc atccgtgggc ccctggagta tgtgccatct
gcaaaagtgg aggtggtgga ggagcgtcag gctatccctc tggaccaaaa tgagggcatc
tatgtgcagg atgtcaagac ggggaaggtg cgggctgtga ttggaagcac ctacatgctg
actcaggatg aagtcctgtg ggaaaaggag ctgccttctg ggtggagga gctgctgaac
ttggggcatg accctctggc agacaggggt cagaagggca cagccaagcc ccttcagccc
tcagctccaa ggaacaagac ccgagtggtc agctaccgtg tcccgcacaa tgcagcggtg
caggtctatg actacagagc caagagagcc cgtgtggtct ttgggcccga gctagtgaca
ctggatcctg aggagcagtt cacagtattg tccctttctg ccgggcgacc caagcgtcct
catgcccgcc gtgcactctg cctactgctg ggacctgatt tctttactga tgtcatcacc
atcgaaactg cagatcatgc caggttgcag ctgcagcttg cctacaactg gcactttgaa
ctgaagaacc ggaatgaccc tgcagaggca gccaagcttt tctccgtgcc tgacttcgtg
ggtgacgcct gcaaggccat tgcatcccga gtccgggggg ctgtagcctc tgtcaccttt
gatgacttcc ataaaaactc agcccggatc attcgaatgg ctgtttttgg ctttgagatg
tctgaagaca caggtcctga tggcacactc ctgcccaagg ctcgagacca ggcagtcttt
ccccaaaacg ggctggtagt cagcagtgtg gatgtgcagt cagtggagcc cgtggaccag
aggacccggg atgcccttca gcgcagcgtt cagctggcca tcgaaattac caccaactcc
caggaggcag cagccaagca cgaggctcag agactggaac aggaagcccg tggtcggctt
gagaggcaga agatcttgga ccagtcagaa gctgaaaaag cccgcaagga actcttggag
cttgaggcta tgagcatggc tgtggagagc acgggtaatg ccaaagcaga ggctgagtcc
cgtgcagagg cagcgaggat cgaaggagaa ggctctgtgc tgcaggccaa gctcaaggca
caggcgctag ccattgagac ggaggctgag ttggagcgag taaagaaagt acgagagatg
gaactgatct atgcccgggc ccagttggag ctggaggtga gcaaggcgca gcagcttgcc
aatgtggagg caaagaagtt caaggagatg acagaggcac tgggccccgg caccatcagg
gacctggctg tggccgggcc agagatgcag gtgaaacttc tccagtccct gggcctgaaa
tccactctca tcaccgatgg ctcgtctccc atcaacctct tcagcacagc cttcgggttg
ctggggctgg ggtctgatgg tcagccgcca gcacagaagt ga Human TEP1, Genbank #AAC51107

SEQ ID NO: 25

Met Glu Lys Leu His Gly His Val Ser Ala His Pro Asp Ile Leu Ser
Leu Glu Asn Arg Cys Leu Ala Met Leu Pro Asp Leu Gln Pro Leu Glu
Lys Leu His Gln His Val Ser Thr His Ser Asp Ile Leu Ser Leu Lys
Asn Gln Cys Leu Ala Thr Leu Pro Asp Leu Lys Thr Met Glu Lys Pro
His Gly Tyr Val Ser Ala His Pro Asp Ile Leu Ser Leu Glu Asn Gln
Cys Leu Ala Thr Leu Ser Asp Leu Lys Thr Met Glu Lys Pro His Gly
His Val Ser Ala His Pro Asp Ile Leu Ser Leu Glu Asn Arg Cys Leu
Ala Thr Leu Pro Ser Leu Lys Ser Thr Val Ser Ala Ser Pro Leu Phe
Gln Ser Leu Gln Ile Ser His Met Thr Gln Ala Asp Leu Tyr Arg Val
Asn Asn Ser Asn Cys Leu Leu Ser Glu Pro Pro Ser Trp Arg Ala Gln
His Phe Ser Lys Gly Leu Asp Leu Ser Thr Cys Pro Ile Ala Leu Lys
Ser Ile Ser Ala Thr Glu Thr Ala Gln Glu Ala Thr Leu Gly Arg Trp
Phe Asp Ser Glu Glu Lys Lys Gly Ala Glu Thr Gln Met Pro Ser Tyr

TABLE 1-continued

| Sequences |
|---|
| Ser Leu Ser Leu Gly Glu Glu Glu Glu Val Glu Asp Leu Ala Val Lys |
| Leu Thr Ser Gly Asp Ser Glu Ser His Pro Glu Pro Thr Asp His Val |
| Leu Gln Glu Lys Lys Met Ala Leu Leu Ser Leu Leu Cys Ser Thr Leu |
| Val Ser Glu Val Asn Met Asn Asn Thr Ser Asp Pro Thr Leu Ala Ala |
| Ile Phe Glu Ile Cys Arg Glu Leu Ala Leu Leu Glu Pro Glu Phe Ile |
| Leu Lys Ala Ser Leu Tyr Ala Arg Gln Gln Leu Asn Val Arg Asn Val |
| Ala Asn Asn Ile Leu Ala Ile Ala Ala Phe Leu Pro Ala Cys Arg Pro |
| His Leu Arg Arg Tyr Phe Cys Ala Ile Val Gln Leu Pro Ser Asp Trp |
| Ile Gln Val Ala Glu Leu Tyr Gln Ser Leu Ala Glu Gly Asp Lys Asn |
| Lys Leu Val Pro Leu Pro Ala Cys Leu Arg Thr Ala Met Thr Asp Lys |
| Phe Ala Gln Phe Asp Glu Tyr Gln Leu Ala Lys Tyr Asn Pro Arg Lys |
| His Arg Ala Lys Arg His Pro Arg Arg Pro Pro Arg Ser Pro Gly Met |
| Glu Pro Pro Phe Ser His Arg Cys Phe Pro Arg Tyr Ile Gly Phe Leu |
| Arg Glu Glu Gln Arg Lys Phe Glu Lys Ala Gly Asp Thr Val Ser Glu |
| Lys Lys Asn Pro Pro Arg Phe Thr Leu Lys Lys Leu Val Gln Arg Leu |
| His Ile His Lys Pro Ala Gln His Val Gln Ala Leu Leu Gly Tyr Arg |
| Tyr Pro Ser Asn Leu Gln Leu Phe Ser Arg Ser Arg Leu Pro Gly Pro |
| Trp Asp Ser Ser Arg Ala Gly Lys Arg Met Lys Leu Ser Arg Pro Glu |
| Thr Trp Glu Arg Glu Leu Ser Leu Arg Gly Asn Lys Ala Ser Val Trp |
| Glu Glu Leu Ile Glu Asn Gly Lys Leu Pro Phe Met Ala Met Leu Arg |
| Asn Leu Cys Asn Leu Leu Arg Val Gly Ile Ser Ser Arg His His Glu |
| Leu Ile Leu Gln Arg Leu Gln His Gly Lys Ser Val Ile His Ser Arg |
| Gln Phe Pro Phe Arg Phe Leu Asn Ala His Asp Ala Ile Asp Ala Leu |
| Glu Ala Gln Leu Arg Asn Gln Ala Leu Pro Phe Pro Ser Asn Ile Thr |
| Leu Met Arg Arg Ile Leu Thr Arg Asn Glu Lys Asn Arg Pro Arg Arg |
| Arg Phe Leu Cys His Leu Ser Arg Gln Gln Leu Arg Met Ala Met Arg |
| Ile Pro Val Leu Tyr Glu Gln Leu Lys Arg Glu Lys Leu Arg Val His |
| Lys Ala Arg Gln Trp Lys Tyr Asp Gly Glu Met Leu Asn Arg Tyr Arg |
| Gln Ala Leu Glu Thr Ala Val Asn Leu Ser Val Lys His Ser Leu Pro |
| Leu Leu Pro Gly Arg Thr Val Leu Val Tyr Leu Thr Asp Ala Asn Ala |
| Asp Arg Leu Cys Pro Lys Ser Asn Pro Gln Gly Pro Pro Leu Asn Tyr |
| Ala Leu Leu Leu Ile Gly Met Met Ile Thr Arg Ala Glu Gln Val Asp |
| Val Val Leu Cys Gly Gly Asp Thr Leu Lys Thr Ala Val Leu Lys Ala |
| Glu Glu Gly Ile Leu Lys Thr Ala Ile Lys Leu Gln Ala Gln Val Gln |
| Glu Phe Asp Glu Asn Asp Gly Trp Ser Leu Asn Thr Phe Gly Lys Tyr |
| Leu Leu Ser Leu Ala Gly Gln Arg Val Pro Val Asp Arg Val Ile Leu |
| Leu Gly Gln Ser Met Asp Asp Gly Met Ile Asn Val Ala Lys Gln Leu |
| Tyr Trp Gln Arg Val Asn Ser Lys Cys Leu Phe Val Gly Ile Leu Leu |
| Arg Arg Val Gln Tyr Leu Ser Thr Asp Leu Asn Pro Asn Asp Val Thr |
| Leu Ser Gly Cys Thr Asp Ala Ile Leu Lys Phe Ile Ala Glu His Gly |
| Ala Ser His Leu Leu Glu His Val Gly Gln Met Asp Lys Ile Phe Lys |
| Ile Pro Pro Pro Pro Gly Lys Thr Gly Val Gln Ser Leu Arg Pro Leu |
| Glu Glu Asp Thr Pro Ser Pro Leu Ala Pro Val Ser Gln Gln Gly Trp |
| Arg Ser Ile Arg Leu Phe Ile Ser Ser Thr Phe Arg Asp Met His Gly |
| Glu Arg Asp Leu Leu Leu Arg Ser Val Leu Pro Ala Leu Gln Ala Arg |
| Ala Ala Pro His Arg Ile Ser Leu His Gly Ile Asp Leu Arg Trp Gly |
| Val Thr Glu Glu Glu Thr Arg Arg Asn Arg Gln Leu Glu Val Cys Leu |
| Gly Glu Val Glu Asn Ala Gln Leu Phe Val Gly Ile Leu Gly Ser Arg |
| Tyr Gly Tyr Ile Pro Pro Ser Tyr Asn Leu Pro Asp His Pro His Phe |
| His Trp Ala Gln Gln Tyr Pro Ser Gly Arg Ser Val Thr Glu Met Glu |
| Val Met Gln Phe Leu Asn Arg Asn Gln Arg Leu Gln Pro Ser Ala |
| Gln Ala Leu Ile Tyr Phe Arg Asp Ser Ser Phe Leu Ser Ser Val |
| Pro Asp Ala Trp Lys Ser Asp Phe Val Ser Glu Ser Glu Glu Ala |
| Ala Cys Arg Ile Ser Glu Leu Lys Ser Tyr Leu Ser Arg Gln Lys |
| Gly Ile Thr Cys Arg Arg Tyr Pro Cys Glu Trp Gly Gly Val Ala |
| Ala Gly Arg Pro Tyr Val Gly Gly Leu Glu Glu Phe Gly Gln Leu |
| Val Leu Gln Asp Val Trp Asn Met Ile Gln Lys Leu Tyr Leu Gln |
| Pro Gly Ala Leu Leu Glu Gln Pro Val Ser Ile Pro Asp Asp Asp |
| Leu Val Gln Ala Thr Phe Gln Gln Leu Gln Lys Pro Pro Ser Pro |
| Ala Arg Pro Arg Leu Leu Gln Asp Thr Val Gln Gln Leu Met Leu |
| Pro His Gly Arg Leu Ser Leu Val Thr Gly Gln Ser Gly Gln Gly |
| Lys Thr Ala Phe Leu Ala Ser Leu Val Ser Ala Leu Gln Ala Pro |
| Asp Gly Ala Lys Val Ala Pro Leu Val Phe Phe His Phe Ser Gly |
| Ala Arg Pro Asp Gln Gly Leu Ala Leu Thr Leu Leu Arg Arg Leu |
| Cys Thr Tyr Leu Arg Gly Gln Leu Lys Glu Pro Gly Ala Leu Pro |
| Ser Thr Tyr Arg Ser Leu Val Trp Glu Leu Gln Gln Arg Leu Leu |
| Pro Lys Ser Ala Glu Ser Leu His Pro Gly Gln Thr Gln Val Leu |
| Ile Ile Asp Gly Ala Asp Arg Leu Val Asp Gln Asn Gly Gln Leu |
| Ile Ser Asp Trp Ile Pro Lys Lys Leu Pro Arg Cys Val His Leu |
| Val Leu Ser Val Ser Ser Asp Ala Gly Leu Gly Glu Thr Leu Glu |
| Gln Ser Gln Gly Ala His Val Leu Ala Leu Gly Pro Leu Glu Ala |
| Ser Ala Arg Ala Arg Leu Val Arg Glu Glu Leu Ala Leu Tyr Gly |
| Lys Arg Leu Glu Glu Ser Pro Phe Asn Asn Gln Met Arg Leu Leu |
| Leu Val Lys Arg Glu Ser Gly Arg Pro Leu Tyr Leu Arg Leu Val |
| Thr Asp His Leu Arg Leu Phe Thr Leu Tyr Glu Gln Val Ser Glu |
| Arg Leu Arg Thr Leu Pro Ala Thr Val Pro Leu Leu Leu Gln His |
| Ile Leu Ser Thr Leu Glu Lys Glu His Gly Pro Asp Val Leu Pro |
| Gln Ala Leu Thr Ala Leu Glu Val Thr Arg Ser Gly Leu Thr Val |

TABLE 1-continued

| Sequences |
|---|
| Asp Gln Leu His Gly Val Leu Ser Val Trp Arg Thr Leu Pro Lys<br>Gly Thr Lys Ser Trp Glu Glu Ala Val Ala Ala Gly Asn Ser Gly<br>Asp Pro Tyr Pro Met Gly Pro Phe Ala Cys Leu Val Gln Ser Leu<br>Arg Ser Leu Leu Gly Glu Gly Pro Leu Glu Arg Pro Gly Ala Arg<br>Leu Cys Leu Pro Asp Gly Pro Leu Arg Thr Ala Ala Lys Arg Cys<br>Tyr Gly Lys Arg Pro Gly Leu Glu Asp Thr Ala His Ile Leu Ile<br>Ala Ala Gln Leu Trp Lys Thr Cys Asp Ala Asp Ala Ser Gly Thr<br>Phe Arg Ser Cys Pro Pro Glu Ala Leu Gly Asp Leu Pro Tyr His<br>Leu Leu Gln Ser Gly Asn Arg Gly Leu Leu Ser Lys Phe Leu Thr<br>Asn Leu His Val Val Ala Ala His Leu Glu Leu Gly Leu Val Ser<br>Arg Leu Leu Glu Ala His Ala Leu Tyr Ala Ser Ser Val Pro Lys<br>Glu Glu Gln Lys Leu Pro Glu Ala Asp Val Ala Val Phe Arg Thr<br>Phe Leu Arg Gln Gln Ala Ser Ile Leu Ser Gln Tyr Pro Arg Leu<br>Leu Pro Gln Gln Ala Ala Asn Gln Pro Leu Asp Ser Pro Leu Cys<br>His Gln Ala Ser Leu Leu Ser Arg Arg Trp His Leu Gln His Thr<br>Leu Arg Trp Leu Asn Lys Pro Arg Thr Met Lys Asn Gln Gln Ser<br>Ser Ser Leu Ser Leu Ala Val Ser Ser Ser Pro Thr Ala Val Ala<br>Phe Ser Thr Asn Gly Gln Arg Ala Ala Val Gly Thr Ala Asn Gly<br>Thr Val Tyr Leu Leu Asp Leu Arg Thr Trp Gln Glu Glu Lys Ser<br>Val Val Ser Gly Cys Asp Gly Ile Ser Ala Cys Leu Phe Leu Ser<br>Asp Asp Thr Leu Phe Leu Thr Ala Phe Asp Gly Leu Leu Glu Leu<br>Trp Asp Leu Gln His Gly Cys Arg Val Leu Gln Thr Lys Ala His<br>Gln Tyr Gln Ile Thr Gly Cys Cys Leu Ser Pro Asp Cys Arg Leu<br>Leu Ala Thr Val Cys Leu Gly Gly Cys Leu Lys Leu Trp Asp Thr<br>Val Arg Gly Gln Leu Ala Phe Gln His Thr Tyr Pro Lys Ser Leu<br>Asn Cys Val Ala Phe His Pro Glu Gly Gln Val Ile Ala Thr Gly<br>Ser Trp Ala Gly Ser Ile Ser Phe Phe Gln Val Asp Gly Leu Lys<br>Val Thr Lys Asp Leu Gly Ala Pro Gly Ala Ser Ile Arg Thr Leu<br>Ala Phe Asn Val Pro Gly Gly Val Val Ala Val Gly Arg Leu Asp<br>Ser Met Val Glu Leu Trp Ala Trp Arg Glu Gly Ala Arg Leu Ala<br>Ala Phe Pro Ala His His Gly Phe Val Ala Ala Ala Leu Phe Leu<br>His Ala Gly Cys Gln Leu Leu Thr Ala Gly Glu Asp Gly Lys Val<br>Gln Val Trp Ser Gly Ser Leu Gly Arg Pro Arg Gly His Leu Gly<br>Ser Leu Ser Leu Ser Pro Ala Leu Ser Val Ala Leu Ser Pro Asp<br>Gly Asp Arg Val Ala Val Gly Tyr Arg Ala Asp Gly Ile Arg Ile<br>Tyr Lys Ile Ser Ser Gly Ser Gln Gly Ala Gln Gly Gln Ala Leu<br>Asp Val Ala Val Ser Ala Leu Ala Trp Leu Ser Pro Lys Val Leu<br>Val Ser Gly Ala Glu Asp Gly Ser Leu Gln Gly Trp Ala Leu Lys<br>Glu Cys Ser Leu Gln Ser Leu Trp Leu Leu Ser Arg Phe Gln Lys<br>Pro Val Leu Gly Leu Ala Thr Ser Gln Glu Leu Leu Ala Ser Ala<br>Ser Glu Asp Phe Thr Val Gln Leu Trp Pro Arg Gln Leu Leu Thr<br>Arg Pro His Lys Ala Glu Asp Phe Pro Cys Gly Thr Glu Leu Arg<br>Gly His Glu Gly Pro Val Ser Cys Cys Ser Phe Ser Thr Asp Gly<br>Gly Ser Leu Ala Thr Gly Gly Arg Asp Arg Ser Leu Leu Cys Trp<br>Asp Val Arg Thr Pro Lys Thr Pro Val Leu Ile His Ser Phe Pro<br>Ala Cys His Arg Asp Trp Val Thr Gly Cys Ala Trp Thr Lys Asp<br>Asn Leu Leu Ile Ser Cys Ser Ser Asp Gly Ser Val Gly Leu Trp<br>Asp Pro Glu Ser Gly Gln Arg Leu Gly Gln Phe Leu Gly His Gln<br>Ser Ala Val Ser Ala Val Ala Ala Val Glu Glu His Val Val Ser<br>Val Ser Arg Asp Gly Thr Leu Lys Val Trp Asp His Gln Gly Val<br>Glu Leu Thr Ser Ile Pro Ala His Ser Gly Pro Ile Ser His Cys<br>Ala Ala Ala Met Glu Pro Arg Ala Ala Gly Gln Pro Gly Ser Glu<br>Leu Leu Val Val Thr Val Gly Leu Asp Gly Ala Thr Arg Leu Trp<br>His Pro Leu Leu Val Cys Gln Thr His Thr Leu Leu Gly His Ser<br>Gly Pro Val Arg Ala Ala Ala Val Ser Glu Thr Ser Gly Leu Met<br>Leu Thr Ala Ser Glu Asp Gly Ser Val Arg Leu Trp Gln Val Pro<br>Lys Glu Ala Asp Asp Thr Cys Ile Pro Arg Ser Ser Ala Ala Val<br>Thr Ala Val Ala Trp Ala Pro Asp Gly Ser Met Ala Val Ser Gly<br>Asn Gln Ala Gly Glu Leu Ile Leu Trp Gln Glu Ala Lys Ala Val<br>Ala Thr Ala Gln Ala Pro Gly His Ile Gly Ala Leu Ile Trp Ser<br>Ser Ala His Thr Phe Phe Val Leu Ser Ala Asp Glu Lys Ile Ser<br>Glu Trp Gln Val Lys Leu Arg Lys Gly Ser Ala Pro Gly Asn Leu<br>Ser Leu His Leu Asn Arg Ile Leu Gln Glu Asp Leu Gly Val Leu<br>Thr Ser Leu Asp Trp Ala Pro Asp Gly His Phe Leu Ile Leu Ala<br>Lys Ala Asp Leu Lys Leu Leu Cys Met Lys Pro Gly Asp Ala Pro<br>Ser Glu Ile Trp Ser Ser Tyr Thr Glu Asn Pro Met Ile Leu Ser<br>Thr His Lys Glu Tyr Gly Ile Phe Val Leu Gln Pro Lys Asp Pro<br>Gly Val Leu Ser Phe Leu Arg Gln Lys Glu Ser Gly Glu Phe Glu<br>Glu Arg Leu Asn Phe Asp Ile Asn Leu Glu Asn Pro Ser Arg Thr<br>Leu Ile Ser Ile Thr Gln Ala Lys Pro Glu Ser Glu Ser Ser Phe<br>Leu Cys Ala Ser Ser Asp Gly Ile Leu Trp Asn Leu Ala Lys Cys<br>Ser Pro Glu Gly Glu Trp Thr Thr Gly Asn Met Trp Gln Lys Lys<br>Ala Asn Thr Pro Glu Thr Gln Thr Pro Gly Thr Asp Pro Ser Thr<br>Cys Arg Glu Ser Asp Ala Ser Met Asp Ser Asp Ala Ser Met Asp<br>Ser Glu Pro Thr Pro His Leu Lys Thr Arg Gln Arg Arg Lys Ile<br>His Ser Gly Ser Val Thr Ala Leu His Val Leu Pro Glu Leu Leu<br>Val Thr Ala Ser Lys Asp Arg Asp Val Lys Leu Trp Glu Arg Pro<br>Ser Met Gln Leu Leu Gly Leu Phe Arg Cys Glu Gly Ser Val Ser |

TABLE 1-continued

Sequences

Cys Leu Glu Pro Trp Leu Gly Ala Asn Ser Thr Leu Gln Leu Ala
Val Gly Asp Val Gln Gly Asn Val Tyr Phe Leu Asn Trp Glu

Human TEP1 cDNA, Genbank #U86136

SEQ ID NO: 26 atggaaaaac tccatgggca tgtgtctgcc catccagaca tcctctcctt ggagaaccgg
tgcctggcta tgctccctga cttacagccc ttggagaaac tacatcagca tgtatctacc
cactcagata tcctctcctt gaagaaccag tgcctagcca cgcttcctga cctgaagacc
atggaaaaac cacatggata tgtgtctgcc cacccagaca tcctctcctt ggagaaccag
tgcctggcca cactttctga cctgaagacc atggagaaac cacatggaca tgtttctgcc
cacccagaca tcctctcctt ggagaaccgg tgcctggcca ccctccctag tctaaagagc
actgtgtctg ccagcccctt gttccagagt ctacagatat ctcacatgac gcaagctgat
ttgtaccgtg tgaacaacag caattgcctg ctctctgagc ctccaagttg gagggctcag
catttctcta agggactaga cctttcaacc tgccctatag ccctgaaatc catctctgcc
acagagacag ctcaggaagc aactttgggt cgttggtttg attcagaaga gaagaaaggg
gcagagaccc aaatgccttc ttatagtctg agcttgggag aggaggagga ggtggaggat
ctggccgtga agctcacctc tggagactct gaatctcatc cagagcctac tgaccatgtc
cttcaggaaa agaagatggc tctactgagc ttgctgtgct ctactctggt ctcagaagta
aacatgaaca atacatctga ccccaccctg gctgccattt ttgaaatctg tcgtgaactt
gccctcctgg agcctgagtt tatcctcaag gcatctttgt atgccaggca gcagctgaac
gtccggaatg tggccaataa catcttggcc attgctgctt tcttgccggc gtgtcgcccc
cacctgcgac gatatttctg tgccattgtc cagctgcctt ctgactggat ccaggtggct
gagctttacc agagcctggc tgagggagat aagaataagc tggtgcccct gcccgcctgt
ctccgtactg ccatgacgga caaatttgcc cagtttgacg agtaccagct ggctaagtac
aaccctcgga agcaccgggc caagagacac ccccgccggc caccccgctc tccagggatg
gagcctccat tttctcacag atgtttttcca aggtacatag ggtttctcag agaagagcag
agaaagtttg agaaggccgg tgatacagtg tcagagaaaa agaatcctcc aaggttcacc
ctgaagaagc tggttcagcg actgcacatc cacaagcctg cccagcacgt tcaagccctg
ctgggttaca gatacccctc caacctacag ctcttttctc gaagtcgcct tcctgggcct
tgggattcta gcagagctgg gaagaggatg aagctgtcta ggccagagac ctgggagcgg
gagctgagcc tacgggggaa caaagcgtcg gtctgggagg aactcattga aaatgggaag
cttcccttca tggccatgct tcggaacctg tgcaacctgc tgcgggttgg aatcagttcc
cgccaccatg agctcattct ccagagactc cagcatggga agtcggtgat ccacagtcgg
cagtttccat tcagatttct taacgcccat gatgccattg atgccctcga ggctcaactc
agaaatcaag cattgccctt tccttcgaat ataacactga tgaggcggat actaactaga
aatgaaaaga accgtcccag gcggaggttt ctttgccacc taagccgtca gcagcttcgt
atggcaatga ggatacctgt gttgtatgag cagctcaaga gggagaagct gagagtacac
aaggccagac agtggaaata tgatggtgag atgctgaaca ggtaccgaca ggccctagag
acagctgtga acctctctgt gaagcacagc ctgcccctgc tgccaggccg cactgtcttg
gtctatctga cagatgctaa tgcagacagg ctctgtccaa agagcaaccc acaagggccc
ccgctgaact atgcactgct gttgattggg atgatgatca cgagggcgga gcaggtggac
gtcgtgctgt gtggaggtga cactctgaag actgcagtgc ttaaggcaga agaaggcatc
ctgaagactg ccatcaagct ccaggctcaa gtccaggagt ttgatgaaaa tgatggatgg
tccctgaata cttttgggaa atacctgctg tctctggctg gccaaagggt tcctgtggac
agggtcatcc tccttggcca aagcatggat gatggaatga taaatgtggc caaacagctt
tactggcagc gtgtgaattc caagtgcctc tttgttggta tcctcctaag aagggtacaa
tacctgtcaa cagatttgaa tcccaatgat gtgacactct caggctgtac tgatgcgata
ctgaagttca ttgcagagca tggggcctcc catcttctgg aacatgtggg ccaaatggac
aaaatattca agattccacc acccccagga aagacagggg tccagtctct ccggccactg
gaagaggaca ctccaagccc cttggctcct gtttcccagc aaggatggcg cagcatccgg
cttttcattt catccacttt ccgagacatg cacggggagc gggacctgct gctgaggtct
gtgctgccag cactgcaggc ccgagcggcc cctcaccgta tcagccttca cggaatcgac
ctccgctggg gcgtcactga ggaggagacc cgtaggaaca gacaactgga agtgtgcctt
ggggaggtgg agaacgcaca gctgtttgtg gggattctgg gctcccgtta tggatacatt
ccccccagct acaaccttcc tgaccatcca cacttccact gggcccagca gtacccttca
gggcgctctg tgacagagat ggaggtgatg cagttcctga accggaacca acgtctgcag
ccctctgccc aagctctcat ctacttccgg gattccagct tcctcagctc tgtgccagat
gcctggaaat ctgactttgt ttctgagtct gaagaggccg catgtcggat ctcagaactg
aagagctacc taagcagaca gaaagggata acctgccgca gatacccctg tgagtggggg
ggtgtggcag ctggccggcc ctatgttggc gggctggagg agtttgggca gttggttctg
caggatgtat ggaatatgat ccagaagctc tacctgcagc ctggggccct gctggagcag
ccagtgtcca tcccagacga tgacttggtc caggccacct tccagcagct gcagaagcca
ccgagtcctg cccggccacg ccttcttcag gacacagtgc aacagctgat gctgccccac
ggaaggctga gcctggtgac ggggcagtca ggacagggca agacagcctt cctggcatct
cttgtgtcag ccctgcaggc tcctgatggg gccaaggtgg caccattagt cttcttccac
ttttctgggg ctcgtcctga ccagggtctt gccctcactc tgctcagacg cctctgtacc
tatctgcgtg gccaactaaa agagccaggt gccctcccca gcacctaccg aagcctggtg
tgggagctgc agcagaggct gctgcccaag tctgctgagt ccctgcatcc tggccagacc
caggtcctga tcatcgatgg ggctgatagg ttagtggacc agaatgggca gctgatttca
gactggatcc caaagaagct tccccggtgt gtacacctgg tgctgagtgt gtctagtgat
gcaggcctag gggagaccct tgagcagagc cagggtgccc acgtgctggc cttggggcct
ctggaggcct ctgctcgggc ccggctggtg agagaggagc tggccctgta cgggaagcgg
ctggaggagt caccatttaa caaccagatg cgactgctgc tggtgaagcg ggaatcaggc
cggccgctct acctgcgctt ggtcaccgat cacctgaggc tcttcacgct gtatgagcag
gtgtctgaga gactccggac cctgcctgcc actgtccccc tgctgctgca gcacatcctg
agcacactgg agaaggagca cgggcctgat gtccttcccc aggccttgac tgccctagaa
gtcacacgga gtggtttgac tgtggaccag ctgcacggag tgctgagtgt gtggcggaca
ctaccgaagg ggactaagag ctgggaagaa gcagtggctg ctggtaacag tggagacccc TABLE 1-continued

| Sequences |
|---|
| taccccatgg gcccgtttgc ctgcctcgtc cagagtctgc gcagtttgct aggggagggc<br>cctctggagc gccctggtgc ccggctgtgc ctccctgatg ggcccctgag aacagcagct<br>aaacgttgct atgggaagag gccagggcta gaggacacgg cacacatcct cattgcagct<br>cagctctgga agacatgtga cgctgatgcc tcaggcacct tccgaagttg ccctcctgag<br>gctctgggag acctgcctta ccacctgctc cagagcggga accgtggact tctttcgaag<br>ttccttacca acctccatgt ggtggctgca cacttggaat tgggtctggt ctctcggctc<br>ttggaggccc atgccctcta tgcttcttca gtccccaaag aggaacaaaa gctccccgag<br>gctgacgttg cagtgtttcg caccttcctg aggcagcagg cttcaatcct cagccagtac<br>ccccggctcc tgccccagca ggcagccaac cagcccctgg actcacctct ttgccaccaa<br>gcctcgctgc tctcccggag atggcacctc caacacacac tacgatggct taataaaccc<br>cggaccatga aaaatcagca aagctccagc ctgtctctgg cagtttcctc atcccctact<br>gctgtggcct tctccaccaa tggcaaaga gcagctgtgg gcactgccaa tgggacagtt<br>tacctgttgg acctgagaac ttggcaggag gagaagtctg tggtgagtgg ctgtgatgga<br>atctctgctt gtttgttcct ctccgatgat acactctttc ttactgcctt cgacgggctc<br>ctggagctct gggacctgca gcatggttgt cgggtgctgc agactaaggc tcaccagtac<br>caaatcactg gctgctgcct gagcccagac tgccggctgc tagccaccgt gtgcttggga<br>ggatgcctaa agctgtggga cacagtccgt gggcagctgg ccttccagca cacctacccc<br>aagtccctga actgtgttgc cttccaccca gaggggcagg taatagccac aggcagctgg<br>gctggcagca tcagcttctt ccaggtggat gggctcaaag tcaccaagga cctgggggca<br>cccggagcct ctatccgtac cttggccttc aatgtgcctg ggggggttgt ggctgtgggc<br>cggctggaca gtatggtgga gctgtgggcc tggcgagaag ggcacggctc ggctgccttc<br>cctgcccacc atggctttgt tgctgctgcg cttttcctgc atgcgggttg ccagttactg<br>acggctggag aggatggcaa ggttcaggtg tggtcagggt ctctgggtcg gccccgtggg<br>cacctgggtt ccctttctct ctctcctgcc ctctctgtgg cactcagccc agatggtgat<br>cgggtggctg ttggatatcg agcggatggc attaggatct acaaaatctc ttcaggttcc<br>cagggggctc agggtcaggc actggatgtg gcagtgtccg ccctggcctg gctaagcccc<br>aaggtattgg tgagtggtgc agaagatggg tccttgcagg gctgggcact caaggaatgc<br>tcccttcagt ccctctggct cctgtccaga ttccagaagc ctgtgctagg actggccact<br>tcccaggagc tcttggcttc tgcctcagag gatttcacag tgcagctgtg gccaaggcag<br>ctgctgacgc ggccacacaa ggcagaagac tttccctgtg gcactgagct gcggggacat<br>gagggccctg tgagctgctg tagtttcagc actgatggag gcagcctggc caccgggggc<br>cgggatcgga gtctcctctg ctgggacgtg aggacaccca aaacccctgt tttgatccac<br>tccttccctg cctgtcaccg tgactgggtc actggctgtg cctggaccaa agataaccta<br>ctgatatcct gctccagtga tggctctgtg gggctctggg acccagagtc aggacagcgg<br>cttggtcagt tcctgggtca tcagagtgct gtgagcgctg tggcagctgt ggaggagcac<br>gtggtgtctg tgagccggga tgggaccttg aaagtgtggg accatcaagg cgtggagctg<br>accagcatcc ctgctcactc aggacccatt agccactgtg cagctgccat ggagccccgt<br>gcagctggac agcctgggtc agagcttctg gtggtaaccg tcgggctaga tggggccaca<br>cggttatggc atccactctt ggtgtgccaa acccacaccc tcctgggaca cagcggccca<br>gtccgtgctg ctgctgtttc agaaacctca ggcctcatgc tgaccgcctc tgaggatggt<br>tctgtacggc tctggcaggt tcctaaggaa gcagatgaca catgtatacc aaggagttct<br>gcagccgtca ctgctgtggc ttgggcacca gatggttcca tggcagtatc tggaaatcaa<br>gctggggaac taatcttgtg gcaggaagct aaggctgtgg ccacagcaca ggctccaggc<br>cacattggtg ctctgatctg gtcctcggca cacacctttt ttgtcctcag tgctgatgag<br>aaaatcagcg agtggcaagt gaaactgcgg aagggttcgg cacccggaaa tttgagtctt<br>cacctgaacc gaattctaca ggaggactta ggggtgctga caagtctgga ttgggctcct<br>gatggtcact ttctcatctt ggccaaagca gatttgaagt tactttgcat gaagccaggg<br>gatgctccat ctgaaatctg gagcagctat acagaaaatc ctatgatatt gtccacccac<br>aaggagtatg gcatatttgt cctgcagccc aaggatcctg gagttctttc tttcttgagg<br>caaaaggaat caggagagtt tgaagagagg ctgaactttg atataaactt agagaatcct<br>agtaggaccc taatatcgat aactcaagcc aaacctgaat ctgagtcctc atttttgtgt<br>gccagctctg atgggatcct atggaacctg gccaaatgca gcccagaagg agaatggacc<br>acaggtaaca tgtggcagaa aaaagcaaac actccagaaa cccaaactcc agggacagac<br>ccatctacct gcagggaatc tgatgccagc atggatagtg atgccagcat ggatagtgag<br>ccaacaccac atctaaagac acggcagcgt agaaagattc actcgggctc tgtcacagcc<br>ctccatgtgc tacctgagtt gctggtgaca gcttcgaagg acagagatgt taagctatgg<br>gagagaccca gtatgcagct gctgggcctg ttccgatgcg aagggtcagt gagctgcctg<br>gaaccttggc tgggcgctaa ctccaccctg cagcttgccg tgggagacgt gcagggcaat<br>gtgtactttc tgaattggga atga<br><br>Rat TEP1, Genbank #AAB51690<br>SEQ ID NO: 27<br><br>Met Glu Lys Leu Cys Gly Tyr Val Pro Val His Pro Asp Ile Leu Ser<br>Leu Lys Asn Arg Cys Leu Thr Met Leu Ser Asp Ile Gln Pro Leu Glu<br>Lys Ile His Gly Gln Arg Ser Val Asn Pro Asp Ile Leu Ser Leu Glu<br>Asn Arg Cys Leu Thr Leu Leu Pro Asp Leu Gln Pro Met Glu Lys Ile<br>His Gly Gln Arg Ser Val His Pro Asp Ile Leu Ser Ser Glu Asn Arg<br>Cys Leu Thr Leu Leu Pro Asp Leu Gln Ser Leu Glu Lys Leu Cys Gly<br>His Met Ser Ser His Pro Asp Val Leu Ser Leu Glu Asn Arg Cys Leu<br>Ala Thr Leu Pro Thr Val Lys Arg Thr Val Ser Ser Gly Pro Leu Leu<br>Gln Cys Leu His Arg Ser His Thr Ala Gln Ala Asp Leu Arg Asp Pro<br>Asn Phe Arg Asn Cys Leu Phe Pro Glu Pro Pro Thr Ile Glu Ala Pro<br>Cys Phe Leu Lys Glu Leu Asp Leu Pro Thr Gly Pro Arg Ala Leu Lys<br>Ser Met Ser Ala Thr Ala Arg Val Gln Glu Val Ala Leu Gly Gln Arg<br>Cys Val Ser Glu Gly Lys Glu Leu Gln Glu Glu Lys Glu Ser Ala Glu<br>Val Pro Met Pro Leu Tyr Ser Leu Ser Leu Gly Gly Glu Glu Glu Glu<br>Val Val Gly Ala Pro Val Leu Lys Leu Thr Ser Gly Asp Ser Asp Ser<br>His Pro Glu Thr Thr Asp Gln Ile Leu Gln Glu Lys Lys Met Ala Leu |

TABLE 1-continued

| Sequences |
|---|
| Leu Thr Leu Leu Cys Ser Ala Met Ala Ser Ser Val Asn Val Lys Asp |
| Ala Ser Asp Pro Thr Arg Ala Ser Ile His Glu Val Cys Ser Ala Leu |
| Ala Pro Leu Glu Pro Glu Phe Ile Leu Lys Ala Ser Leu Tyr Ala Arg |
| Gln Gln Leu Asn Leu Arg Asp Ile Ala Asn Ile Val Leu Ala Val Ala |
| Ala Leu Leu Pro Ala Cys Arg Pro His Val Arg Arg Tyr Tyr Ser Ala |
| Ile Val His Leu Pro Ser Asp Trp Ile Gln Val Ala Glu Phe Tyr Gln |
| Ser Leu Ala Glu Gly Asp Glu Lys Lys Leu Val Pro Leu Pro Ala Cys |
| Leu Arg Ala Ala Met Thr Asp Lys Phe Ala Gln Phe Asp Glu Tyr Gln |
| Leu Ala Lys Tyr Asn Pro Arg Lys His Arg Ser Lys Thr Arg Ser Arg |
| Gln Pro Pro Arg Pro Gln Arg Thr Lys Pro Pro Phe Ser Glu Ser Gly |
| Lys Cys Phe Pro Lys Ser Val Trp Pro Leu Lys Asn Glu Gln Ile Ser |
| Phe Glu Ala Ala Tyr Asn Ala Val Ser Glu Lys Lys Arg Leu Pro Arg |
| Phe Thr Leu Lys Lys Leu Val Glu Gln Leu His Ile His Glu Pro Ala |
| Gln His Val Gln Ala Leu Leu Gly Tyr Arg Tyr Pro Ser Thr Leu Glu |
| Leu Phe Ser Arg Ser His Leu Pro Gly Pro Trp Asp Ser Ser Arg Ala |
| Gly Gln Arg Met Lys Leu Gln Arg Pro Glu Thr Trp Glu Arg Glu Leu |
| Ser Leu Arg Gly Asn Arg Ala Ser Val Trp Glu Glu Leu Ile Asp Asn |
| Gly Lys Leu Pro Phe Met Ala Met Leu Arg Asn Leu Cys Asn Leu Leu |
| Arg Thr Gly Ile Ser Ala His His His Glu Leu Val Leu Gln Arg Leu |
| Gln His Glu Lys Ser Val Ile His Ser Arg Gln Phe Pro Phe Arg Phe |
| Leu Asn Ala His Asp Ser Leu Asp Arg Leu Glu Ala Gln Leu Arg Ser |
| Lys Ala Ser Pro Phe Pro Ser Asn Thr Thr Leu Met Lys Arg Ile Met |
| Ile Arg Asn Ser Lys Lys Ile Lys Arg Pro Ala Asn Pro Arg Tyr Leu |
| Cys Thr Leu Thr Gln Arg Gln Leu Arg Ala Ala Met Ala Ile Pro Val |
| Met Tyr Glu His Leu Lys Arg Glu Lys Leu Arg Leu His Lys Ala Arg |
| Gln Trp Thr Cys Asp Leu Glu Leu Leu Glu Arg Tyr Arg Gln Ala Leu |
| Glu Thr Ala Val Asn Ile Ser Val Lys His Asn Leu Pro Pro Leu Pro |
| Gly Arg Thr Leu Leu Val Tyr Leu Thr Asp Ala Asn Ala Asn Arg Leu |
| Cys Pro Lys Ser His Leu Gln Gly Pro Pro Leu Asn Tyr Val Leu Leu |
| Leu Ile Gly Met Met Met Ala Arg Ala Glu Gln Thr Thr Val Trp Leu |
| Cys Gly Thr Gly Thr Val Lys Thr Pro Val Leu Thr Ala Asp Glu Gly |
| Ile Leu Lys Thr Ala Ile Lys Leu Gln Ala Gln Val Gln Glu Leu Glu |
| Glu Asn Asp Glu Trp Pro Leu Glu Thr Phe Glu Lys Tyr Leu Leu Ser |
| Leu Ala Val Arg Arg Thr Pro Ile Asp Arg Val Ile Leu Phe Gly Gln |
| Arg Met Asp Thr Glu Leu Leu Asn Val Ala Lys Gln Ile Ile Trp Gln |
| His Val Asn Ser Lys Cys Leu Phe Val Ser Val Leu Leu Arg Lys Met |
| Gln Tyr Met Ser Pro Asn Leu Asn Pro Asn Asp Val Thr Leu Ser Gly |
| Cys Thr Asp Gly Ile Leu Lys Phe Ile Ala Glu His Gly Ala Ser Arg |
| Leu Leu Glu His Val Gly Gln Leu Asp Lys Ile Phe Lys Ile Pro Pro |
| Pro Pro Gly Lys Thr Lys Val Ser Pro Leu Arg Pro Leu Glu Glu Asn |
| Asn Pro Gly Pro Phe Val Pro Ile Ser Gln His Gly Trp Arg Asn Ile |
| Arg Leu Phe Ile Ser Ser Thr Phe Arg Asp Met His Gly Glu Arg Asp |
| Leu Leu Met Arg Ser Val Leu Pro Ala Leu Gln Ala Arg Ala Phe Pro |
| His Arg Ile Ser Leu His Ala Ile Asp Leu Arg Trp Gly Ile Thr Glu |
| Glu Glu Thr Arg Arg Asn Arg Gln Leu Glu Val Cys Leu Gly Glu Val |
| Glu Asn Ser Gln Leu Phe Val Gly Ile Leu Gly Ser Arg Tyr Gly Tyr |
| Thr Pro Pro Ser Tyr Asp Leu Pro Asp His Pro His Phe His Trp Thr |
| Gln Arg Tyr Pro Ser Gly Arg Ser Val Thr Glu Met Glu Val Met |
| Gln Phe Leu Asn Arg Gly Gln Arg Ser Glu Pro Ser Asp Gln Ala |
| Leu Ile Tyr Phe Arg Asp Pro Gly Phe Leu Ser Ser Val Pro Asp |
| Val Trp Lys Pro Asp Phe Ile Ser Glu Ser Glu Glu Ala Ala His |
| Arg Val Ser Glu Leu Lys Arg Phe Leu Gln Glu Gln Lys Glu Val |
| Thr Cys Arg Arg Tyr Ser Cys Glu Trp Gly Gly Val Ala Ala Gly |
| Arg Pro Tyr Thr Gly Gly Leu Glu Glu Phe Gly Gln Leu Val Leu |
| Gln Asp Val Trp Ser Val Ile Gln Lys Arg Tyr Leu Gln Pro Gly |
| Ala Gln Leu Glu Gln Pro Gly Ser Ile Ser Glu Glu Asp Leu Ile |
| Gln Ala Ser Phe Gln Gln Leu Lys Ser Pro Pro Ser Pro Ala Arg |
| Pro Arg Leu Leu Gln Asp Thr Val Gln Gln Leu Met Leu Pro His |
| Gly Arg Leu Ser Leu Val Ile Gly Gln Ala Gly Gln Gly Lys Thr |
| Ala Phe Leu Ala Ser Leu Val Ser Ala Leu Lys Val Pro Asp Gln |
| Pro Asn Val Ala Pro Phe Val Phe Phe His Phe Ser Ala Ala Arg |
| Pro Asp Gln Cys Leu Ala Phe Asn Leu Leu Arg Arg Leu Cys Thr |
| His Leu His Gln Lys Leu Gly Glu Pro Ser Ala Leu Pro Ser Thr |
| Tyr Arg Gly Leu Val Trp Glu Leu Gln Gln Lys Leu Leu Leu Lys |
| Ser Ala Gln Trp Leu Gln Pro Gly Gln Thr Leu Val Leu Ile Ile |
| Asp Gly Ala Asp Lys Leu Val Asp His Asn Gly Gln Leu Ile Ser |
| Asp Trp Ile Pro Lys Ser Leu Pro Arg Arg Val His Leu Val Leu |
| Ser Val Ser Ser Asp Ser Gly Leu Gly Glu Thr Leu Gln Gln Ser |
| Gln Ser Ala Tyr Val Val Ala Leu Gly Ser Leu Val Pro Ser Ser |
| Arg Ala Gln Leu Val Arg Glu Glu Leu Ala Leu Tyr Gly Lys Arg |
| Leu Glu Glu Ser Pro Phe Asn Asn Gln Met Arg Leu Leu Leu Ala |
| Lys Gln Gly Ser Ser Leu Pro Leu Tyr Leu His Leu Val Thr Asp |
| Tyr Leu Arg Leu Phe Thr Leu Tyr Glu Gln Val Ser Glu Arg Leu |
| Arg Thr Leu Pro Ala Thr Leu Pro Leu Leu Leu Gln His Ile Leu |
| Ser Thr Leu Glu Gln Glu His Gly His Asn Val Leu Pro Gln Ala |
| Leu Thr Ala Leu Glu Val Thr His Ser Gly Leu Thr Val Asp Gln |
| Leu His Ala Val Leu Ser Thr Trp Leu Thr Leu Pro Lys Glu Thr |
| Lys Ser Trp Glu Glu Ala Val Ala Ala Ser His Ser Gly Asn Leu |

TABLE 1-continued

| Sequences |
|---|
| Tyr Pro Leu Ala Pro Phe Ala Tyr Leu Val Gln Ser Leu Arg Ser |
| Leu Leu Gly Glu Gly Pro Val Glu Arg Pro Gly Ala Arg Leu Cys |
| Leu Ser Asp Gly Pro Leu Arg Thr Ala Val Lys Arg Arg Tyr Gly |
| Lys Arg Leu Gly Leu Glu Lys Thr Ala His Val Leu Ile Ala Ala |
| His Leu Trp Lys Met Cys Asp Pro Asp Ala Ser Gly Thr Phe Arg |
| Ser Cys Pro Pro Glu Ala Leu Lys Asp Leu Pro Tyr His Leu Leu |
| Gln Ser Gly Asn His Gly Leu Leu Ala Lys Phe Leu Thr Asn Leu |
| His Val Val Ala Ala Tyr Leu Glu Val Gly Leu Val Pro Asp Leu |
| Leu Glu Ala Tyr Glu Leu Tyr Ala Ser Ser Lys Pro Glu Val Asn |
| Gln Lys Leu Pro Glu Ala Asp Val Ala Val Phe His Asn Phe Leu |
| Lys Gln Gln Ala Ser Leu Leu Thr Gln Tyr Pro Leu Leu Leu Leu |
| Gln Gln Ala Ala Ser Gln Pro Glu Glu Ser Pro Val Cys Cys Gln |
| Ala Pro Leu Leu Thr Gln Arg Trp His Asn Gln Cys Ile Leu Lys |
| Trp Ile Asn Lys Pro Gln Thr Leu Lys Gly Gln Gln Ser Leu Ser |
| Leu Pro Ile Ser Ser Ser Pro Thr Ala Val Ala Phe Ser Pro Asn |
| Gly Gln Arg Ala Ala Val Gly Thr Ala Gly Gly Thr Ile Tyr Leu |
| Leu Asn Leu Arg Thr Trp Gln Glu Glu Lys Ala Leu Val Ser Gly |
| Cys Asp Gly Ile Ser Ser Phe Ala Phe Leu Ser Asp Thr Ala Leu |
| Phe Leu Thr Thr Phe Asp Gly Leu Leu Glu Leu Trp Asp Leu Gln |
| His Gly Cys Trp Val Phe Gln Thr Lys Ala His Gln Tyr Gln Ile |
| Thr Gly Cys Cys Leu Ser Pro Asp Arg Arg Leu Leu Ala Thr Val |
| Cys Leu Gly Gly Tyr Val Lys Leu Trp Asp Thr Val Gln Gly Gln |
| Leu Ala Phe Gln Tyr Thr His Pro Lys Ser Leu Asn Cys Ile Thr |
| Phe His Pro Glu Gly Gln Val Val Ala Thr Gly Asn Trp Ser Gly |
| Ile Val Thr Phe Phe Gln Ala Asp Gly Leu Lys Val Thr Lys Glu |
| Leu Gly Gly Pro Gly Pro Ser Val Arg Thr Leu Ala Phe Ser Ala |
| Pro Gly Lys Val Val Ala Leu Gly Arg Ile Asp Gly Thr Val Glu |
| Leu Trp Ala Trp Gln Glu Gly Thr Arg Leu Ala Ala Phe Pro Ala |
| Gln Cys Gly Gly Val Ser Thr Val Leu Phe Leu His Ala Gly Gly |
| Arg Phe Leu Thr Ala Gly Glu Asp Gly Lys Ala Gln Leu Trp Ser |
| Gly Phe Leu Gly Arg Pro Arg Gly Cys Leu Gly Ser Leu Tyr Leu |
| Ser Pro Ala Leu Ser Val Ala Leu Asn Pro Asp Gly Asp Gln Val |
| Ala Val Gly Tyr Arg Gly Asp Gly Ile Lys Ile Tyr Arg Ile Ser |
| Ser Gly Pro Gln Glu Ala Gln Cys Gln Glu Leu Asn Val Ala Val |
| Ser Ala Leu Val Trp Leu Ser Pro Ser Val Leu Val Ser Gly Ala |
| Glu Asp Gly Ser Leu His Gly Trp Met Leu Arg Arg Asn Ser Leu |
| Gln Ser Leu Trp Leu Ser Ser Val Cys Gln Lys Pro Val Leu Gly |
| Leu Ala Ala Ser Gln Glu Phe Leu Ala Ser Ala Ser Glu Asp Phe |
| Thr Val Arg Leu Trp Pro Arg Gln Leu Leu Thr Gln Pro His Ala |
| Val Glu Glu Leu Pro Cys Ala Ala Glu Leu Arg Gly His Glu Gly |
| Pro Val Cys Cys Cys Ser Phe Ser Pro Asp Gly Arg Ile Leu Ala |
| Thr Ala Gly Arg Asp Arg Asn Leu Leu Cys Trp Asp Val Lys Val |
| Ala Gln Ala Pro Leu Leu Ile His Thr Phe Ser Ser Cys His Arg |
| Asp Trp Ile Thr Gly Cys Thr Trp Thr Lys Asp Asn Ile Leu Ile |
| Ser Cys Ser Ser Asp Gly Ser Val Gly Leu Trp Asn Pro Glu Ala |
| Gly Gln Gln Leu Gly Gln Phe Pro Gly His Gln Ser Ala Val Ser |
| Ala Val Val Ala Val Glu Glu His Ile Val Ser Val Ser Arg Asp |
| Gly Thr Leu Lys Val Trp Asp Arg Gln Gly Val Glu Leu Thr Ser |
| Ile Pro Ala His Ser Gly Pro Ile Ser Gln Cys Ala Ala Ala Leu |
| Glu Pro Arg Pro Ala Gly Gln Pro Gly Ser Glu Leu Met Val Val |
| Thr Val Gly Leu Asp Gly Ala Thr Lys Leu Trp His Pro Leu Leu |
| Val Cys Gln Ile His Thr Leu Gln Gly His Ser Gly Pro Val Thr |
| Ala Ala Ala Ala Ser Glu Ala Ser Gly Leu Leu Leu Thr Ser Asp |
| Asn Ser Ser Val Arg Leu Trp Gln Ile Pro Lys Glu Ala Asp Asp |
| Thr Cys Lys Pro Arg Ser Ser Ala Val Ile Thr Ala Val Ala Trp |
| Ala Pro Asp Gly Ser Leu Val Val Ser Gly Asn Glu Ala Gly Glu |
| Leu Thr Leu Trp Gln Lys Ala Gln Ala Val Ala Thr Ala Arg Ala |
| Pro Gly Arg Val Ser Asp Leu Ile Trp Cys Ser Ala Asn Ala Phe |
| Phe Val Leu Ser Ala Asn Glu Asn Val Ser Glu Trp Gln Val Glu |
| Leu Arg Lys Gly Ser Thr Cys Thr Asn Phe Arg Leu Tyr Leu Lys |
| Arg Val Leu Gln Glu Asp Leu Gly Val Leu Thr Gly Met Ala Leu |
| Ala Pro Asp Gly Gln Ser Leu Ile Leu Met Lys Glu Asp Val Glu |
| Leu Leu Gln Met Lys Pro Gly Ser Thr Pro Ser Ser Ile Cys Arg |
| Arg Tyr Ala Val His Ser Ser Ile Leu Cys Thr Ser Lys Asp Tyr |
| Gly Leu Phe Tyr Leu Gln Gln Gly Asn Ser Gly Ser Leu Ser Ile |
| Leu Glu Gln Glu Glu Ser Gly Lys Phe Glu Lys Thr Leu Asp Phe |
| Asn Leu Asn Leu Asn Asn Pro Asn Gly Ser Pro Val Ser Ile Thr |
| Gln Ala Glu Pro Glu Ser Gly Ser Ser Leu Leu Cys Ala Thr Ser |
| Asp Gly Met Leu Trp Asn Leu Ser Glu Cys Thr Pro Glu Gly Glu |
| Trp Val Val Asp Asn Ile Trp Gln Lys Lys Ser Arg Asn Pro Lys |
| Ser Arg Thr Pro Gly Thr Asp Ser Ser Pro Gly Leu Phe Cys Met |
| Asp Ser Trp Val Glu Pro Thr His Leu Lys Ala Arg Gln Cys Lys |
| Lys Ile His Leu Gly Ser Val Thr Ala Leu His Val Leu Pro Gly |
| Leu Leu Val Thr Ala Ser Glu Asp Arg Asp Val Lys Leu Trp Glu |
| Arg Pro Ser Met Gln Leu Leu Gly Leu Phe Arg Cys Glu Gly Pro |
| Val Ser Cys Leu Glu Pro Trp Met Glu Pro Ser Ser Pro Leu Gln |
| Leu Ala Val Gly Asp Ala Gln Gly Asn Leu Tyr Phe Leu Ser Trp |
| Glu |

TABLE 1-continued

| Sequences |
|---|

Rat TEP1 cDNA, Genbank #U89282

SEQ ID NO: 28 atggagaaac tctgtggtta tgtgcctgtc cacccagaca tcctctcctt gaagaatcgg
tgcctgacca tgctctctga catccaaccc ctggagaaaa tacatggaca gagatctgtc
aacccagaca tcctgtcctt ggagaaccgg tgcctgacct tgctccctga tctccagccc
atggagaaaa tacatggaca gagatctgtc cacccagaca tcctctcctc agagaaccgg
tgtctgacct tgctccctga cctccagtcc ctggagaagc tatgtggaca tatgtctagt
cacccagacg tcctctcttt ggagaaccga tgtcttgcta ccctcccgac tgtaaagaga
actgtttcga gtggcccctt gctccagtgt cttcacagat ctcatacggc acaagctgat
ctgcgtgacc cgaactttcg caactgcctg ttccctgagc ctcctaccat agaggctcca
tgtttcttga aggaactaga ccttccaact ggacccaggg ccctgaaatc catgtctgct
acagctcgag ttcaggaagt agctttgggt cagcggtgcg tctcagaagg aaaggaattg
caggaagaaa aagaaagcgc agaagtcccg atgcctttgt acagtctaag cttgggggga
gaagaagaag aagtggtggg ggcaccggtc ctaaaactca catctggaga ctctgactct
caccctgaaa ccactgacca gatcctgcag gagaagaaga tggctctctt gaccttgctg
tgctcagcta tggcctcaag tgtgaatgtg aaagatgcct ccgatcctac ccgggcatct
atccatgaag tctgcagtgc gctggccccc ttggaacctg agttcatcct taaggcatct
ttgtatgcta ggcagcagct taacctccgg gacatagcca atatagtgtt ggccgtggct
gccctcttgc cagcctgccg cccccatgta cgacggtatt actctgccat tgttcacctg
ccttcagact ggatccaggt agccgagttc taccagagcc tggcagaagg ggatgagaag
aagttggtgc ccctgcctgc ctgcctccgt gctgccatga ctgacaaatt tgcccagttt
gatgagtacc agctagcgaa gtacaaccca cggaaacacc gatccaagac acgttcccgc
cagccacccc gccctcaaag gacaaaacct ccattttcag agagtgggaa atgttttcca
aagagcgttt ggccccttaa aaacgaacag atttcgttcg aagcagctta taatgcagtg
tcagagaaga aaaggctacc aaggttcact ctgaagaagt tggtagagca actgcatatc
catgagcctg cgcagcatgt ccaggccctg ctgggctaca ggtacccatc caccctagag
ctcttttctc ggagtcatct ccctgggcca tgggactcta gcagggctgg gcaacggatg
aagctccaaa ggccagagac ctgggagcgg gagctgagct tacgtggaaa cagagcttct
gtgtgggagg aactcataga caatgggaaa ctccccttca tggccatgct ccggaacctg
tgtaacctgc tgcggactgg gatcagtgcc caccaccatg aactcgttct ccagagactc
cagcatgaga aatctgtgat tcacagtcgg cagtttccat tcagattcct taatgctcac
gactctctcg atagactcga ggctcagctc agaagtaaag catcgccctt cccttccaat
acaacattga tgaagcggat aatgattaga aactcaaaaa aaatcaagag acctgccaac
ccgaggtacc tgtgcaccct gacgcagcgg cagcttcggg cggcaatggc tatcccggtg
atgtatgagc atctcaagcg ggagaaactg aggctgcaca aggccagaca gtggacctgt
gaccttgagt tgctggagcg gtatcgccag gccctggaaa cggccgtgaa catctctgta
aagcacaacc tacccccgct gccaggccga accctcttgg tctatctcac agatgcaaat
gccaacagac tttgtcccaa gagtcacttg caagggcctc ccctgaacta tgtgctgctg
ttgatcggga tgatgatggc tcgggcggag cagacgacag tttggctgtg tgggacagga
actgtgaaga caccagtact tacagccgac gaaggtatcc tgaagactgc catcaaactt
caggctcaag tccaggagtt agaagaaaat gatgagtggc cctggaaaac ttttgagaag
tacctgctat ctctggctgt gcgaaggacc cctattgaca gggtcatcct gttcggccaa
aggatggata cggagctgct gaatgtagcc aaacagatta tctggcagca tgtgaattcc
aagtgcctct tcgtcagtgt cctcctacgg aaaatgcagt acatgtcacc aaatttgaat
cccaatgatg tgacgctctc gggctgcact gacgggatcc tgaagttcat tgcggagcat
ggagcctctc gtcttctgga acatgtgggc caactagata agatattcaa gatccctcca
cccccaggaa agacaaaggt ctcacctctc cggccgctgg aggagaacaa ccctggtccc
ttcgttccta tttcccagca tggatggcgc aacatccggc ttttcatttc gtccactttc
cgagacatgc atggggaacg agacttgctg atgcgatctg ttctgccagc gctgcaggcc
cgagcgttcc cccaccgcat cagccttcac gccattgacc tgcgctgggg aatcacggag
gaagagaccc gcaggaacag acaactggaa gtgtgccttg gggaggtgga gaactctcag
ctgttcgtgg ggatcctggg ctcccgctat ggctatactc cccccagcta tgatctgcct
gaccaccccc actttcactg gacccagcga tacccttcgg ggcgctctgt aacagagatg
gaggtgatgc agttcctgaa ccgtggccaa cgctcggaac cctctgacca agctctcatc
tacttccgag atcctggttt ccttagctct gtgccagatg tctggaaacc tgactttatt
tccgagtcag aagaggctgc acatcgggtc tcagaactga agagattcct acaggaacag
aaagaggtta cctgccgcag gtactcctgt gaatggggag gcgtagcagc cggccggccc
tatactgggg gcctggagga gtttggacag ttggttctcc aagatgtgtg gagcgtgatc
cagaagcgtt acctgcagcc tgggggccag ttggagcagc caggatccat ctcagaagag
gatttgatcc aggccagctt tcagcagctg aagagcccac cgagtcccgc acggccacgc
cttcttcagg ataccgtgca acagctgatg ctgccccacg ggaggctgag cctagtgatt
gggcaggcag gacagggaaa gactgccttc ctggcatccc ttgtgtcggc cctgaaggtt
cccgaccagc ccaatgtggc cccgttcgtt ttcttccact tttcagcagc ccgccctgac
cagtgtcttg ctttcaacct cctcagacgc ctctgtaccc atctgcatca aaaactggga
gagccgagcg ctctccccag cacttacaga ggcctggtgt gggaactgca gcagaagctg
ctcctcaaat ctgcccagtg gctgcaacca ggccagactt tggtccttat tatcgacggg
gcagataagt tggtggacca taatggacag ctgatttcag actggatccc caagtctctt
ccgcggcgag tacacctggt gctgagtgtg tctagtgact caggcctggg agagaccctt
cagcaaagtc agagtgctta tgtggtggcc ttggggtctt tggtcccgtc ttcaagggct
cagcttgtga gagaagagct agcactgtat gggaaacggc tggaggagtc acctttttaac
aaccagatgc ggctgctgct ggcaaagcag gggtcaagcc tgccactgta cctgcacctc
gtcactgact acctgaggct tttcacactg tacgaacagg tgtctgagag acttcgaacc
ctgcccgcca ctctcccact gctgctgcag cacatcctga gcaccttgga gcaagagcat
ggccataacg tccttcctca agctttgact gcccttgagg tcacgcacag tggtctgact
gtggaccagc tgcatgcagt cctgagcacg tggttgactt tgcccaagga gactaagagc
tgggaagagg cagtggctgc cagtcacagt ggaaacctct acccccttggc tccatttgcc
taccttgtcc agagtctacg cagtttacta ggcgagggcc ccgtggagcg ccctggcgcc TABLE 1-continued

| Sequences |
| --- |
| cgtctctgcc tctctgatgg gcctctgagg acagcagtta aacgtcgcta tgggaaaagg<br>ctggggctag agaagactgc gcatgtcctc attgcagctc acctctggaa gatgtgtgac<br>cctgatgcct caggcacctt ccgaagttgc cctcccgagg ctctgaaaga tttaccttac<br>cacctgctcc agagcgggaa ccatggtctc cttgcaaagt tccttaccaa cctccatgtg<br>gtggctgcat atctggaagt gggtctagtc ccggacctct tggaggctta cgagctctat<br>gcttcttcaa agcctgaagt gaaccagaag ctcccggagg cagatgttgc tgtattccac<br>aacttcctga aacaacaggc ttcactcctt acccagtatc ctttgctcct gctccagcag<br>gcagctagcc agcctgaaga gtcacctgtt tgctgccagg cccccctgct cacccagcgg<br>tggcacaacc agtgcatact gaaatggatt aataaacccc agaccttgaa gggtcagcaa<br>agcttgtctc tgccaatttc ctcatcccca actgctgtgg ccttctctcc taatgggcaa<br>agagcagctg tggggactgc tggtgggaca atttacctgt tgaacttgag aacctggcag<br>gaggagaagg ctctggtgag tggctgtgat gggatttcct ctttcgcgtt cctgtcagac<br>actgctcttt tccttaccac cttcgatggg ctcctggagc tttgggacct gcaacatggt<br>tgttgggtgt tccagaccaa ggcccaccag taccaaatca ctggctgctg cctgagccca<br>gaccgccgcc tgctggccac cgtgtgtttg ggaggatacg taaagctgtg ggacacagtc<br>cagggccagc tggctttcca gtacacccat cccaagtctc taaactgcat caccttccac<br>ccagaggggc aggtggtagc cacaggcaac tggtctggca tcgtgacctt cttccaggca<br>gatggactca aagtcaccaa ggaactaggg ggcccaggac cctctgttcg tacgctggca<br>ttcagtgcac ccgggaaggt tgtggctcta ggccggatag atgggacagt ggagctgtgg<br>gcctggcaag agggcacacg gctggcagcc ttccctgcac agtgtggcgg tgtctccacc<br>gttcttttct tgcatgctgg aggccggttc ctgacggctg gggaagatgg caaggctcag<br>ttatggtcag gatttcttgg ccggcccagg ggttgcctgg gctctcttta tctttctcct<br>gcgctctctg tggctctcaa cccagacggt gaccaggtgg ctgttgggta ccgaggagat<br>ggcattaaaa tctacagaat ttcttcaggt ccccaggagg ctcaatgcaa agagctaaat<br>gtggcggtgt ctgcactggt ctggctgagt cccagcgtct tggtgagtgg tgcagaagat<br>ggctccctgc atggctggat gctcaggaga aactcccttc agtccctgtg gctgtcatcc<br>gtgtgccaga agcctgtgct ggggctggct gcctcccagg agttcttggc ttctgcctca<br>gaggacttca cggtgcgact gtggccaaga cagctgctga cacagccaca tgcagtagaa<br>gagttgccct gtgcggctga actccgggga cacgaggggc cggtgtgctg ctgtagcttc<br>agcccggatg gacgcatctt ggccacagcg ggcagggatc ggaatctcct ctgctgggac<br>gtcaaggtag cccaagcccc tctcctgatt cacacgttct cgtcctgtca tcgagactgg<br>atcactggct gtacgtggac caaagacaac atcctgatct cctgctctag tgatggctct<br>gtgggactct ggaacccaga ggcaggacag caacttggcc agttcccagg tcaccagagt<br>gccgtgagcg ctgtggttgc tgtggaggaa cacattgtat ctgtgagtcg ggatgggacc<br>ttgaaagtgt gggaccgtca gggtgtggag ctgaccagca tccctgccca ttccggaccc<br>attagccagt gtgcggctgc tctggaaccc cgtccagctg gacagcctgg atcagagctt<br>atggtggtga ctgttggact ggatggggcc acaaagctgt ggcatcccct gttggtgtgc<br>caaatacata ccctgcaggg acacagtggt ccagtcacag ctgctgctgc ttcagaggcc<br>tcaggcctcc tgctgacctc agacaatagc tctgtacgac tctggcagat ccctaaggaa<br>gcagatgata cctgcaaacc taggagttct gcggtcatca ccgctgtggc gtgggcacca<br>gatggttctc tggtggtgtc tggaaatgaa gctggggaac taacgctgtg gcagaaagcg<br>caggctgtgg ctacggcacg ggctccaggc cgcgtcagtg acctgatctg gtgctccgca<br>aatgcattct ttgttctcag tgctaatgaa aatgtcagtg agtggcaagt ggaactgagg<br>aaaggttcaa catgcaccaa tttcagactt tatctgaaga gagttctgca ggaggacttg<br>ggagtcttga caggtatggc cctggcgcct gacggccagt ctctcatttt gatgaaagag<br>gatgtagaat tgctacagat gaagcccggg tctactccat cttcgatctg caggaggtat<br>gcagtgcatt cttctatact gtgcaccagc aaagactatg gcctgtttta cctgcagcag<br>ggaaactctg gatctctttc tatcttggag caggaggagt cagggaagtt tgaaaagacc<br>ctggacttca atctgaactt aaataatcct aatgggtccc cagtatcaat cactcaggct<br>gaacctgagt ctgggtcctc gcttttgtgt gctacctctg atgggatgct gtggaactta<br>tctgagtgta ccccagaagg agagtgggtc gtagataaca tctggcagaa aaaatcaaga<br>aaccctaaaa gtcgaactcc ggggacagat tcgtccccag gcttattctg catggatagc<br>tgggtagaac ccacacattt aaaggcacgg cagtgtaaaa agattcactt gggctctgtc<br>acggccctcc atgtgctgcc cggattgctg gtgactgctt cagaggacag agatgttaag<br>ctgtgggaga gacccagtat gcagctgctc ggcttgttcc gatgtgaagg gccggtgagc<br>tgtctggaac cttggatgga gcccagctct cccctgcagc ttgctgtggg agatgcacaa<br>ggaaacttgt attttctatc ttgggaatga |
| Human vRNA, Genbank #AF045143<br>SEQ ID NO: 29<br>ggcuggcuuu agcucagcgg uuacuucgac aguucuuuaa uugaaacaag caaccugucu<br>ggguuguucg agacccgcgg gcgcucucca gcuuuuuu |
| Human vRNA, Genbank #AF045144<br>SEQ ID NO: 30<br>ggcuggcuuu agcucagcgg uuacuucgag uacauuguaa ccaccucucu gggugguucg<br>agacccgcgg gugcuuucca gcucuuuu |
| Human vRNA, Genbank #AF045145<br>SEQ ID NO: 31<br>ggcuggcuuu agcucagcgg uuacuucgcg ugucaucaaa ccaccucucu ggguuguucg<br>agacccgcgg gcgcucucca gccccucuu |
| Rat vRNA, Genbank #Z1171<br>SEQ ID NO: 32<br>ggccagcuuu agcucagcgg uuacuucgac gugcuccagu uugagcaggc uauguaacgu<br>ggucgguucg agcaacacaa ccagccgcuu gccuaucugg ugagugguug guucgagacc<br>cgcgggcgcu cucuggcccu uuu |

TABLE 1-continued

| Sequences |
|---|
| Human IL-2 cDNA Sequence, Genbank #BC070338.1, coding sequence: 48-509<br>SEQ ID NO: 33<br>1 atcactctct ttaatcacta ctcacagtaa cctcaactcc tgccacaatg tacaggatgc<br>61 aactcctgtc ttgcattgca ctaagtcttg cacttgtcac aaacagtgca cctacttcaa<br>121 gttctacaaa gaaaacacag ctacaactgg agcatttact gctggattta cagatgattt<br>181 tgaatggaat taataattac aagaatccca aactcaccag gatgctcaca tttaagtttt<br>241 acatgcccaa gaaggccaca gaactgaaac atcttcagtg tctagaagaa gaactcaaac<br>301 ctctggagga agtgctaaat ttagctcaaa gcaaaaactt tcacttaaga cccagggact<br>361 taatcagcaa tatcaacgta atagttctgg aactaaaggg atctgaaaca acattcatgt<br>421 gtgaatatgc tgatgagaca gcaaccattg tagaatttct gaacagatgg attacctttt<br>481 gtcaaagcat catctcaaca ctgacttgat aattaagtgc ttcccactta aaacgtatca<br>541 ggccttctat ttatttaaat atttaaattt tatatttatt gttgaatgta tggtttgcta<br>601 cctattgtaa ctattattct taatcttaaa actataaata tggatctttt atgattcttt<br>661 ttgtaagccc taggggctct aaaatggttt cacttattta tcccaaaata tttattatta<br>721 tgttgaatgt taaatatagt atctatgtag attggttagt aaaactattt aataaatttg<br>781 ataaatataa aaaaaaaaaa aaaaaaaaaa aaaa |
| Human IL-2 Protein sequence, Genbank #AAH70338.1<br>SEQ ID NO: 34<br>MYRMQLLSCIALSLALVTNSAPTSSSTKKTQLQLEHLLLDLQMILNGINNYKNPKLTRMLTFKFYMPKKA<br>TELKHLQCLEEELKPLEEVLNLAQSKNFHLRFRDLISNINVIVLELKGSETTFMCEYADETATIVEFLNR<br>WITFCQSIISTLT |
| Human IL-7 cDNA sequence, Genbank #J04156.1; coding sequence: 385-918<br>SEQ ID NO: 35<br>1 gaattcctct ggtcctcatc caggtgcgcg ggaagcaggt gcccaggaga gaggggataa<br>61 tgaagattcc atgctgatga tcccaaagat tgaacctgca gaccaagcgc aaagtagaaa<br>121 ctgaaagtac actgctggcg gatcctacgg aagttatgga aaaggcaaag cgcagagcca<br>181 cgccgtagtg tgtgccgccc cccttgggat ggatgaaact gcagtcgcgg cgtgggtaag<br>241 aggaaccagc tgcagagatc accctgccca acacagactc ggcaactccg cggaagacca<br>301 gggtcctggg agtgactatg ggcggtgaga gcttgctcct gctccagttg cggtcatcat<br>361 gactacgccc gcctcccgca gaccatgttc catgtttctt ttaggtatat ctttggactt<br>421 cctcccctga tccttgttct gttgccagta gcatcatctg attgtgatat tgaaggtaaa<br>481 gatggcaaac aatatgagag tgttctaatg gtcagcatcg atcaattatt ggacagcatg<br>541 aaagaaattg gtagcaattg cctgaataat gaatttaact tttttaaaag acatatctgt<br>601 gatgctaata aggaaggtat gttttattc cgtgctgctc gcaagttgag gcaatttctt<br>661 aaaatgaata gcactggtga ttttgatctc cacttattaa aagtttcaga aggcacaaca<br>721 atactgttga actgcactgg ccaggttaaa ggaagaaaac cagctgccct gggtgaagcc<br>781 caaccaacaa agagtttgga agaaaataaa tctttaaagg aacagaaaaa actgaatgac<br>841 ttgtgtttcc taaagagact attacaagag ataaaaactt gttggaataa aattttgatg<br>901 ggcactaaag aacactgaaa aatatggagt ggcaatatag aaacacgaac tttagctgca<br>961 tcctccaaga atctatctgc ttatgcagtt tttcagagtg gaatgcttcc tagaagttac<br>1021 tgaatgcacc atggtcaaaa cggattaggg catttgagaa atgcatattg tattactaga<br>1081 agatgaatac aaacaatgga aactgaatgc tccagtcaac aaactatttc ttatatatgt<br>1141 gaacatttat caatcagtat aattctgtac tgatttttgt aagacaatcc atgtaaggta<br>1201 tcagttgcaa taatacttct caaacctgtt taaatatttc aagacattaa atctatgaag<br>1261 tatataatgg tttcaaagat tcaaaattga cattgcttta ctgtcaaaat aattttatgg<br>1321 ctcactatga atctattata ctgtattaag agtgaaaatt gtcttcttct gtgctggaga<br>1381 tgttttagag ttaacaatga tatatggata atgccggtga gaataagaga gtcataaacc<br>1441 ttaagtaagc aacagcataa caaggtccaa gatacctaaa agagatttca agagatttaa<br>1501 ttaatcatga atgtgtaaca cagtgccttc aataaatggt atagcaaatg ttttgacatg<br>1561 aaaaaaggac aatttcaaaa aaataaaat |
| Human IL-7 Protein sequence, Genbank #AAA59156.1<br>SEQ ID NO: 36<br>MFHVSFRYIFGLPPLILVLLPVASSDCDIEGKDGKQYESVLMVSIDQLLDSMKEIGSNCLNNEFNFFKRH<br>ICDANKEGMFLFRAARKLRQFLKMNSTGDFDLHLLKVSEGTTILLNCTGQVKGRKFAALGEAQFTKSLEE<br>NKSLKEQKKLNDLCFLKRLLQEIKTCWNKILMGTKEH |
| Human IL-15 cDNA sequence, Genbank #BC018149.2; coding sequence: 845-1333<br>SEQ ID NO: 37<br>1 actccgggtg gcaggcgccc gggggaatcc cagctgactc gctcactgcc ttcgaagtcc<br>61 ggcgcccccc gggagggaac tgggtggccg caccctcccg gctgcggtgg ctgtcgcccc<br>121 ccaccctgca gccaggactc gatggaggta cagagctcgg cttctttgcc ttgggagggg<br>181 agtggtggtg gttgaaaggg cgatggaatt ttccccgaaa gcctacgccc agggcccctc<br>241 ccagctccag cgttaccctc cggtctatcc tactggccga gctgccccgc cttctcatgg<br>301 ggaaaactta gccgcaactt caatttttgg tttttccttt aatgacactt ctgaggctct<br>361 cctagccatc ctcccgcttc cggaggagcg cagatcgcag gtccctttgc ccctggcgtg<br>421 cgactcccta ctgcgctgcg ctcttacggc gttccaggct gctggctagc gcaaggcggg<br>481 ccgggcaccc cgcgctccgc tgggagggtg agggacgcgc gtctggcggc cccagccaag<br>541 ctgcgggttt ctgagaagac gctgtcccgc agccctgagg gctgagttct gcacccagtc<br>601 aagctcagga aggccaagaa aagaatccat tccaatatat ggccatgtgg ctctttggag<br>661 caatgttcca tcatgttcca tgctgctgac gtcacatgga gcacagaaat caatgttagc<br>721 agatagccag cccatacaag atcgtattgt attgtaggag gcatcgtgga tggatggctg<br>781 ctggaaaccc cttgccatag ccagctcttc ttcaatactt aaggatttac cgtggctttg<br>841 agtaatgaga atttcgaaac cacatttgag aagtatttcc atccagtgct acttgtgttt<br>901 acttctaaac agtcattttc taactgaagc tggcattcat gtcttcattt tgggctgttt |

TABLE 1-continued

Sequences

```
 961 cagtgcaggg cttcctaaaa cagaagccaa ctgggtgaat gtaataagtg atttgaaaaa
1021 aattgaagat cttattcaat ctatgcatat tgatgctact ttatatacgg aaagtgatgt
1081 tcaccccagt tgcaaagtaa cagcaatgaa gtgctttctc ttggagttac aagttatttc
1141 acttgagtcc ggagatgcaa gtattcatga tacagtagaa aatctgatca tcctagcaaa
1201 caacagtttg tcttctaatg ggaatgtaac agaatctgga tgcaaagaat gtgaggaact
1261 ggaggaaaaa aatattaaag aatttttgca gagttttgta catattgtcc aaatgttcat
1321 caacacttct tgattgcaat tgattctttt taaagtgttt ctgttattaa caaacatcac
1381 tctgctgctt agacataaca aaacactcgg catttcaaat gtgctgtcaa aacaagtttt
1441 tctgtcaaga agatgatcag accttggatc agatgaactc ttagaaatga aggcagaaaa
1501 atgtcattga gtaatatagt gactatgaac ttctctcaga cttactttac tcattttttt
1561 aatttattat tgaaattgta catatttgtg gaataatgta aaatgttgaa taaaaatatg
1621 tacaagtgtt gtttttttaag ttgcactgat attttacctc ttattgcaaa atagcatttg
1681 tttaagggtg atagtcaaat tatgtattgg tggggctggg taccaatgct gcaggtcaac
1741 agctatgctg gtaggctcct gcctgtgtgg aaccactgac tactggctct cattgacttc
1801 cttactaagc atagcaaaca gaggaagaat ttgttatcag taagaaaaag aagaactata
1861 tgtgaatcct cttctttaca ctgtaattta gttattgatg tataaagcaa ctgttatgaa
1921 ataaagaaat tgcaataact ggcaaaaaaa aaaaaaaaaa aaaaaaaa
```

Human IL-15 protein sequence, Genbank #AAH18149.1

SEQ ID NO: 38

```
MRISKPHLRSISIQCYLCLLLNSHFLTEAGIHVFILGCFSAGLPKTEANWVNVISDLKKIEDLIQSMHIDATLYTESDVHPSC
KVTAMKCFLLELQVISLESGDASIHDTVENLIILANNSLSSNGNVTESGCKECEELEEKNIKEFLQSFVHIVQMFIN
```

Human IL-12B cDNA Sequence, Genbank #NM_002187.2; coding sequence: 43-1029

SEQ ID NO: 39

```
   1 ctgtttcagg gccattggac tctccgtcct gcccagagca agatgtgtca ccagcagttg
  61 gtcatctctt ggttttccct ggtttttctg gcatctcccc tcgtggccat atgggaactg
 121 aagaaagatg tttatgtcgt agaattggat tggtatccgg atgcccctgg agaaatggtg
 181 gtcctcacct gtgacacccc tgaagaagat ggtatcacct ggaccttgga ccagagcagt
 241 gaggtcttag gctctggcaa aaccctgacc atccaagtca aagagtttgg agatgctggc
 301 cagtacacct gtcacaaagg aggcgaggtt ctaagccatt cgctcctgct gcttcacaaa
 361 aaggaagatg gaatttggtc cactgatatt ttaaaggacc agaaagaacc caaaaataag
 421 acctttctaa gatgcgaggc caagaattat tctggacgtt tcacctgctg gtggctgacg
 481 acaatcagta ctgatttgac attcagtgtc aaaagcagca gaggctcttc tgacccccaa
 541 ggggtgacgt gcggagctgc tacactctct gcagagagag tcagagggga caacaaggag
 601 tatgagtact cagtggagtg ccaggaggac agtgcctgcc cagctgctga ggagagtctg
 661 cccattgagg tcatggtgga tgccgttcac aagctcaagt atgaaaacta caccagcagc
 721 ttcttcatca gggacatcat caaacctgac ccacccaaga acttgcagct gaagccatta
 781 aagaattctc ggcaggtgga ggtcagctgg gagtaccctg acacctggag tactccacat
 841 tcctacttct ccctgacatt ctgcgttcag gtccagggca agagcaagag agaaaagaaa
 901 gatagagtct tcacggacaa gacctcagcc acggtcatct gccgcaaaaa tgccagcatt
 961 agcgtgcggg cccaggaccg ctactatagc tcatcttgga gcgaatgggc atctgtgccc
1021 tgcagttagg ttctgatcca ggatgaaaat ttggaggaaa agtggaagat attaagcaaa
1081 atgtttaaag acacaacgga atagacccaa aaagataatt tctatctgat ttgctttaaa
1141 acgttttttt aggatcacaa tgatatcttt gctgtatttg tatagttaga tgctaaatgc
1201 tcattgaaac aatcagctaa tttatgtata gattttccag ctctcaagtt gccatgggcc
1261 ttcatgctat ttaaatattt aagtaattta tgtatttatt agtatattac tgttatttaa
1321 cgtttgtctg ccaggatgta tggaatgttt catactctta tgacctgatc catcaggatc
1381 agtccctatt atgcaaaatg tgaatttaat tttatttgta ctgacaactt ttcaagcaag
1441 gctgcaagta catcagtttt atgacaatca ggaagaatgc agtgttctga taccagtgcc
1501 atcatacact tgtgatggat gggaacgcaa gagatactta catggaaacc tgacaatgca
1561 aacctgttga gaagatccag gagaacaaga tgctagttcc catgtctgtg aagacttcct
1621 ggagatggtg ttgataaagc aatttagggc cacttacact tctaagcaag tttaatcttt
1681 ggatgcctga attttaaaag ggctagaaaa aaatgattga ccagcctggg aaacataaca
1741 agaccccgtc tctacaaaaa aaatttaaaa ttagccaggc gtggtggctc atgcttgtgg
1801 tcccagctgt tcaggaggat gaggcaggag gatctcttga gcccaggagg tcaaggctat
1861 ggtgagccgt gattgtgcca ctgcatacca gcctaggtga cagaatgaga ccctgtctca
1921 aaaaaaaaaa tgattgaaat taaaattcag ctttagcttc catggcagtc ctcaccccca
1981 cctctctaaa agacacagga ggatgacaca gaaacaccgt aagtgtctgg aaggcaaaaa
2041 gatcttaaga ttcaagagag aggacaagta gttatggcta aggacatgaa attgtcagaa
2101 tggcaggtgg cttcttaaca gccctgtgag aagcagacag atgcaaagaa aatctggaat
2161 ccctttctca ttagcatgaa tgaacctgat acacaattat gaccagaaaa tatggctcca
2221 tgaaggtgct acttttaagt aatgtatgtg cgctctgtaa agtgattaca tttgtttcct
2281 gtttgtttat ttatttattt atttttgcat tctgaggctg aactaataaa aactcttctt
2341 tgtaatc
```

Human IL-12B Protein Sequence, Genbank #NP_002178.2

SEQ ID NO: 40

```
MCHQQLVISWFSLVFLASPLVAIWELKKDVYVVELDWYPDAPGEMVVLTCDTPEEDGITWTLDQSSEVLGSGKT
LTIQVKEFGDAGQYTCHKGGEVLSHSLLLLHKKEDGIWSTDILKDQKEPKNKTFLRCEAKNYSGRFTCWWLTTI
STDLTFSVKSSRGSSDPQGVTCGAATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLTFCVQVQGKSKREKKDRVFTDKTSA
TVICRKNASISVRAQDRYYSSSWSEWASVPCS
```

Human IL-12A cDNA sequence, Genbank #NM_000882.2; coding sequence: 216-977

SEQ ID NO: 41

```
   1 tttcattttg ggccgagctg gaggcggcgg ggccgtcccg gaacggctgc ggccgggcac
  61 cccgggagtt aatccgaaag cgccgcaagc cccgcgggcc ggccgcaccg cacgtgtcac
```

TABLE 1-continued

Sequences

```
 121 cgagaagctg atgtagagag agacacagaa ggagacagaa agcaagagac cagagtcccg
 181 ggaaagtcct gccgcgcctc gggacaatta taaaaatgtg gccccctggg tcagcctccc
 241 agccaccgcc ctcacctgcc gcggccacag gtctgcatcc agcggctcgc cctgtgtccc
 301 tgcagtgccg gctcagcatg tgtccagcgc gcagcctcct ccttgtggct accctggtcc
 361 tcctggacca cctcagtttg gccagaaacc tccccgtggc cactccagac ccaggaatgt
 421 tcccatgcct tcaccactcc caaaacctgc tgagggccgt cagcaacatg ctccagaagg
 481 ccagacaaac tctagaattt taccctgca cttctgaaga gattgatcat gaagatatca
 541 caaaagataa aaccagcaca gtggaggcct gtttaccatt ggaattaacc aagaatgaga
 601 gttgcctaaa ttccagagag acctctttca taactaatgg gagttgcctg gcctccagaa
 661 agacctcttt tatgatggcc ctgtgcctta gtagtattta tgaagacttg aagatgtacc
 721 aggtggagtt caagaccatg aatgcaaagc ttctgatgga tcctaagagg cagatctttc
 781 tagatcaaaa catgctggca gttattgatg agctgatgca ggccctgaat ttcaacagtg
 841 agactgtgcc acaaaaatcc tcccttgaag aaccggattt ttataaaact aaaatcaagc
 901 tctgcatact tcttcatgct ttcagaattc gggcagtgac tattgataga gtgatgagct
 961 atctgaatgc ttcctaaaaa gcgaggtccc tccaaaccgt tgtcattttt ataaaacttt
1021 gaaatgagga aactttgata ggatgtggat taagaactag ggagggggaa agaaggatgg
1081 gactattaca tccacatgat acctctgatc aagtattttt gacatttact gtggataaat
1141 tgtttttaag ttttcatgaa tgaattgcta agaagggaaa atatccatcc tgaaggtgtt
1201 tttcattcac tttaatagaa gggcaaatat ttataagcta tttctgtacc aaagtgtttg
1261 tggaaacaaa catgtaagca taacttattt taaaatattt atttatataa cttggtaatc
1321 atgaaagcat ctgagctaac ttatatttat ttatgttata tttattaaat tatttatcaa
1381 gtgtatttga aaaatatttt taagtgttct aaaaataaaa gtattgaatt aaagtgaaaa
1441 aaaa
```

Human IL-12A Protein sequence, Genbank #NP_000873.2

SEQ ID NO: 42

```
MWPPGSASQPPPSPAAATGLHPAARPVSLQCRLSMCPARSLLLVATLVLLDHLSLARNLPVATPDPGMFPCLHH
SQNLLRAVSNMLQKARQTLEFYPCTSEEIDHEDITKDKTSTVEACLPLELTKNESCLNSRETSFITNGSCLASR
KTSFMMALCLSSIYEDLKMYQVEFKTMNAKLLMDPKRQIFLDQNMLAVIDELMQALNFNSETVPQKSSLEEPDF
YKTKIKLCILLHAFRIRAVTIDRVMSYLNAS
```

Human CSF2 cDNA Sequence, Genbank #BC108724.1; coding sequence: 20-454

SEQ ID NO: 43

```
   1 ggctaaagtt ctctggagga tgtggctgca gagcctgctg ctcttgggca ctgtggcctg
  61 cagcatctct gcacccgccc gctcgcccag ccccagcacg cagccctggg agcatgtgaa
 121 tgccatccag gaggcccggc gtctcctgaa cctgagtaga gacactgctg ctgagatgaa
 181 tgaaacagta gaagtcatct cagaaatgtt tgacctccag gagccgacct gcctacagac
 241 ccgcctggag ctgtacaagc agggcctgcg gggcagcctc accaagctca agggcccctt
 301 gaccatgatg gccagccact acaagcagca ctgccctcca accccggaaa cttcctgtgc
 361 aacccagatt atcacctttg aaagtttcaa agagaacctg aaggactttc tgcttgtcat
 421 cccctttgac tgctgggagc cagtccagga gtgagaccgg ccagatgagg ctggccaagc
 481 cggggagctg ctctctcatg aaacaagagc tagaaactca ggatggtcat cttggaggga
 541 ccaaggggtg ggccacagcc atggtgggag tggcctggac ctgccctggg ccacactgac
 601 cctgatacag gcatggcaga agaatgggaa tattttatac tgacagaaat cagtaatatt
 661 tatatattta tatttttaaa atatttattt atttatttat ttaagttcat attccatatt
 721 tattcaagat gttttaccgt aataattatt attaaaaata tgcttctact tgaaaaaaaa
 781 aaaaaaa
```

Human CSF2 Protein Sequence, Genbank #AAI08725.1

SEQ ID NO: 44

```
MWLQSLLLLGTVACSISAPARSPSPSTQPWEHVNAIQEARRLLNLSRDTAAEMNETVEVISEMFDLQEPTCLQT
RLELYKQGLRGSLTKLKGPLTMMASHYKQHCPPTPETSCATQIITFESFKENLKDFLLVIPFDCWEPVQE
```

Human CXCL9 cDNA Sequence, Genbank #NM_002416.1; coding sequence: 40-417

SEQ ID NO: 45

```
   1 atccaataca ggagtgactt ggaactccat tctatcacta tgaagaaaag tggtgttctt
  61 ttcctcttgg gcatcatctt gctggttctg attggagtgc aaggaacccc agtagtgaga
 121 aagggtcgct gttcctgcat cagcaccaac caagggacta tccacctaca atccttgaaa
 181 gaccttaaac aatttgcccc aagcccttcc tgcgagaaaa ttgaaatcat tgctacactg
 241 aagaatggag ttcaaacatg tctaaaccca gattcagcag atgtgaagga actgattaaa
 301 aagtgggaga aacaggtcag ccaaaagaaa aagcaaaaga atgggaaaaa acatcaaaaa
 361 aagaaagttc tgaaagttcg aaaatctcaa cgttctcgtc aaaagaagac tacataagag
 421 accacttcac caataagtat tctgtgttaa aaatgttcta ttttaattat accgctatca
 481 ttccaaagga ggatggcata taatacaaag gcttattaat ttgactagaa aatttaaaac
 541 attactctga aattgtaact aaagttagaa agttgatttt aagaatccaa acgttaagaa
 601 ttgttaaagg ctatgattgt ctttgttctt ctaccaccca ccagttgaat ttcatcatgc
 661 ttaaggccat gattttagca atacccatgt ctacacagat gttcacccaa ccacatccca
 721 ctcacaacag ctgcctggaa gagcagccct aggcttccac gtactgcagc ctccagagag
 781 tatctgaggc acatgtcagc aagtcctaag cctgttagca tgctggtgag ccaagcagtt
 841 tgaaattgag ctggacctca ccaagctgct gtggccatca acctctgtat ttgaatcagc
 901 ctacaggcct cacacacaat gtgtctgaga gattcatgct gattgttatt gggtatcacc
 961 actggagatc accagtgtgt ggctttcaga gcctcctttc tggctttgga agccatgtga
1021 ttccatcttg cccgctcagg ctgaccactt tatttctttt tgttcccctt tgcttcattc
1081 aagtcagctc ttctccatcc taccacaatg cagtgccttt cttctctcca gtgcacctgt
1141 catatgctct gatttatctg agtcaactcc tttctcatct tgtccccaac accccacaga
1201 agtgctttct tctcccaatt catcctcact cagtccagct tagttcaagt cctgcctctt
1261 aaataaacct ttttggacac acaaattatc ttaaaactcc tgtttcactt ggttcagtac
1321 cacatgggtg aacactcaat ggttaactaa ttcttgggtg tttatcctat ctctccaacc
```

TABLE 1-continued

| Sequences |
|---|

```
1381 agattgtcag ctccttgagg gcaagagcca cagtatattt ccctgtttct tccacagtgc
1441 ctaataatac tgtggaacta ggttttaata atttttaat tgatgttgtt atgggcagga
1501 tggcaaccag accattgtct cagagcaggt gctggctctt tcctggctac tccatgttgg
1561 ctagcctctg gtaacctctt acttattatc ttcaggacac tcactacagg gaccagggat
1621 gatgcaacat ccttgtcttt ttatgacagg atgtttgctc agcttctcca acaataagaa
1681 gcacgtggta aaacacttgc ggatattctg gactgttttt aaaaaatata cagtttaccg
1741 aaaatcatat aatcttacaa tgaaaaggac tttatagatc agccagtgac caaccttttc
1801 ccaaccatac aaaaattcct tttcccgaag gaaaagggct ttctcaataa gcctcagctt
1861 tctaagatct aacaagatag ccaccgagat ccttatcgaa actcatttta ggcaaatatg
1921 agttttattg tccgtttact tgtttcagag tttgtattgt gattatcaat taccacacca
1981 tctcccatga agaaagggaa cggtgaagta ctaagcgcta gaggaagcag ccaagtcggt
2041 tagtggaagc atgattggtg cccagttagc ctctgcagga tgtggaaacc tccttccagg
2101 ggaggttcag tgaattgtgt aggagaggtt gtctgtggcc agaatttaaa cctatactca
2161 ctttcccaaa ttgaatcact gctcacactg ctgatgattt agagtgctgt ccggtggaga
2221 tcccacccga acgtcttatc taatcatgaa actccctagt tccttcatgt aacttccctg
2281 aaaaatctaa gtgtttcata aatttgagag tctgtgaccc acttaccttg catctcacag
2341 gtagacagta tataactaac aaccaaagac tacatattgt cactgacaca cacgttataa
2401 tcatttatca tatatataca tacatgcata cactctcaaa gcaaataatt tttcacttca
2461 aaacagtatt gacttgtata ccttgtaatt tgaaatattt tctttgttaa aatagaatgg
2521 tatcaataaa tagaccatta atcag
```

Human CXCL9 Protein Sequence, Genbank #NP_002407.1

SEQ ID NO: 46

```
MKKSGVLFLLGIILLVLIGVQGTPVVRKGRCSCISTNQGTIHLQSLKDLKQFAPSPSCEKIEIIATLKNGVQTCLNPDSADVK
ELIKKWEKQVSQKKKQKNGKKHQKKKVLKVRKSQRSRQKKTT
```

Human CXCL10 cDNA Sequence, Genbank #NM_001565.2; coding sequence: 71-367

SEQ ID NO: 47

```
   1 gggggagaca ttcctcaatt gcttagacat attctgagcc tacagcagag gaacctccag
  61 tctcagcacc atgaatcaaa ctgccattct gatttgctgc cttatctttc tgactctaag
 121 tggcattcaa ggagtacctc tctctagaac tgtacgctgt acctgcatca gcattagtaa
 181 tcaacctgtt aatccaaggt ctttagaaaa acttgaaatt attcctgcaa gccaattttg
 241 tccacgtgtt gagatcattg ctacaatgaa aaagaagggt gagaagagat gtctgaatcc
 301 agaatcgaag gccatcaaga atttactgaa agcagttagc aaggaaaggt ctaaaagatc
 361 tccttaaaac cagaggggag caaaatcgat gcagtgcttc caaggatgga ccacacagag
 421 gctgcctctc ccatcacttc cctacatgga gtatatgtca agccataatt gttcttagtt
 481 tgcagttaca ctaaaaggtg accaatgatg gtcaccaaat cagctgctac tactcctgta
 541 ggaaggttaa tgttcatcat cctaagctat tcagtaataa ctctaccctg gcactataat
 601 gtaagctcta ctgaggtgct atgttcttag tggatgttct gaccctgctt caaatatttc
 661 cctcaccttt cccatcttcc aagggtacta aggaatcttt ctgctttggg gtttatcaga
 721 attctcagaa tctcaaataa ctaaaaggta tgcaatcaaa tctgcttttt aaagaatgct
 781 ctttacttca tggacttcca ctgccatcct cccaaggggc ccaaattctt tcagtggcta
 841 cctacataca attccaaaca catacaggaa ggtagaaata tctgaaaatg tatgtgtaag
 901 tattcttatt taatgaaaga ctgtacaaag tagaagtctt agatgtatat atttcctata
 961 ttgttttcag tgtacatgga ataacatgta attaagtact atgtatcaat gagtaacagg
1021 aaaattttaa aaatacagat agatatatgc tctgcatgtt acataagata aatgtgctga
1081 atggttttca aaataaaaat gaggtactct cctggaaata ttaagaaaga ctatctaaat
1141 gttgaaagat caaaaggtta ataaagtaat tataactaaa aaaa
```

Human CXCL10 Protein Sequence, Genbank #NP_001556.2

SEQ ID NO: 48

```
MNQTAILICCLIFLTLSGIQGVPLSRTVRCTCISISNQPVNPRSLEKLEIIPASQFCPRVEIIATMKKKGEKRCLNPESKAIK
NLLKAVSKERSKRSP
```

Human IFN-alpha cDNA Sequence, Genbank #J00210.1; coding sequence: 221-790

SEQ ID NO: 49

```
   1 aaaacaaaac atttgagaaa cacggctcta aactcatgta aagagtgcat gaaggaaagc
  61 aaaaacagaa atggaaagtg gcccagaagc attaagaaag tggaaatcag tatgttccct
 121 atttaaggca tttgcaggaa gcaaggcctt cagagaacct agagcccaag gttcagagtc
 181 acccatctca gcaagcccag aagtatctgc aatatctacg atggcctcgc cctttgcttt
 241 actgatggtc ctggtggtgc tcagctgcaa gtcaagctgc tctctgggct gtgatctccc
 301 tgagacccac agcctggata acaggaggac cttgatgctc ctggcacaaa tgagcagaat
 361 ctctccttcc tcctgtctga tggacagaca tgactttgga tttccccagg aggagtttga
 421 tggcaaccag ttccagaagg ctccagccat ctctgtcctc catgagctga tccagcagat
 481 cttcaacctc tttaccacaa aagattcatc tgctgcttgg gatgaggacc tcctagacaa
 541 attctgcacc gaactctacc agcagctgaa tgacttggaa gcctgtgtga tgcaggagga
 601 gagggtggga gaaactcccc tgatgaatgc ggactccatc ttggctgtga agaaatactt
 661 ccgaagaatc actctctatc tgacagagaa gaaatacagc ccttgtgcct gggaggttgt
 721 cagagcagaa atcatgagat ccctctcttt atcaacaaac ttgcaagaaa gattaaggag
 781 gaaggaataa catctggtcc aacatgaaaa caattcttat tgactcatac accaggtcac
 841 gctttcatga attctgtcat ttcaaagact ctcacccctg ctataactat gaccatgctg
 901 ataaactgat ttatctattt aaatatttat ttaactattc ataagattta aattattttt
 961 gttcatataa cgtcatgtgc acctttacac tgtggttagt gtaataaaac atgttcctta
1021 tatttactca atccattatt ttgtgttgtt cattaaactt ttactatagg aacttcctgt
1081 atgtgttcat tctttaatat gaaattccta gcctgactgt gcaacctgat tagagaataa
1141 agggtatatt ttatttgctt atcattatta tatgtaaga
```

TABLE 1-continued

| Sequences |
| --- |

Human IFN-alpha Protein Sequence, Genbank #AAB59403.1
SEQ ID NO: 50
MASPFALLMVLVVLSCKSSCSLGCDLPETHSLDNRRTLMLLAQMSRISPSSCLMDRHDFGFPQEEFDGNQFQKAPAISVLHEL
IQQIFNLFTTKDSSAAWDEDLLDKFCTELYQQLNDLEACVMQEERVGETPLMNADSILAVKKYFRRITLYLTEKKYSPCAWEV
VRAEIMRSLSLSTNLQERLRRKE Human IFN-gamma IEF SSP 5111 cDNA Sequence, Genbank #L07633.1; coding sequence: 93-842
SEQ ID NO: 51
```
  1 gcggagctgg gtgcgagcgc cctaccgctt tcgctttccc ttcgcggtgc ccactccact
 61 ccttgtgcgg cgctaggccc cccgtcccgg tcatggccat gctcagggtc cagcccgagg
121 cccaagccaa ggtggatgtg tttcgtgaag acctctgtac caagacagag aacctgctcg
181 ggagctattt ccccaagaag atttctgagc tggatgcatt tttaaaggag ccagctctca
241 atgaagccaa cttgagcaat ctgaaggccc cattggacat cccagtgcct gatccagtca
301 aggagaaaga gaaagaggag cggaagaaac agcaggagaa ggaagacaag gatgaaaaga
361 agaaggggga ggatgaagac aaaggtcctc cctgtggccc agtgaactgc aatgaaaaga
421 tcgtggtcct tctgcagcgc ttgaagcctg agatcaagga tgtcattgag cagctcaacc
481 tggtcaccac ctggttgcag ctgcagatac ctcggattga ggatggtaac aattttggag
541 tggctgtcca ggagaaggtg tttgagctga tgaccagcct ccacaccaag ctagaaggct
601 tccacactca aatctctaag tatttctctg agcgtggtga tgcagtgact aaagcagcca
661 agcagcccca tgtgggtgat tatcggcagc tggtgcacga gctggatgag gcagagtacc
721 gggacatccg gctgatggtc atggagatcc gcaatgctta tgctgtgtta tatgacatca
781 tcctgaagaa cttcgagaag ctcaagaagc ccaggggaga aacaaaggga atgatctatt
841 gagagccctc tctcccattc tgtgatgagt acagcagaga ccttcctgct tttactggg
901 gactccagat tttccccaaa cttgcttctg ttgagatttt tccctcacct tgcctctcag
961 gcacaataaa tatagttata ccact
```

Human IFN-gamma IEF SSP 5111 Protein Sequence, Genbank #AAA16521.1
SEQ ID NO: 52
MAMLRVQPEAQAKVDVFREDLCTKTENLLGSYFPKKISELDAFLKEPALNEANLSNLKAPLDIPVPDPVKEKEK
EERKKQQEKEDKDEKKKGEDEDKGPPCGPVNCNEKIVVLLQRLKPEIKDVIEQLNLVTTWLQLQIPRIEDGNNF
GVAVQEKVFELMTSLHTKLEGFHTQISKYFSERGDAVTKAAKQPHVGDYRQLVHELDEAEYRDIRLMVMEIRNA
YAVLYDIILKNFEKLKKPRGETKGMIY Human CCL-19 cDNA Sequence, Genbank #BC027968.1; coding sequence: 125-421
SEQ ID NO: 53
```
  1 catcactcac accttgcatt tcacccctgc atcccagtcg ccctgcagcc tcacacagat
 61 cctgcacaca cccagacagc tggcgctcac acattcaccg ttggcctgcc tctgttcacc
121 ctccatggcc ctgctactgg ccctcagcct gctggttctc tggacttccc cagccccaac
181 tctgagtggc accaatgatg ctgaagactg ctgcctgtct gtgacccaga aacccatccc
241 tgggtacatc gtgaggaact tccactacct tctcatcaag gatggctgca gggtgcctgc
301 tgtagtgttc accacactga ggggccgcca gctctgtgca cccccagacc agccctgggt
361 agaacgcatc atccagagac tgcagaggac ctcagccaag atgaagcgcc gcagcagtta
421 acctatgacc gtgcagaggg agcccggagt ccgagtcaag cattgtgaat tattacctaa
481 cctggggaac cgaggaccag aaggaaggac caggcttcca gctcctctgc accagacctg
541 accagccagg acagggcctg gggtgtgtgt gagtgtgagt gtgagcgaga gggtgagtgt
601 ggtcagagta aagctgctcc acccccagat tgcaatgcta ccaataaagc cgcctggtgt
661 ttacaactaa aaaaaaaaaa aaaaaaaaaa aaaa
```

Human CCL-19 Protein Sequence, Genbank #AAH27968.1
SEQ ID NO: 54
ALLLALSLLVLWTSPAPTLSGTNDAEDCCLSVTQKPIPGYIVRNFHYLLIKDGCRVPAVVFTTLRGRQLCAPPDQPWVERIIQ
RLQRTSAKMKRRSS Human CCL-21 cDNA Sequence, Genbank #BC027918.1; coding sequence: 8-412
SEQ ID NO: 55
```
  1 cacagacatg gctcagtcac tggctctgag cctccttatc ctggttctgg cctttggcat
 61 ccccaggacc caaggcagtg atggaggggc tcaggactgt tgcctcaagt acagccaaag
121 gaagattccc gccaaggttg tccgcagcta ccggaagcag gaaccaagct taggctgctc
181 catcccagct atcctgttct tgccccgcaa gcgctctcag gcagagctat gtgcagaccc
241 aaaggagctc tgggtgcagc agctgatgca gcatctggac aagacaccat ccccacagaa
301 accagcccag ggctgcagga aggacagggg ggcctccaag actggcaaga aaggaaaggg
361 ctccaaaggc tgcaagagga ctgagcggtc acagacccct aaagggccat agcccagtga
421 gcagcctgga gccctggaga ccccaccagc ctcaccagcg cttgaagcct gaacccaaga
481 tgcaagaagg aggctatgct caggggccct ggagcagcca ccccatgctg gccttgccac
541 actctttctc ctgctttaac caccccatct gcattcccag ctctaccctg catggctgag
601 ctgcccacag caggccaggt ccagagagac cgaggaggga gagtctccca gggagcatga
661 gaggaggcag caggactgtc cccttgaagg agaatcatca ggaccctgga cctgatacgg
721 ctccccagta caccccacct cttccttgta aatatgattt atacctaact gaataaaaag
781 ctgttctgtc ttcccaccca aaaaaaaaaa aaaaaaaaaa aaaaaaaaaa aaaaaaaaaa
841 aaaaaaaaaa aaaaaa
```

Human CCL-21 Protein Sequence, Genbank #AAH27918.1
SEQ ID NO: 56
MAQSLALSLLILVLAFGIPRTQGSDGGAQDCCLKYSQRKIPAKVVRSYRKQEPSLGCSIPAILFLPRKRSQAELCADP
KELWVQQLMQHLDKTPSPQKPAQGCRKDRGASKTGKKGKGSKGCKRTERSQTPKGP TABLE 1-continued

| Sequences |
|---|

Human TNF DNA Sequence, Genbank #NM_000594.2; coding sequence: 170-871

SEQ ID NO: 57

```
   1 ctccctcagc aaggacagca gaggaccagc taagagggag agaagcaact acagaccccc
  61 cctgaaaaca accctcagac gccacatccc ctgacaagct gccaggcagg ttctcttcct
 121 ctcacatact gacccacggc tccaccctct ctcccctgga aaggacacca tgagcactga
 181 aagcatgatc cgggacgtgg agctggccga ggaggcgctc cccaagaaga caggggggcc
 241 ccagggctcc aggcggtgct tgttcctcag cctcttctcc ttcctgatcg tggcaggcgc
 301 caccacgctc ttctgcctgc tgcactttgg agtgatcggc ccccagaggg aagagttccc
 361 cagggacctc tctctaatca gccctctggc ccaggcagtc agatcatctt ctcgaacccc
 421 gagtgacaag cctgtagccc atgttgtagc aaaccctcaa gctgaggggc agctccagtg
 481 gctgaaccgc cgggccaatg ccctcctggc caatggcgtg gagctgagag ataaccagct
 541 ggtggtgcca tcagagggcc tgtacctcat ctactcccag gtcctcttca agggccaagg
 601 ctgcccctcc acccatgtgc tcctcaccca caccatcagc cgcatcgccg tctcctacca
 661 gaccaaggtc aacctcctct ctgccatcaa gagcccctgc cagagggaga ccccagaggg
 721 ggctgaggcc aagccctggt atgagcccat ctatctggga ggggtcttcc agctggagaa
 781 gggtgaccga ctcagcgctg agatcaatcg gcccgactat ctcgactttg ccgagtctgg
 841 gcaggtctac tttgggatca ttgccctgtg aggaggacga acatccaacc ttcccaaacg
 901 cctcccctgc cccaatccct ttattacccc ctccttcaga caccctcaac ctcttctggc
 961 tcaaaaagag aattgggggc ttagggtcgg aacccaagct tagaacttta agcaacaaga
1021 ccaccacttc gaaacctggg attcaggaat gtgtggcctg cacagtgaag tgctggcaac
1081 cactaagaat tcaaactggg gcctccagaa ctcactgggg cctacagctt tgatccctga
1141 catctggaat ctggagacca gggagccttt ggttctggcc agaatgctgc aggacttgag
1201 aagacctcac ctagaaattg acacaagtgg accttaggcc ttcctctctc cagatgtttc
1261 cagacttcct tgagacacgg agcccagccc tccccatgga gccagctccc tctatttatg
1321 tttgcacttg tgattattta ttatttattt attatttatt tatttacaga tgaatgtatt
1381 tatttgggag accggggtat cctgggggac ccaatgtagg agctgccttg gctcagacat
1441 gttttccgtg aaaacggagc tgaacaatag gctgttccca tgtagccccc tggcctctgt
1501 gccttctttt gattatgttt tttaaaatat ttatctgatt aagttgtcta aacaatgctg
1561 atttggtgac caactgtcac tcattgctga gcctctgctc cccaggggag ttgtgtctgt
1621 aatcgcccta ctattcagtg gcgagaaata aagtttgctt agaaaagaa
```

Human TNF Protein Sequence, Genbank #NP_000585.2

SEQ ID NO: 58

```
MSTESMIRDVELAEEALPKKTGGPQGSRRCLFLSLFSFLIVAGATTLFCLLHFGVIGPQREEFPRDLSLISPLAQAVRSSSRT
PSDKPVAHVVANPQAEGQLQWLNRRANALLANGVELRDNQLVVPSEGLYLIYSQVLFKGQGCPSTHVLLTHTISRIAVSYQTK
VNLLSAIKSPCQRETPEGAEAKPWYEPIYLGGVFQLEKGDRLSAEINRPDYLDFAESGQVYFGIIAL
```

Human IL-27 cDNA Sequence, Genbank #BC062422.1; coding sequence: 27-758

SEQ ID NO: 59

```
   1 ggggaccaaa gaggctgggc cccgccatgg gccagacggc aggcgacctt ggctggcggc
  61 tcagcctgtt gctgcttccc ttgctcctgg ttcaagctgg tgtctgggga ttcccaaggc
 121 ccccagggag gccccagctg agcctgcagg agctgcggag ggagttcaca gtcagcctgc
 181 atctcgccag gaagctgctc gccgaggttc ggggccaggc ccaccgcttt gcggaatctc
 241 acctgccagg agtgaacctg tacctcctgc ccctgggaga gcagctccct gatgtttccc
 301 tgaccttcca ggcctggcgc cgcctctctg acccggagcg tctctgcttc atctccacca
 361 cgcttcagcc cttccatgcc ctgctgggag ggctggggac ccagggccgc tggaccaaca
 421 tggagaggat gcagctgtgg gccatgaggc tggacctccg cgatctgcag cggcacctcc
 481 gcttccaggt gctggctgca ggattcaacc tcccggagga ggaggaggag gaagaggagg
 541 aggaggagga ggagaggaag ggctgctcc caggggcact gggcagcgcc ttacagggcc
 601 cggcccaggt gtcctggccc cagctcctct ccacctaccg cctgctgcac tccttggagc
 661 tcgtcttatc tcgggccgtg cgggagttgc tgctgctgtc caaggctggg cactcagtct
 721 ggcccttggg gttcccaaca ttgagccccc agccctgatc ggtggcttct tagccccctg
 781 ccccccaccc tttagaactt taggactgga gtcttggcat cagggcagcc ttcgcatcat
 841 cagccttgga caagggaggg ctcttccagc cccctgcccc aggccctacc cagtaactga
 901 aagcccctct ggtcctcgcc agctatttat ttcttggata tttatttatt gtttagggag
 961 atgatggttt atttattgtc ttggggcccg atggtcctcc tcgggccaag cccccatgct
1021 gggtgcccaa taaagcactc tcatccataa aaaaaaaaaa aaaaaaaaaa aaaaaaa
```

Human IL-27 Protein Sequence, Genbank #AAH62422.1

SEQ ID NO: 60

```
MGQTAGDLGWRLSLLLLPLLLVQAGVWGFPRPPGRPQLSLQELRREFTVSLHLARKLLAEVRGQAHRFAESHLPGVNLYLLPL
GEQLPDVSLTFQAWRRLSDPERLCFISTTLQPFHALLGGLGTQGRWTNMERMQLWAMRLDLRDLQRHLRFQVLAAGFNLPEEE
EEEEEEEEERKGLLPGALGSALQGPAQVSWPQLLSTYRLLHSLELVLSRAVRELLLLSKAGHSVWFLGFPTLSPQP
```

mCherry sequence

SEQ ID NO: 61

```
ATGGTGAGCA AGGGCGAGGA GGATAACATG GCCATCATCA AGGAGTTCAT GCGCTTCAAG GTGCACATGG
AGGGCTCCGT GAACGGCCAC GAGTTCGAGA TCGAGGGCGA GGGCGAGGGC CGCCCCTACG AGGGCACCCA
GACCGCCAAG CTGAAGGTGA CCAAGGGTGG CCCCCTGCCC TTCGCCTGGG ACATCCTGTC CCCTCAGTTC
ATGTACGGCT CCAAGGCCTA CGTGAAGCAC CCCGCCGACA TCCCCGACTA CTTGAAGCTG TCCTTCCCCG
AGGGCTTCAA GTGGGAGCGC GTGATGAACT TCGAGGACGG CGGCGTGGTG ACCGTGACCC AGGACTCCTC
CCTGCAGGAC GGCGAGTTCA TCTACAAGGT GAAGCTGCGC GGCACCAACT TCCCCTCCGA CGGCCCCGTA
ATGCAGAAGA AGACCATGGG CTGGGAGGCC TCCTCCGAGC GGATGTACCC CGAGGACGGC GCCCTGAAGG
GCGAGATCAA GCAGAGGCTG AAGCTGAAGG ACGGCGGCCA CTACGACGCT GAGGTCAAGA CCACCTACAA
GGCCAAGAAG CCCGTGCAGC TGCCCGGCGC CTACAACGTC AACATCAAGT TGGACATCAC CTCCCACAAC
GAGGACTACA CCATCGTGGA ACAGTACGAA CGCGCCGAGG GCCGCCACTC CACCGGCGGC ATGGACGAGC
TGTACAAGTA A
```

TABLE 1-continued

| Sequences |
|---|
| Mouse CCL-21-mCherry-mINT fusion DNA sequence<br>SEQ ID NO: 62<br>**ATGGCTCAGATGATGACTCTGAGCCTCCTTAGCCTGGTCCTGGCTCTCTGCATCCCCTGGACCCAAGGCAGTGATGGAGGGGG**<br>**TCAGGACTGCTGCCTTAAGTACAGCCAGAAGAAAATTCCCTACAGTATTGTCCGAGGCTATAGGAAGCAAGAACCAAGTTTAG**<br>**GCTGTCCCATCCCGGCAATCCTGTTCTCACCCCGGAAGCACTCTAAGCCTGAGCTATGTGCAAACCCTGAGGAAGGCTGGGTG**<br>**CAGAACCTGATGCGCCGCCTGGACCAGCCTCCAGCCCCAGGGAAACAAAGCCCCGGCTGCAGGAAGAACCGGGGAACCTCTAA**<br>**GTCTGGAAAGAAAGGAAAGGGCTCCAAGGGCTGCAAGAGAACTGAACAGACACAGCCCTCAAGAGGA**AGATCC<br>ATGGTGAGCA AGGGCGAGGA GGATAACATG GCCATCATCA AGGAGTTCAT GCGCTTCAAG GTGCACATGG<br>AGGGCTCCGT GAACGGCCAC GAGTTCGAGA TCGAGGGCGA GGGCGAGGGC CGCCCCTACG AGGGCACCCA<br>GACCGCCAAG CTGAAGGTGA CCAAGGGTGG CCCCCTGCCC TTCGCCTGGG ACATCCTGTC CCCTCAGTTC<br>ATGTACGGCT CCAAGGCCTA CGTGAAGCAC CCCGCCGACA TCCCCGACTA CTTGAAGCTG TCCTTCCCCG<br>AGGGCTTCAA GTGGGAGCGC GTGATGAACT TCGAGGACGG CGGCGTGGTG ACCGTGACCC AGGACTCCTC<br>CCTGCAGGAC GGCGAGTTCA TCTACAAGGT GAAGCTGCGC GGCACCAACT TCCCCTCCGA CGGCCCCGTA<br>ATGCAGAAGA AGACCATGGG CTGGGAGGCC TCCTCCGAGC GGATGTACCC CGAGGACGGC GCCCTGAAGG<br>GCGAGATCAA GCAGAGGCTG AAGCTGAAGG ACGGCGGCCA CTACGACGCT GAGGTCAAGA CCACCTACAA<br>GGCCAAGAAG CCCGTGCAGC TGCCCGGCGC CTACAACGTC AACATCAAGT TGGACATCAC CTCCCACAAC<br>GAGGACTACA CCATCGTGGA ACAGTACGAA CGCGCCGAGG GCCGCCACTC CACCGGCGGC ATGGACGAGC<br>TGTACAAGTA Atgcacacaacactg gcaggatgct gtgccttgga cagaactcct cagtctacag acagaggatg<br>gcttctggaa acttacacca gaactgggac ttatattaaa<br>tcttaataca aatggtttgc acagctttct taaacaaaaa ggcattcaat ctctaggtgt aaaaggaaga<br>gaatgtctcc tggacctaat tgccacaatg ctggtactac agtttattcg caccaggttg gaaaaagagg<br>gaatagtgtt caaatcactg atgaaaatgg atgacccttc tatttccagg aatattccct gggcttttga<br>ggcaataaag caagcaagtg aatgggtaag aagaactgaaggacagtacc catctatctg cccacggctt<br>gaactgggga acgactggga ctctgccacc aagcagttgc tgggactcca gcccataagc actgtgtccc<br>ctcttcatag agtcctccat tacagtcaag gctaa |
| Mouse CCL21-forward primer<br>SEQ ID NO: 63<br>GCGCGGATCCCCATGGCTCAGATGATG |
| Mouse CCL-21-reverse primer<br>SEQ ID NO: 64<br>GCGCAGATCTTCCTCTTGAGGGCTGTGTCTG |
| Human CCL21 primer<br>SEQ ID NO: 65<br>CCCCACTAGTCCAGTTCTCAGTCACTGGCTCTG |
| Human CCL21 primer<br>SEQ ID NO: 66<br>CCCCGCTAGCTGGCCCTTTAGGGGTCTGTG |
| Human CCL21 primer<br>SEQ ID NO: 67<br>CCCCGCTAGCTGCACACAACACTGGCAGGA |
| Human CCL21 primer<br>SEQ ID NO: 68<br>GGGGCTCGAGTTAGCCTTGACTGTAATGGA |
| Human mINT protein sequence (residues 1473-1724 of human VPARP protein sequence)<br>SEQ ID NO: 69<br>Ala Asn Leu Arg Leu Pro Met Ala Ser Ala Leu Pro Glu Ala Leu Cys<br>Ser Gln Ser Arg Thr Thr Pro Val Asp Leu Cys Leu Leu Glu Glu<br>Ser Val Gly Ser Leu Glu Gly Ser Arg Cys Pro Val Phe Ala Phe<br>Gln Ser Ser Asp Thr Glu Ser Asp Glu Leu Ser Glu Val Leu Gln<br>Asp Ser Cys Phe Leu Gln Ile Lys Cys Asp Thr Lys Asp Asp Ser<br>Ile Pro Cys Phe Leu Glu Leu Lys Glu Glu Asp Glu Ile Val Cys<br>Thr Gln His Trp Gln Asp Ala Val Pro Trp Thr Glu Leu Leu Ser<br>Leu Gln Thr Glu Asp Gly Phe Trp Lys Leu Thr Pro Glu Leu Gly<br>Leu Ile Leu Asn Leu Asn Thr Asn Gly Leu His Ser Phe Leu Lys<br>Gln Lys Gly Ile Gln Ser Leu Gly Val Lys Gly Arg Glu Cys Leu<br>Leu Asp Leu Ile Ala Thr Met Leu Val Leu Gln Phe Ile Arg Thr<br>Arg Leu Glu Lys Glu Gly Ile Val Phe Lys Ser Leu Met Lys Met<br>Asp Asp Pro Ser Ile Ser Arg Asn Ile Pro Trp Ala Phe Glu Ala<br>Ile Lys Gln Ala Ser Glu Trp Val Arg Arg Thr Glu Gly Gln Tyr<br>Pro Ser Ile Cys Pro Arg Leu Glu Leu Gly Asn Asp Trp Asp Ser<br>Ala Thr Lys Gln Leu Leu Gly Leu Gln Pro Ile Ser Thr Val Ser<br>Pro Leu His Arg Val Leu His Tyr Ser Gln Gly |

REFERENCES CITED

1. Kedersha N L, Rome L H: *Isolation and characterization of a novel ribonucleoprotein particle: large structures contain a single species of small RNA. J Cell Biol* 1986, 103 (3):699-709.
2. Kong L B, Siva A C, Rome L H, Stewart P L: *Structure of the vault, a ubiquitous cellular component. Structure* 1999, 7(4):371-379.
3. Kedersha N L, Heuser J E, Chugani D C, Rome L H: Vaults. III. *Vault ribonucleoprotein particles open into flower-like structures with octagonal symmetry. J Cell Biol* 1991, 112 (2):225-235.
4. Suprenant K A: *Vault ribonucleoprotein particles: sarcophagi, gondolas, or safety deposit boxes? Biochemistry* 2002, 41(49):14447-14454.
5. Berger W, Steiner E, Grusch M, Elbling L, Micksche M: *Vaults and the major vault protein: novel roles in signal pathway regulation and immunity. Cell Mol Life Sci* 2009, 66(1):43-61.
6. Champion C I, Kickhoefer V A, Liu G, Moniz R J, Freed A S, Bergmann L L, Vaccari D, Raval-Fernandes S, Chan A M, Rome L H et al: *A vault nanoparticle vaccine induces protective mucosal immunity. PLoS One* 2009, 4(4):e5409. Epub 2009 April 5430.
7. Stephen A G, Raval-Fernandes S, Huynh T, Tones M, Kickhoefer V A, Rome L H: *Assembly of vault-like particles in insect cells expressing only the major vault protein. J Biol Chem* 2001, 276(26):23217-23220. Epub 22001 May 23210.
8. Kickhoefer V A, Garcia Y, Mikyas Y, Johansson E, Zhou J C, Raval-Fernandes S, Minoofar P, Zink J I, Dunn B, Stewart P L et al: *Engineering of vault nanocapsules with enzymatic and fluorescent properties. Proc Natl Acad Sci USA* 2005, 102(12):4348-4352. Epub 2005 March 4347.
9. Gunn M, Tangemann K, Tam C, Cyster J, Rosen S, Williams L: *A chemokine expressed in lymphoid high endothelial venules promotes the adhesion and chemotaxis of naive T lymphocytes. Proceedings of the National Academy of Sciences of the United States of America* 1998, 695(1):259-263.
10. Warnock R A, Campbell J J, Dorf M E, Matsuzawa A, McEvoy L M, Butcher E C: *The role of chemokines in the microenvironmental control of T versus B cell arrest in Peyer's patch high endothelial venules. J Exp Med* 2000, 191(1):77-88.
11. Willimann K, Legler D F, Loetscher M, Roos R S, Delgado M B, Clark-Lewis I, Baggiolini M, Moser B: *The chemokine SLC is expressed in T cell areas of lymph nodes and mucosal lymphoid tissues and attracts activated T cells via CCR*7. *Eur J Immunol* 1998, 28(6):2025-2034.
12. Sharma S, Stolina M, Luo J, Strieter R M, Burdick M, Zhu L X, Batra R K, Dubinett S M: *Secondary lymphoid tissue chemokine mediates T cell-dependent antitumor responses in vivo. J Immunol* 2000, 164(9):4558-4563.
13. Yang S C, Hillinger S, Riedl K, Zhang L, Zhu L, Huang M, Atianzar K, Kuo B Y, Gardner B, Batra R K et al: *Intratumoral administration of dendritic cells overexpressing CCL*21 *generates systemic antitumor responses and confers tumor immunity. Clin Cancer Res* 2004, 10(8):2891-2901.
14. Yang S C, Batra R K, Hillinger S, Reckamp K L, Strieter R M, Dubinett S M, Sharma S: *Intrapulmonary administration of CCL*21 *gene-modified dendritic cells reduces tumor burden in spontaneous murine bronchoalveolar cell carcinoma. Cancer Res* 2006, 66(6):3205-3213.
15. Kirk C J, Hartigan-O'Connor D, Mule J J: *The dynamics of the T-cell antitumor response: chemokine-secreting dendritic cells can prime tumor-reactive T cells extranodally. Cancer Res* 2001, 61(24):8794-8802.
16. Novak L, Igoucheva O, Cho S, Alexeev V: *Characterization of the CCL*21*-mediated melanoma-specific immune responses and in situ melanoma eradication. Mol Cancer Ther* 2007, 6(6):1755-1764.
17. Liang C M, Zhong C P, Sun R X, Liu B B, Huang C, Qin J, Zhou S, Shan J, Liu Y K, Ye S L: *Local expression of secondary lymphoid tissue chemokine delivered by adeno-associated virus within the tumor bed stimulates strong anti-liver tumor immunity. J Virol* 2007, 81(17):9502-9511. Epub 2007 June 9513.
18. Wu S, Xing W, Peng J, Yuan X, Zhao X, Lei P, Li W, Wang M, Zhu H, Huang B et al: *Tumor transfected with CCL*21 *enhanced reactivity and apoptosis resistance of human monocyte-derived dendritic cells. Immunobiology* 2008, 213(5):417-426. *Epub* 2007 November 2028.
19. Yousefieh N, Hahto S M, Stephens A L, Ciavarra R P: *Regulated Expression of CCL*21 *in the Prostate Tumor Microenvironment Inhibits Tumor Growth and Metastasis in an Orthotopic Model of Prostate Cancer. Cancer Microenviron* 2009, 6:6.
20. Baratelli F, Takedatsu H, Hazra S, Peebles K, Luo J, Kurimoto P S, Zeng G, Batra R K, Sharma S, Dubinett S M et al: *Pre-clinical characterization of GMP grade CCL*21*-gene modified dendritic cells for application in a phase I trial in Non-Small Cell Lung Cancer. J Transl Med* 2008, 6(1):38.
21. Lai C Y, Wiethoff C M, Kickhoefer V A, Rome L H, Nemerow G R: *Vault nanoparticles containing an adenovirus-derived membrane lytic protein facilitate toxin and gene transfer. ACS Nano* 2009, 3(3):691-699.
22. Siva A C, Raval-Fernandes S, Stephen A G, LaFemina M J, Scheper R J, Kickhoefer V A, Rome L H: *Up-regulation of vaults may be necessary but not sufficient for multidrug resistance. Int J Cancer* 2001, 92(2):195-202.
23. Kickhoefer V A, Siva A C, Kedersha N L, Inman E M, Ruland C, Streuli M, Rome L H: *The* 193*-kD vault protein, VPARP, is a novel poly*(*ADP-ribose*) *polymerase. J Cell Biol* 1999, 146(5):917-928.
24. Andersson A, Yang S C, Huang M, Zhu L, Kar U K, Batra R K, Elashoff D, Strieter R M, Dubinett S M, Sharma S: *IL-*7 *promotes CXCR*3 *ligand-dependent T cell antitumor reactivity in lung cancer. J Immunol* 2009, 182(11):6951-6958.
25. Chen H, Liakou C I, Kamat A, Pettaway C, Ward J F, Tang D N, Sun J, Jungbluth A A, Troncoso P, Logothetis C et al: *Anti-CTLA-*4 *therapy results in higher CD*4+*ICOShi T cell frequency and IFN-gamma levels in both nonmalignant and malignant prostate tissues. Proc Natl Acad Sci USA* 2009, 106(8):2729-2734. Epub 2009 February 2726.
26. Mikyas Y, Makabi M, Raval-Fernandes S, Harrington L, Kickhoefer V A, Rome L H, Stewart P L: *Cryoelectron microscopy imaging of recombinant and tissue derived vaults: localization of the MVP N termini and VPARP. J Mol Biol* 2004, 344(1):91-105.
27. Sharma S, Stolina M, Zhu L, Lin Y, Batra R, Huang M, Strieter R, Dubinett S M: *Secondary lymphoid organ chemokine reduces pulmonary tumor burden in spontaneous murine bronchoalveolar cell carcinoma. Cancer research* 2001, 61(17):6406-6412.
28. Sharma S, Yang S C, Hillinger S, Zhu L X, Huang M, Batra R K, Lin J F, Burdick M D, Strieter R M, Dubinett S M: *SLC/CCL*21*-mediated anti-tumor responses require IFNgamma, MIG/CXCL*9 *and IP-*10*/CXCL*10. *Molecular cancer* 2003, 2(1):22.

29. Kickhoefer V A, Han M, Raval-Fernandes S, Poderycki M J, Moniz R J, Vaccari D, Silvestry M, Stewart P L, Kelly K A, Rome L H: *Targeting vault nanoparticles to specific cell surface receptors. ACS Nano* 2009, 3(1):27-36.
30. Johnson S K, Kerr K M, Chapman A D, Kennedy M M, King G, Cockburn J S, Jeffrey R R: *Immune cell infiltrates and prognosis in primary carcinoma of the lung. Lung Cancer* 2000, 27(1):27-35.
31. Hiraoka K, Miyamoto M, Cho Y, Suzuoki M, Oshikiri T, Nakakubo Y, Itoh T, Ohbuchi T, Kondo S, Katoh H: *Concurrent infiltration by CD8+ T cells and CD4+ T cells is a favourable prognostic factor in non-small-cell lung carcinoma. Br J Cancer* 2006, 94(2):275-280.
32. Dieu-Nosjean M C, Antoine M, Danel C, Heudes D, Wislez M, Poulot V, Rabbe N, Laurans L, Tartour E, de Chaisemartin L et al: *Long-term survival for patients with non-small-cell lung cancer with intratumoral lymphoid structures. J Clin Oncol* 2008, 26(27):4410-4417.
33. Woo E Y, Yeh H, Chu C S, Schlienger K, Carroll R G, Riley J L, Kaiser L R, June C H: Cutting edge: *Regulatory T cells from lung cancer patients directly inhibit autologous T cell proliferation. J Immunol* 2002, 168(9):4272-4276.
34. Yannelli J R, Tucker J A, Hidalgo G, Perkins S, Kryscio R, Hirschowitz E A: *Characteristics of PBMC obtained from leukapheresis products and tumor biopsies of patients with non-small cell lung cancer. Oncol Rep* 2009, 22(6):1459-1471.
35. Li L, Chao Q G, Ping L Z, Xue C, Xia Z Y, Qian D, Shi-ang H: *The prevalence of FOXP3+ regulatory T-cells in peripheral blood of patients with NSCLC. Cancer Biother Radiopharm* 2009, 24(3):357-367.
36. Ju S, Qiu H, Zhou X, Zhu B, Lv X, Huang X, Li J, Zhang Y, Liu L, Ge Y et al: *CD13+CD4+CD25hi regulatory T cells exhibit higher suppressive function and increase with tumor stage in non-small cell lung cancer patients. Cell cycle* (Georgetown, Tex. 2009, 8(16):2578-2585.
37. Sakaguchi S: *Regulatory T cells: key controllers of immunologic self-tolerance. Cell* 2000, 101(5):455-458.
38. Boon T, Cerottini J-C, Van den Eynde B, van der Bruggen P, Van Pel A: *Tumor antigens recognized by T lymphocytes. Annu Rev Immunol* 1994, 12:337-365.
39. Li C, Heidt D G, Dalerba P, Burant C F, Zhang L, Adsay V, Wicha M, Clarke M F, Simeone D M: Identification of pancreatic cancer stem cells. Cancer research 2007, 67(3): 1030-1037.
40. Smyth M J, Teng M W, Swann J, Kyparissoudis K, Godfrey D I, Hayakawa Y: *CD4+CD25+ T regulatory cells suppress NK cell-mediated immunotherapy of cancer. J Immunol* 2006, 176(3):1582-1587.
41. Young M R, Wright M A, Pandit R: *Myeloid differentiation treatment to diminish the presence of immune-suppressive CD34+ cells within human head and neck squamous cell carcinomas. J Immunol* 1997, 159(2):990-996.
42. Kusmartsev S A, Kusmartseva I N, Afanasyev S G, Cherdyntseva N V: *Immunosuppressive cells in bone marrow of patients with stomach cancer. Adv Exp Med Biol* 1998, 451:189-194.
43. Almand B, Clark J I, Nikitina E, van Beynen J, English N R, Knight S C, Carbone D P, Gabrilovich D I: *Increased production of immature myeloid cells in cancer patients: a mechanism of immunosuppression in cancer. J Immunol* 2001, 166(1):678-689.
44. Diaz-Montero C M, Salem M L, Nishimura M I, Garrett-Mayer E, Cole D J, Montero A J: *Increased circulating myeloid-derived suppressor cells correlate with clinical cancer stage, metastatic tumor burden, and doxorubicin-cyclophosphamide chemotherapy. Cancer Immunol Immunother* 2009, 58(1):49-59.
45. Liu C Y, Wang Y M, Wang C L, Feng P H, Ko H W, Liu Y H, Wu Y C, Chu Y, Chung F T, Kuo C H et al: *Population alterations of L: -arginase-and inducible nitric oxide synthase-expressed CD11b(+)/CD14 (−)/CD15 (+)/CD33 (+) myeloid-derived suppressor cells and CD8 (+) T lymphocytes in patients with advanced-stage non-small cell lung cancer. J Cancer Res Clin Oncol* 2009.
46. Srivastava M K, Bosch J J, Thompson J A, Ksander B R, Edelman M J, Ostrand-Rosenberg S: *Lung cancer patients' CD4(+) T cells are activated in vitro by MHC II cell-based vaccines despite the presence of myeloid-derived suppressor cells. Cancer Immunol Immunother* 2008, 57(10): 1493-1504.
47. Young M R, Newby M, Wepsic H T: *Hematopoiesis and suppressor bone marrow cells in mice bearing large metastatic Lewis lung carcinoma tumors. Cancer Res* 1987, 47(1):100-105.
48. Subiza J L, Vinuela J E, Rodriguez R, Gil J, Figueredo M A, De La Concha E G: *Development of splenic natural suppressor (NS) cells in Ehrlich tumor-bearing mice. Int J Cancer* 1989, 44(2):307-314.
49. Kusmartsev S A, Ogreba V I: *[Suppressor activity of bone marrow and spleen cells in C57B1/6 mice during carcinogenesis induced by 7,12-dimethylbenz(a)anthracene]. Eksp Onkol* 1989, 11(5):23-26.
50. Kusmartsev S A, Li Y, Chen S H: *Gr-1+ myeloid cells derived from tumor-bearing mice inhibit primary T cell activation induced through CD3/CD28 costimulation. J Immunol* 2000, 165(2):779-785.
51. Sinha P, Clements V K, Ostrand-Rosenberg S: *Reduction of myeloid-derived suppressor cells and induction of M1 macrophages facilitate the rejection of established metastatic disease. J Immunol* 2005, 174(2):636-645.
52. Liu C, Yu S, Kappes J, Wang J, Grizzle W E, Zinn K R, Zhang H G: *Expansion of spleen myeloid suppressor cells represses NK cell cytotoxicity in tumor-bearing host. Blood* 2007, 109(10):4336-4342.
53. Maeda et al., *Tumor vascular* permeability and the EPR effect in macromolecular therapeutics: a review. *J. of Controlled Release* 2000, 65: 271-284.
54. Griesh, K., *Enhanced permeability and retention of macromolecular drugs in solid tumors: A royal gate for targeted anticancer nanomedicines. J. of Drug Targeting* 2007, 15(7-8): 457-464
55. Allen et al., *Drug Delivery Systems: Entering the Mainstream. Science* 2004, 303:1818-1822.

The invention claimed is:

1. A composition comprising a vault complex comprising a major vault protein and a fusion protein comprising a cytokine and a vault targeting domain, wherein the vault targeting domain is a vault poly ADP-ribose polymerase (VPARP) sequence or a portion thereof that interacts with the major vault protein, or a telomerase/vault associated protein 1 (TEP 1) sequence or a portion thereof that interacts with the major vault protein, wherein the fusion protein is non-covalently associated with the vault complex.

2. The composition of claim 1, wherein the cytokine is a chemokine.

3. The composition of claim 1, wherein the cytokine is a cysteine-cysteine chemokine.

4. The composition of claim 1, wherein the cytokine is a CCL-21 chemokine.

5. The composition of claim 1, wherein the cytokine comprises the amino acid sequence of SEQ ID NO:2.

6. The composition of claim 1, wherein the vault targeting domain is a portion of the VPARP that is a major vault protein interaction (mINT) domain.

7. The composition of claim 6, wherein the mINT domain comprises the amino acid sequence of SEQ ID NO:8.

8. The composition of claim 1, wherein the fusion protein comprises the amino acid sequence of SEQ ID NO:13.

9. A method of delivering a cytokine to a cell, comprising introducing the composition of claim 1 to the cell.

10. The method of claim 9, wherein the composition is introduced into the extracellular environment surrounding the cell.

11. A method for stimulating an immune response in a cell, the method comprising contacting the cell with the composition of claim 1.

12. The method of claim 11, wherein the cell is a human cell.

13. The method of claim 11, wherein the immune response induces migration of T cells and dendritic cells.

14. The method of claim 11, wherein contacting the cell with the composition of claim 2 increases T cell migration to the cell by at least 5% compared to administration of CCL-21 cytokine alone.

15. A method for stimulating an immune response in a subject, the method comprising administering the composition of claim 1 to the subject.

16. The method of claim 15, wherein the subject is a human.

17. A method of treating or managing cancer in a subject in need of treatment or management of cancer, comprising administering to a subject a therapeutically effective amount of the composition of claim 1.

* * * * *